United States Patent
Han et al.

(10) Patent No.: US 7,511,012 B2
(45) Date of Patent: Mar. 31, 2009

(54) MYOSTATIN BINDING AGENTS

(75) Inventors: Hq Han, Thousand Oaks, CA (US); Hosung Min, Newbury Park, CA (US); Thomas Charles Boone, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 581 days.

(21) Appl. No.: 10/742,379

(22) Filed: Dec. 19, 2003

(65) Prior Publication Data
US 2004/0181033 A1 Sep. 16, 2004

Related U.S. Application Data

(60) Provisional application No. 60/435,923, filed on Dec. 20, 2002.

(51) Int. Cl.
*A61K 38/03* (2006.01)
*A61K 38/04* (2006.01)
*A61K 38/02* (2006.01)
*A61K 38/08* (2006.01)
*A61K 38/10* (2006.01)
*A61K 38/16* (2006.01)
*C07K 19/00* (2006.01)
*C07K 16/00* (2006.01)
*C07K 16/22* (2006.01)
*C07K 14/00* (2006.01)

(52) U.S. Cl. .............................. 514/2; 514/12; 514/13; 514/14; 514/15; 530/300; 530/324; 530/325; 530/326; 530/327; 530/328; 530/350

(58) Field of Classification Search ........................ None
See application file for complete search history.

(56) References Cited

U.S. PATENT DOCUMENTS

| 6,284,882 B1 * | 9/2001 | Wu-Wong et al. .......... 536/24.1 |
| 6,369,201 B1 | 4/2002 | Barker et al. |
| 6,660,843 B1 | 12/2003 | Feige et al. |
| 2003/0140356 A1 | 7/2003 | Bass et al. |
| 2004/0087778 A1 | 5/2004 | Feige et al. |
| 2006/0140934 A1 * | 6/2006 | Gegg et al. .............. 424/133.1 |

FOREIGN PATENT DOCUMENTS

| GB | 2 333 706 A | 8/1999 |
| WO | WO 93/06843 | 4/1993 |
| WO | WO 99/02667 | 1/1999 |
| WO | WO 99/56768 A1 | 11/1999 |
| WO | WO 00/07038 A2 | 2/2000 |
| WO | WO 00/24782 A3 | 5/2000 |
| WO | WO 00/43781 A2 | 7/2000 |
| WO | WO 00/77206 A3 | 12/2000 |
| WO | WO 01/53350 A1 | 7/2001 |
| WO | WO 02/09641 A2 | 2/2002 |

OTHER PUBLICATIONS

Ngo et al., 1994, The Protein Folding Problem and Tertiary Structure Prediction, Merz and Le Grnad, eds., Birkhauser, Boston, pp. 491-495.*
Wells, 1990, Biochemistry 29:8509-8517.*
Thies et al., 2001, Growth Factors 8 (4): 251-259.*
Se-Jin Lee et al., "Regulation of myostatin activity and muscle growth," *Proc. Natl. Acad. Sci. USA* 98:9306-9311, 2001.
Supplementary European Search Report, EP 03 81 4258, mailed Sep. 9, 2008.

* cited by examiner

*Primary Examiner*—Elizabeth C. Kemmerer
(74) *Attorney, Agent, or Firm*—Christine M. Bellas

(57) ABSTRACT

The present invention provides binding agents comprising peptides capable of binding myostatin and inhibiting its activity. In one embodiment the binding agent comprises at least one myostatin-binding peptide attached directly or indirectly to at least one vehicle such as a polymer or an Fc domain. The binding agents of the present invention produced increased lean muscle mass when administered to animals and decreased fat to muscle ratios. Therapeutic compositions containing the binding agents of the present invention are useful for treating muscle-wasting disorders and metabolic disorders including diabetes and obesity.

22 Claims, 6 Drawing Sheets

SEQUENCE LISTING

```
<160> NUMBER OF SEQ ID NOS: 634

<210> SEQ ID NO 1
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 1

Lys Asp Lys Cys Lys Met Trp His Trp Met Cys Lys Pro Pro
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 2

Lys Asp Leu Cys Ala Met Trp His Trp Met Cys Lys Pro Pro
1               5                   10

<210> SEQ ID NO 3
<211> LENGTH: 13
<212> TYPE: PRT
```

```
<213> ORGANISM: Artificial Sequence
<220> FEATURE:
<223> OTHER INFORMATION: Myostatin Binding Peptide

<400> SEQUENCE: 3

Asp Leu Cys Lys Met Trp Lys Trp Met Cys Lys Pro Pro
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 4

Lys Asp Leu Cys Lys Met Trp His Trp Met Cys Lys Pro Lys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 5

Trp Tyr Pro Cys Tyr Glu Phe His Phe Trp Cys Tyr Asp Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 6

Trp Tyr Pro Cys Tyr Glu Gly His Phe Trp Cys Tyr Asp Leu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 7

Ile Phe Gly Cys Lys Trp Trp Asp Val Gln Cys Tyr Gln Phe
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 8

Ile Phe Gly Cys Lys Trp Trp Asp Val Asp Cys Tyr Gln Phe
1               5                   10

<210> SEQ ID NO 9
<211> LENGTH: 14
<212> TYPE: PRT
<213> ORGANISM: Artificial Sequence
```

```
<220> FEATURE:
<223> OTHER INFORMATION: Myostatin Binding Peptide

<400> SEQUENCE: 9

Ala Asp Trp Cys Val Ser Pro Asn Trp Phe Cys Met Val Met
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 10

His Lys Phe Cys Pro Trp Trp Ala Leu Phe Cys Trp Asp Phe
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 11

Lys Asp Leu Cys Lys Met Trp His Trp Met Cys Lys Pro Pro
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 12

Ile Asp Lys Cys Ala Ile Trp Gly Trp Met Cys Pro Pro Leu
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 13

Trp Tyr Pro Cys Gly Glu Phe Gly Met Trp Cys Leu Asn Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Myostatin Binding Peptide

<400> SEQUENCE: 14

Trp Phe Thr Cys Leu Trp Asn Cys Asp Asn Glu
1               5                   10

<210> SEQ ID NO 15
<211> LENGTH: 14
<212> TYPE: PRT
<213> ORGANISM: Artificial Sequence
<220> FEATURE:
```

<223> OTHER INFORMATION: Myostatin Binding Peptide

<400> SEQUENCE: 15

His Thr Pro Cys Pro Trp Phe Ala Pro Leu Cys Val Glu Trp
1 5 10

<210> SEQ ID NO 16
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 16

Lys Glu Trp Cys Trp Arg Trp Lys Trp Met Cys Lys Pro Glu
1 5 10

<210> SEQ ID NO 17
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 17

Phe Glu Thr Cys Pro Ser Trp Ala Tyr Phe Cys Leu Asp Ile
1 5 10

<210> SEQ ID NO 18
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 18

Ala Tyr Lys Cys Glu Ala Asn Asp Trp Gly Cys Trp Trp Leu
1 5 10

<210> SEQ ID NO 19
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 19

Asn Ser Trp Cys Glu Asp Gln Trp His Arg Cys Trp Trp Leu
1 5 10

<210> SEQ ID NO 20
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 20

Trp Ser Ala Cys Tyr Ala Gly His Phe Trp Cys Tyr Asp Leu
1 5 10

<210> SEQ ID NO 21
<211> LENGTH: 14
<212> TYPE: PRT
<213> ORGANISM: Artificial Sequence
<220> FEATURE:
<223> OTHER INFORMATION: Myostatin Binding Peptide

```
<400> SEQUENCE: 21

Ala Asn Trp Cys Val Ser Pro Asn Trp Phe Cys Met Val Met
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 22

Trp Thr Glu Cys Tyr Gln Gln Glu Phe Trp Cys Trp Asn Leu
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 23

Glu Asn Thr Cys Glu Arg Trp Lys Trp Met Cys Pro Pro Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 24

Trp Leu Pro Cys His Gln Glu Gly Phe Trp Cys Met Asn Phe
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 25

Ser Thr Met Cys Ser Gln Trp His Trp Met Cys Asn Pro Phe
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 26

Ile Phe Gly Cys His Trp Trp Asp Val Asp Cys Tyr Gln Phe
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Myostatin Binding Peptide
```

```
<400> SEQUENCE: 27

Ile Tyr Gly Cys Lys Trp Trp Asp Ile Gln Cys Tyr Asp Ile
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 28

Pro Asp Trp Cys Ile Asp Pro Asp Trp Trp Cys Lys Phe Trp
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 29

Gln Gly His Cys Thr Arg Trp Pro Trp Met Cys Pro Pro Tyr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 30

Trp Gln Glu Cys Tyr Arg Glu Gly Phe Trp Cys Leu Gln Thr
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 31

Trp Phe Asp Cys Tyr Gly Pro Gly Phe Lys Cys Trp Ser Pro
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 32

Gly Val Arg Cys Pro Lys Gly His Leu Trp Cys Leu Tyr Pro
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 33
```

```
His Trp Ala Cys Gly Tyr Trp Pro Trp Ser Cys Lys Trp Val
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 34

```
Gly Pro Ala Cys His Ser Pro Trp Trp Trp Cys Val Phe Gly
1               5                   10
```

<210> SEQ ID NO 35
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 35

```
Thr Thr Trp Cys Ile Ser Pro Met Trp Phe Cys Ser Gln Gln
1               5                   10
```

<210> SEQ ID NO 36
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 36

```
His Lys Phe Cys Pro Pro Trp Ala Ile Phe Cys Trp Asp Phe
1               5                   10
```

<210> SEQ ID NO 37
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 37

```
Pro Asp Trp Cys Val Ser Pro Arg Trp Tyr Cys Asn Met Trp
1               5                   10
```

<210> SEQ ID NO 38
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 38

```
Val Trp Lys Cys His Trp Phe Gly Met Asp Cys Glu Pro Thr
1               5                   10
```

<210> SEQ ID NO 39
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 39

```
Lys Lys His Cys Gln Ile Trp Thr Trp Met Cys Ala Pro Lys
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 40

Trp Phe Gln Cys Gly Ser Thr Leu Phe Trp Cys Tyr Asn Leu
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 41

Trp Ser Pro Cys Tyr Asp His Tyr Phe Tyr Cys Tyr Thr Ile
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 42

Ser Trp Met Cys Gly Phe Phe Lys Glu Val Cys Met Trp Val
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 43

Glu Met Leu Cys Met Ile His Pro Val Phe Cys Asn Pro His
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 44

Leu Lys Thr Cys Asn Leu Trp Pro Trp Met Cys Pro Pro Leu
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 45

Val Val Gly Cys Lys Trp Tyr Glu Ala Trp Cys Tyr Asn Lys
```

```
<210> SEQ ID NO 46
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 46

Pro Ile His Cys Thr Gln Trp Ala Trp Met Cys Pro Pro Thr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 47

Asp Ser Asn Cys Pro Trp Tyr Phe Leu Ser Cys Val Ile Phe
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 48

His Ile Trp Cys Asn Leu Ala Met Met Lys Cys Val Glu Met
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 49

Asn Leu Gln Cys Ile Tyr Phe Leu Gly Lys Cys Ile Tyr Phe
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 50

Ala Trp Arg Cys Met Trp Phe Ser Asp Val Cys Thr Pro Gly
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 51

Trp Phe Arg Cys Phe Leu Asp Ala Asp Trp Cys Thr Ser Val
1               5                   10
```

<210> SEQ ID NO 52
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 52

Glu Lys Ile Cys Gln Met Trp Ser Trp Met Cys Ala Pro Pro
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 53

Trp Phe Tyr Cys His Leu Asn Lys Ser Glu Cys Thr Glu Pro
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 54

Phe Trp Arg Cys Ala Ile Gly Ile Asp Lys Cys Lys Arg Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 55

Asn Leu Gly Cys Lys Trp Tyr Glu Val Trp Cys Phe Thr Tyr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 56

Ile Asp Leu Cys Asn Met Trp Asp Gly Met Cys Tyr Pro Pro
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 57

Glu Met Pro Cys Asn Ile Trp Gly Trp Met Cys Pro Pro Val
1               5                   10

```
<210> SEQ ID NO 58
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 58

Trp Phe Arg Cys Val Leu Thr Gly Ile Val Asp Trp Ser Glu Cys Phe
 1               5                  10                  15

Gly Leu

<210> SEQ ID NO 59
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 59

Trp Phe Arg Cys Val Leu Thr Gly Ile Val Asp Trp Ser Glu Cys Phe
 1               5                  10                  15

Gly Leu

<210> SEQ ID NO 60
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 60

Leu Pro Trp Cys His Asp Gln Val Asn Ala Asp Trp Gly Phe Cys Met
 1               5                  10                  15

Leu Trp

<210> SEQ ID NO 61
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 61

Tyr Pro Thr Cys Ser Glu Lys Phe Trp Ile Tyr Gly Gln Thr Cys Val
 1               5                  10                  15

Leu Trp

<210> SEQ ID NO 62
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 62

Leu Gly Pro Cys Pro Ile His His Gly Pro Trp Pro Gln Tyr Cys Val
 1               5                  10                  15

Tyr Trp

<210> SEQ ID NO 63
<211> LENGTH: 18
<212> TYPE: PRT
```

```
<213> ORGANISM: Artificial Sequence
<220> FEATURE:
<223> OTHER INFORMATION: Myostatin Binding Peptide

<400> SEQUENCE: 63

Pro Phe Pro Cys Glu Thr His Gln Ile Ser Trp Leu Gly His Cys Leu
1               5                   10                  15

Ser Phe

<210> SEQ ID NO 64
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 64

His Trp Gly Cys Glu Asp Leu Met Trp Ser Trp His Pro Leu Cys Arg
1               5                   10                  15

Arg Pro

<210> SEQ ID NO 65
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 65

Leu Pro Leu Cys Asp Ala Asp Met Met Pro Thr Ile Gly Phe Cys Val
1               5                   10                  15

Ala Tyr

<210> SEQ ID NO 66
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 66

Ser His Trp Cys Glu Thr Thr Phe Trp Met Asn Tyr Ala Lys Cys Val
1               5                   10                  15

His Ala

<210> SEQ ID NO 67
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 67

Leu Pro Lys Cys Thr His Val Pro Phe Asp Gln Gly Gly Phe Cys Leu
1               5                   10                  15

Trp Tyr

<210> SEQ ID NO 68
<211> LENGTH: 18
<212> TYPE: PRT
<213> ORGANISM: Artificial Sequence
<220> FEATURE:
<223> OTHER INFORMATION: Myostatin Binding Peptide
```

```
<400> SEQUENCE: 68

Phe Ser Ser Cys Trp Ser Pro Val Ser Arg Gln Asp Met Phe Cys Val
1               5                   10                  15

Phe Tyr

<210> SEQ ID NO 69
<211> LENGTH: 17
<212> TYPE: PRT
<213> ORGANISM: Artificial Sequence
<220> FEATURE:
<223> OTHER INFORMATION: Myostatin Binding Peptide

<400> SEQUENCE: 69

Ser His Lys Cys Glu Tyr Ser Gly Trp Leu Gln Pro Leu Cys Tyr Arg
1               5                   10                  15

Pro

<210> SEQ ID NO 70
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 70

Pro Trp Trp Cys Gln Asp Asn Tyr Val Gln His Met Leu His Cys Asp
1               5                   10                  15

Ser Pro

<210> SEQ ID NO 71
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 71

Trp Phe Arg Cys Met Leu Met Asn Ser Phe Asp Ala Phe Gln Cys Val
1               5                   10                  15

Ser Tyr

<210> SEQ ID NO 72
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 72

Pro Asp Ala Cys Arg Asp Gln Pro Trp Tyr Met Phe Met Gly Cys Met
1               5                   10                  15

Leu Gly

<210> SEQ ID NO 73
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 73

Phe Leu Ala Cys Phe Val Glu Phe Glu Leu Cys Phe Asp Ser
1               5                   10
```

<210> SEQ ID NO 74
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 74

Ser Ala Tyr Cys Ile Ile Thr Glu Ser Asp Pro Tyr Val Leu Cys Val
1               5                   10                  15

Pro Leu

<210> SEQ ID NO 75
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 75

Pro Ser Ile Cys Glu Ser Tyr Ser Thr Met Trp Leu Pro Met Cys Gln
1               5                   10                  15

His Asn

<210> SEQ ID NO 76
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 76

Trp Leu Asp Cys His Asp Asp Ser Trp Ala Trp Thr Lys Met Cys Arg
1               5                   10                  15

Ser His

<210> SEQ ID NO 77
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 77

Tyr Leu Asn Cys Val Met Met Asn Thr Ser Pro Phe Val Glu Cys Val
1               5                   10                  15

Phe Asn

<210> SEQ ID NO 78
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 78

Tyr Pro Trp Cys Asp Gly Phe Met Ile Gln Gln Gly Ile Thr Cys Met
1               5                   10                  15

Phe Tyr

<210> SEQ ID NO 79
<211> LENGTH: 18

```
<212> TYPE: PRT
<213> ORGANISM: Artificial Sequence
<220> FEATURE:
<223> OTHER INFORMATION: Myostatin Binding Peptide

<400> SEQUENCE: 79

Phe Asp Tyr Cys Thr Trp Leu Asn Gly Phe Lys Asp Trp Lys Cys Trp
1               5                   10                  15

Ser Arg

<210> SEQ ID NO 80
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 80

Leu Pro Leu Cys Asn Leu Lys Glu Ile Ser His Val Gln Ala Cys Val
1               5                   10                  15

Leu Phe

<210> SEQ ID NO 81
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 81

Ser Pro Glu Cys Ala Phe Ala Arg Trp Leu Gly Ile Glu Gln Cys Gln
1               5                   10                  15

Arg Asp

<210> SEQ ID NO 82
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 82

Tyr Pro Gln Cys Phe Asn Leu His Leu Leu Glu Trp Thr Glu Cys Asp
1               5                   10                  15

Trp Phe

<210> SEQ ID NO 83
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 83

Arg Trp Arg Cys Glu Ile Tyr Asp Ser Glu Phe Leu Pro Lys Cys Trp
1               5                   10                  15

Phe Phe

<210> SEQ ID NO 84
<211> LENGTH: 14
<212> TYPE: PRT
<213> ORGANISM: Artificial Sequence
<220> FEATURE:
<223> OTHER INFORMATION: Myostatin Binding Peptide
```

-continued

```
<400> SEQUENCE: 84

Leu Val Gly Cys Asp Asn Val Trp His Arg Cys Lys Leu Phe
1               5                   10

<210> SEQ ID NO 85
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 85

Ala Gly Trp Cys His Val Trp Gly Glu Met Phe Gly Met Gly Cys Ser
1               5                   10                  15

Ala Leu

<210> SEQ ID NO 86
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 86

His His Glu Cys Glu Trp Met Ala Arg Trp Met Ser Leu Asp Cys Val
1               5                   10                  15

Gly Leu

<210> SEQ ID NO 87
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 87

Phe Pro Met Cys Gly Ile Ala Gly Met Lys Asp Phe Asp Cys Val
1               5                   10                  15

Trp Tyr

<210> SEQ ID NO 88
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 88

Arg Asp Asp Cys Thr Phe Trp Pro Glu Trp Leu Trp Lys Leu Cys Glu
1               5                   10                  15

Arg Pro

<210> SEQ ID NO 89
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 89

Tyr Asn Phe Cys Ser Tyr Leu Phe Gly Val Ser Lys Glu Ala Cys Gln
1               5                   10                  15
```

Leu Pro

<210> SEQ ID NO 90
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 90

Ala His Trp Cys Glu Gln Gly Pro Trp Arg Tyr Gly Asn Ile Cys Met
1               5                   10                  15

Ala Tyr

<210> SEQ ID NO 91
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 91

Asn Leu Val Cys Gly Lys Ile Ser Ala Trp Gly Asp Glu Ala Cys Ala
1               5                   10                  15

Arg Ala

<210> SEQ ID NO 92
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 92

His Asn Val Cys Thr Ile Met Gly Pro Ser Met Lys Trp Phe Cys Trp
1               5                   10                  15

Asn Asp

<210> SEQ ID NO 93
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 93

Asn Asp Leu Cys Ala Met Trp Gly Trp Arg Asn Thr Ile Trp Cys Gln
1               5                   10                  15

Asn Ser

<210> SEQ ID NO 94
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 94

Pro Pro Phe Cys Gln Asn Asp Asn Asp Met Leu Gln Ser Leu Cys Lys
1               5                   10                  15

Leu Leu

<210> SEQ ID NO 95

```
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 95

Trp Tyr Asp Cys Asn Val Pro Asn Glu Leu Leu Ser Gly Leu Cys Arg
1               5                   10                  15

Leu Phe

<210> SEQ ID NO 96
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 96

Tyr Gly Asp Cys Asp Gln Asn His Trp Met Trp Pro Phe Thr Cys Leu
1               5                   10                  15

Ser Leu

<210> SEQ ID NO 97
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 97

Gly Trp Met Cys His Phe Asp Leu His Asp Trp Gly Ala Thr Cys Gln
1               5                   10                  15

Pro Asp

<210> SEQ ID NO 98
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 98

Tyr Phe His Cys Met Phe Gly Gly His Glu Phe Glu Val His Cys Glu
1               5                   10                  15

Ser Phe

<210> SEQ ID NO 99
<211> LENGTH: 12
<212> TYPE: PRT
<213> ORGANISM: Artificial Sequence
<220> FEATURE:
<223> OTHER INFORMATION: Myostatin Binding Peptide

<400> SEQUENCE: 99

Ala Tyr Trp Cys Trp His Gly Gln Cys Val Arg Phe
1               5                   10

<210> SEQ ID NO 100
<211> LENGTH: 19
<212> TYPE: PRT
<213> ORGANISM: Artificial Sequence
<220> FEATURE:
<223> OTHER INFORMATION: Myostatin Binding Peptide
```

```
<400> SEQUENCE: 100

Ser Glu His Trp Thr Phe Thr Asp Trp Asp Gly Asn Glu Trp Trp Val
1               5                   10                  15

Arg Pro Phe

<210> SEQ ID NO 101
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 101

Met Glu Met Leu Asp Ser Leu Phe Glu Leu Leu Lys Asp Met Val Pro
1               5                   10                  15

Ile Ser Lys Ala
            20

<210> SEQ ID NO 102
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 102

Ser Pro Pro Glu Glu Ala Leu Met Glu Trp Leu Gly Trp Gln Tyr Gly
1               5                   10                  15

Lys Phe Thr

<210> SEQ ID NO 103
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 103

Ser Pro Glu Asn Leu Leu Asn Asp Leu Tyr Ile Leu Met Thr Lys Gln
1               5                   10                  15

Glu Trp Tyr Gly
            20

<210> SEQ ID NO 104
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 104

Phe His Trp Glu Glu Gly Ile Pro Phe His Val Val Thr Pro Tyr Ser
1               5                   10                  15

Tyr Asp Arg Met
            20

<210> SEQ ID NO 105
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 105
```

Lys Arg Leu Leu Glu Gln Phe Met Asn Asp Leu Ala Glu Leu Val Ser
1               5                   10                  15

Gly His Ser

<210> SEQ ID NO 106
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 106

Asp Thr Arg Asp Ala Leu Phe Gln Glu Phe Tyr Glu Phe Val Arg Ser
1               5                   10                  15

Arg Leu Val Ile
            20

<210> SEQ ID NO 107
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 107

Arg Met Ser Ala Ala Pro Arg Pro Leu Thr Tyr Arg Asp Ile Met Asp
1               5                   10                  15

Gln Tyr Trp His
            20

<210> SEQ ID NO 108
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 108

Asn Asp Lys Ala His Phe Phe Glu Met Phe Met Phe Asp Val His Asn
1               5                   10                  15

Phe Val Glu Ser
            20

<210> SEQ ID NO 109
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 109

Gln Thr Gln Ala Gln Lys Ile Asp Gly Leu Trp Glu Leu Leu Gln Ser
1               5                   10                  15

Ile Arg Asn Gln
            20

<210> SEQ ID NO 110
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 110

```
Met Leu Ser Glu Phe Glu Glu Phe Leu Gly Asn Leu Val His Arg Gln
1               5                   10                  15

Glu Ala

<210> SEQ ID NO 111
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 111

Tyr Thr Pro Lys Met Gly Ser Glu Trp Thr Ser Phe Trp His Asn Arg
1               5                   10                  15

Ile His Tyr Leu
            20

<210> SEQ ID NO 112
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 112

Leu Asn Asp Thr Leu Leu Arg Glu Leu Lys Met Val Leu Asn Ser Leu
1               5                   10                  15

Ser Asp Met Lys
            20

<210> SEQ ID NO 113
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 113

Phe Asp Val Glu Arg Asp Leu Met Arg Trp Leu Glu Gly Phe Met Gln
1               5                   10                  15

Ser Ala Ala Thr
            20

<210> SEQ ID NO 114
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 114

His His Gly Trp Asn Tyr Leu Arg Lys Gly Ser Ala Pro Gln Trp Phe
1               5                   10                  15

Glu Ala Trp Val
            20

<210> SEQ ID NO 115
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 115
```

-continued

```
Val Glu Ser Leu His Gln Leu Gln Met Trp Leu Asp Gln Lys Leu Ala
1               5                   10                  15

Ser Gly Pro His
            20

<210> SEQ ID NO 116
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 116

Arg Ala Thr Leu Leu Lys Asp Phe Trp Gln Leu Val Glu Gly Tyr Gly
1               5                   10                  15

Asp Asn

<210> SEQ ID NO 117
<211> LENGTH: 16
<212> TYPE: PRT
<213> ORGANISM: Artificial Sequence
<220> FEATURE:
<223> OTHER INFORMATION: Myostatin Binding Peptide

<400> SEQUENCE: 117

Glu Glu Leu Leu Arg Glu Phe Tyr Arg Phe Val Ser Ala Phe Asp Tyr
1               5                   10                  15

<210> SEQ ID NO 118
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 118

Gly Leu Leu Asp Glu Phe Ser His Phe Ile Ala Glu Gln Phe Tyr Gln
1               5                   10                  15

Met Pro Gly Gly
            20

<210> SEQ ID NO 119
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 119

Tyr Arg Glu Met Ser Met Leu Glu Gly Leu Leu Asp Val Leu Glu Arg
1               5                   10                  15

Leu Gln His Tyr
            20

<210> SEQ ID NO 120
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 120

His Asn Ser Ser Gln Met Leu Leu Ser Glu Leu Ile Met Leu Val Gly
1               5                   10                  15

Ser Met Met Gln
          20

<210> SEQ ID NO 121
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 121

Trp Arg Glu His Phe Leu Asn Ser Asp Tyr Ile Arg Asp Lys Leu Ile
1               5                   10                  15

Ala Ile Asp Gly
          20

<210> SEQ ID NO 122
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 122

Gln Phe Pro Phe Tyr Val Phe Asp Asp Leu Pro Ala Gln Leu Glu Tyr
1               5                   10                  15

Trp Ile Ala

<210> SEQ ID NO 123
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 123

Glu Phe Phe His Trp Leu His Asn His Arg Ser Glu Val Asn His Trp
1               5                   10                  15

Leu Asp Met Asn
          20

<210> SEQ ID NO 124
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 124

Glu Ala Leu Phe Gln Asn Phe Phe Arg Asp Val Leu Thr Leu Ser Glu
1               5                   10                  15

Arg Glu Tyr

<210> SEQ ID NO 125
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 125

Gln Tyr Trp Glu Gln Gln Trp Met Thr Tyr Phe Arg Glu Asn Gly Leu
1               5                   10                  15

His Val Gln Tyr
            20

<210> SEQ ID NO 126
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 126

Asn Gln Arg Met Met Leu Glu Asp Leu Trp Arg Ile Met Thr Pro Met
1               5                   10                  15

Phe Gly Arg Ser
            20

<210> SEQ ID NO 127
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 127

Phe Leu Asp Glu Leu Lys Ala Glu Leu Ser Arg His Tyr Ala Leu Asp
1               5                   10                  15

Asp Leu Asp Glu
            20

<210> SEQ ID NO 128
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 128

Gly Lys Leu Ile Glu Gly Leu Leu Asn Glu Leu Met Gln Leu Glu Thr
1               5                   10                  15

Phe Met Pro Asp
            20

<210> SEQ ID NO 129
<211> LENGTH: 15
<212> TYPE: PRT
<213> ORGANISM: Artificial Sequence
<220> FEATURE:
<223> OTHER INFORMATION: Myostatin Binding Peptide

<400> SEQUENCE: 129

Ile Leu Leu Leu Asp Glu Tyr Lys Lys Asp Trp Lys Ser Trp Phe
1               5                   10                  15

<210> SEQ ID NO 130
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 130

Gln Gly His Cys Thr Arg Trp Pro Trp Met Cys Pro Pro Tyr Gly Ser
1               5                   10                  15

Gly Ser Ala Thr Gly Gly Ser Gly Ser Thr Ala Ser Ser Gly Ser Gly
            20                  25                  30

-continued

Ser Ala Thr Gly Gln Gly His Cys Thr Arg Trp Pro Trp Met Cys Pro
            35                  40                  45

Pro Tyr
    50

<210> SEQ ID NO 131
<211> LENGTH: 43
<212> TYPE: PRT
<213> ORGANISM: Artificial Sequence
<220> FEATURE:
<223> OTHER INFORMATION: Myostatin Binding Peptide

<400> SEQUENCE: 131

Trp Tyr Pro Cys Tyr Glu Gly His Phe Trp Cys Tyr Asp Leu Gly Ser
1               5                   10                  15

Gly Ser Thr Ala Ser Ser Gly Ser Gly Ser Ala Thr Gly Trp Tyr Pro
            20                  25                  30

Cys Tyr Glu Gly His Phe Trp Cys Tyr Asp Leu
            35                  40

<210> SEQ ID NO 132
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 132

His Thr Pro Cys

```
Ala Asn Trp Cys Val Ser Pro Asn Trp Phe Cys Met Val Met Gly Ser
1               5                   10                  15

Gly Ser Ala Thr Gly Gly Ser Gly Ser Thr Ala Ser Ser Gly Ser Gly
            20                  25                  30

Ser Ala Thr Gly Ala Asn Trp Cys Val Ser Pro Asn Trp Phe Cys Met
        35                  40                  45

Val Met
    50

<210> SEQ ID NO 135
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 135

Pro Asp Trp Cys Ile Asp Pro Asp Trp Trp Cys Lys Phe Trp Gly Ser
1               5                   10                  15

Gly Ser Ala Thr Gly Gly Ser Gly Ser Thr Ala Ser Ser Gly Ser Gly
            20                  25                  30

Ser Ala Thr Gly Pro Asp Trp Cys Ile Asp Pro Asp Trp Trp Cys Lys
        35                  40                  45

Phe Trp
    50

<210> SEQ ID NO 136
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 136

His Trp Ala Cys Gly Tyr Trp Pro Trp Ser Cys Lys Trp Val Gly Ser
1               5                   10                  15

Gly Ser Ala Thr Gly Gly Ser Gly Ser Thr Ala Ser Ser Gly Ser Gly
            20                  25                  30

Ser Ala Thr Gly His Trp Ala Cys Gly Tyr Trp Pro Trp Ser Cys Lys
        35                  40                  45

Trp Val
    50

<210> SEQ ID NO 137
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 137

Lys Lys His Cys Gln Ile Trp Thr Trp Met Cys Ala Pro Lys Gly Ser
1               5                   10                  15

Gly Ser Ala Thr Gly Gly Ser Gly Ser Thr Ala Ser Ser Gly Ser Gly
            20                  25                  30

Ser Ala Thr Gly Gln Gly His Cys Thr Arg Trp Pro Trp Met Cys Pro
        35                  40                  45

Pro Tyr
    50
```

<210> SEQ ID NO 138
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 138

```
Gln Gly His Cys Thr Arg Trp Pro Trp Met Cys Pro Pro Tyr Gly Ser
1               5                   10                  15

Gly Ser Ala Thr Gly Gly Ser Gly Ser Thr Ala Ser Ser Gly Ser Gly
            20                  25                  30

Ser Ala Thr Gly Lys Lys His Cys Gln Ile Trp Thr Trp Met Cys Ala
        35                  40                  45

Pro Lys
    50
```

<210> SEQ ID NO 139
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 139

```
Lys Lys His Cys Gln Ile Trp Thr Trp Met Cys Ala Pro Lys Gly Ser
1               5                   10                  15

Gly Ser Ala Thr Gly Gly Ser Gly Ser Thr Ala Ser Ser Gly Ser Gly
            20                  25                  30

Ser Ala Thr Gly Gln Gly His Cys Thr Arg Trp Pro Trp Met Cys Pro
        35                  40                  45

Pro Tyr
    50
```

<210> SEQ ID NO 140
<211> LENGTH: 36
<212> TYPE: PRT
<213> ORGANISM: Artificial Sequence
<220> FEATURE:
<223> OTHER INFORMATION: Myostatin Binding Peptide

<400> SEQUENCE: 140

```
Lys Lys His Cys Gln Ile Trp Thr Trp Met Cys Ala Pro Lys Gly Gly
1               5                   10                  15

Gly Gly Gly Gly Gly Gly Gln Gly His Cys Thr Arg Trp Pro Trp Met
            20                  25                  30

Cys Pro Pro Tyr
        35
```

<210> SEQ ID NO 141
<211> LENGTH: 34
<212> TYPE: PRT
<213> ORGANISM: Artificial Sequence
<220> FEATURE:
<223> OTHER INFORMATION: Myostatin Binding Peptide

<400> SEQUENCE: 141

```
Gln Gly His Cys Thr Arg Trp Pro Trp Met Cys Pro Pro Tyr Gly Gly
1               5                   10                  15

Gly Gly Gly Gly Lys Lys His Cys Gln Ile Trp Thr Trp Met Cys Ala
            20                  25                  30
```

Pro Lys

<210> SEQ ID NO 142
<211> LENGTH: 14
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(6)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = any amino acid

<400> SEQUENCE: 142

Lys Asp Xaa Cys Xaa Xaa Trp His Trp Met Cys Lys Pro Xaa
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(7)
<223> OTHER INFORMATION: Xaa = any amino acid

<400> SEQUENCE: 143

Trp Xaa Xaa Cys Xaa Xaa Xaa Gly Phe Trp Cys Leu Asn Val
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (9)..(10)
<223> OTHER INFORMATION: Xaa = any amino acid
<220> FEATURE:
<221> NAME/KEY: MISC_FEATURE
<222> LOCATION: (13)..(14)
<223> OTHER INFORMATION: Xaa = any amino acid

<400> SEQUENCE: 144

Ile Xaa Gly Cys Xaa Trp Trp Asp Xaa Xaa Cys Tyr Xaa Xaa
1               5                   10

<210> SEQ ID NO 145

```
<211> LENGTH: 14
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (1)..(2)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid
<220> FEATURE:
<221> NAME/KEY: MISC_FEATURE
<222> LOCATION: (12)..(14)
<223> OTHER INFORMATION: Xaa = any amino acid

<400> SEQUENCE: 145

Xaa Xaa Trp Cys Val Ser Pro Xaa Trp Phe Cys Xaa Xaa Xaa
 1               5                  10

<210> SEQ ID NO 146
<211> LENGTH: 14
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (9)..(10)
<223> OTHER INFORMATION: Xaa = any amino acid

<400> SEQUENCE: 146

Xaa Xaa Xaa Cys Pro Trp Phe Ala Xaa Xaa Cys Val Asp Trp
 1               5                  10

<210> SEQ ID NO 147
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 147
aaagacaaat gcaaaatgtg gcactggatg tgcaaaccgc cg                          42

<210> SEQ ID NO 148
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 148
aaagacctgt gcgctatgtg gcactggatg tgcaaaccgc cg                          42

<210> SEQ ID NO 149
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide
```

```
<400> SEQUENCE: 149
aaagacctgt gcaaaatgtg gaaatggatg tgcaaaccgc cg                             42

<210> SEQ ID NO 150
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 150
aaagacctgt gcaaaatgtg gcactggatg tgcaaaccga aa                             42

<210> SEQ ID NO 151
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 151
tggtacccgt gctacgaatt ccacttctgg tgctacgacc tg                             42

<210> SEQ ID NO 152
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 152
tggtacccgt gctacgaatt ccacttctgg tgctacgacc tg                             42

<210> SEQ ID NO 153
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 153
tggtacccgt gctacgaagg tcacttctgg tgctacgacc tg                             42

<210> SEQ ID NO 154
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 154
tggtacccgt gctacgaagg tcacttctgg tgctacgacc tg                             42

<210> SEQ ID NO 155
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 155
```
atcttcggtt gcaaatggtg ggacgttcag tgctaccagt tc          42

<210> SEQ ID NO 156
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 156
atcttcggtt gcaaatggtg ggacgttgac tgctaccagt tc          42

<210> SEQ ID NO 157
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 157
atcttcggtt gcaaatggtg ggacgttgac tgctaccagt tc          42

<210> SEQ ID NO 158
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 158
gctgactggt gcgtttcccc gaactggttc tgcatggtta tg          42

<210> SEQ ID NO 159
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 159
cacaaattct gcccgtggtg ggctctgttc tgctgggact tc          42

<210> SEQ ID NO 160
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 160
aaagacctgt gcaaaatgtg gcactggatg tgcaaaccgc cg          42

<210> SEQ ID NO 161
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 161

-continued atcgacaaat gcgctatctg gggttggatg tgcccgccgc tg                              42

<210> SEQ ID NO 162
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 162
tggtacccgt gcggtgaatt cggtatgtgg tgcctgaacg tt                              42

<210> SEQ ID NO 163
<211> LENGTH: 33
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 163
tggttcacct gcctgtggaa ctgcgacaac gaa                                       33

<210> SEQ ID NO 164
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 164
cacaccccgt gcccgtggtt cgctccgctg tgcgttgaat gg                              42

<210> SEQ ID NO 165
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 165
aaagaatggt gctggcgttg gaaatggatg tgcaaaccgg aa                              42

<210> SEQ ID NO 166
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 166
ttcgaaacct gcccgtcctg ggcttacttc tgcctggaca tc                              42

<210> SEQ ID NO 167
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 167
ttcgaaacct gcccgtcctg ggcttacttc tgcctggaca tc                              42

<210> SEQ ID NO 168
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 168
gcttacaaat gcgaagctaa cgactggggt tgctggtggc tg                             42

<210> SEQ ID NO 169
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 169
aactcctggt gcgaagacca gtggcaccgt tgctggtggc tg                             42

<210> SEQ ID NO 170
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 170
tggtccgctt gctacgctgg tcacttctgg tgctacgacc tg                             42

<210> SEQ ID NO 171
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 171
gctaactggt gcgtttcccc gaactggttc tgcatggtta tg                             42

<210> SEQ ID NO 172
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 172
tggaccgaat gctaccagca ggaattctgg tgctggaacc tg                             42

<210> SEQ ID NO 173
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 173
gaaaacacct gcgaacgttg gaaatggatg tgcccgccga aa                             42

<210> SEQ ID NO 174
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 174
tggctgccgt gccaccagga aggtttctgg tgcatgaact tc                        42

<210> SEQ ID NO 175
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 175
tccaccatgt gctcccagtg gcactggatg tgcaacccgt tc                        42

<210> SEQ ID NO 176
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 176
atcttcggtt gccactggtg ggacgttgac tgctaccagt tc                        42

<210> SEQ ID NO 177
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 177
atctacggtt gcaaatggtg ggacatccag tgctacgaca tc                        42

<210> SEQ ID NO 178
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 178
ccggactggt gcatcgatcc ggactggtgg tgcaaattct gg                        42

<210> SEQ ID NO 179
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 179
cagggtcact gcacccgttg gccgtggatg tgcccgccgt ac                        42

<210> SEQ ID NO 180
<211> LENGTH: 42
<212> TYPE: DNA
<213> ORGANISM: Artificial Sequence
<220> FEATURE:
<223> OTHER INFORMATION: Nucleotide sequence encoding Myostatin Binding Peptide

<400> SEQUENCE: 180
tggcaggaat gctaccgtga aggtttctgg tgcctgcaga cc        42

<210> SEQ ID NO 181
<211> LENGTH: 42
<212> TYPE: DNA
<213> ORGANISM: Artificial Sequence
<220> FEATURE:
<223> OTHER INFORMATION: Nucleotide sequence encoding Myostatin Binding Peptide

<400> SEQUENCE: 181
tggttcgact gctacggtcc gggtttcaaa tgctggtccc cg        42

<210> SEQ ID NO 182
<211> LENGTH: 42
<212> TYPE: DNA
<213> ORGANISM: Artificial Sequence
<220> FEATURE:
<223> OTHER INFORMATION: Nucleotide sequence encoding Myostatin Binding Peptide

<400> SEQUENCE: 182
ggtgttcgtt gcccgaaagg tcacctgtgg tgcctgtacc cg        42

<210> SEQ ID NO 183
<211> LENGTH: 42
<212> TYPE: DNA
<213> ORGANISM: Artificial Sequence
<220> FEATURE:
<223> OTHER INFORMATION: Nucleotide sequence encoding Myostatin Binding Peptide

<400> SEQUENCE: 183
cactgggctt gcggttactg gccgtggtcc tgcaaatggg tt 42

<210> SEQ ID NO 184
<211> LENGTH: 42
<212> TYPE: DNA
<213> ORGANISM: Artificial Sequence
<220> FEATURE:
<223> OTHER INFORMATION: Nucleotide sequence encoding Myostatin Binding Peptide

<400> SEQUENCE: 184
ggtccggctt gccactcccc gtggtggtgg tgcgttttcg gt 42

<210> SEQ ID NO 185
<211> LENGTH: 42
<212> TYPE: DNA
<213> ORGANISM: Artificial Sequence
<220> FEATURE:
<223> OTHER INFORMATION: Nucleotide sequence encoding Myostatin Binding Peptide

<400> SEQUENCE: 185
accacctggt gcatctcccc gatgtggttc tgctcccagc ag 42

<210> SEQ ID NO 186

```
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 186
cacaaattct gcccgccgtg ggctatcttc tgctgggact tc                               42

<210> SEQ ID NO 187
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 187
ccggactggt gcgtttcccc gcgttggtac tgcaacatgt gg                               42

<210> SEQ ID NO 188
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 188
gtttggaaat gccactggtt cggtatggac tgcgaaccga cc                               42

<210> SEQ ID NO 189
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 189
aaaaaacact gccagatctg gacctggatg tgcgctccga aa                               42

<210> SEQ ID NO 190
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 190
tggttccagt gcggttccac cctgttctgg tgctacaacc tg                               42

<210> SEQ ID NO 191
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 191
tggtccccgt gctacgacca ctacttctac tgctacacca tc                               42

<210> SEQ ID NO 192
<211> LENGTH: 42
```

<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 192
tcctggatgt gcggtttctt caaagaagtt tgcatgtggg tt                    42

<210> SEQ ID NO 193
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 193
gaaatgctgt gcatgatcca cccggttttc tgcaacccgc ac                    42

<210> SEQ ID NO 194
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 194
ctgaaaacct gcaacctgtg gccgtggatg tgcccgccgc tg                    42

<210> SEQ ID NO 195
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 195
gttgttggtt gcaaatggta cgaagcttgg tgctacaaca aa                    42

<210> SEQ ID NO 196
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 196
ccgatccact gcacccagtg ggcttggatg tgcccgccga cc                    42

<210> SEQ ID NO 197
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 197
gactccaact gcccgtggta cttcctgtcc tgcgttatct tc                    42

<210> SEQ ID NO 198
<211> LENGTH: 42
<212> TYPE: DNA

<213> ORGANISM: Artificial Sequence
<220> FEATURE:
<223> OTHER INFORMATION: Nucleotide sequence encoding Myost

```
<220> FEATURE:
<223> OTHER INFORMATION: Nucleotide sequence encoding Myostatin Binding
      Peptide

<400> SEQUENCE: 204
ttttggcgtt gtgctattgg tattgataaa tgtaaacgtg tt                              42

<210> SEQ ID NO 205
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 205
ttttggcgtt gtgctattgg tattgataaa tgtaaacgtg tt                              42

<210> SEQ ID NO 206
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 206
attgatcttt gtaatatgtg ggatggtatg tgttatccac ca                              42

<210> SEQ ID NO 207
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 207
gaaatgccat gtaatatttg gggttggatg tgtccaccag tt                              42

<210> SEQ ID NO 208
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 208
tggttccgtt gcgttctgac cggtatcgtt gactggtccg aatgcttcgg tctg                 54

<210> SEQ ID NO 209
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 209
ggtttctcct gcaccttcgg tctggacgaa ttctacgttg actgctcccc gttc                 54

<210> SEQ ID NO 210
<211> LENGTH: 54
<212> TYPE: DNA
<213> ORGANISM: Artificial Sequence
<220> FEATURE:
```

<223> OTHER INFORMATION: Nucleotide sequence encoding Myostatin
     Peptide

<400> SEQUENCE: 210
ctgccgtggt gccacgacca ggttaacgct gactggggtt tctgcatgct gtgg      54

<210> SEQ ID NO 211
<211> LENGTH: 54
<212> TYPE: DNA
<213> ORGANISM: Artificial Sequence
<220> FEATURE:
<223> OTHER INFORMATION: Nucleotide sequence encoding Myostatin
     Peptide

<400> SEQUENCE: 211
tacccgacct gctccgaaaa attctggatc tacggtcaga cctgcgttct gtgg      54

<210> SEQ ID NO 212
<211> LENGTH: 54
<212> TYPE: DNA
<213> ORGANISM: Artificial Sequence
<220> FEATURE:
<223> OTHER INFORMATION: Nucleotide sequence encoding Myostatin
     Peptide

<400> SEQUENCE: 212
ctgggtccgt gcccgatcca ccacggtccg tggccgcagt actgcgttta ctgg      54

<210> SEQ ID NO 213
<211> LENGTH: 54
<212> TYPE: DNA
<213> ORGANISM: Artificial Sequence
<220> FEATURE:
<223> OTHER INFORMATION: Nucleotide sequence encoding Myostatin
     Peptide

<400> SEQUENCE: 213
ccgttcccgt gcgaaaccca ccagatctcc tggctgggtc actgcctgtc cttc      54

<210> SEQ ID NO 214
<211> LENGTH: 54
<212> TYPE: DNA
<213> ORGANISM: Artificial Sequence
<220> FEATURE:
<223> OTHER INFORMATION: Nucleotide sequence encoding Myostatin
     Peptide

<400> SEQUENCE: 214
cactggggtt gcgaagacct gatgtggtcc tggcacccgc tgtgccgtcg tccg      54

<210> SEQ ID NO 215
<211> LENGTH: 54
<212> TYPE: DNA
<213> ORGANISM: Artificial Sequence
<220> FEATURE:
<223> OTHER INFORMATION: Nucleotide sequence encoding Myostatin
     Peptide

<400> SEQUENCE: 215
ctgccgctgt gcgacgctga catgatgccg accatcggtt tctgcgttgc ttac      54

<210> SEQ ID NO 216
<211> LENGTH: 54
<212> TYPE: DNA
<213> ORGANISM: Artificial Sequence
<220> FEATURE:
<223> OTHER INFORMATION: Nucleotide sequence encoding Myostatin Binding -continued Peptide

<400> SEQUENCE: 216
tcccactggt gcgaaaccac cttctggatg aactacgcta aatgcgttca cgct        54

<210> SEQ ID NO 217
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 217
ctgccgaaat gcacccacgt tccgttcgac cagggtggtt tctgcctgtg gtac        54

<210> SEQ ID NO 218
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 218
ttctcctcct gctggtcccc ggtttcccgt caggacatgt tctgcgtttt ctac        54

<210> SEQ ID NO 219
<211> LENGTH: 51
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 219
tcccacaaat gcgaatactc cggttggctg cagccgctgt gctaccgtcc g           51

<210> SEQ ID NO 220
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 220
ccgtggtggt gccaggacaa ctacgttcag cacatgctgc actgcgactc cccg        54

<210> SEQ ID NO 221
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 221
tggttccgtt gcatgctgat gaactccttc gacgctttcc agtgcgtttc ctac        54

<210> SEQ ID NO 222
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

```
<400> SEQUENCE: 222
ccggacgctt gccgtgacca gccgtggtac atgttcatgg gttgcatgct gggt            54

<210> SEQ ID NO 223
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 223
ttcctggctt gcttcgttga attcgaactg tgcttcgact cc                        42

<210> SEQ ID NO 224
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 224
tccgcttact gcatcatcac cgaatccgac ccgtacgttc tgtgcgttcc gctg            54

<210> SEQ ID NO 225
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 225
ccgtccatct gcgaatccta ctccaccatg tggctgccga tgtgccagca caac            54

<210> SEQ ID NO 226
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 226
tggctggact gccacgacga ctcctgggct tggaccaaaa tgtgccgttc ccac            54

<210> SEQ ID NO 227
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 227
tacctgaact gcgttatgat gaacacctcc ccgttcgttg aatgcgtttt caac            54

<210> SEQ ID NO 228
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide
```

<400> SEQUENCE: 228
tacccgtggt gcgacggttt catgatccag cagggtatca cctgcatgtt ctac        54

<210> SEQ ID NO 229
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 229
ttcgactact gcacctggct gaacggtttc aaagactgga atgctggtc ccgt          54

<210> SEQ ID NO 230
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 230
ctgccgctgt gcaacctgaa agaaatctcc cacgttcagg cttgcgttct gttc        54

<210> SEQ ID NO 231
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 231
tccccggaat gcgctttcgc tcgttggctg ggtatcgaac agtgccagcg tgac        54

<210> SEQ ID NO 232
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 232
tacccgcagt gcttcaacct gcacctgctg gaatggaccg aatgcgactg gttc        54

<210> SEQ ID NO 233
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 233
cgttggcgtt gcgaaatcta cgactccgaa ttcctgccga atgctggtt cttc         54

<210> SEQ ID NO 234
<211> LENGTH: 42
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 234
ctggttggtt gcgacaacgt ttggcaccgt tgcaaactgt tc 42

<210> SEQ ID NO 235
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 235
gctggttggt gccacgtttg gggtgaaatg ttcggtatgg gttgctccgc tctg 54

<210> SEQ ID NO 236
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 236
caccacgaat gcgaatggat ggctcgttgg atgtccctgg actgcgttgg tctg 54

<210> SEQ ID NO 237
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 237
ttcccgatgt gcggtatcgc tggtatgaaa gacttcgact tctgcgtttg gtac 54

<210> SEQ ID NO 238
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 238
cgtgatgatt gtactttttg gccagaatgg ctttggaaac tttgtgaacg tcca 54

<210> SEQ ID NO 239
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 239
tataattttt gttcttatct ttttggtgtt tctaaagaag cttgtcaact tcca 54

<210> SEQ ID NO 240
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 240

```
gctcattggt gtgaacaagg tccatggcgt tatggtaata tttgtatggc ttat      54
```

<210> SEQ ID NO 241
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 241

```
aatcttgttt gtggtaaaat ttctgcttgg ggtgatgaag cttgtgctcg tgct      54
```

<210> SEQ ID NO 242
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 242

```
cataatgttt gtactattat gggtccatct atgaaatggt tttgttggaa tgat      54
```

<210> SEQ ID NO 243
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 243

```
aatgatcttt gtgctatgtg gggttggcgt aatactattt ggtgtcaaaa ttct      54
```

<210> SEQ ID NO 244
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 244

```
ccaccatttt gtcaaaatga taatgatatg cttcaatctc tttgtaaact tctt      54
```

<210> SEQ ID NO 245
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 245

```
tggtatgatt gtaatgttcc aaatgaactt ctttctggtc tttgtcgtct tttt      54
```

<210> SEQ ID NO 246
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 246

```
tatggtgatt gtgatcaaaa tcattggatg tggccattta cttgtctttc tctt      54
```

<210> SEQ ID NO 247
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 247
ggttggatgt gtcattttga tcttcatgat tggggtgcta cttgtcaacc agat            54

<210> SEQ ID NO 248
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 248
tattttcatt gtatgtttgg tggtcatgaa tttgaagttc attgtgaatc tttt            54

<210> SEQ ID NO 249
<211> LENGTH: 36
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 249
gcttattggt gttggcatgg tcaatgtgtt cgtttt                                36

<210> SEQ ID NO 250
<211> LENGTH: 57
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 250
tccgaacact ggaccttcac cgactgggac ggtaacgaat ggtgggttcg tccgttc         57

<210> SEQ ID NO 251
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 251
atggaaatgc tggactccct gttcgaactg ctgaaagaca tggttccgat ctccaaagct      60

<210> SEQ ID NO 252
<211> LENGTH: 57
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 252
tccccgccgg aagaagctct gatggaatgg ctgggttggc agtacggtaa attcacc         57

<210> SEQ ID NO 253
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 253
tccccggaaa acctgctgaa cgacctgtac atcctgatga ccaaacagga atggtacggt    60

<210> SEQ ID NO 254
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 254
ttccactggg aagaaggtat cccgttccac gttgttaccc cgtactccta cgaccgtatg    60

<210> SEQ ID NO 255
<211> LENGTH: 57
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 255
aaacgtctgc tggaacagtt catgaacgac ctggctgaac tggtttccgg tcactcc       57

<210> SEQ ID NO 256
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 256
gacacccgtg acgctctgtt ccaggaattc tacgaattcg ttcgttcccg tctggttatc    60

<210> SEQ ID NO 257
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 257
cgtatgtccg ctgctccgcg tccgctgacc taccgtgaca tcatggacca gtactggcac    60

<210> SEQ ID NO 258
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 258
aacgacaaag ctcacttctt cgaaatgttc atgttcgacg ttcacaactt cgttgaatcc    60

```
<210> SEQ ID NO 259
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 259
cagacccagg ctcagaaaat cgacggtctg tgggaactgc tgcagtccat ccgtaaccag     60

<210> SEQ ID NO 260
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 260
atgctgtccg aattcgaaga attcctgggt aacctggttc accgtcagga agct           54

<210> SEQ ID NO 261
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 261
tacaccccga aaatgggttc cgaatggacc tccttctggc acaaccgtat ccactacctg     60

<210> SEQ ID NO 262
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 262
ctgaacgaca ccctgctgcg tgaactgaaa atggttctga actccctgtc cgacatgaaa     60

<210> SEQ ID NO 263
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 263
ttcgacgttg aacgtgacct gatgcgttgg ctggaaggtt tcatgcagtc cgctgctacc     60

<210> SEQ ID NO 264
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 264
caccacggtt ggaactacct gcgtaaaggt tccgctccgc agtggttcga agcttgggtt     60

<210> SEQ ID NO 265
```

<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 265
gttgaatccc tgcaccagct gcagatgtgg ctggaccaga aactggcttc cggtccgcac    60

<210> SEQ ID NO 266
<211> LENGTH: 54
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 266
cgtgctaccc tgctgaaaga cttctggcag ctggttgaag gttacggtga caac          54

<210> SEQ ID NO 267
<211> LENGTH: 48
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 267
gaagaactgc tgcgtgaatt ctaccgtttc gtttccgctt tcgactac                 48

<210> SEQ ID NO 268
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 268
ggtctgctgg acgaattctc ccacttcatc gctgaacagt tctaccagat gccgggtggt    60

<210> SEQ ID NO 269
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 269
taccgtgaaa tgtccatgct ggaaggtctg ctggacgttc tggaacgtct gcagcactac    60

<210> SEQ ID NO 270
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 270
cacaactcct cccagatgct gctgtccgaa ctgatcatgc tggttggttc catgatgcag    60

<210> SEQ ID NO 271
<211> LENGTH: 60

```
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 271
tggcgtgaac acttcctgaa ctccgactac atccgtgaca aactgatcgc tatcgacggt    60

<210> SEQ ID NO 272
<211> LENGTH: 57
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 272
cagttcccgt tctacgtttt cgacgacctg ccggctcagc tggaatactg gatcgct       57

<210> SEQ ID NO 273
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 273
gaattcttcc actggctgca caaccaccgt tccgaagtta accactggct ggacatgaac    60

<210> SEQ ID NO 274
<211> LENGTH: 57
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 274
gaagctcttt ttcaaaattt ttttcgtgat gttcttactc tttctgaacg tgaatat       57

<210> SEQ ID NO 275
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 275
caatattggg aacaacaatg gatgacttat tttcgtgaaa atggtcttca tgttcaatat    60

<210> SEQ ID NO 276
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 276
aatcaacgta tgatgcttga agatctttgg cgtattatga ctccaatgtt tggtcgttct    60

<210> SEQ ID NO 277
<211> LENGTH: 60
<212> TYPE: DNA
```

<213> ORGANISM: Artificial Sequence
<220> FEATURE:
<223> OTHER INFORMATION: Nucleotide sequence encoding Myostatin Binding
      Peptide

<400> SEQUENCE: 277
tttcttgatg aacttaaagc tgaactttct cgtcattatg ctcttgatga tcttgatgaa     60

<210> SEQ ID NO 278
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 278
ggtaaactta ttgaaggtct tcttaatgaa cttatgcaac ttgaaacttt tatgccagat     60

<210> SEQ ID NO 279
<211> LENGTH: 45
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 279
attcttcttc ttgatgaata taaaaaagat tggaaatctt ggttt                     45

<210> SEQ ID NO 280
<211> LENGTH: 150
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 280
cagggccact gtactcgctg gccgtggatg tgcccgccgt acggttctgg ttccgctacc     60
ggtggttctg gttccactgc ttcttctggt tccggttctg ctactggtca gggtcactgc    120
actcgttggc catggatgtg tccaccgtat                                     150

<210> SEQ ID NO 281
<211> LENGTH: 129
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 281
tggtatccgt gttatgaggg tcacttctgg tgctacgatc tgggttctgg ttccactgct     60
tcttctggtt ccggttccgc tactggttgg tacccgtgct acgaaggtca cttttggtgt    120
tatgatctg                                                            129

<210> SEQ ID NO 282
<211> LENGTH: 150
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 282

-continued

```
cacactccgt gtccgtggtt tgctccgctg tgcgttgaat ggggttctgg ttccgctact      60
ggtggttccg gttccactgc ttcttctggt tccggttctg caactggtca caccccgtgc     120
ccgtggtttg caccgctgtg tgtagagtgg                                      150
```

<210> SEQ ID NO 283
<211> LENGTH: 150
<212> TYPE: DNA
<213> ORGANISM: Artificial Sequence
<220> FEATURE:
<223> OTHER INFORMATION: Nucleotide sequence encoding Myostatin Binding
    Peptide

<400> SEQUENCE: 283

```
ccggattggt gtatcgaccc ggactggtgg tgcaaattct ggggttctgg ttccgctacc      60
ggtggttccg gttccactgc ttcttctggt tccggttctg caactggtcc ggactggtgc     120
atcgacccgg attggtggtg taaattttgg                                      150
```

<210> SEQ ID NO 284
<211> LENGTH: 150
<212> TYPE: DNA
<213> ORGANISM: Artificial Sequence
<220> FEATURE:
<223> OTHER INFORMATION: Nucleotide sequence encoding Myostatin Binding
    Peptide

<400> SEQUENCE: 284

```
ccggattggt gtatcgaccc ggactggtgg tgcaaattct ggggttctgg ttccgctacc      60
ggtggttccg gttccactgc ttcttctggt tccggttctg caactggtcc ggactggtgc     120
atcgacccgg attggtggtg taaattttgg                                      150
```

<210> SEQ ID NO 285
<211> LENGTH: 129
<212> TYPE: DNA
<213> ORGANISM: Artificial Sequence
<220> FEATURE:
<223> OTHER INFORMATION: Nucleotide sequence encoding Myostatin Binding
    Peptide

<400> SEQUENCE: 285

```
accacttggt gcatctctcc gatgtggttc tgctctcagc agggttctgg ttccactgct      60
tcttctggtt ccggttctgc aactggtact acttggtgta tctctccaat gtggttttgt     120
tctcagcaa                                                             129
```

<210> SEQ ID NO 286
<211> LENGTH: 150
<212> TYPE: DNA
<213> ORGANISM: Artificial Sequence
<220> FEATURE:
<223> OTHER INFORMATION: Nucleotide sequence encoding Myostatin Binding
    Peptide

<400> SEQUENCE: 286

```
cactgggcat gtggctattg gccgtggtcc tgcaaatggg ttggttctgg ttccgctacc      60
ggtggttccg gttccactgc ttcttctggt tccggttctg caactggtca ctgggcttgc     120
ggttactggc cgtggtcttg taaatgggtt                                      150
```

<210> SEQ ID NO 287
<211> LENGTH: 150
<212> TYPE: DNA

```
<213> ORGANISM: Artificial Sequence
<220> FEATURE:
<223> OTHER INFORMATION: Nucleotide sequence encoding Myostatin Binding
      Peptide

<400> SEQUENCE: 287
aaaaaacact gtcagatctg gacttggatg tgcgctccga aaggttctgg ttccgctacc    60
ggtggttctg gttccactgc ttcttctggt tccggttccg ctactggtca gggtcactgc   120
actcgttggc catggatgtg tccgccgtat                                    150

<210> SEQ ID NO 288
<211> LENGTH: 150
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 288
cagggtcact gcacccgttg gccgtggatg tgcccgccgt acggttctgg ttccgctacc    60
ggtggttctg gttccactgc ttcttctggt tccggttctg ctactggtaa aaaacactgc   120
cagatctgga cttggatgtg cgctccgaaa                                    150

<210> SEQ ID NO 289
<211> LENGTH: 150
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 289
aaaaaacact gtcagatctg gacttggatg tgcgctccga aaggttctgg ttccgctacc    60
ggtggttctg gttccactgc ttcttctggt tccggttccg ctactggtca gggtcactgc   120
actcgttggc catggatgtg tccgccgtat                                    150

<210> SEQ ID NO 290
<211> LENGTH: 108
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 290
aaaaaacact gccagatctg gacttggatg tgcgctccga aggtggtgg tggtggtggc     60 ggtggccagg gtcactgcac ccgttggccg tggatgtgtc cgccgtat               108

<210> SEQ ID NO 291
<211> LENGTH: 102
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 291
cagggtcact gcacccgttg gccgtggatg tgcccgccgt acggtggtgg tggtggtggc    60
aaaaaacact gccagatctg gacttggatg tgcgctccga aa                      102
```

<210> SEQ ID NO 292
<211> LENGTH: 37
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 292
gagagagagc atatgaatga gaacagtgag caaaaag                               37

<210> SEQ ID NO 293
<211> LENGTH: 34
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 293
agagagggat ccattatgag cacccacagc ggtc                                  34

<210> SEQ ID NO 294
<211> LENGTH: 25
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 294
cggcgcaact atcggtatca agctg                                            25

<210> SEQ ID NO 295
<211> LENGTH: 26
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 295
catgtaccgt aacactgagt ttcgtc                                           26

<210> SEQ ID NO 296
<211> LENGTH: 227
<212> TYPE: PRT
<213> ORGANISM: Artificial Sequence
<220> FEATURE:
<223> OTHER INFORMATION: Myostatin Binding Peptide

<400> SEQUENCE: 296

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly

```
                85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 297
<211> LENGTH: 67
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 297
acaaacaaac atatgggtgc acagaaagcg gccgcaaaaa aactcgaggg tggaggcggt      60
ggggaca                                                               67

<210> SEQ ID NO 298
<211> LENGTH: 20
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 298
ggtcattact ggaccggatc                                                 20

<210> SEQ ID NO 299
<211> LENGTH: 25
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 299
cgtacaggtt tacgcaagaa aatgg                                           25

<210> SEQ ID NO 300
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide
```

```
<210> SEQ ID NO 301
<211> LENGTH: 681
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 301
gacaaaactc acacatgtcc accttgccca gcacctgaac tcctgggggg accgtcagtt      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaaccatctc caaagccaaa     360
gggcagcccc gagaaccaca ggtgtacacc ctgcccccat cccgggatga gctgaccaag     420
aaccaggtca gcctgacctg cctggtcaaa ggcttctatc ccagcgacat cgccgtggag     480
tgggagagca atgggcagcc ggagaacaac tacaagacca cgcctcccgt gctggactcc     540
gacggctcct tcttcctcta cagcaagctc accgtggaca agagcaggtg gcagcagggg     600
aacgtcttct catgctccgt gatgcatgag gctctgcaca accactacac gcagaagagc     660 ctctcccctgt ctccgggtaa a                                              681

<210> SEQ ID NO 302
<211> LENGTH: 15
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 302
ggtggaggtg gtggt                                                       15

<210> SEQ ID NO 303
<211> LENGTH: 22
<212> TYPE: PRT
<213> ORGANISM: Artificial Sequence
<220> FEATURE:
<223> OTHER INFORMATION: Peptibody

<400> SEQUENCE: 303

Met Phe Cys Gly Gly Gly Gly Gly Lys Asp Lys Cys Lys Met Trp His
1               5                   10                  15

Trp Met Cys Lys Pro Pro
            20

<210> SEQ ID NO 304
<211> LENGTH: 740
<212> TYPE: DNA
<213> ORGANISM: Artificial Sequence
<220> FEATURE:
<223> OTHER INFORMATION: Nucleotide sequence encoding Myostatin Binding
      Peptide
```

<400> SEQUENCE: 304

```
atggacaaaa ctcacacatg tccaccttgc ccagcacctg aactcctggg gggaccgtca      60
gttttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca gcccccatcg agaaaaccat ctccaaagcc     360
aaagggcagc cccgagaacc acaggtgtac accctgcccc catcccggga tgagctgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaaggtgga ggtggtggta agacaaatgc aaaatgtggc     720
actggatgtg caaaccgccg                                                 740
```

<210> SEQ ID NO 305
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 305

```
Val Ala Leu His Gly Gln Cys Thr Arg Trp Pro Trp Met Cys Pro Pro
1               5                   10                  15
Gln Arg Glu Gly
            20
```

<210> SEQ ID NO 306
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 306

```
Tyr Pro Glu Gln Gly Leu Cys Thr Arg Trp Pro Trp Met Cys Pro Pro
1               5                   10                  15
Gln Thr Leu Ala
            20
```

<210> SEQ ID NO 307
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 307

```
Gly Leu Asn Gln Gly His Cys Thr Arg Trp Pro Trp Met Cys Pro Pro
1               5                   10                  15
Gln Asp Ser Asn
            20
```

<210> SEQ ID NO 308
<211> LENGTH: 20

<212> TYPE: PRT
<213> ORGANISM: Artificial Sequence
<220> FEATURE:
<223> OTHER INFORMATION: Myostatin Binding Peptide

<400> SEQUENCE: 308

Met Ile Thr Gln Gly Gln Cys Thr Arg Trp Pro Trp Met Cys Pro Pro
1               5                   10                  15

Gln Pro Ser Gly
            20

<210> SEQ ID NO 309
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 309

Ala Gly Ala Gln Glu His Cys Thr Arg Trp Pro Trp Met Cys Ala Pro
1               5                   10                  15

Asn Asp Trp Ile
            20

<210> SEQ ID NO 310
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 310

Gly Val Asn Gln Gly Gln Cys Thr Arg Trp Arg Trp Met Cys Pro Pro
1               5                   10                  15

Asn Gly Trp Glu
            20

<210> SEQ ID NO 311
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 311

Leu Ala Asp His Gly Gln Cys Ile Arg Trp Pro Trp Met Cys Pro Pro
1               5                   10                  15

Glu Gly Trp Glu
            20

<210> SEQ ID NO 312
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 312

Ile Leu Glu Gln Ala Gln Cys Thr Arg Trp Pro Trp Met Cys Pro Pro
1               5                   10                  15

Gln Arg Gly Gly
            20

<210> SEQ ID NO 313

```
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 313

Thr Gln Thr His Ala Gln Cys Thr Arg Trp Pro Trp Met Cys Pro Pro
1               5                   10                  15

Gln Trp Glu Gly
            20

<210> SEQ ID NO 314
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 314

Val Val Thr Gln Gly His Cys Thr Leu Trp Pro Trp Met Cys Pro Pro
1               5                   10                  15

Gln Arg Trp Arg
            20

<210> SEQ ID NO 315
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 315

Ile Tyr Pro His Asp Gln Cys Thr Arg Trp Pro Trp Met Cys Pro Pro
1               5                   10                  15

Gln Pro Tyr Pro
            20

<210> SEQ ID NO 316
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 316

Ser Tyr Trp Gln Gly Gln Cys Thr Arg Trp Pro Trp Met Cys Pro Pro
1               5                   10                  15

Gln Trp Arg Gly
            20

<210> SEQ ID NO 317
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 317

Met Trp Gln Gln Gly His Cys Thr Arg Trp Pro Trp Met Cys Pro Pro
1               5                   10                  15

Gln Gly Trp Gly
            20
```

```
<210> SEQ ID NO 318
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 318

Glu Phe Thr Gln Trp His Cys Thr Arg Trp Pro Trp Met Cys Pro Pro
1               5                   10                  15

Gln Arg Ser Gln
            20

<210> SEQ ID NO 319
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 319

Leu Asp Asp Gln Trp Gln Cys Thr Arg Trp Pro Trp Met Cys Pro Pro
1               5                   10                  15

Gln Gly Phe Ser
            20

<210> SEQ ID NO 320
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 320

Tyr Gln Thr Gln Gly Leu Cys Thr Arg Trp Pro Trp Met Cys Pro Pro
1               5                   10                  15

Gln Ser Gln Arg
            20

<210> SEQ ID NO 321
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 321

Glu Ser Asn Gln Gly Gln Cys Thr Arg Trp Pro Trp Met Cys Pro Pro
1               5                   10                  15

Gln Gly Gly Trp
            20

<210> SEQ ID NO 322
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 322

Trp Thr Asp Arg Gly Pro Cys Thr Arg Trp Pro Trp Met Cys Pro Pro
1               5                   10                  15

Gln Ala Asn Gly
            20
```

```
<210> SEQ ID NO 323
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 323

Val Gly Thr Gln Gly Gln Cys Thr Arg Trp Pro Trp Met Cys Pro Pro
1               5                   10                  15

Tyr Glu Thr Gly
            20

<210> SEQ ID NO 324
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 324

Pro Tyr Glu Gln Gly Lys Cys Thr Arg Trp Pro Trp Met Cys Pro Pro
1               5                   10                  15

Tyr Glu Val Glu
            20

<210> SEQ ID NO 325
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 325

Ser Glu Tyr Gln Gly Leu Cys Thr Arg Trp Pro Trp Met Cys Pro Pro
1               5                   10                  15

Gln Gly Trp Lys
            20

<210> SEQ ID NO 326
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 326

Thr Phe Ser Gln Gly His Cys Thr Arg Trp Pro Trp Met Cys Pro Pro
1               5                   10                  15

Gln Gly Trp Gly
            20

<210> SEQ ID NO 327
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 327

Pro Gly Ala His Asp His Cys Thr Arg Trp Pro Trp Met Cys Pro Pro
1               5                   10                  15

Gln Ser Arg Tyr
            20
```

<210> SEQ ID NO 328
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 328

Val Ala Glu Glu Trp His Cys Arg Arg Trp Pro Trp Met Cys Pro Pro
1               5                   10                  15

Gln Asp Trp Arg
            20

<210> SEQ ID NO 329
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 329

Val Gly Thr Gln Gly His Cys Thr Arg Trp Pro Trp Met Cys Pro Pro
1               5                   10                  15

Gln Pro Ala Gly
            20

<210> SEQ ID NO 330
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 330

Glu Glu Asp Gln Ala His Cys Arg Ser Trp Pro Trp Met Cys Pro Pro
1               5                   10                  15

Gln Gly Trp Val
            20

<210> SEQ ID NO 331
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 331

Ala Asp Thr Gln Gly His Cys Thr Arg Trp Pro Trp Met Cys Pro Pro
1               5                   10                  15

Gln His Trp Phe
            20

<210> SEQ ID NO 332
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 332

Ser Gly Pro Gln Gly His Cys Thr Arg Trp Pro Trp Met Cys Ala Pro
1               5                   10                  15

Gln Gly Trp Phe

-continued

```
            20

<210> SEQ ID NO 333
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 333

Thr Leu Val Gln Gly His Cys Thr Arg Trp Pro Trp Met Cys Pro Pro
1               5                   10                  15

Gln Arg Trp Val
            20

<210> SEQ ID NO 334
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 334

Gly Met Ala His Gly Lys Cys Thr Arg Trp Ala Trp Met Cys Pro Pro
1               5                   10                  15

Gln Ser Trp Lys
            20

<210> SEQ ID NO 335
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 335

Glu Leu Tyr His Gly Gln Cys Thr Arg Trp Pro Trp Met Cys Pro Pro
1               5                   10                  15

Gln Ser Trp Ala
            20

<210> SEQ ID NO 336
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 336

Val Ala Asp His Gly His Cys Thr Arg Trp Pro Trp Met Cys Pro Pro
1               5                   10                  15

Gln Gly Trp Gly
            20

<210> SEQ ID NO 337
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 337

Pro Glu Ser Gln Gly His Cys Thr Arg Trp Pro Trp Met Cys Pro Pro
1               5                   10                  15
```

```
Gln Gly Trp Gly
        20

<210> SEQ ID NO 338
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 338

Ile Pro Ala His Gly His Cys Thr Arg Trp Pro Trp Met Cys Pro Pro
1               5                   10                  15

Gln Arg Trp Arg
        20

<210> SEQ ID NO 339
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 339

Phe Thr Val His Gly His Cys Thr Arg Trp Pro Trp Met Cys Pro Pro
1               5                   10                  15

Tyr Gly Trp Val
        20

<210> SEQ ID NO 340
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 340

Pro Asp Phe Pro Gly His Cys Thr Arg Trp Arg Trp Met Cys Pro Pro
1               5                   10                  15

Gln Gly Trp Glu
        20

<210> SEQ ID NO 341
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 341

Gln Leu Trp Gln Gly Pro Cys Thr Gln Trp Pro Trp Met Cys Pro Pro
1               5                   10                  15

Lys Gly Arg Tyr
        20

<210> SEQ ID NO 342
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 342

His Ala Asn Asp Gly His Cys Thr Arg Trp Gln Trp Met Cys Pro Pro
1               5                   10                  15
```

```
Gln Trp Gly Gly
            20

<210> SEQ ID NO 343
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 343

Glu Thr Asp His Gly Leu Cys Thr Arg Trp Pro Trp Met Cys Pro Pro
1               5                   10                  15

Tyr Gly Ala Arg
            20

<210> SEQ ID NO 344
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 344

Gly Thr Trp Gln Gly Leu Cys Thr Arg Trp Pro Trp Met Cys Pro Pro
1               5                   10                  15

Gln Gly Trp Gln
            20

<210> SEQ ID NO 345
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 345

Val Ala Thr Gln Gly Gln Cys Thr Arg Trp Pro Trp Met Cys Pro Pro
1               5                   10                  15

Gln Gly Trp Gly
            20

<210> SEQ ID NO 346
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 346

Val Ala Thr Gln Gly Gln Cys Thr Arg Trp Pro Trp Met Cys Pro Pro
1               5                   10                  15

Gln Arg Trp Gly
            20

<210> SEQ ID NO 347
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 347

Gln Arg Glu Trp Tyr Pro Cys Tyr Gly Gly His Leu Trp Cys Tyr Asp
```

```
1               5                  10                  15

Leu His Lys Ala
            20

<210> SEQ ID NO 348
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 348

Ile Ser Ala Trp Tyr Ser Cys Tyr Ala Gly His Phe Trp Cys Trp Asp
1               5                  10                  15

Leu Lys Gln Lys
            20

<210> SEQ ID NO 349
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 349

Trp Thr Gly Trp Tyr Gln Cys Tyr Gly Gly His Leu Trp Cys Tyr Asp
1               5                  10                  15

Leu Arg Arg Lys
            20

<210> SEQ ID NO 350
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 350

Lys Thr Phe Trp Tyr Pro Cys Tyr Asp Gly His Phe Trp Cys Tyr Asn
1               5                  10                  15

Leu Lys Ser Ser
            20

<210> SEQ ID NO 351
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 351

Glu Ser Arg Trp Tyr Pro Cys Tyr Glu Gly His Leu Trp Cys Phe Asp
1               5                  10                  15

Leu Thr Glu Thr
            20

<210> SEQ ID NO 352
<211> LENGTH: 10
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (2)..(3)
```

<223> OTHER INFORMATION: Xaa is selected from a neutral hydrophobic,
      neutral polar, or
      basic amino acid
<220> FEATURE:
<221> NAME/KEY: MISC_FEATURE
<222> LOCATION: (5)..(5)
<223> OTHER INFORMATION: Xaa is selected from a neutral hydrophobic,
      neutral polar, or
      basic amino acid

<400> SEQUENCE: 352

Cys Xaa Xaa Trp Xaa Trp Met Cys Pro Pro
1               5                   10

<210> SEQ ID NO 353
<211> LENGTH: 10
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (2)..(2)
<223> OTHER INFORMATION: Xaa is selected from any one of the amino
      acids T, I, or R.
<220> FEATURE:
<221> NAME/KEY: MISC_FEATURE
<222> LOCATION: (3)..(3)
<223> OTHER INFORMATION: Xaa is selected from any one of R, S, Q.
<220> FEATURE:
<221> NAME/KEY: MISC_FEATURE
<222> LOCATION: (5)..(5)
<223> OTHER INFORMATION: Xaa is selected from any one of P, R, and Q.

<400> SEQUENCE: 353

Cys Xaa Xaa Trp Xaa Trp Met Cys Pro Pro
1               5                   10

<210> SEQ ID NO 354
<211> LENGTH: 20
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (1)..(1)
<223> OTHER INFORMATION: Xaa is absent or any amino acid
<220> FEATURE:
<221> NAME/KEY: MISC_FEATURE
<222> LOCATION: (2)..(3)
<223> OTHER INFORMATION: Xaa is absent or a neutral hydrophobic,
      neutral polar, or acidic
      amino acid
<220> FEATURE:
<221> NAME/KEY: MISC_FEATURE
<222> LOCATION: (4)..(4)
<223> OTHER INFORMATION: Xaa is absent or any amino acid
<220> FEATURE:
<221> NAME/KEY: MISC_FEATURE
<222> LOCATION: (5)..(5)
<223> OTHER INFORMATION: Xaa is absent or a neutral hydrophobic,
      neutral polar, or acidic
      amino acid
<220> FEATURE:
<221> NAME/KEY: MISC_FEATURE
<222> LOCATION: (6)..(6)
<223> OTHER INFORMATION: Xaa is absent or a neutral hydrophobic,
      neutral polar, or basic
      amino acid
<220> FEATURE:
<221> NAME/KEY: MISC_FEATURE
<222> LOCATION: (8)..(9)
<223> OTHER INFORMATION: Xaa is a neutral hydrophobic, neutral polar,
      or basic amino acid

```
<220> FEATURE:
<221> NAME/KEY: MISC_FEATURE
<222> LOCATION: (11)..(11)
<223> OTHER INFORMATION: Xaa is a neutral hydrophobic, neutral polar,
      or basic amino acid
<220> FEATURE:
<221> NAME/KEY: MISC_FEATURE
<222> LOCATION: (17)..(20)
<223> OTHER INFORMATION: Xaa is any amino acid

<400> SEQUENCE: 354

Xaa Xaa Xaa Xaa Xaa Xaa Cys Xaa Xaa Trp Xaa Trp Met Cys Pro Pro
1               5                   10                  15

Xaa Xaa Xaa Xaa
            20

<210> SEQ ID NO 355
<211> LENGTH: 20
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (1)..(1)
<223> OTHER INFORMATION: Xaa is absent or any amino acid
<220> FEATURE:
<221> NAME/KEY: MISC_FEATURE
<222> LOCATION: (2)..(3)
<223> OTHER INFORMATION: Xaa  is absent or a neutral hydrophobic,
      neutral polar, or acidic
      amino acid
<220> FEATURE:
<221> NAME/KEY: MISC_FEATURE
<222> LOCATION: (4)..(4)
<223> OTHER INFORMATION: Xaa is absent or any amino acid
<220> FEATURE:
<221> NAME/KEY: MISC_FEATURE
<222> LOCATION: (5)..(5)
<223> OTHER INFORMATION: Xaa is absent or a neutral hydrophobic,
      neutral polar, or acidic
      amino acid
<220> FEATURE:
<221> NAME/KEY: MISC_FEATURE
<222> LOCATION: (6)..(6)
<223> OTHER INFORMATION: Xaa is absent or a neutral hydrophobic,
      neutral polar, or basic
      amino acid
<220> FEATURE:
<221> NAME/KEY: MISC_FEATURE
<222> LOCATION: (8)..(8)
<223> OTHER INFORMATION: Xaa is selected from any one of the amino
      acids T, I, or R
<220> FEATURE:
<221> NAME/KEY: MISC_FEATURE
<222> LOCATION: (9)..(9)
<223> OTHER INFORMATION: Xaa is selected from any one of R, S, Q
<220> FEATURE:
<221> NAME/KEY: MISC_FEATURE
<222> LOCATION: (11)..(11)
<223> OTHER INFORMATION: Xaa is selected from any one of P, R and Q
<220> FEATURE:
<221> NAME/KEY: MISC_FEATURE
<222> LOCATION: (17)..(20)
<223> OTHER INFORMATION: Xaa is any amino acid

<400> SEQUENCE: 355

Xaa Xaa Xaa Xaa Xaa Xaa Cys Xaa Xaa Trp Xaa Trp Met Cys Pro Pro
1               5                   10                  15

Xaa Xaa Xaa Xaa
            20

<210> SEQ ID NO 356
```

```
<211> LENGTH: 7
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (3)..(3)
<223> OTHER INFORMATION: Xaa is P,S or Y
<220> FEATURE:
<221> NAME/KEY: MISC_FEATURE
<222> LOCATION: (4)..(4)
<223> OTHER INFORMATION: Xaa is C or Q
<220> FEATURE:
<221> NAME/KEY: MISC_FEATURE
<222> LOCATION: (6)..(6)
<223> OTHER INFORMATION: Xaa is G or H

<400> SEQUENCE: 356

Trp Tyr Xaa Xaa Tyr Xaa Gly
1               5

<210> SEQ ID NO 357
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 357

Arg Met Glu Met Leu Glu Ser Leu Leu Glu Leu Leu Lys Glu Ile Val
1               5                   10                  15

Pro Met Ser Lys Ala Gly
            20

<210> SEQ ID NO 358
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 358

Arg Met Glu Met Leu Glu Ser Leu Leu Glu Leu Leu Lys Glu Ile Val
1               5                   10                  15

Pro Met Ser Lys Ala Arg
            20

<210> SEQ ID NO 359
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 359

Arg Met Glu Met Leu Glu Ser Leu Leu Glu Leu Leu Lys Asp Ile Val
1               5                   10                  15

Pro Met Ser Lys Pro Ser
            20

<210> SEQ ID NO 360
<211> LENGTH: 22
<212> TYPE: PRT
<213> ORGANISM: Artificial Sequence
<220> FEATURE:
<223> OTHER INFORMATION: Myostatin Binding Peptide
```

-continued

<400> SEQUENCE: 360

Gly Met Glu Met Leu Glu Ser Leu Phe Glu Leu Leu Gln Glu Ile Val
1               5                   10                  15

Pro Met Ser Lys Ala Pro
            20

<210> SEQ ID NO 361
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 361

Arg Met Glu Met Leu Glu Ser Leu Leu Glu Leu Leu Lys Asp Ile Val
1               5                   10                  15

Pro Ile Ser Asn Pro Pro
            20

<210> SEQ ID NO 362
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 362

Arg Ile Glu Met Leu Glu Ser Leu Leu Glu Leu Leu Gln Glu Ile Val
1               5                   10                  15

Pro Ile Ser Lys Ala Glu
            20

<210> SEQ ID NO 363
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 363

Arg Met Glu Met Leu Gln Ser Leu Leu Glu Leu Leu Lys Asp Ile Val
1               5                   10                  15

Pro Met Ser Asn Ala Arg
            20

<210> SEQ ID NO 364
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 364

Arg Met Glu Met Leu Glu Ser Leu Leu Glu Leu Leu Lys Glu Ile Val
1               5                   10                  15

Pro Thr Ser Asn Gly Thr
            20

<210> SEQ ID NO 365
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 365

Arg Met Glu Met Leu Glu Ser Leu Phe Glu Leu Leu Lys Glu Ile Val
1               5                   10                  15

Pro Met Ser Lys Ala Gly
            20

<210> SEQ ID NO 366
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 366

Arg Met Glu Met Leu Gly Ser Leu Leu Glu Leu Leu Lys Glu Ile Val
1               5                   10                  15

Pro Met Ser Lys Ala Arg
            20

<210> SEQ ID NO 367
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 367

Gln Met Glu Leu Leu Asp Ser Leu Phe Glu Leu Leu Lys Glu Ile Val
1               5                   10                  15

Pro Lys Ser Gln Pro Ala
            20

<210> SEQ ID NO 368
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 368

Arg Met Glu Met Leu Asp Ser Leu Leu Glu Leu Leu Lys Glu Ile Val
1               5                   10                  15

Pro Met Ser Asn Ala Arg
            20

<210> SEQ ID NO 369
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 369

Arg Met Glu Met Leu Glu Ser Leu Leu Glu Leu Leu His Glu Ile Val
1               5                   10                  15

Pro Met Ser Gln Ala Gly
            20

<210> SEQ ID NO 370
<211> LENGTH: 22
<212> TYPE: PRT
<213> ORGANISM: Artificial Sequence
<220> FEATURE:

-continued

<223> OTHER INFORMATION: Myostatin Binding Peptide

<400> SEQUENCE: 370

Gln Met Glu Met Leu Glu Ser Leu Leu Gln Leu Leu Lys Glu Ile Val
1 5 10 15

Pro Met Ser Lys Ala Ser
20

<210> SEQ ID NO 371
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 371

Arg Met Glu Met Leu Asp Ser Leu Leu Glu Leu Leu Lys Asp Met Val
1 5 10 15

Pro Met Thr Thr Gly Ala
20

<210> SEQ ID NO 372
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 372

Arg Ile Glu Met Leu Glu Ser Leu Leu Glu Leu Leu Lys Asp Met Val
1 5 10 15

Pro Met Ala Asn Ala Ser
20

<210> SEQ ID NO 373
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 373

Arg Met Glu Met Leu Glu Ser Leu Leu Gln Leu Leu Asn Glu Ile Val
1 5 10 15

Pro Met Ser Arg Ala Arg
20

<210> SEQ ID NO 374
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 374

Arg Met Glu Met Leu Glu Ser Leu Phe Asp Leu Leu Lys Glu Leu Val
1 5 10 15

Pro Met Ser Lys Gly Val
20

<210> SEQ ID NO 375
<211> LENGTH: 22
<212> TYPE: PRT
<213> ORGANISM: Artificial Sequence

```
<220> FEATURE:
<223> OTHER INFORMATION: Myostatin Binding Peptide

<400> SEQUENCE: 375

Arg Ile Glu Met Leu Glu Ser Leu Leu Glu Leu Leu Lys Asp Ile Val
1               5                   10                  15

Pro Ile Gln Lys Ala Arg
            20

<210> SEQ ID NO 376
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 376

Arg Met Glu Leu Leu Glu Ser Leu Phe Glu Leu Leu Lys Asp Met Val
1               5                   10                  15

Pro Met Ser Asp Ser Ser
            20

<210> SEQ ID NO 377
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 377

Arg Met Glu Met Leu Glu Ser Leu Leu Glu Val Leu Gln Glu Ile Val
1               5                   10                  15

Pro Arg Ala Lys Gly Ala
            20

<210> SEQ ID NO 378
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 378

Arg Met Glu Met Leu Asp Ser Leu Leu Gln Leu Leu Asn Glu Ile Val
1               5                   10                  15

Pro Met Ser His Ala Arg
            20

<210> SEQ ID NO 379
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 379

Arg Met Glu Met Leu Glu Ser Leu Leu Glu Leu Leu Lys Asp Ile Val
1               5                   10                  15

Pro Met Ser Asn Ala Gly
            20

<210> SEQ ID NO 380
<211> LENGTH: 22
<212> TYPE: PRT
```

```
<213> ORGANISM: Artificial Sequence
<220> FEATURE:
<223> OTHER INFORMATION: Myostatin Binding Peptide

<400> SEQUENCE: 380

Arg Met Glu Met Leu Gln Ser Leu Phe Glu Leu Leu Lys Gly Met Val
1               5                   10                  15

Pro Ile Ser Lys Ala Gly
            20

<210> SEQ ID NO 381
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 381

Arg Met Glu Met Leu Glu Ser Leu Leu Glu Leu Leu Lys Glu Ile Val
1               5                   10                  15

Pro Asn Ser Thr Ala Ala
            20

<210> SEQ ID NO 382
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 382

Arg Met Glu Met Leu Gln Ser Leu Leu Glu Leu Leu Lys Glu Ile Val
1               5                   10                  15

Pro Ile Ser Lys Ala Gly
            20

<210> SEQ ID NO 383
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 383

Arg Ile Glu Met Leu Asp Ser Leu Leu Glu Leu Leu Asn Glu Leu Val
1               5                   10                  15

Pro Met Ser Lys Ala Arg
            20

<210> SEQ ID NO 384
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 384

Gln Val Glu Ser Leu Gln Gln Leu Leu Met Trp Leu Asp Gln Lys Leu
1               5                   10                  15

Ala Ser Gly Pro Gln Gly
            20

<210> SEQ ID NO 385
<211> LENGTH: 22
```

```
<212> TYPE: PRT
<213> ORGANISM: Artificial Sequence
<220> FEATURE:
<223> OTHER INFORMATION: Myostatin Binding Peptide

<400> SEQUENCE: 385

Arg Met Glu Leu Leu Glu Ser Leu Phe Glu Leu Leu Lys Glu Met Val
1               5                   10                  15

Pro Arg Ser Lys Ala Val
            20

<210> SEQ ID NO 386
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 386

Gln Ala Val Ser Leu Gln His Leu Leu Met Trp Leu Asp Gln Lys Leu
1               5                   10                  15

Ala Ser Gly Pro Gln His
            20

<210> SEQ ID NO 387
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 387

Asp Glu Asp Ser Leu Gln Gln Leu Leu Met Trp Leu Asp Gln Lys Leu
1               5                   10                  15

Ala Ser Gly Pro Gln Leu
            20

<210> SEQ ID NO 388
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 388

Pro Val Ala Ser Leu Gln Gln Leu Leu Ile Trp Leu Asp Gln Lys Leu
1               5                   10                  15

Ala Gln Gly Pro His Ala
            20

<210> SEQ ID NO 389
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 389

Glu Val Asp Glu Leu Gln Gln Leu Leu Asn Trp Leu Asp His Lys Leu
1               5                   10                  15

Ala Ser Gly Pro Leu Gln
            20

<210> SEQ ID NO 390
```

-continued

```
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 390

Asp Val Glu Ser Leu Glu Gln Leu Leu Met Trp Leu Asp His Gln Leu
1               5                   10                  15

Ala Ser Gly Pro His Gly
            20

<210> SEQ ID NO 391
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 391

Gln Val Asp Ser Leu Gln Gln Val Leu Leu Trp Leu Glu His Lys Leu
1               5                   10                  15

Ala Leu Gly Pro Gln Val
            20

<210> SEQ ID NO 392
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 392

Gly Asp Glu Ser Leu Gln His Leu Leu Met Trp Leu Glu Gln Lys Leu
1               5                   10                  15

Ala Leu Gly Pro His Gly
            20

<210> SEQ ID NO 393
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 393

Gln Ile Glu Met Leu Glu Ser Leu Leu Asp Leu Leu Arg Asp Met Val
1               5                   10                  15

Pro Met Ser Asn Ala Phe
            20

<210> SEQ ID NO 394
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 394

Glu Val Asp Ser Leu Gln Gln Leu Leu Met Trp Leu Asp Gln Lys Leu
1               5                   10                  15

Ala Ser Gly Pro Gln Ala
            20
```

```
<210> SEQ ID NO 395
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 395

Glu Asp Glu Ser Leu Gln Gln Leu Leu Ile Tyr Leu Asp Lys Met Leu
1               5                   10                  15

Ser Ser Gly Pro Gln Val
            20

<210> SEQ ID NO 396
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 396

Ala Met Asp Gln Leu His Gln Leu Leu Ile Trp Leu Asp His Lys Leu
1               5                   10                  15

Ala Ser Gly Pro Gln Ala
            20

<210> SEQ ID NO 397
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 397

Arg Ile Glu Met Leu Glu Ser Leu Leu Glu Leu Leu Asp Glu Ile Ala
1               5                   10                  15

Leu Ile Pro Lys Ala Trp
            20

<210> SEQ ID NO 398
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 398

Glu Val Val Ser Leu Gln His Leu Leu Met Trp Leu Glu His Lys Leu
1               5                   10                  15

Ala Ser Gly Pro Asp Gly
            20

<210> SEQ ID NO 399
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 399

Gly Gly Glu Ser Leu Gln Gln Leu Leu Met Trp Leu Asp Gln Gln Leu
1               5                   10                  15

Ala Ser Gly Pro Gln Arg
            20
```

```
<210> SEQ ID NO 400
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 400

Gly Val Glu Ser Leu Gln Gln Leu Leu Ile Phe Leu Asp His Met Leu
1               5                   10                  15

Val Ser Gly Pro His Asp
            20

<210> SEQ ID NO 401
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 401

Asn Val Glu Ser Leu Glu His Leu Met Met Trp Leu Glu Arg Leu Leu
1               5                   10                  15

Ala Ser Gly Pro Tyr Ala
            20

<210> SEQ ID NO 402
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 402

Gln Val Asp Ser Leu Gln Gln Leu Leu Ile Trp Leu Asp His Gln Leu
1               5                   10                  15

Ala Ser Gly Pro Lys Arg
            20

<210> SEQ ID NO 403
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 403

Glu Val Glu Ser Leu Gln Gln Leu Leu Met Trp Leu Glu His Lys Leu
1               5                   10                  15

Ala Gln Gly Pro Gln Gly
            20

<210> SEQ ID NO 404
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 404

Glu Val Asp Ser Leu Gln Gln Leu Leu Met Trp Leu Asp Gln Lys Leu
1               5                   10                  15

Ala Ser Gly Pro His Ala
            20
```

<210> SEQ ID NO 405
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 405

Glu Val Asp Ser Leu Gln Gln Leu Leu Met Trp Leu Asp Gln Gln Leu
1               5                   10                  15

Ala Ser Gly Pro Gln Lys
            20

<210> SEQ ID NO 406
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 406

Gly Val Glu Gln Leu Pro Gln Leu Leu Met Trp Leu Glu Gln Lys Leu
1               5                   10                  15

Ala Ser Gly Pro Gln Arg
            20

<210> SEQ ID NO 407
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 407

Gly Glu Asp Ser Leu Gln Gln Leu Leu Met Trp Leu Asp Gln Gln Leu
1               5                   10                  15

Ala Ala Gly Pro Gln Val
            20

<210> SEQ ID NO 408
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 408

Ala Asp Asp Ser Leu Gln Gln Leu Leu Met Trp Leu Asp Arg Lys Leu
1               5                   10                  15

Ala Ser Gly Pro His Val
            20

<210> SEQ ID NO 409
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 409

Pro Val Asp Ser Leu Gln Gln Leu Leu Ile Trp Leu Asp Gln Lys Leu
1               5                   10                  15

Ala Ser Gly Pro Gln Gly

```
                20

<210> SEQ ID NO 410
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 410

Asp Trp Arg Ala Thr Leu Leu Lys Glu Phe Trp Gln Leu Val Glu Gly
1               5                   10                  15

Leu Gly Asp Asn Leu Val
            20

<210> SEQ ID NO 411
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 411

Gln Ser Arg Ala Thr Leu Leu Lys Glu Phe Trp Gln Leu Val Glu Gly
1               5                   10                  15

Leu Gly Asp Lys Gln Ala
            20

<210> SEQ ID NO 412
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 412

Asp Gly Arg Ala Thr Leu Leu Thr Glu Phe Trp Gln Leu Val Gln Gly
1               5                   10                  15

Leu Gly Gln Lys Glu Ala
            20

<210> SEQ ID NO 413
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 413

Leu Ala Arg Ala Thr Leu Leu Lys Glu Phe Trp Gln Leu Val Glu Gly
1               5                   10                  15

Leu Gly Glu Lys Val Val
            20

<210> SEQ ID NO 414
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 414

Gly Ser Arg Asp Thr Leu Leu Lys Glu Phe Trp Gln Leu Val Val Gly
1               5                   10                  15
```

Leu Gly Asp Met Gln Thr
            20

<210> SEQ ID NO 415
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 415

Asp Ala Arg Ala Thr Leu Leu Lys Glu Phe Trp Gln Leu Val Asp Ala
1               5                   10                  15

Tyr Gly Asp Arg Met Val
            20

<210> SEQ ID NO 416
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 416

Asn Asp Arg Ala Gln Leu Leu Arg Asp Phe Trp Gln Leu Val Asp Gly
1               5                   10                  15

Leu Gly Val Lys Ser Trp
            20

<210> SEQ ID NO 417
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 417

Gly Val Arg Glu Thr Leu Leu Tyr Glu Leu Trp Tyr Leu Leu Lys Gly
1               5                   10                  15

Leu Gly Ala Asn Gln Gly
            20

<210> SEQ ID NO 418
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 418

Gln Ala Arg Ala Thr Leu Leu Lys Glu Phe Cys Gln Leu Val Gly Cys
1               5                   10                  15

Gln Gly Asp Lys Leu Ser
            20

<210> SEQ ID NO 419
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 419

Gln Glu Arg Ala Thr Leu Leu Lys Glu Phe Trp Gln Leu Val Ala Gly
1               5                   10                  15

```
Leu Gly Gln Asn Met Arg
            20

<210> SEQ ID NO 420
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 420

Ser Gly Arg Ala Thr Leu Leu Lys Glu Phe Trp Gln Leu Val Gln Gly
1               5                   10                  15

Leu Gly Glu Tyr Arg Trp
            20

<210> SEQ ID NO 421
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 421

Thr Met Arg Ala Thr Leu Leu Lys Glu Phe Trp Leu Phe Val Asp Gly
1               5                   10                  15

Gln Arg Glu Met Gln Trp
            20

<210> SEQ ID NO 422
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 422

Gly Glu Arg Ala Thr Leu Leu Asn Asp Phe Trp Gln Leu Val Asp Gly
1               5                   10                  15

Gln Gly Asp Asn Thr Gly
            20

<210> SEQ ID NO 423
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 423

Asp Glu Arg Glu Thr Leu Leu Lys Glu Phe Trp Gln Leu Val His Gly
1               5                   10                  15

Trp Gly Asp Asn Val Ala
            20

<210> SEQ ID NO 424
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 424

Gly Gly Arg Ala Thr Leu Leu Lys Glu Leu Trp Gln Leu Leu Glu Gly
```

```
                1               5                  10                  15

Gln Gly Ala Asn Leu Val
            20

<210> SEQ ID NO 425
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 425

Thr Ala Arg Ala Thr Leu Leu Asn Glu Leu Val Gln Leu Val Lys Gly
1               5                  10                  15

Tyr Gly Asp Lys Leu Val
            20

<210> SEQ ID NO 426
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 426

Gly Met Arg Ala Thr Leu Leu Gln Glu Phe Trp Gln Leu Val Gly Gly
1               5                  10                  15

Gln Gly Asp Asn Trp Met
            20

<210> SEQ ID NO 427
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 427

Ser Thr Arg Ala Thr Leu Leu Asn Asp Leu Trp Gln Leu Met Lys Gly
1               5                  10                  15

Trp Ala Glu Asp Arg Gly
            20

<210> SEQ ID NO 428
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 428

Ser Glu Arg Ala Thr Leu Leu Lys Glu Leu Trp Gln Leu Val Gly Gly
1               5                  10                  15

Trp Gly Asp Asn Phe Gly
            20

<210> SEQ ID NO 429
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 429
```

Val Gly Arg Ala Thr Leu Leu Lys Glu Phe Trp Gln Leu Val Glu Gly
1               5                   10                  15

Leu Val Gly Gln Ser Arg
            20

<210> SEQ ID NO 430
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 430

Glu Ile Arg Ala Thr Leu Leu Lys Glu Phe Trp Gln Leu Val Asp Glu
1               5                   10                  15

Trp Arg Glu Gln Pro Asn
            20

<210> SEQ ID NO 431
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 431

Gln Leu Arg Ala Thr Leu Leu Lys Glu Phe Leu Gln Leu Val His Gly
1               5                   10                  15

Leu Gly Glu Thr Asp Ser
            20

<210> SEQ ID NO 432
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 432

Thr Gln Arg Ala Thr Leu Leu Lys Glu Phe Trp Gln Leu Ile Glu Gly
1               5                   10                  15

Leu Gly Gly Lys His Val
            20

<210> SEQ ID NO 433
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 433

His Tyr Arg Ala Thr Leu Leu Lys Glu Phe Trp Gln Leu Val Asp Gly
1               5                   10                  15

Leu Arg Glu Gln Gly Val
            20

<210> SEQ ID NO 434
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 434

Gln Ser Arg Val Thr Leu Leu Arg Glu Phe Trp Gln Leu Val Glu Ser
1               5                   10                  15

Tyr Arg Pro Ile Val Asn
            20

<210> SEQ ID NO 435
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 435

Leu Ser Arg Ala Thr Leu Leu Asn Glu Phe Trp Gln Phe Val Asp Gly
1               5                   10                  15

Gln Arg Asp Lys Arg Met
            20

<210> SEQ ID NO 436
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 436

Trp Asp Arg Ala Thr Leu Leu Asn Asp Phe Trp His Leu Met Glu Glu
1               5                   10                  15

Leu Ser Gln Lys Pro Gly
            20

<210> SEQ ID NO 437
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 437

Gln Glu Arg Ala Thr Leu Leu Lys Glu Phe Trp Arg Met Val Glu Gly
1               5                   10                  15

Leu Gly Lys Asn Arg Gly
            20

<210> SEQ ID NO 438
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 438

Asn Glu Arg Ala Thr Leu Leu Arg Glu Phe Trp Gln Leu Val Gly Gly
1               5                   10                  15

Tyr Gly Val Asn Gln Arg
            20

<210> SEQ ID NO 439
<211> LENGTH: 22
<212> TYPE: PRT
<213> ORGANISM: Artificial Sequence
<220> FEATURE:
<223> OTHER INFORMATION: Myostatin Binding Peptide

```
<400> SEQUENCE: 439

His Gln Arg Asp Met Ser Met Leu Trp Glu Leu Leu Asp Val Leu Asp
1               5                   10                  15

Gly Leu Arg Gln Tyr Ser
            20

<210> SEQ ID NO 440
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 440

Thr Gln Arg Asp Met Ser Met Leu Asp Gly Leu Leu Glu Val Leu Asp
1               5                   10                  15

Gln Leu Arg Gln Gln Arg
            20

<210> SEQ ID NO 441
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 441

Thr Ser Arg Asp Met Ser Leu Leu Trp Glu Leu Leu Glu Glu Leu Asp
1               5                   10                  15

Arg Leu Gly His Gln Arg
            20

<210> SEQ ID NO 442
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 442

Met Gln His Asp Met Ser Met Leu Tyr Gly Leu Val Glu Leu Leu Glu
1               5                   10                  15

Ser Leu Gly His Gln Ile
            20

<210> SEQ ID NO 443
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 443

Trp Asn Arg Asp Met Arg Met Leu Glu Ser Leu Phe Glu Val Leu Asp
1               5                   10                  15

Gly Leu Arg Gln Gln Val
            20

<210> SEQ ID NO 444
<211> LENGTH: 22
<212> TYPE: PRT
<213> ORGANISM: Artificial Sequence
<220> FEATURE:
<223> OTHER INFORMATION: Myostatin Binding Peptide
```

<400> SEQUENCE: 444

Gly Tyr Arg Asp Met Ser Met Leu Glu Gly Leu Leu Ala Val Leu Asp
1               5                   10                  15

Arg Leu Gly Pro Gln Leu
            20

<210> SEQ ID NO 445
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 445

Thr Gln Arg Asp Met Ser Met Leu Glu Gly Leu Leu Glu Val Leu Asp
1               5                   10                  15

Arg Leu Gly Gln Gln Arg
            20

<210> SEQ ID NO 446
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 446

Trp Tyr Arg Asp Met Ser Met Leu Glu Gly Leu Leu Glu Val Leu Asp
1               5                   10                  15

Arg Leu Gly Gln Gln Arg
            20

<210> SEQ ID NO 447
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 447

Thr Gln Asn Ser Arg Gln Met Leu Leu Ser Asp Phe Met Met Leu Val
1               5                   10                  15

Gly Ser Met Ile Gln Gly
            20

<210> SEQ ID NO 448
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 448

Met Gln Thr Ser Arg His Ile Leu Leu Ser Glu Phe Met Met Leu Val
1               5                   10                  15

Gly Ser Ile Met His Gly
            20

<210> SEQ ID NO 449
<211> LENGTH: 22
<212> TYPE: PRT
<213> ORGANISM: Artificial Sequence
<220> FEATURE:

<223> OTHER INFORMATION: Myostatin Binding Peptide

<400> SEQUENCE: 449

His Asp Asn Ser Arg Gln Met Leu Leu Ser Asp Leu Leu His Leu Val
1 5 10 15

Gly Thr Met Ile Gln Gly
20

<210> SEQ ID NO 450
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 450

Met Glu Asn Ser Arg Gln Asn Leu Leu Arg Glu Leu Ile Met Leu Val
1 5 10 15

Gly Asn Met Ser His Gln
20

<210> SEQ ID NO 451
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 451

Gln Asp Thr Ser Arg His Met Leu Leu Arg Glu Phe Met Met Leu Val
1 5 10 15

Gly Glu Met Ile Gln Gly
20

<210> SEQ ID NO 452
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 452

Asp Gln Asn Ser Arg Gln Met Leu Leu Ser Asp Leu Met Ile Leu Val
1 5 10 15

Gly Ser Met Ile Gln Gly
20

<210> SEQ ID NO 453
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 453

Asn Val Phe Phe Gln Trp Val Gln Lys His Gly Arg Val Val Tyr Gln
1 5 10 15

Trp Leu Asp Ile Asn Val
20

<210> SEQ ID NO 454
<211> LENGTH: 22
<212> TYPE: PRT
<213> ORGANISM: Artificial Sequence

```
<220> FEATURE:
<223> OTHER INFORMATION: Myostatin Binding Peptide

<400> SEQUENCE: 454

Phe Asp Phe Leu Gln Trp Leu Gln Asn His Arg Ser Glu Val Glu His
1               5                   10                  15

Trp Leu Val Met Asp Val
            20

<210> SEQ ID NO 455
<211> LENGTH: 11
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (1)..(1)
<223> OTHER INFORMATION: Xaa is M or I
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is L or F
<220> FEATURE:
<221> NAME/KEY: MISC_FEATURE
<222> LOCATION: (9)..(9)
<223> OTHER INFORMATION: Xaa is E, Q or D

<400> SEQUENCE: 455

Xaa Glu Met Leu Xaa Ser Leu Xaa Xaa Leu Leu
1               5                   10

<210> SEQ ID NO 456
<211> LENGTH: 8
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (2)..(2)
<223> OTHER INFORMATION: Xaa is Q, D or E
<220> FEATURE:
<221> NAME/KEY: MISC_FEATURE
<222> LOCATION: (3)..(3)
<223> OTHER INFORMATION: Xaa is S, Q, D or E
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is L, W, F or Y

<400> SEQUENCE: 456

Leu Xaa Xaa Leu Leu Xaa Xaa Leu
1               5

<210> SEQ ID NO 457
<211> LENGTH: 9
<212> TYPE: PRT
<213> ORGANISM: Artificial Sequence
<220> FEATURE:
<223> OTHER INFORMATION: Myostatin Binding Peptide
<220> FEATURE:
<221> NAME/KEY: MISC_FEATURE
<222> LOCATION: (1)..(1)
```

```
<223> OTHER INFORMATION: Xaa is R or D
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is A, T, S or Q
<220> FEATURE:
<221> NAME/KEY: MISC_FEATURE
<222> LOCATION: (4)..(4)
<223> OTHER INFORMATION: Xaa is L or M
<220> FEATURE:
<221> NAME/KEY: MISC_FEATURE
<222> LOCATION: (5)..(5)
<223> OTHER INFORMATION: Xaa is L or S
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is F or E
<220> FEATURE:
<221> NAME/KEY: MISC_FEATURE
<222> LOCATION: (8)..(8)
<223> OTHER INFORMATION: Xaa is W, F or C
<220> FEATURE:
<221> NAME/KEY: MISC_FEATURE
<222> LOCATION: (9)..(9)
<223> OTHER INFORMATION: Xaa is L, F, M or K

<400> SEQUENCE: 457

Xaa Xaa Xaa Xaa Xaa Xaa Xaa Xaa Xaa
1               5

<210> SEQ ID NO 458
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 458
cgtatggaaa tgcttgaatc tcttcttgaa cttcttaaag aaattgttcc aatgtctaaa      60
gctggt                                                                66

<210> SEQ ID NO 459
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 459
cgtatggaaa tgcttgaatc tcttcttgaa cttcttaaag aaattgttcc aatgtctaaa      60
gctcgt                                                                66

<210> SEQ ID NO 460
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 460
```

```
cgtatggaaa tgcttgaatc tcttcttgaa cttcttaaag atattgttcc aatgtctaaa    60
ccatct                                                                66
```

<210> SEQ ID NO 461
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 461

```
ggtatggaaa tgcttgaatc tcttttttgaa cttcttcaag aaattgttcc aatgtctaaa    60
gctcca                                                                66
```

<210> SEQ ID NO 462
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 462

```
cgtatggaaa tgcttgaatc tcttcttgaa cttcttaaag atattgttcc aatttctaat    60
ccacca                                                                66
```

<210> SEQ ID NO 463
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 463

```
cgtattgaaa tgcttgaatc tcttcttgaa cttcttcaag aaattgttcc aatttctaaa    60
gctgaa                                                                66
```

<210> SEQ ID NO 464
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 464

```
cgtatggaaa tgcttcaatc tcttcttgaa cttcttaaag atattgttcc aatgtctaat    60
gctcgt                                                                66
```

<210> SEQ ID NO 465
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 465

```
cgtatggaaa tgcttgaatc tcttcttgaa cttcttaaag aaattgttcc aacttctaat    60
ggtact                                                                66
```

<210> SEQ ID NO 466
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 466
cgtatggaaa tgcttgaatc tcttttgaa cttcttaaag aaattgttcc aatgtctaaa      60
gctggt                                                                66

<210> SEQ ID NO 467
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 467
cgtatggaaa tgcttggttc tcttcttgaa cttcttaaag aaattgttcc aatgtctaaa      60
gctcgt                                                                66

<210> SEQ ID NO 468
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 468
caaatggaac ttcttgattc tcttttgaa cttcttaaag aaattgttcc aaaatctcaa      60
ccagct                                                                66

<210> SEQ ID NO 469
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 469
cgtatggaaa tgcttgattc tcttcttgaa cttcttaaag aaattgttcc aatgtctaat      60
gctcgt                                                                66

<210> SEQ ID NO 470
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 470
cgtatggaaa tgcttgaatc tcttcttgaa cttcttcatg aaattgttcc aatgtctcaa      60
gctggt                                                                66

<210> SEQ ID NO 471
<211> LENGTH: 66

<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 471
caaatggaaa tgcttgaatc tcttcttcaa cttcttaaag aaattgttcc aatgtctaaa    60
gcttct                                                              66

<210> SEQ ID NO 472
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 472
cgtatggaaa tgcttgattc tcttcttgaa cttcttaaag atatggttcc aatgactact    60
ggtgct                                                              66

<210> SEQ ID NO 473
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 473
cgtattgaaa tgcttgaatc tcttcttgaa cttcttaaag atatggttcc aatggctaat    60
gcttct                                                              66

<210> SEQ ID NO 474
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 474
cgtatggaaa tgcttgaatc tcttcttcaa cttcttaatg aaattgttcc aatgtctcgt    60
gctcgt                                                              66

<210> SEQ ID NO 475
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 475
cgtatggaaa tgcttgaatc tcttttttgat cttcttaaag aacttgttcc aatgtctaaa    60
ggtgtt                                                              66

<210> SEQ ID NO 476
<211> LENGTH: 66
<212> TYPE: DNA
<213> ORGANISM: Artificial Sequence
<220> FEATURE:
<223> OTHER INFORMATION: Nucleotide sequence encoding Myostatin Binding Peptide

<400> SEQUENCE: 476
cgtattgaaa tgcttgaatc tcttcttgaa cttcttaaag atattgttcc aattcaaaaa    60
gctcgt                                                              66

<210> SEQ ID NO 477
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 477
cgtatggaac ttcttgaatc tctttttgaa cttcttaaag atatggttcc aatgtctgat    60
tcttct                                                              66

<210> SEQ ID NO 478
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 478
cgtatggaaa tgcttgaatc tcttcttgaa gttcttcaag aaattgttcc acgtgctaaa    60
ggtgct                                                              66

<210> SEQ ID NO 479
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 479
cgtatggaaa tgcttgattc tcttcttcaa cttcttaatg aaattgttcc aatgtctcat    60
gctcgt                                                              66

<210> SEQ ID NO 480
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 480
cgtatggaaa tgcttgaatc tcttcttgaa cttcttaaag atattgttcc aatgtctaat    60
gctggt                                                              66

<210> SEQ ID NO 481
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 481

```
cgtatggaaa tgcttcaatc tcttttttgaa cttcttaaag gtatggttcc aatttctaaa    60
gctggt                                                                66

<210> SEQ ID NO 482
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 482
cgtatggaaa tgcttgaatc tcttcttgaa cttcttaaag aaattgttcc aaattctact    60
gctgct                                                                66

<210> SEQ ID NO 483
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 483
cgtatggaaa tgcttcaatc tcttcttgaa cttcttaaag aaattgttcc aatttctaaa    60
gctggt                                                                66

<210> SEQ ID NO 484
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 484
cgtattgaaa tgcttgattc tcttcttgaa cttcttaatg aacttgttcc aatgtctaaa    60
gctcgt                                                                66

<210> SEQ ID NO 485
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 485
gattggcgtg ctactcttct taaagaattt tggcaacttg ttgaaggtct tggtgataat    60
cttgtt                                                                66

<210> SEQ ID NO 486
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 486
gatggtcgtg ctactcttct tactgaattt tggcaacttg ttcaaggtct tggtcaaaaa    60
gaagct                                                                66
```

<210> SEQ ID NO 487
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 487
cttgctcgtg ctactcttct taaagaattt tggcaacttg ttgaaggtct tggtgaaaaa    60
gttgtt                                                                66

<210> SEQ ID NO 488
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 488
ggttctcgtg atactcttct taaagaattt tggcaacttg ttgttggtct tggtgatatg    60
caaact                                                                66

<210> SEQ ID NO 489
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 489
gatgctcgtg ctactcttct taaagaattt tggcaacttg ttgatgctta tggtgatcgt    60
atggtt                                                                66

<210> SEQ ID NO 490
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 490
aatgatcgtg ctcaacttct tcgtgatttt tggcaacttg ttgatggtct tggtgttaaa    60
tcttgg                                                                66

<210> SEQ ID NO 491
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 491
ggtgttcgtg aaactcttct ttatgaactt tggtatcttc ttaaaggtct tggtgctaat    60
caaggt                                                                66

<210> SEQ ID NO 492
<211> LENGTH: 66
<212> TYPE: DNA

```
<213> ORGANISM: Artificial Sequence
<220> FEATURE:
<223> OTHER INFORMATION: Nucleotide sequence encoding Myostatin Binding
      Peptide

<400> SEQUENCE: 492
caagctcgtg ctactcttct taaagaattt tgtcaacttg ttggttgtca aggtgataaa      60
ctttct                                                                66

<210> SEQ ID NO 493
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 493
caagaacgtg ctactcttct taaagaattt tggcaacttg ttgctggtct tggtcaaaat      60
atgcgt                                                                66

<210> SEQ ID NO 494
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 494
tctggtcgtg ctactcttct taaagaattt tggcaacttg ttcaaggtct tggtgaatat      60
cgttgg                                                                66

<210> SEQ ID NO 495
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 495
actatgcgtg ctactcttct taaagaattt tggctttttg ttgatggtca acgtgaaatg      60
caatgg                                                                66

<210> SEQ ID NO 496
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 496
ggtgaacgtg ctactcttct taatgatttt tggcaacttg ttgatggtca aggtgataat      60
actggt                                                                66

<210> SEQ ID NO 497
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide
```

<400> SEQUENCE: 497
gatgaacgtg aaactcttct taaagaattt tggcaacttg ttcatggttg gggtgataat    60
gttgct    66

<210> SEQ ID NO 498
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 498
ggtggtcgtg ctactcttct taaagaactt tggcaacttc ttgaaggtca aggtgctaat    60
cttgtt    66

<210> SEQ ID NO 499
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 499
actgctcgtg ctactcttct taatgaactt gttcaacttg ttaaaggtta tggtgataaa    60
cttgtt    66

<210> SEQ ID NO 500
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 500
ggtatgcgtg ctactcttct tcaagaattt tggcaacttg ttggtggtca aggtgataat    60
tggatg    66

<210> SEQ ID NO 501
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 501
tctactcgtg ctactcttct taatgatctt tggcaactta tgaaaggttg ggctgaagat    60
cgtggt    66

<210> SEQ ID NO 502
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 502
tctgaacgtg ctactcttct taaagaactt tggcaacttg ttggtggttg gggtgataat    60

```
<210> SEQ ID NO 503
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 503
gttggtcgtg ctactcttct taaagaattt tggcaacttg ttgaaggtct tgttggtcaa      60
tctcgt                                                                66

<210> SEQ ID NO 504
<211> LENGTH: 62
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (62)..(62)
<223> OTHER INFORMATION: Xaa = Fc

<400> SEQUENCE: 504

Met Gly Ala Gln Trp Tyr Pro Cys Tyr Glu Gly His Phe Trp Cys Tyr
1               5                   10                  15

Asp Leu Gly Ser Gly Ser Ala Thr Gly Gly Ser Gly Ser Thr Ala Ser
            20                  25                  30

Ser Gly Ser Gly Ser Ala Thr Gly Trp Tyr Pro Cys Tyr Glu Gly His
        35                  40                  45

Phe Trp Cys Tyr Asp Leu Leu Glu Gly Gly Gly Gly Xaa
    50                  55                  60

<210> SEQ ID NO 505
<211> LENGTH: 129
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 505
tggtatccgt gttatgaggg tcacttctgg tgctacgatc tgggttctgg ttccactgct      60
tcttctggtt ccggttccgc tactggttgg tacccgtgct acgaaggtca cttttggtgt     120
tatgatctg                                                            129

<210> SEQ ID NO 506
<211> LENGTH: 60
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 506

Xaa Gly Gly Gly Gly Gly Ala Gln Trp Tyr Pro Cys Tyr Glu Gly His
1               5                   10                  15

Phe Trp Cys Tyr Asp Leu Gly Ser Gly Ser Ala Thr Gly Gly Ser Gly
```

```
                20              25                  30
Ser Thr Ala Ser Ser Gly Ser Gly Ser Ala Thr Gly Trp Tyr Pro Cys
            35                  40                  45

Tyr Glu Gly His Phe Trp Cys Tyr Asp Leu Leu Glu
    50                  55                  60

<210> SEQ ID NO 507
<211> LENGTH: 129
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 507
tggtatccgt gttatgaggg tcacttctgg tgctacgatc tgggttctgg ttccactgct      60
tcttctggtt ccggttccgc tactggttgg tacccgtgct acgaaggtca cttttggtgt    120
tatgatctg                                                             129

<210> SEQ ID NO 508
<211> LENGTH: 62
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (62)..(62)
<223> OTHER INFORMATION: Xaa = Fc

<400> SEQUENCE: 508

Met Gly Ala Gln Ile Phe Gly Cys Lys Trp Trp Asp Val Gln Cys Tyr
1               5                   10                  15

Gln Phe Gly Ser Gly Ser Ala Thr Gly Gly Ser Gly Ser Thr Ala Ser
            20                  25                  30

Ser Gly Ser Gly Ser Ala Thr Gly Ile Phe Gly Cys Lys Trp Trp Asp
        35                  40                  45

Val Gln Cys Tyr Gln Phe Leu Glu Gly Gly Gly Gly Xaa
    50                  55                  60

<210> SEQ ID NO 509
<211> LENGTH: 129
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 509
atctttggct gtaaatggtg ggacgttcag tgctaccagt tcggttctgg ttccactgct      60
tcttctggtt ccggttccgc tactggtatc ttcggttgca gtggtgggat gtacagtgt     120 tatcagttt                                                             129

<210> SEQ ID NO 510
<211> LENGTH: 60
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc
```

```
<400> SEQUENCE: 510

Xaa Gly Gly Gly Gly Ala Gln Ile Phe Gly Cys Lys Trp Trp Asp
1               5                   10                  15

Val Gln Cys Tyr Gln Phe Gly Ser Gly Ser Ala Thr Gly Gly Ser Gly
            20                  25                  30

Ser Thr Ala Ser Ser Gly Ser Gly Ser Ala Thr Gly Ile Phe Gly Cys
        35                  40                  45

Lys Trp Trp Asp Val Gln Cys Tyr Gln Phe Leu Glu
    50                  55                  60

<210> SEQ ID NO 511
<211> LENGTH: 129
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 511
atctttggct gtaaatggtg ggacgttcag tgctaccagt tcggttctgg ttccactgct    60
tcttctggtt ccggttccgc tactggtatc ttcggttgca agtggtggga tgtacagtgt   120
tatcagttt                                                           129

<210> SEQ ID NO 512
<211> LENGTH: 62
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (62)..(62)
<223> OTHER INFORMATION: Xaa = Fc

<400> SEQUENCE: 512

Met Gly Ala Gln Ile Phe Gly Cys Lys Trp Trp Asp Val Asp Cys Tyr
1               5                   10                  15

Gln Phe Gly Ser Gly Ser Ala Thr Gly Gly Ser Gly Ser Thr Ala Ser
            20                  25                  30

Ser Gly Ser Gly Ser Ala Thr Gly Ile Phe Gly Cys Lys Trp Trp Asp
        35                  40                  45

Val Asp Cys Tyr Gln Phe Leu Glu Gly Gly Gly Gly Xaa
    50                  55                  60

<210> SEQ ID NO 513
<211> LENGTH: 129
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 513
atctttggct gtaagtggtg ggacgttgac tgctaccagt tcggttctgg ttccactgct    60
tcttctggtt ccggttccgc tactggtatc ttcggttgca aatggtggga cgttgattgt   120
tatcagttt                                                           129

<210> SEQ ID NO 514
<211> LENGTH: 60
<212> TYPE: PRT
```

```
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 514

Xaa Gly Gly Gly Gly Ala Gln Ile Phe Gly Cys Lys Trp Trp Asp
1               5                   10                  15

Val Asp Cys Tyr Gln Phe Gly Ser Gly Ser Ala Thr Gly Ser Gly
                20                  25                  30

Ser Thr Ala Ser Ser Gly Ser Gly Ser Ala Thr Gly Ile Phe Gly Cys
            35                  40                  45

Lys Trp Trp Asp Val Asp Cys Tyr Gln Phe Leu Glu
        50                  55                  60

<210> SEQ ID NO 515
<211> LENGTH: 129
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 515
atctttggct gtaagtggtg ggacgttgac tgctaccagt tcggttctgg ttccactgct     60
tcttctggtt ccggttccgc tactggtatc ttcggttgca aatggtggga cgttgattgt    120
tatcagttt                                                            129

<210> SEQ ID NO 516
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 516
caggttgaat ccctgcagca gctgctgatg tggctggacc agaaactggc ttccggtccg     60
cagggt                                                               66

<210> SEQ ID NO 517
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 517
cgtatggaac tgctggaatc cctgttcgaa ctgctgaaag aaatggttcc gcgttccaaa     60
gctgtt                                                               66

<210> SEQ ID NO 518
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 518
```

```
caggctgttt ccctgcagca cctgctgatg tggctggacc agaaactggc ttccggtccg    60
cagcac                                                               66
```

<210> SEQ ID NO 519
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 519

```
gacgaagact ccctgcagca gctgctgatg tggctggacc agaaactggc ttccggtccg    60
cagctg                                                               66
```

<210> SEQ ID NO 520
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 520

```
ccggttgctt ccctgcagca gctgctgatc tggctggacc agaaactggc tcagggtccg    60
cacgct                                                               66
```

<210> SEQ ID NO 521
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 521

```
gaagttgacg aactgcagca gctgctgaac tggctggacc acaaactggc ttccggtccg    60
ctgcag                                                               66
```

<210> SEQ ID NO 522
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 522

```
gacgttgaat ccctggaaca gctgctgatg tggctggacc accagctggc ttccggtccg    60
cacggt                                                               66
```

<210> SEQ ID NO 523
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 523

```
caggttgact ccctgcagca ggttctgctg tggctggaac acaaactggc tctgggtccg    60
caggtt                                                               66
```

<210> SEQ ID NO 524
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 524
ggtgacgaat ccctgcagca cctgctgatg tggctggaac agaaactggc tctgggtccg    60
cacggt                                                                66

<210> SEQ ID NO 525
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 525
cagatcgaaa tgctggaatc cctgctggac ctgctgcgtg acatggttcc gatgtccaac    60
gctttc                                                                66

<210> SEQ ID NO 526
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 526
gaagttgact ccctgcagca gctgctgatg tggctggacc agaaactggc ttccggtccg    60
caggct                                                                66

<210> SEQ ID NO 527
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 527
gaagacgaat ccctgcagca gctgctgatc tacctggaca aaatgctgtc ctccggtccg    60
caggtt                                                                66

<210> SEQ ID NO 528
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 528
gctatggacc agctgcacca gctgctgatc tggctggacc acaaactggc ttccggtccg    60
caggct                                                                66

<210> SEQ ID NO 529
<211> LENGTH: 66

<210> SEQ ID NO 529
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 529
cgtatcgaaa tgctggaatc cctgctggaa ctgctggacg aaatcgctct gatcccgaaa     60
gcttgg                                                                66

<210> SEQ ID NO 530
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 530
gaagttgttt ccctgcagca cctgctgatg tggctggaac acaaactggc ttccggtccg     60
gacggt                                                                66

<210> SEQ ID NO 531
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 531
ggtggtgaat ccctgcagca gctgctgatg tggctggacc agcagctggc ttccggtccg     60
cagcgt                                                                66

<210> SEQ ID NO 532
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 532
ggtgttgaat ccctgcagca gctgctgatc ttcctggacc acatgctggt ttccggtccg     60
cacgac                                                                66

<210> SEQ ID NO 533
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 533
aacgttgaat ccctggaaca cctgatgatg tggctggaac gtctgctggc ttccggtccg     60
tacgct                                                                66

<210> SEQ ID NO 534
<211> LENGTH: 66
<212> TYPE: DNA
<213> ORGANISM: Artificial Sequence
<220> FEATURE:
<223> OTHER INFORMATION: Nucleotide sequence encoding Myostatin Binding -continued

```
        Peptide

<400> SEQUENCE: 534
caggttgact ccctgcagca gctgctgatc tggctggacc accagctggc ttccggtccg      60
aaacgt                                                                 66

<210> SEQ ID NO 535
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 535
gaagttgaat ccctgcagca gctgctgatg tggctggaac acaaactggc tcagggtccg      60
cagggt                                                                 66

<210> SEQ ID NO 536
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 536
gaagttgact ccctgcagca gctgctgatg tggctggacc agaaactggc ttccggtccg      60
cacgct                                                                 66

<210> SEQ ID NO 537
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 537
gaagttgact ccctgcagca gctgctgatg tggctggacc agcagctggc ttccggtccg      60
cagaaa                                                                 66

<210> SEQ ID NO 538
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 538
ggtgttgaac agctgccgca gctgctgatg tggctggaac agaaactggc ttccggtccg      60
cagcgt                                                                 66

<210> SEQ ID NO 539
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 539
```

```
ggtgaagact ccctgcagca gctgctgatg tggctggacc agcagctggc tgctggtccg    60
caggtt                                                               66
```

<210> SEQ ID NO 540
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 540

```
gctgacgact ccctgcagca gctgctgatg tggctggacc gtaaactggc ttccggtccg    60
cacgtt                                                               66
```

<210> SEQ ID NO 541
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 541

```
ccggttgact ccctgcagca gctgctgatc tggctggacc agaaactggc ttccggtccg    60
cagggt                                                               66
```

<210> SEQ ID NO 542
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 542

```
cagtcccgtg ctaccctgct gaaagaattc tggcagctgg ttgaaggtct gggtgacaaa    60
caggct                                                               66
```

<210> SEQ ID NO 543
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 543

```
gaaatccgtg ctaccctgct gaaagaattc tggcagctgg ttgacgaatg gcgtgaacag    60
ccgaac                                                               66
```

<210> SEQ ID NO 544
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 544

```
cagctgcgtg ctaccctgct gaaagaattc ctgcagctgg ttcacggtct gggtgaaacc    60
gactcc                                                               66
```

```
<210> SEQ ID NO 545
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 545
acccagcgtg ctaccctgct gaaagaattc tggcagctga tcgaaggtct gggtggtaaa      60
cacgtt                                                                 66

<210> SEQ ID NO 546
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 546
cactaccgtg ctaccctgct gaaagaattc tggcagctgg ttgacggtct gcgtgaacag      60
ggtgtt                                                                 66

<210> SEQ ID NO 547
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 547
cagtcccgtg ttaccctgct gcgtgaattc tggcagctgg ttgaatccta ccgtccgatc      60
gttaac                                                                 66

<210> SEQ ID NO 548
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 548
ctgtcccgtg ctaccctgct gaacgaattc tggcagttcg ttgacggtca gcgtgacaaa      60
cgtatg                                                                 66

<210> SEQ ID NO 549
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 549
tgggaccgtg ctaccctgct gaacgacttc tggcacctga tggaagaact gtcccagaaa      60
ccgggt                                                                 66

<210> SEQ ID NO 550
<211> LENGTH: 66
<212> TYPE: DNA
```

<213> ORGANISM: Artificial Sequence
<220> FEATURE:
<223> OTHER INFORMATION: Nucleotide sequence encoding Myostatin Binding
      Peptide

<400> SEQUENCE: 550
caggaacgtg ctaccctgct gaaagaattc tggcgtatgg ttgaaggtct gggtaaaaac    60
cgtggt                                                              66

<210> SEQ ID NO 551
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 551
aacgaacgtg ctaccctgct gcgtgaattc tggcagctgg ttggtggtta cggtgttaac    60
cagcgt                                                              66

<210> SEQ ID NO 552
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 552
cagcgtgaat ggtacccgtg ctacggtggt cacctgtggt gctacgacct gcacaaagct    60

<210> SEQ ID NO 553
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 553
atctccgctt ggtactcctg ctacgctggt cacttctggt gctgggacct gaaacagaaa    60

<210> SEQ ID NO 554
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 554
tggaccggtt ggtaccagtg ctacggtggt cacctgtggt gctacgacct gcgtcgtaaa    60

<210> SEQ ID NO 555
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 555
aaaaccttct ggtacccgtg ctacgacggt cacttctggt gctacaacct gaaatcctcc    60

```
<210> SEQ ID NO 556
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 556
gaatcccgtt ggtacccgtg ctacgaaggt cacctgtggt gcttcgacct gaccgaaacc      60

<210> SEQ ID NO 557
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 557
aatgtttttt ttcaatgggt tcaaaaacat ggtcgtgttg tttatcaatg gcttgatatt      60
aatgtt                                                                 66

<210> SEQ ID NO 558
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 558
tttgattttc ttcaatggct tcaaaatcat cgttctgaag ttgaacattg gcttgttatg      60
gatgtt                                                                 66

<210> SEQ ID NO 559
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 559
catcaacgtg atatgtctat gctttgggaa cttcttgatg ttcttgatgg tcttcgtcaa      60
tattct                                                                 66

<210> SEQ ID NO 560
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 560
actcaacgtg atatgtctat gcttgatggt cttcttgaag ttcttgatca acttcgtcaa      60
caacgt                                                                 66

<210> SEQ ID NO 561
<211> LENGTH: 66
<212> TYPE: DNA
<213> ORGANISM: Artificial Sequence
<220> FEATURE:
<223> OTHER INFORMATION: Nucleotide sequence encoding Myostatin Binding
```

Peptide

<400> SEQUENCE: 561
acctcccgtg acatgtccct gctgtgggaa ctgctggaag aactggaccg tctgggtcac    60
cagcgt    66

<210> SEQ ID NO 562
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 562
atgcaacatg atatgtctat gctttatggt cttgttgaac ttcttgaatc tcttggtcat    60
caaatt    66

<210> SEQ ID NO 563
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 563
tggaatcgtg atatgcgtat gcttgaatct cttttttgaag ttcttgatgg tcttcgtcaa    60
caagtt    66

<210> SEQ ID NO 564
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 564
ggttatcgtg atatgtctat gcttgaaggt cttcttgctg ttcttgatcg tcttggtcca    60
caactt    66

<210> SEQ ID NO 565
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 565
actcaacgtg atatgtctat gcttgaaggt cttcttgaag ttcttgatcg tcttggtcaa    60
caacgt    66

<210> SEQ ID NO 566
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 566

```
tggtaccgtg acatgtccat gctggaaggt ctgctggaag ttctggaccg tctgggtcag    60
cagcgt                                                               66

<210> SEQ ID NO 567
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 567
actcaaaatt ctcgtcaaat gcttctttct gattttatga tgcttgttgg ttctatgatt    60
caaggt                                                               66

<210> SEQ ID NO 568
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 568
atgcaaactt ctcgtcatat tcttctttct gaatttatga tgcttgttgg ttctattatg    60
catggt                                                               66

<210> SEQ ID NO 569
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 569
cacgacaact cccgtcagat gctgctgtcc gacctgctgc acctggttgg taccatgatc    60
cagggt                                                               66

<210> SEQ ID NO 570
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 570
atggaaaact cccgtcagaa cctgctgcgt gaactgatca tgctggttgg taacatgtcc    60
caccag                                                               66

<210> SEQ ID NO 571
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 571
caggacacct cccgtcacat gctgctgcgt gaattcatga tgctggttgg tgaaatgatc    60
cagggt                                                               66
```

<210> SEQ ID NO 572
<211> LENGTH: 66
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 572
gaccagaact cccgtcagat gctgctgtcc gacctgatga tcctggttgg ttccatgatc    60
cagggt                                                              66

<210> SEQ ID NO 573
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 573
gttgctcttc atggtcaatg tactcgttgg ccatggatgt gtccaccaca acgtgaaggt    60

<210> SEQ ID NO 574
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 574
tatccagaac aaggtctttg tactcgttgg ccatggatgt gtccaccaca aactcttgct    60

<210> SEQ ID NO 575
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 575
ggtctgaacc agggtcactg cacccgttgg ccgtggatgt gcccgccgca ggactccaac    60

<210> SEQ ID NO 576
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 576
atgattactc aaggtcaatg tactcgttgg ccatggatgt gtccaccaca accatctggt    60

<210> SEQ ID NO 577
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 577
gctggtgctc aggaacactg cacccgttgg ccgtggatgt gcgctccgaa cgactggatc    60

<210> SEQ ID NO 578
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 578
ggtgttaacc agggtcagtg cacccgttgg cgttggatgt gcccgccgaa cggttgggaa     60

<210> SEQ ID NO 579
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 579
ctggctgacc acggtcagtg catccgttgg ccgtggatgt gcccgccgga aggttgggaa     60

<210> SEQ ID NO 580
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 580
atcctggaac aggctcagtg cacccgttgg ccgtggatgt gcccgccgca gcgtggtggt     60

<210> SEQ ID NO 581
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 581
actcaaactc atgctcaatg tactcgttgg ccatggatgt gtccaccaca atgggaaggt     60

<210> SEQ ID NO 582
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 582
gttgttactc aaggtcattg tactctttgg ccatggatgt gtccaccaca acgttggcgt     60

<210> SEQ ID NO 583
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 583
atttatccac atgatcaatg tactcgttgg ccatggatgt gtccaccaca accatatcca     60

```
<210> SEQ ID NO 584
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 584
tcttattggc aaggtcaatg tactcgttgg ccatggatgt gtccaccaca atggcgtggt      60

<210> SEQ ID NO 585
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 585
atgtggcaac aaggtcattg tactcgttgg ccatggatgt gtccaccaca aggttggggt      60

<210> SEQ ID NO 586
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 586
gaattcaccc agtggcactg cacccgttgg ccgtggatgt gcccgccgca gcgttcccag      60

<210> SEQ ID NO 587
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 587
ctggacgacc agtggcagtg cacccgttgg ccgtggatgt gcccgccgca gggtttctcc      60

<210> SEQ ID NO 588
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 588
tatcaaactc aaggtctttg tactcgttgg ccatggatgt gtccaccaca atctcaacgt      60

<210> SEQ ID NO 589
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 589
gaatctaatc aaggtcaatg tactcgttgg ccatggatgt gtccaccaca aggtggttgg      60
```

<210> SEQ ID NO 590
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 590
tggaccgacc gtggtccgtg cacccgttgg ccgtggatgt gcccgccgca ggctaacggt    60

<210> SEQ ID NO 591
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 591
gttggtaccc agggtcagtg cacccgttgg ccgtggatgt gcccgccgta cgaaaccggt    60

<210> SEQ ID NO 592
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 592
ccgtacgaac agggtaaatg cacccgttgg ccgtggatgt gcccgccgta cgaagttgaa    60

<210> SEQ ID NO 593
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 593
tccgaatacc agggtctgtg cacccgttgg ccgtggatgt gcccgccgca gggttggaaa    60

<210> SEQ ID NO 594
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 594
accttctccc agggtcactg cacccgttgg ccgtggatgt gcccgccgca gggttggggt    60

<210> SEQ ID NO 595
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 595
ccgggtgctc acgaccactg cacccgttgg ccgtggatgt gcccgccgca gtcccgttac    60

<210> SEQ ID NO 596

```
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 596
gttgctgaag aatggcactg ccgtcgttgg ccgtggatgt gcccgccgca ggactggcgt    60

<210> SEQ ID NO 597
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 597
gttggtaccc agggtcactg cacccgttgg ccgtggatgt gcccgccgca gccggctggt    60

<210> SEQ ID NO 598
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 598
gaagaagacc aggctcactg ccgttcctgg ccgtggatgt gcccgccgca gggttgggtt    60

<210> SEQ ID NO 599
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 599
gctgacaccc agggtcactg cacccgttgg ccgtggatgt gcccgccgca gcactggttc    60

<210> SEQ ID NO 600
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 600
tccggtccgc agggtcactg cacccgttgg ccgtggatgt gcgctccgca gggttggttc    60

<210> SEQ ID NO 601
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 601
accctggttc agggtcactg cacccgttgg ccgtggatgt gcccgccgca gcgttgggtt    60

<210> SEQ ID NO 602
<211> LENGTH: 60
```

```
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 602
ggtatggctc acggtaaatg cacccgttgg gcttggatgt gcccgccgca gtcctggaaa    60

<210> SEQ ID NO 603
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 603
gaactgtacc acggtcagtg cacccgttgg ccgtggatgt gcccgccgca gtcctgggct    60

<210> SEQ ID NO 604
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 604
gttgctgacc acggtcactg cacccgttgg ccgtggatgt gcccgccgca gggttggggt    60

<210> SEQ ID NO 605
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 605
ccggaatccc agggtcactg cacccgttgg ccgtggatgt gcccgccgca gggttggggt    60

<210> SEQ ID NO 606
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 606
atcccggctc acggtcactg cacccgttgg ccgtggatgt gcccgccgca gcgttggcgt    60

<210> SEQ ID NO 607
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 607
ttcaccgttc acggtcactg cacccgttgg ccgtggatgt gcccgccgta cggttgggtt    60

<210> SEQ ID NO 608
<211> LENGTH: 60
<212> TYPE: DNA
```

```
<213> ORGANISM: Artificial Sequence
<220> FEATURE:
<223> OTHER INFORMATION: Nucleotide sequence encoding Myostatin Binding
      Peptide

<400> SEQUENCE: 608
ccagattttc caggtcattg tactcgttgg cgttggatgt gtccaccaca aggttgggaa      60

<210> SEQ ID NO 609
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 609
cagctgtggc agggtccgtg cacccagtgg ccgtggatgt gcccgccgaa aggtcgttac      60

<210> SEQ ID NO 610
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 610
cacgctaacg acggtcactg cacccgttgg cagtggatgt gcccgccgca gtggggtggt      60

<210> SEQ ID NO 611
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 611
gaaaccgacc acggtctgtg cacccgttgg ccgtggatgt gcccgccgta cggtgctcgt      60

<210> SEQ ID NO 612
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 612
ggtacctggc agggtctgtg cacccgttgg ccgtggatgt gcccgccgca gggttggcag      60

<210> SEQ ID NO 613
<211> LENGTH: 60
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 613
gttgctaccc agggtcagtg cacccgttgg ccgtggatgt gcccgccgca gggttggggt      60

<210> SEQ ID NO 614
<211> LENGTH: 60
<212> TYPE: DNA
<213> ORGANISM: Artificial Sequence
```

<220> FEATURE:
<223> OTHER INFORMATION: Nucleotide sequence encoding Myostatin Binding
      Peptide

<400> SEQUENCE: 614
gttgctaccc agggtcagtg cacccgttgg ccgtggatgt gcccgccgca gcgttggggt    60

<210> SEQ ID NO 615
<211> LENGTH: 74
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 615

Xaa Gly Gly Gly Gly Gly Ala Gln Leu Ala Asp His Gly Gln Cys Ile
1               5                   10                  15

Arg Trp Pro Trp Met Cys Pro Pro Glu Gly Trp Glu Leu Glu Gly Ser
            20                  25                  30

Gly Ser Ala Thr Gly Gly Ser Gly Ser Thr Ala Ser Ser Gly Ser Gly
        35                  40                  45

Ser Ala Thr Gly Leu Ala Asp His Gly Gln Cys Ile Arg Trp Pro Trp
    50                  55                  60

Met Cys Pro Pro Glu Gly Trp Glu Leu Glu
65                  70

<210> SEQ ID NO 616
<211> LENGTH: 198
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 616
cttgctgatc atggtcaatg tattcgttgg ccatggatgt gtccaccaga aggttgggaa    60
ctcgagggtt ccggttccgc taccggcggc tctggctcca ctgcttcttc cggttccggt   120
tctgctactg gtctggctga ccacggtcag tgcatccgtt ggccgtggat gtgcccgccg   180
gaaggttggg aactggaa                                                198

<210> SEQ ID NO 617
<211> LENGTH: 70
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 617

Xaa Gly Gly Gly Gly Gly Ala Gln Leu Ala Asp His Gly Gln Cys Ile
1               5                   10                  15

Arg Trp Pro Trp Met Cys Pro Pro Glu Gly Trp Glu Gly Ser Gly Ser
            20                  25                  30

Ala Thr Gly Gly Ser Gly Gly Ala Ser Ser Gly Ser Gly Ser Ala
        35                  40                  45

Thr Gly Leu Ala Asp His Gly Gln Cys Ile Arg Trp Pro Trp Met Cys
            50                  55                  60

Pro Pro Glu Gly Trp Glu
65                  70

<210> SEQ ID NO 618
<211> LENGTH: 186
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 618
cttgctgatc atggtcaatg tattcgttgg ccatggatgt gtccaccaga aggttgggaa      60
ggttccggtt ccgctaccgg cggctctggc ggtggcgctt cttccggttc cggttctgct     120
actggtctgg ctgaccacgg tcagtgcatc cgttggccgt ggatgtgtcc accagaaggt     180
tgggaa                                                                186

<210> SEQ ID NO 619
<211> LENGTH: 74
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 619

Xaa Gly Gly Gly Gly Ala Gln Ser Glu Tyr Gln Gly Leu Cys Thr
1               5                   10                  15

Arg Trp Pro Trp Met Cys Pro Pro Gln Gly Trp Lys Leu Glu Gly Ser
                20                  25                  30

Gly Ser Ala Thr Gly Gly Ser Gly Ser Thr Ala Ser Ser Gly Ser Gly
            35                  40                  45

Ser Ala Thr Gly Ser Glu Tyr Gln Gly Leu Cys Thr Arg Trp Pro Trp
        50                  55                  60

Met Cys Pro Pro Gln Gly Trp Lys Leu Glu
65                  70

<210> SEQ ID NO 620
<211> LENGTH: 198
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 620
tctgaatatc aaggtctttg tactcgttgg ccatggatgt gtccaccaca aggttggaaa      60
ctcgagggtt ccggttccgc taccggcggc tctggctcca ctgcttcttc cggttccggt     120
tctgctactg gttctgagta tcaaggcctc tgtactcgct ggccatggat gtgtccacca     180
caaggctgga agctggaa                                                   198

<210> SEQ ID NO 621
<211> LENGTH: 70
<212> TYPE: PRT
<213> ORGANISM: Artificial Sequence
<220> FEATURE:

<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 621

Xaa Gly Gly Gly Gly Gly Ala Gln Ser Glu Tyr Gln Gly Leu Cys Thr
1               5                   10                  15

Arg Trp Pro Trp Met Cys Pro Pro Gln Gly Trp Lys Gly Ser Gly Ser
            20                  25                  30

Ala Thr Gly Gly Ser Gly Gly Ala Ser Ser Gly Gly Ser Ala
        35                  40                  45

Thr Gly Ser Glu Tyr Gln Gly Leu Cys Thr Arg Trp Pro Trp Met Cys
    50                  55                  60

Pro Pro Gln Gly Trp Lys
65                  70

<210> SEQ ID NO 622
<211> LENGTH: 186
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 622
tctgaatatc aaggtctttg tactcgttgg ccatggatgt gtccaccaca aggttggaaa      60
ggttccggtt ccgctaccgg cggctctggc ggtggcgctt cttccggttc cggttctgct     120
actggttctg agtatcaagg cctctgtact cgctggccat ggatgtgtcc accacaaggt     180
tggaaa                                                                186

<210> SEQ ID NO 623
<211> LENGTH: 74
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 623

Xaa Gly Gly Gly Gly Gly Ala Gln Thr Phe Ser Gln Gly His Cys Thr
1               5                   10                  15

Arg Trp Pro Trp Met Cys Pro Pro Gln Gly Trp Gly Leu Glu Gly Ser
            20                  25                  30

Gly Ser Ala Thr Gly Gly Ser Gly Ser Thr Ala Ser Ser Gly Ser Gly
        35                  40                  45

Ser Ala Thr Gly Thr Phe Ser Gln Gly His Cys Thr Arg Trp Pro Trp
    50                  55                  60

Met Cys Pro Pro Gln Gly Trp Gly Leu Glu
65                  70

<210> SEQ ID NO 624
<211> LENGTH: 198
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 624 acttttctc aaggtcattg tactcgttgg ccatggatgt gtccaccaca aggttggggt    60
ctcgagggtt ccggttccgc taccggcggc tctggctcca ctgcttcttc cggttccggt   120
tctgctactg gtactttttc tcaaggccat tgtactcgct ggccatggat gtgtccacca   180
caaggctggg gcctggaa                                                 198

<210> SEQ ID NO 625
<211> LENGTH: 74
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 625

Xaa Gly Gly Gly Gly Gly Ala Gln Val Ala Asp His Gly His Cys Thr
1               5                   10                  15

Arg Trp Pro Trp Met Cys Pro Pro Gln Gly Trp Gly Leu Glu Ser
            20                  25                  30

Gly Ser Ala Thr Gly Gly Ser Gly Ser Thr Ala Ser Ser Gly Ser Gly
        35                  40                  45

Ser Ala Thr Gly Val Ala Asp His Gly His Cys Thr Arg Trp Pro Trp
    50                  55                  60

Met Cys Pro Pro Gln Gly Trp Gly Leu Glu
65                  70

<210> SEQ ID NO 626
<211> LENGTH: 198
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 626
gttgctgatc atggtcattg tactcgttgg ccatggatgt gtccaccaca aggttggggt    60
ctcgagggtt ccggttccgc aaccggcggc tctggctcca ctgcttcttc cggttccggt   120
tctgctactg gtgttgctga ccacggtcac tgcacccgtt ggccgtggat gtgcccgccg   180
cagggttggg gtctggaa                                                 198

<210> SEQ ID NO 627
<211> LENGTH: 70
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 627

Xaa Gly Gly Gly Gly Gly Ala Gln Val Ala Asp His Gly His Cys Thr
1               5                   10                  15

Arg Trp Pro Trp Met Cys Pro Pro Gln Gly Trp Gly Gly Ser Gly Ser
            20                  25                  30

```
Ala Thr Gly Gly Ser Gly Gly Ala Ser Ser Gly Ser Gly Ser Ala
         35                  40                  45

Thr Gly Val Ala Asp His Gly His Cys Thr Arg Trp Pro Trp Val Cys
     50                  55                  60

Pro Pro Gln Gly Trp Gly
65                  70

<210> SEQ ID NO 628
<211> LENGTH: 186
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 628
gttgctgatc atggtcattg tactcgttgg ccatggatgt gtccaccaca aggttggggt      60
ggttccggtt ccgctaccgg cggctctggc ggtggtgctt cttccggttc cggttctgct     120
actggtgttg ctgaccacgg tcactgcacc cgttggccgt gggtgtgtcc accacaaggt     180
tggggt                                                                186

<210> SEQ ID NO 629
<211> LENGTH: 74
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa = Fc

<400> SEQUENCE: 629

Xaa Gly Gly Gly Gly Ala Gln Pro Glu Ser Gln Gly His Cys Thr
1               5                  10                  15

Arg Trp Pro Trp Met Cys Pro Pro Gln Gly Trp Gly Leu Glu Ser
                 20                  25                  30

Gly Ser Ala Thr Gly Gly Ser Gly Ser Thr Ala Ser Ser Gly Ser Gly
             35                  40                  45

Ser Ala Thr Gly Pro Glu Ser Gln Gly His Cys Thr Arg Trp Pro Trp
         50                  55                  60

Met Cys Pro Pro Gln Gly Trp Gly Leu Glu
65                  70

<210> SEQ ID NO 630
<211> LENGTH: 198
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 630
ccagaatctc aaggtcattg tactcgttgg ccatggatgt gtccaccaca aggttggggt      60
ctcgagggtt ccggttccgc taccggcggc tctggctcca ctgcttcttc cggttccggt     120
tctgctactg gtccggaatc ccagggtcac tgcacccgtt ggccgtggat gtgcccgccg     180
cagggttggg gtctggaa                                                   198

<210> SEQ ID NO 631
<211> LENGTH: 70
```

```
<212> TYPE: PRT
<213> ORGANISM: Artificial Sequence
<220> FEATURE:
<223> OTHER INFORMATION: Peptibody
<220> FEATURE:
<221> NAME/KEY: MISC_FEATURE
<222> LOCATION: (1)..(1)
<223> OTHER INFORMATION: Xaa= Fc

<400> SEQUENCE: 631

Xaa Gly Gly Gly Gly Ala Gln Pro Glu Ser Gln Gly His Cys Thr
1               5                   10                  15

Arg Trp Pro Trp Met Cys Pro Pro Gln Gly Trp Gly Ser Gly Ser
            20                  25                  30

Ala Thr Gly Gly Ser Gly Gly Gly Ala Ser Ser Gly Ser Gly Ser Ala
        35                  40                  45

Thr Gly Pro Glu Ser Gln Gly His Cys Thr Arg Trp Pro Trp Met Cys
    50                  55                  60

Pro Pro Gln Gly Trp Gly
65                  70

<210> SEQ ID NO 632
<211> LENGTH: 186
<212> TYPE: DNA
<213> ORGANISM: Artificial Sequence
<220> FEATURE:
<223> OTHER INFORMATION: Nucleotide sequence encoding Myostatin Binding
      Peptide

<400> SEQUENCE: 632
ccagaatctc aaggtcattg tactcgttgg ccatggatgt gtccaccaca aggttggggt    60
ggttccggtt ccgctaccgg cggctctggc ggtggtgctt cttccggttc cggttctgct   120
actggtccgg aatcccaggg tcactgcacc cgttggccgt ggatgtgtcc accacaaggt   180
tggggt                                                              186

<210> SEQ ID NO 633
<211> LENGTH: 5
<212> TYPE: PRT
<213> ORGANISM: Artificial Sequence
<220> FEATURE:
<223> OTHER INFORMATION: Myostatin Binding Peptide

<400> SEQUENCE: 633

Trp Met Cys Pro Pro
1               5

<210> SEQ

```
<222> LOCATION: (21)..(21)
<223> OTHER INFORMATION: K = G and T are equally represented
<220> FEATURE:
<221> NAME/KEY: misc_feature
<222> LOCATION: (22)..(23)
<223> OTHER INFORMATION: N =  A, T, C, or G are equally represented
<220> FEATURE:
<221> NAME/KEY: misc_feature
<222> LOCATION: (27)..(27)
<223> OTHER INFORMATION: K = G and T are equally represented
<220> FEATURE:
<221> NAME/KEY: misc_feature
<222> LOCATION: (30)..(30)
<223> OTHER INFORMATION: K = G and T are equally represented
<220> FEATURE:
<221> NAME/KEY: misc_feature
<222> LOCATION: (33)..(33)
<223> OTHER INFORMATION: K = G and T are equally represented
<220> FEATURE:
<221> NAME/KEY: misc_feature
<222> LOCATION: (36)..(36)
<223> OTHER INFORMATION: K = G and T are equally represented
<220> FEATURE:
<221> NAME/KEY: misc_feature
<222> LOCATION: (39)..(39)
<223> OTHER INFORMATION: K = G and T are equally represented
<220> FEATURE:
<221> NAME/KEY: misc_feature
<222> LOCATION: (42)..(42)
<223> OTHER INFORMATION: K = G and T are equally represented
<220> FEATURE:
<221> NAME/KEY: misc_feature
<222> LOCATION: (45)..(45)
<223> OTHER INFORMATION: K = G and T are equally represented
<220> FEATURE:
<221> NAME/KEY: misc_feature
<222> LOCATION: (48)..(48)
<223> OTHER INFORMATION: K = G and T are equally represented
<220> FEATURE:
<221> NAME/KEY: misc_feature
<222> LOCATION: (51)..(51)
<223> OTHER INFORMATION: K = G and T are equally represented
<220> FEATURE:
<221> NAME/KEY: misc_feature
<222> LOCATION: (54)..(54)
<223> OTHER INFORMATION: K = G and T are equally represented
<220> FEATURE:
<221> NAME/KEY: misc_feature
<222> LOCATION: (57)..(57)
<223> OTHER INFORMATION: K = G and T are equally represented
<220> FEATURE:
<221> NAME/KEY: misc_feature
<222> LOCATION: (60)..(60)
<223> OTHER INFORMATION: K = G and T are equally represented
<220> FEATURE:
<221> NAME/KEY: misc_feature
<222> LOCATION: (63)..(63)
<223> OTHER INFORMATION: K = G and T are equally represented
<220> FEATURE:
<221> NAME/KEY: misc_feature
<222> LOCATION: (66)..(66)
<223> OTHER INFORMATION: K = G and T are equally represented
<220> FEATURE:
<221> NAME/KEY: misc_feature
<222> LOCATION: (67)..(68)
<223> OTHER INFORMATION: N =  A, T, C, or G are equally represented
<220> FEATURE:
<221> NAME/KEY: misc_feature
<222> LOCATION: (69)..(69)
<223> OTHER INFORMATION: K = G and T are equally represented
<220> FEATURE:
<221> NAME/KEY: misc_feature
<222> LOCATION: (70)..(71)
<223> OTHER INFORMATION: N =  A, T, C, or G are equally represented
<220> FEATURE:
<221> NAME/KEY: misc_feature
<222> LOCATION: (72)..(72)
<223> OTHER INFORMATION: K = G and T are equally represented
<220> FEATURE:
```

```
-continued
<221> NAME/KEY: misc_feature
<222> LOCATION: (73)..(74)
<223> OTHER INFORMATION: N = A, T, C, or G are equally represented
<220> FEATURE:
<221> NAME/KEY: misc_feature
<222> LOCATION: (75)..(75)
<223> OTHER INFORMATION: K = G and T are equally represented

<400> SEQUENCE: 634
cacagtgcac agggtnnknn knnkcakggk caktgkackc gktgkccktg katktgkcck    60
ccktaknnkn nknnkcattc tctcgagatc                                    90
```

US 7,511,012 B2

MYOSTATIN BINDING AGENTS

This application hereby claims benefit of U.S. provisional application Ser. No. 60/435,923, filed Dec. 20, 2002, the entire disclosure of which is relied upon and incorporated by reference.

FIELD OF THE INVENTION

The invention relates to growth factors and in particular to the growth factor myostatin and agents which bind myostatin and inhibit its activity.

BACKGROUND

Myostatin, also known as growth/differentiation factor 8 (GDF-8), is a transforming growth factor-β (TGF-β) family member known to be involved in regulation of skeletal muscle mass. Most members of the TGF-β-GDF family are expressed non-specifically in many tissue types and exert a variety of pleitrophic actions. However, myostatin is largely expressed in the cells of developing and adult skeletal muscle tissue and plays an essential role in negatively controlling skeletal muscle growth (McPherron et al. *Nature* (London) 387, 83-90 (1997)). Recent studies, however, indicate that low levels of myostatin expression can be measured in cardiac, adipose and pre-adipose tissues.

The myostatin protein has been highly conserved evolutionarily (McPherron et al. *PNAS USA* 94:12457-12461 (1997)). The biologically active C-terminal region of myostatin has 100 percent sequence identity between human, mouse, rat, cow, chicken, and turkey sequences. The function of myostatin also appears to be conserved across species as well. This is evident from the phenotypes of animals having a mutation in the myostatin gene. Two breeds of cattle, the Belgian Blue (Hanset R., *Muscle Hypertrophy of Genetic Origin and its Use to Improve Beef Production*, eds, King, J. W. G. & Menissier, F. (Nijhoff, The Hague, The Netherlands) pp. 437-449) and the Piedmontese (Masoero, G. & Poujardieu, B, *Muscle Hypertrophy of Genetic Origin and its Use to Improve Beef Production.*, eds, King, J. W. G. & Menissier, F. (Nijhoff, The Hague, The Netherlands) pp. 450-459) are characterized by a "double muscling" phenotype and increase in muscle mass. These breeds were shown to contain mutations in the coding region of the myostatin gene (McPherron et al.(1997) supra). In addition, mice containing a targeted deletion of the gene encoding myostatin (Mstn) demonstrate a dramatic increase in muscle mass without a corresponding increase in fat. Individual muscles of Mstn $^{-/-}$ mice weigh approximately 100 to 200 percent more than those of control animals as a result of muscle fiber hypertrophy and hyperplasia (Zimmers et al. *Science* 296, 1486 (2002)).

Administration of myostatin to certain strains of mice has been shown to create a condition similar to muscle wasting disorders found associated with cancer, AIDS, and muscular dystrophy, for example. Myostatin administered as myostatin-producing CHO cells to athymic nude mice resulted in a wasting effect with a high degree of weight loss, a decrease of as much as 50% of skeletal muscle mass in addition to fat wasting, and severe hypoglycemia (Zimmers et al. supra).

Loss of myostatin appears to result in the retention of muscle mass and reduction in fat accumulation with aging. It has been shown that age-related increases in adipose tissue mass and decrease in muscle mass were proportional to myostatin levels, as determined by a comparison of fat and muscle mass in Mstn $^{+/+}$ when compared with Mstn $^{-/-}$ adult knockout mice (McFerron et al. *J. Clin. Invest* 109, 595 (2002)). Mstn $^{-/-}$ mice showed decreased fat accumulation with age compared with Mstn $^{+/+}$ mice.

In addition myostatin may play a role in maintaining blood glucose levels and may influence the development of diabetes in certain cases. It is known that, for example, skeletal muscle resistance to insulin-stimulated glucose uptake is the earliest known manifestation of non-insulin-dependent (type 2) diabetes mellitus (Corregan et al. *Endocrinology* 128:1682 (1991)). It has now been shown that the lack of myostatin partially attenuates the obese and diabetes phenotypes of two mouse models, the agouti lethal yellow ($A^y$) (Yen et al. *FASEB J.* 8:479 (1994)), and obese ($Lep^{ob/ob}$). Fat accumulation and total body weight of the $A^{y/a}$, Mstn $^{-/-}$ double mutant mouse was dramatically reduced compared with the $A^{y/a}$ Mstn $^{+/+}$ mouse (McFerron et al., (2002) supra). In addition, blood glucose levels in the $A^{y/a}$, Mstn $^{-/-}$ mice was dramatically lower than in $A^{y/a}$ Mstn $^{+/+}$ mice following exogenous glucose load, indicating that the lack of myostatin improved glucose metabolism. Similarly $Lep^{ob/ob}$ Mstn $^{-/-}$ mice showed decreased fat accumulation when compared with the $Lep^{ob/ob}$ Mstn $^{+/+}$ phenotype.

Therefore, there is considerable evidence from the phenotypes of over-expressing and knockout animals that myostatin may play a role in contributing to a number of metabolic disorders including disorders resulting in muscle wasting, diabetes, obesity and hyperglycemia.

SUMMARY OF THE INVENTION

The present invention is directed to binding agents which bind myostatin and inhibit its activity. The binding agents comprise at least one peptide capable of binding myostatin. The myostatin-binding peptides are preferably between about 5 and about 50 amino acids in length, more preferably between about 10 and 30 amino acids in length, and most preferably between about 10 and 25 amino acids in length. In one embodiment the myostatin-binding peptide comprises the amino acid sequence WMCPP (SEQ ID NO: 633). In another embodiment the myostatin binding peptides comprise the amino acid sequence $\underline{C}a_1a_2\underline{Wa_3WMCPP}$ (SEQ ID NO: 352), wherein $a_1$, $a_2$ and $a_3$ are selected from a neutral hydrophobic, neutral polar, or basic amino acid. In another embodiment the myostatin binding peptide comprises the sequence $\underline{C}b_1b_2\underline{Wb_3WMCPP}$ (SEQ ID NO: 353), wherein $b_1$ is selected from any one of the amino acids T, I, or R; $b_2$ is selected from any one of R, S, Q; $b_3$ is selected from any one of P, R and Q, and wherein the peptide is between 10 and 50 amino acids in length, and physiologically acceptable salts thereof. In another embodiment, the myostatin binding peptide comprises the formula:

$$c_1c_2c_3c_4c_5c_6\underline{C}c_7c_8\underline{W}c_9\underline{WMCPP}c_{10}c_{11}c_{12}c_{13} \quad \text{(SEQ ID NO: 354)},$$

wherein:

$c_1$ is absent or any amino acid;

$c_2$ is absent or a neutral hydrophobic, neutral polar, or acidic amino acid;

$c_3$ is absent or a neutral hydrophobic, neutral polar, or acidic amino acid;

$c_4$ is absent or any amino acid;

$c_5$ is absent or a neutral hydrophobic, neutral polar, or acidic amino acid;

$c_6$ is absent or a neutral hydrophobic, neutral polar, or basic amino acid;

$c_7$ is a neutral hydrophobic, neutral polar, or basic amino acid;

$c_8$ is a neutral hydrophobic, neutral polar, or basic amino acid;

$c_9$ is a neutral hydrophobic, neutral polar or basic amino acid; and $c_{10}$ to $c_{13}$ is any amino acid; and wherein the peptide is between 20 and 50 amino acids in length, and physiologically acceptable salts thereof.

A related embodiment the myostatin binding peptide comprises the formula:

$$d_1d_2d_3d_4d_5d_6\underline{C}d_7d_8\underline{Wd_9WMCPP}\ d_{10}d_{11}d_{12}d_{13} \quad \text{(SEQ ID NO: 355)},$$

wherein:

$d_1$ is absent or any amino acid;

$d_2$ is absent or a neutral hydrophobic, neutral polar, or acidic amino acid;

$d_3$ is absent or a neutral hydrophobic, neutral polar, or acidic amino acid;

$d_4$ is absent or any amino acid;

$d_5$ is absent or a neutral hydrophobic, neutral polar, or acidic amino acid;

$d_6$ is absent or a neutral hydrophobic, neutral polar, or basic amino acid;

$d_7$ is selected from any one of the amino acids T, I, or R;

$d_8$ is selected from any one of R, S, Q;

$d_9$ is selected from any one of P, R and Q, and $d_{10}$ to $d_{13}$ is selected from any amino acid, and wherein the peptide is between 20 and 50 amino acids in length, and physiologically acceptable salts thereof.

Additional embodiments of binding agents comprise at least one of the following peptides:

(1) a peptide capable of binding myostatin, wherein the peptide comprises the sequence $\underline{WY}e_1e_2\underline{Y}e_3\underline{G}$, (SEQ ID NO: 356), wherein $e_1$ is P, S or Y, $e_2$ is C or Q, and $e_3$ is G or H, wherein the peptide is between 7 and 50 amino acids in length, and physiologically acceptable salts thereof;

(2) a peptide capable of binding myostatin, wherein the peptide comprises the sequence $f_1\underline{EML}f_2\underline{SL}f_3f_4\underline{LL}$, (SEQ ID NO: 455), wherein $f_1$ is M or I, $f_2$ is any amino acid, $f_3$ is L or F, $f_4$ is E, Q or D;

and wherein the peptide is between 7 and 50 amino acids in length, and physiologically acceptable salts thereof;

(3) a peptide capable of binding myostatin wherein the peptide comprises the sequence $\underline{L}g_1g_2\underline{LL}g_3g_4\underline{L}$, (SEQ ID NO: 456), wherein $g_1$ is Q, D or E, $g_2$ is S, Q, D or E, $g_3$ is any amino acid, $g_4$ is L, W, F, or Y, and wherein the peptide is between 8 and 50 amino acids in length, and physiologically acceptable salts thereof;

(4) a peptide capable of binding myostatin, wherein the peptide comprises the sequence $h_1h_2h_3h_4h_5h_6h_7h_8h_9$ (SEQ ID NO: 457), wherein $h_1$ is R or D, $h_2$ is any amino acid, $h_3$ is A, T S or Q, $h_4$ is L or M, $h_5$ is L or S, $h_6$ is any amino acid, $h_7$ is F or E, $h_8$ is W, F or C, $h_9$ is L, F, M or K, and wherein the peptide is between 9 and 50 amino acids in length, and physiologically acceptable salts thereof.

In one embodiment, the binding agents of the present invention further comprise at least one vehicle such as a polymer or an Fc domain, and may further comprise at least one linker sequence. In this embodiment, the binding agents of the present invention are constructed so that at least one myostatin-binding peptide is attached to at least one vehicle. The peptide or peptides are attached directly or indirectly through a linker sequence, to the vehicle at the N-terminal, C-terminal or an amino acid sidechain of the peptide. In this embodiment, the binding agents of the present invention have the following generalized structure:

$$(X^1)_a\text{-}F^1\text{-}(X^2)_b, \text{ or multimers thereof};$$

wherein $F^1$ is a vehicle; and $X^1$ and $X^2$ are each independently selected from $-(L^1)_c\text{-}P^1$;

$-(L^1)_c\text{-}P^1\text{-}(L^2)_d\text{-}P^2$;

$-(L^1)_c\text{-}P^1\text{-}(L^2)_d\text{-}P^2\text{-}(L^3)_e\text{-}P^3$;

and $-(L^1)_c\text{-}P^1\text{-}(L^2)_d\text{-}P^2\text{-}(L^3)_e\text{-}P^3\text{-}(L^4)_f\text{-}P^4$;

wherein $P^1$, $P^2$, $P^3$, and $P^4$ are peptides capable of binding myostatin; and $L^1$, $L^2$, $L^3$, and $L^4$ are each linkers; and a, b, c, d, e, and f are each independently 0 or 1, provided that at least one of a and b is 1, and physiologically acceptable salts thereof.

In various embodiments of binding agents having this generalized structure, the peptides $P^1$, $P^2$, $P^3$, and $P^4$ can be independently selected from one or more of any of the peptides comprising the sequences provided above. $P^1$, $P^2$, $P^3$, and $P^4$ are independently selected from one or more peptides comprising any of the following sequences: SEQ ID NO: 633, SEQ ID NO: 352, SEQ ID NO: 353, SEQ ID NO: 354, SEQ ID NO: 355, SEQ ID NO: 356, SEQ ID NO: 455, SEQ ID NO: 456, or SEQ ID NO: 457.

In a further embodiment, the binding agents comprise peptides fused to an Fc domain, either directly or indirectly, thereby providing peptibodies. The peptibodies of the present invention display a high binding affinity for myostatin and can inhibit the activity of myostatin as demonstrated both in vitro using cell based assays and in animals.

The present invention also provides nucleic acid molecules comprising polynucleotides encoding the peptides, peptibodies, and peptide and peptibody variants and derivatives of the present invention.

The present invention provides pharmaceutically acceptable compositions comprising one or more binding agents of the present invention.

The binding agents of the present invention inhibit myostatin activity in vitro and in vivo. The binding agents of the present invention increase lean muscle mass in a treated animal and decreases fat mass as a percentage of body weight of the animal. The myostatin binding agents of the present invention increase muscular strength in treated animal models.

The present invention provides methods of inhibiting myostatin activity in animals including humans by administering an effective dosage of one or more binding agents to the subject. The present invention provides methods of increasing lean muscle mass in animals including humans by administering an effective dosage of one or more binding agents. The present invention further provides methods of treating myostatin-related disorders by administering an therapeutically effective dosage of one or more myostatin binding agents in a pharmaceutically acceptable composition to a subject. The present invention provides methods of treating muscle wasting disorders including muscular dystrophy, muscle wasting due to cancer, AIDS, rheumatoid arthritis, renal failure, uremia, chronic heart failure, age-related sarcopenia, prolonged bed-rest, spinal chord injury, stroke, bone fracture. The present invention also provides methods of treating metabolic disorders including obesity, diabetes, hyperglycemia, and bone loss.

The present invention also provides a method of increasing muscle mass in food animals by administering an effective dosage of one or more myostatin binding agents to the animal.

The present invention provides assays utilizing one or more myostatin binding agents to identify and quantitate myostatin in a sample. The assays may be diagnostic assays for measuring or monitoring myostatin levels in individuals with a myostatin related disorder or disease.

DETAILED DESCRIPTION OF THE INVENTION

Figure 1:
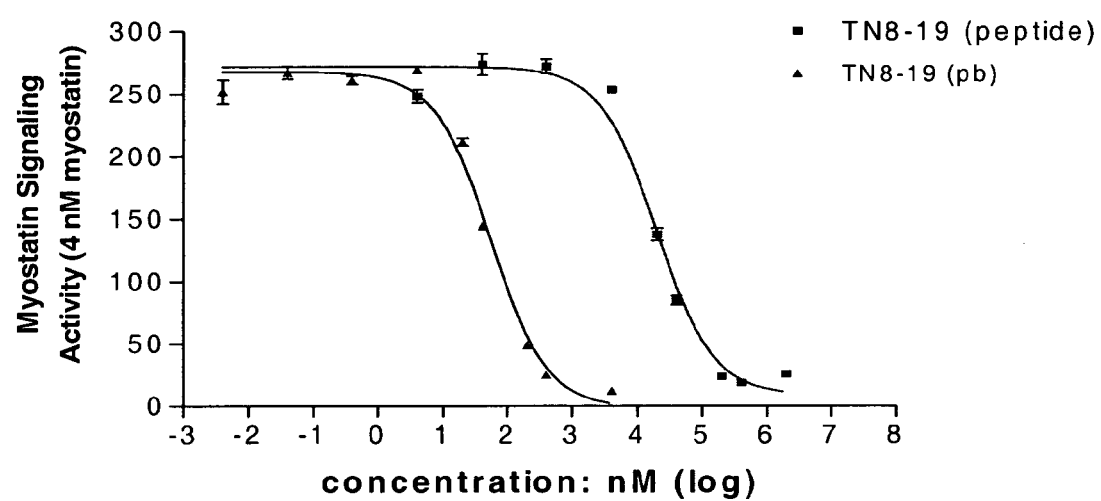
FIG. 1 shows myostatin activity as measured by expressed luciferase activity (y-axis) vs. concentration (x-axis) for the TN8-19 peptide QGHCTRWPWMCPPY (SEQ ID No: 32) and the TN8-19 peptibody (pb) to determine the $IC_{50}$ for each using the C2C12 pMARE luciferase assay described in the Examples below. The peptibody has a lower $IC_{50}$ value compared with the peptide.

The present invention provides binding agents capable of binding myostatin and inhibiting its activity. The myostatin binding agents can be used in assays, to identify, quantitate, or monitor the level of myostatin in an animal. The myostatin binding agents of the present invention reduce myostatin activity. The myostatin binding agents of the present invention increase lean muscle mass in animals, decrease fat mass as a percentage of body weight, and increase muscle strength. The myostatin binding agents of the present invention can be used to treat a variety of metabolic disorders in which myostatin plays a role, including muscle wasting disorders such as muscular dystrophies, muscle wasting due to cancer, AIDS, rheumatoid arthritis, renal failure, uremia, chronic heart failure, prolonged bed-rest, spinal chord injury, stroke, and age-related sarcopenia as well as other metabolic disorders including diabetes, obesity, hyperglycemia, and bone loss, by administering a therapeutic dosage of one or more binding agents in a pharmaceutically acceptable composition to a subject.

Myostatin

Myostatin, a growth factor also known as GDF-8, is known to be a negative regulator of skeletal muscle tissue. Myostatin is synthesized as an inactive preproprotein which is activated by proteolyic cleavage (Zimmers et al., supra (2002)). The precurser protein is cleaved to produce an $NH_2$-terminal inactive prodomain and an approximately 109 amino acid COOH-terminal protein in the form of a homodimer of about 25 kDa, which is the mature, active form (Zimmers et al, supra (2002)). It is now believed that the mature dimer circulates in the blood as an inactive latent complex bound to the propeptide (Zimmers et al, supra (2002).

As used herein the term "full-length myostatin" refers to the full-length human preproprotein sequence described in McPherron et al. supra (1997), as well as related full-length polypeptides including allelic variants and interspecies homologs which are also described in McPherron et al. (1997). As used herein, the term "prodomain" or "propeptide" refers to the inactive $NH_2$-terminal protein which is cleaved off to release the active COOH-terminal protein. As used herein the term "myostatin" or "mature myostatin" refers to the mature, biologically active COOH-terminal polypeptide, in monomer, dimer, multimeric form or other form. "Myostatin" or "mature myostatin" also refers to fragments of the biologically active mature myostatin, as well as related polypeptides including allelic variants, splice variants, and fusion peptides and polypeptides. The mature myostatin COOH-terminal protein has been reported to have 100% sequence identity among many species including human, mouse, chicken, porcine, turkey, and rat (Lee et al., *PNAS* 98, 9306 (2001)). Myostatin may or may not include additional terminal residues such as targeting sequences, or methionine and lysine residues and/or tag or fusion protein sequences, depending on how it is prepared.

As used herein the term "capable of binding to myostatin" or "having a binding affinity for myostatin" refers to a binding agent or peptide which binds to myostatin as demonstrated by as the phage ELISA assay, the BIAcore® or KinExA™ assays described in the Examples below.

As used herein, the term "capable of modifying myostatin activity" refers to the action of an agent as either an agonist or an antagonist with respect to at least one biological activity of myostatin. As used herein, "agonist" or "mimetic" activity refers an agent having biological activity comparable to a protein that interacts with the protein of interest, as described, for example, in International application WO 01/83525, filed May 2, 2001, which is incorporated herein by reference.

As used herein, the term "inhibiting myostatin activity" or "having antagonist activity" refers to the ability of a peptide or binding agent to reduce or block myostatin activity or signaling as demonstrated by or in vitro assays such as, for example, the pMARE C2C12 cell-based myostatin activity assay or by in vivo animal testing as described below.

Structure of Myostatin Binding Agents

In one embodiment, the binding agents of the present invention comprise at least one myostatin binding peptide covalently attached to at least one vehicle such as a polymer or an Fc domain. The attachment of the myostatin-binding peptides to at least one vehicle is intended to increase the effectiveness of the binding agent as a therapeutic by increasing the biological activity of the agent and/or decreasing degradation in vivo, increasing half-life in vivo, reducing toxicity or immunogenicity in vivo. The binding agents of the present invention may further comprise a linker sequence connecting the peptide and the vehicle. The peptide or peptides are attached directly or indirectly through a linker sequence to the vehicle at the N-terminal, C-terminal or an amino acid sidechain of the peptide. In this embodiment, the binding agents of the present invention have the following structure:

$(X^1)_a$-$F^1$-$(X^2)_b$, or multimers thereof;

wherein $F^1$ is a vehicle; and $X^1$ and $X^2$ are each independently selected from -$(L^1)_c$-$P^1$;

-$(L^1)_c$-$P^1$-$(L^2)_d$-$P^2$;

-$(L^1)_c$-$P^1$-$(L^2)_d$-$P^2$-$(L^3)_e$-$P^3$;

and -$(L^1)_c$-$P^1$-$(L^2)_d$-$P^2$-$(L^3)_e$-$P^3$-$(L^4)_f$-$P^4$;

wherein $P^1$, $P^2$, $P^3$, and $P^4$ are peptides capable of binding myostatin; and $L^1$, $L^2$, $L^3$, and $L^4$ are each linkers; and a, b, c, d, e, and f are each independently 0 or 1, provided that at least one of a and b is 1.

Any peptide containing a cysteinyl residue may be cross-linked with another Cys-containing peptide, either or both of which may be linked to a vehicle. Any peptide having more than one Cys residue may form an intrapeptide disulfide bond, as well.

In one embodiment, the vehicle is an Fc domain, defined below. This embodiment is referred to as a "peptibody". As used herein, the term "peptibody" refers to a molecule comprising an antibody Fc domain attached to at least one peptide. The production of peptibodies is generally described in PCT publication WO 00/24782, published May 4, 2000, which is herein incorporated by reference. Exemplary peptibodies are provided as 1× and 2× configurations with one copy and two copies of the peptide (attached in tandem) respectively, as described in the Examples below.

Peptides

As used herein the term "peptide" refers to molecules of about 5 to about 90 amino acids linked by peptide bonds. The peptides of the present invention are preferably between about 5 to about 50 amino acids in length, more preferably between about 10 and 30 amino acids in length, and most preferably between about 10 and 25 amino acids in length, and ate capable of binding to the myostatin protein.

The peptides of the present invention may comprise part of a sequence of naturally occuring proteins, may be randomized sequences derived from naturally occuring proteins, or may be entirely randomized sequences. The peptides of the present invention may be generated by any methods known in the art including chemical synthesis, digestion of proteins, or recombinant technology. Phage display and RNA-peptide screening, and other affinity screening techniques are particularly useful for generating peptides capable of binding myostatin.

Phage display technology is described, for example, in Scott et al. *Science* 249: 386 (1990); Devlin et al., *Science* 249: 404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998, each of which is incorporated herein by reference. Using phage libraries, random peptide sequences are displayed by fusion with coat proteins of filamentous phage. Typically, the displayed peptides are affinity-eluted either specifically or non-specifically against the target molecule. The retained phages may be enriched by successive rounds of affinity purification and repropagation. The best binding peptides are selected for further analysis, for example, by using phage ELISA, described below, and then sequenced. Optionally, mutagenesis libraries may be created and screened to further optimize the sequence of the best binders (Lowman, *Ann Rev Biophys Biomol Struct* 26:401-24 (1997)).

Other methods of generating the myostatin binding peptides include additional affinity selection techniques known in the art. A peptide library can be fused in the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA. See, for example, Roberts and Szostak, *Proc Natl Acad Sci USA*, 94: 12297-303 (1997). Hereinafter, this and related methods are collectively referred to as "RNA-peptide screening." Yeast two-hybrid screening methods also may be used to identify peptides of the invention that bind to myostatin. In addition, chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other analogues, as well as non-peptide elements. Both biological and chemical methods are reviewed in Wells and Lowman, *Curr Opin Biotechnol* 3: 355-62 (1992).

Additionally, selected peptides capable of binding myostatin can be further improved through the use of "rational design". In this approach, stepwise changes are made to a peptide sequence and the effect of the substitution on the binding affinity or specificity of the peptide or some other property of the peptide is observed in an appropriate assay. One example of this technique is substituting a single residue at a time with alanine, referred to as an "alanine walk" or an "alanine scan". When two residues are replaced, it is referred to as a "double alanine walk". The resultant peptide containing amino acid substitutions are tested for enhanced activity or some additional advantageous property.

In addition, analysis of the structure of a protein-protein interaction may also be used to suggest peptides that mimic the interaction of a larger protein. In such an analysis, the crystal structure of a protein may suggest the identity and relative orientation of critical residues of the protein, from which a peptide may be designed. See, for example, Takasaki et al., *Nature Biotech* 15:1266 (1977). These methods may also be used to investigate the interaction between a targeted protein and peptides selected by phage display or other affinity selection processes, thereby suggesting further modifications of peptides to increase binding affinity and the ability of the peptide to inhibit the activity of the protein.

In one embodiment, the peptides of the present invention are generated as families of related peptides. Exemplary peptides are represented by SEQ ID NO: 1 through 132. These exemplary peptides were derived through an selection process in which the best binders generated by phage display technology were further analyzed by phage ELISA to obtain candidate peptides by an affinity selection technique such as phage display technology as described herein. However, the peptides of the present invention may be produced by any number of known methods including chemical synthesis as described below.

The peptides of the present invention can be further improved by the process of "affinity maturation". This procedure is directed to increasing the affinity or the activity of the peptides and peptibodies of the present invention using phage display or other selection technologies. Based on a consensus sequence, directed secondary phage display libraries, for example, can be generated in which the "core" amino acids (determined from the consensus sequence) are held constant or are biased in frequency of occurrence. Alternatively, an individual peptide sequence can be used to generate a biased, directed phage display library. Panning of such libraries under more stringent conditions can yield peptides with enhanced binding to myostatin, selective binding to myostatin, or with some additional desired property. However, peptides having the affinity matured sequences may then be produced by any number of known methods including chemical synthesis or recombinantly. These peptides are used to generate binding agents such as peptibodies of various configurations which exhibit greater inhibitory activity in cell-based assays and in vivo assays.

Example 6 below describes affinity maturation of the "first round" peptides described above to produce affinity matured peptides. Exemplary affinity matured peptibodies are presented in Tables IV and V. The resultant 1× and 2× peptibodies made from these peptides were then further characterized for binding affinity, ability to neutralize myostatin activity, specificity to myostatin as opposed to other TNFβ family members, and for additional in vitro and in vivo activity, as described below. Affinity-matured peptides and peptibodies are referred to by the prefix "m" before their family name to distinguish them from first round peptides of the same family.

Exemplary first round peptides chosen for further affinity maturation according to the present invention included the following peptides: TN8-19 QGHCTRWPWMCPPY (SEQ ID NO: 33), and the linear peptides Linear-2 MEMLDSLFELLKDMVPISKA (SEQ ID NO: 104), Linear-15 HHGWNYLRKGSAPQWFEAWV (SEQ ID NO: 117), Linear-17, RATLLKDFWQLVEGYGDN (SEQ ID NO: 119), Linear-20 YREMSMLEGLLDVLERLQHY (SEQ ID NO: 122), Linear-21 HNSSQMLLSELIMLVGSMMQ (SEQ ID NO: 123), Linear-24 EFFHWLHNHRSEVNHWLDMN (SEQ ID NO: 126). The affinity matured families of each of these is presented below in Tables IV and V.

The peptides of the present invention also encompass variants and derivatives of the selected peptides which are capable of binding myostatin. As used herein the term "variant" refers to peptides having one or more amino acids inserted, deleted, or substituted into the original amino acid sequence, and which are still capable of binding to myostatin. Insertional and substitutional variants may contain natural amino acids as well as non-naturally occuring amino acids. As used herein the term "variant" includes fragments of the peptides which still retain the ability to bind to myostatin. As used herein, the term "derivative" refers to peptides which have been modified chemically in some manner distinct from insertion, deletion, and substitution variants. Variants and derivatives of the peptides and peptibodies of the present invention are described more fully below.

Vehicles

As used herein the term "vehicle" refers to a molecule that may be attached to one or more peptides of the present invention. Preferably, vehicles confer at least one desired property on the binding agents of the present invention. Peptides alone are likely to be removed in vivo either by renal filtration, by cellular clearance mechanisms in the reticuloendothelial system, or by proteolytic degradation. Attachment to a vehicle improves the therapeutic value of a binding agent by reducing degradation of the binding agent and/or increasing half-life, reducing toxicity, reducing immunogenicity, and/or increasing the biological activity of the binding agent.

Exemplary vehicles include Fc domains; linear polymers such as polyethylene glycol (PEG), polylysine, dextran; a branched chain polymer (see for example U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide; or any natural or synthetic protein, polypeptide or peptide that binds to a salvage receptor.

In one embodiment, the myostatin binding agents of the present invention have at least one peptide attached to at least one vehicle ($F^1$, $F^2$) through the N-terminus, C-terminus or a side chain of one of the amino acid residues of the peptide(s). Multiple vehicles may also be used; such as an Fc domain at each terminus or an Fc domain at a terminus and a PEG group at the other terminus or a side chain.

An Fc domain is one preferred vehicle. As used herein, the term "Fc domain" encompasses native Fc and Fc variant molecules and sequences as defined below. As used herein the term "native Fc" refers to a non-antigen binding fragment of an antibody or the amino acid sequence of that fragment which is produced by recombinant DNA techniques or by enzymatic or chemical cleavage of intact antibodies. A preferred Fc is a fully human Fc and may originate from any of the immunoglobulins, such as IgG1 and IgG2. However, Fc molecules that are partially human, or originate from non-human species are also included herein. Native Fc molecules are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucl Acids Res* 10: 4071-9). The term "native Fc" as used herein is used to refer to the monomeric, dimeric, and multimeric forms.

As used herein, the term "Fc variant" refers to a modified form of a native Fc sequence provided that binding to the salvage receptor is maintained, as described, for example, in WO 97/34631 and WO 96/32478, both of which are incorporated herein by reference. Fc variants may be constructed for example, by substituting or deleting residues, inserting residues or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionyl residue, especially when the molecule is expressed recombinantly in a bacterial cell such as *E. coli*.

3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art. See, for example, *Molec Immunol* 29 (5):633-9 (1992) with regard to ADCC sites in IgG1. These sites, as well, are not required for the fusion molecules of the present invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

The term "Fc domain" includes molecules in monomeric or multimeric form, whether digested from whole antibody or produced by other means. As used herein the term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing such a native Fc. The term "dimer" as applied to Fc domains or molecules comprising Fc domains refers to molecules having two polypeptide chains associated covalently or non-covalently.

Additionally, an alternative vehicle according to the present invention is a non-Fc domain protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle", and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

In addition, polymer vehicles may also be used to construct the binding agents of the present invention. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kDa to about 100 kDa, more preferably from about 5 kDa to about 50 kDa, most preferably from about 5 kDa to about 10 kDa. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group). A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis as known in the art. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by a1-6 linkages. The dextran itself is available in many molecular weight ranges, and is readily available in molecular weights from about 1 kDa to about 70 kDa. Dextran is a suitable water-soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kDa to about 20 kDa is preferred when dextran is used as a vehicle in accordance with the present invention.

Linkers

The binding agents of the present invention may optionally further comprise a "linker" group. Linkers serve primarily as a spacer between a peptide and a vehicles or between two peptides of the binding agents of the present invention. In one embodiment, the linker is made up of amino acids linked together by peptide bonds, preferably from 1 to 20 amino acids linked by peptide bonds, wherein the amino acids are selected from the 20 naturally occurring amino acids. One or more of these amino acids may be glycosylated, as is understood by those in the art. In one embodiment, the 1 to 20 amino acids are selected from glycine, alanine, proline, asparagine, glutamine, and lysine. Preferably, a linker is made up of a majority of amino acids that are sterically unhindered, such as glycine and alanine. Thus, exemplary linkers are polyglycines (particularly $(Gly)_5$, $(Gly)_8$), poly(Gly-Ala), and polyalanines. As used herein, the designation "g" refers to a glycine homopeptide linkers. As shown in Table II, "gn" refers to a 5×gly linker at the N terminus, while "gc" refers to 5×gly linker at the C terminus. Combinations of Gly and Ala are also preferred. One exemplary linker sequence useful for constructing the binding agents of the present invention is the following: gsgsatggsgstassgsgsatg (Seq ID No: 305). This linker sequence is referred to as the "k" or 1k sequence. The designations "kc", as found in Table II, refers to the k linker at the C-terminus, while the designation "kn", refers to the k linker at the N-terminus.

The linkers of the present invention may also be non-peptide linkers. For example, alkyl linkers such as —NH—$(CH_2)s$-C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker, and has a molecular weight of 100 to 5000 kDa, preferably 100 to 500 kDa. The peptide linkers may be altered to form derivatives in the same manner as above.

Exemplary Binding Agents

The binding agents of the present invention comprise at least one peptide capable of binding myostatin. In one embodiment, the myostatin binding peptide is between about 5 and about 50 amino acids in length, in another, between about 10 and 30 amino acids in length, and in another, between about 10 and 25 amino acids in length. In one embodiment the myostatin binding peptide comprises the amino acid sequence WMCPP (SEQ ID NO: 633). In other embodiment, the myostatin binding peptide comprises the amino acid sequence $\underline{C}a_1a_2\underline{W}a_3\underline{WMCPP}$ (SEQ ID NO: 352), wherein $a_1$, $a_2$ and $a_3$ are selected from a neutral hydrophobic, neutral polar, or basic amino acid. In another embodiment the myostatin binding peptide comprises the amino acid sequence $\underline{C}b_1b_2\underline{W}b_3\underline{WMCPP}$ (SEQ ID NO: 353), wherein $b_1$ is selected from any one of the amino acids T, I, or R; $b_2$ is selected from any one of R, S, Q; $b_3$ is selected from any one of P, R and Q, and wherein the peptide is beween 10 and 50 amino acids in length, and physiologically acceptable salts thereof.

In another embodiment, the myostatin binding peptide comprises the formula:

$c_1c_2c_3c_4c_5c_6\underline{C}c_7c_8\underline{W}c_9\underline{WMCPP}c_{10}c_{11}c_{12}c_{13}$ (SEQ ID NO: 354), wherein:
$c_1$ is absent or any amino acid;
$c_2$ is absent or a neutral hydrophobic, neutral polar, or acidic amino acid;
$c_3$ is absent or a neutral hydrophobic, neutral polar, or acidic amino acid;
$c_4$ is absent or any amino acid;
$c_5$ is absent or a neutral hydrophobic, neutral polar, or acidic amino acid;
$c_6$ is absent or a neutral hydrophobic, neutral polar, or basic amino acid;
$c_7$ is a neutral hydrophobic, neutral polar, or basic amino acid;
$c_8$ is a neutral hydrophobic, neutral polar, or basic amino acid;
$c_9$ is a neutral hydrophobic, neutral polar or basic amino acid; and
$c_{10}$ to $c_{13}$ is any amino acid; and wherein the peptide is between 20 and 50 amino acids in length, and physiologically acceptable salts thereof.

A related embodiment the myostatin binding peptide comprises the formula:

$d_1d_2d_3d_4d_5d_6\underline{C}d_7d_8\underline{W}d_9\underline{WMCPP}d_{10}d_{11}d_{12}d_{13}$ (SEQ ID NO: 355), wherein:
$d_1$ is absent or any amino acid;
$d_2$ is absent or a neutral hydrophobic, neutral polar, or acidic amino acid;
$d_3$ is absent or a neutral hydrophobic, neutral polar, or acidic amino acid;
$d_4$ is absent or any amino acid;
$d_5$ is absent or a neutral hydrophobic, neutral polar, or acidic amino acid;
$d_6$ is absent or a neutral hydrophobic, neutral polar, or basic amino acid;
$d_7$ is selected from any one of the amino acids T, I, or R;
$d_8$ is selected from any one of R, S, Q;
$d_9$ is selected from any one of P, R and Q, and
$d_{10}$ to $d_{13}$ is selected from any amino acid,
and wherein the peptide is between 20 and 50 amino acids in length, and physiologically acceptable salts thereof.

Additional embodiments of binding agents comprise at least one of the following peptides:

(1) a peptide capable of binding myostatin, wherein the peptide comprises the sequence $\underline{WY}e_1e_2\underline{Y}e_3\underline{G}$, (SEQ ID NO: 356),
wherein $e_1$ is P, S or Y.
$e_2$ is C or Q, and
$e_3$ is G or H, wherein the peptide is between 7 and 50 amino acids in length, and physiologically acceptable salts thereof;

(2) a peptide capable of binding myostatin, wherein the peptide comprises the sequence $f_1\underline{EML}f_2\underline{SL}f_3f_4\underline{LL}$, (SEQ ID NO: 455),
wherein $f_1$ is M or I,
$f_2$ is any amino acid,
$f_3$ is L or F,
$f_4$ is E, Q or D;
and wherein the peptide is between 7 and 50 amino acids in length, and physiologically acceptable salts thereof;

(3) a peptide capable of binding myostatin wherein the peptide comprises the sequence $\underline{Lg_1g_2LLg_3g_4L}$, (SEQ ID NO: 456), wherein $g_1$ is Q, D or E,
$g_2$ is S, Q, D or E,
$g_3$ is any amino acid,
$g_4$ is L, W, F, or Y, and wherein the peptide is between 8 and 50 amino acids in length, and physiologically acceptable salts thereof;

(4) a peptide capable of binding myostatin, wherein the peptide comprises the sequence $h_1h_2h_3h_4h_5h_6h_7h_8h_9$ (SEQ ID NO: 457), wherein $h_1$ is R or D,
$h_2$ is any amino acid,
$h_3$ is A, T S or Q.
$h_4$ is L or M,
$h_5$ is L or S,
$h_6$ is any amino acid,
$h_7$ is F or E,
$h_8$ is W, F or C,
$h_9$ is L, F, M or K, and wherein the peptide is between 9 and 50 amino acids in length, and physiologically acceptable salts thereof.

In one embodiment, the binding agents of the present invention-further comprise at least one vehicle such as a polymer or an Fc domain, and may further comprise at least one linker sequence. In this embodiment, the binding agents of the present invention are constructed so that at least one myostatin-binding peptide is covalently attached to at least one vehicle. The peptide or peptides are attached directly or indirectly through a linker sequence, to the vehicle at the N-terminal, C-terminal or an amino acid sidechain of the peptide. In this embodiment, the binding agents of the present invention have the following generalized structure:

$(X^1)_a$-$F^1$-$(X^2)_b$, or multimers thereof;

wherein $F^1$ is a vehicle; and $X^1$ and $X^2$ are each independently selected from -$(L^1)_c$-$P^1$;

-$(L^1)_c$-$P^1$-$(L^2)_d$-$P^2$;

-$(L^1)_c$-$P^1$-$(L^2)_d$-$P^2$-$(L^3)_e$-$P^3$;

and -$(L^1)_c$-$P^1$-$(L^2)_d$-$P^2$-$(L^3)_e$-$P^3$-$(L^4)_f$-$P^4$;

wherein $P^1$, $P^2$, $P^3$, and $P^4$ are peptides capable of binding myostatin; and $L^1$, $L^2$, $L^3$, and $L^4$ are each linkers; and a, b, c, d, e, and f are each independently 0 or 1, provided that at least one of a and b is 1.

In one embodiment of the binding agents having this generalized structure, the peptides $P^1$, $P^2$, $P^3$, and $P^4$ can be selected from one or more of any of the peptides comprising the sequences provided above. Peptides $P^1$, $P^2$, $P^3$, and $P^4$ can be selected from one or more peptides comprising any of the following sequences: SEQ ID NO: 633, SEQ ID NO: 352, SEQ ID NO: 353, SEQ ID NO: 354, SEQ ID NO: 355, SEQ ID NO: 356, SEQ ID NO: 455, SEQ ID NO: 456, or SEQ ID NO: 457.

In a further embodiment, the vehicles of binding agents having the general formula above are Fc domains. The peptides are therefore fused to an Fc domain, either directly or indirectly, thereby providing peptibodies. The peptibodies of the present invention display a high binding affinity for myostatin and can inhibit the activity of myostatin as demonstrated by in vitro assays and in vivo testing in animals provided herein.

The present invention also provides nucleic acid molecules comprising polynucleotides encoding the peptides, peptibodies, and peptide and peptibody variants and derivatives of the present invention. Exemplary nucleotides sequences are given below.

Variants and Derivatives of Peptides and Peptibodies

The binding agents of the present invention also encompass variants and derivatives of the peptides and peptibodies described herein. Since both the peptides and peptibodies of the present invention can be described in terms of their amino acid sequence, the terms "variants" and "derivatives" can be said to apply to a peptide alone, or a peptide as a component of a peptibody. As used herein, the term "peptide variants" refers to peptides or peptibodies having one or more amino acid residues inserted, deleted or substituted into the original amino acid sequence and which retain the ability to bind to myostatin and modify its activity. As used herein, fragments of the peptides or peptibodies are included within the definition of "variants".

It is understood that any given peptide or peptibody may contain one or two or all three types of variants. Insertional and substitutional variants may contain natural amino acids, as well as non-naturally occurring amino acids or both.

Peptide and peptibody variants also include mature peptides and peptibodies wherein leader or signal sequences are removed, and the resulting proteins having additional amino terminal residues, which amino acids may be natural or non-natural. Peptibodies with an additional methionyl residue at amino acid position −1 ($Met^{-1}$-peptibody) are contemplated, as are peptibodies with additional methionine and lysine residues at positions −2 and −1 ($Met^{-2}$-$Lys^{-1}$-). Variants having additional Met, Met-Lys, Lys residues (or one or more basic residues, in general) are particularly useful for enhanced recombinant protein production in bacterial host cells.

Peptide or peptibody variants of the present invention also includes peptides having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position-1 after cleavage of the GST component from the desired polypeptide. Variants which result from expression in other vector systems are also contemplated, including those wherein histidine tags are incorporated into the amino acid sequence, generally at the carboxy and/or amino terminus of the sequence.

In one example, insertional variants are provided wherein one or more amino acid residues, either naturally occurring or non-naturally occurring amino acids, are added to a peptide amino acid sequence. Insertions may be located at either or both termini of the protein, or may be positioned within internal regions of the peptibody amino acid sequence. Insertional variants with additional residues at either or both termini can include, for example, fusion proteins and proteins including amino acid tags or labels. Insertional variants include peptides in which one or more amino acid residues are added to the peptide amino acid sequence or fragment thereof.

Insertional variants also include fusion proteins wherein the amino and/or carboxy termini of the peptide or peptibody is fused to another polypeptide, a fragment thereof or amino acids which are not generally recognized to be part of any specific protein sequence. Examples of such fusion proteins are immunogenic polypeptides, proteins with long circulating half lives, such as immunoglobulin constant regions, marker proteins, proteins or polypeptides that facilitate purification of the desired peptide or peptibody, and polypeptide sequences that promote formation of multimeric proteins (such as leucine zipper motifs that are useful in dimer formation/stability).

This type of insertional variant generally has all or a substantial portion of the native molecule, linked at the N— or C-terminus, to all or a portion of a second polypeptide. For example, fusion proteins typically employ leader sequences from other species to permit the recombinant expression of a protein in a heterologous host. Another useful fusion protein includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione-S-transferase (GST) system (Pharmacia), the maltose binding protein system (NEB, Beverley, Mass.), the FLAG system (IBI, New Haven, Conn.), and the 6×His system (Qiagen, Chatsworth, Calif.). These systems are capable of producing recombinant peptides and/or peptibodies bearing only a small number of additional amino acids, which are unlikely to significantly affect the activity of the peptide or peptibody. For example, both the FLAG system and the 6×His system add only short sequences, both of which are known to be poorly antigenic and which do not adversely affect folding of a polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

Other fusion systems produce polypeptide hybrids where it is desirable to excise the fusion partner from the desired peptide or peptibody. In one embodiment, the fusion partner is linked to the recombinant peptibody by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The invention also provides fusion polypeptides which comprise all or part of a peptide or peptibody of the present invention, in combination with truncated tissue factor (tTF). tTF is a vascular targeting agent consisting of a truncated form of a human coagulation-inducing protein that acts as a tumor blood vessel clotting agent, as described U.S. Pat. Nos.: 5,877,289; 6,004,555; 6,132,729; 6,132,730; 6,156,321; and European Patent No. EP 0988056. The fusion of tTF to the anti-myostatin peptibody or peptide, or fragments thereof facilitates the delivery of anti-myostatin antagonists to target cells, for example, skeletal muscle cells, cardiac muscle cells, fibroblasts, pre-adipocytes, and possibly adipocytes.

In another aspect, the invention provides deletion variants wherein one or more amino acid residues in a peptide or peptibody are removed. Deletions can be effected at one or both termini of the peptibody, or from removal of one or more residues within the peptibody amino acid sequence. Deletion variants necessarily include all fragments of a peptide or peptibody.

In still another aspect, the invention provides substitution variants of peptides and peptibodies of the invention. Substitution variants include those peptides and peptibodies wherein one or more amino acid residues are removed and replaced with one or more alternative amino acids, which amino acids may be naturally occurring or non-naturally occurring. Substitutional variants generate peptides or peptibodies that are "similar" to the original peptide or peptibody, in that the two molecules have a certain percentage of amino acids that are identical. Substitution variants include substitutions of 1, 2, 3, 4, 5, 6, 7, 8, 9, 10, 15, and 20 amino acids within a peptide or peptibody, wherein the number of substitutions may be up to ten percent of the amino acids of the peptide or peptibody. In one aspect, the substitutions are conservative in nature, however, the invention embraces substitutions that are also non-conservative and also includes unconventional amino acids.

Identity and similarity of related peptides and peptibodies can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Preferred methods to determine the relatedness or percent identity of two peptides or polypeptides, or a polypeptide and a peptide, are designed to give the largest match between the sequences tested. Methods to determine identity are described in publicly available computer programs. Preferred computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method will result in an alignment that spans at least ten percent of the full length of the target polypeptide being compared, i.e., at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared. For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure,* 5(3)(1978) for the PAM 250 comparison matrix; Henikoff et al., *Proc. Natl. Acad. Sci USA,* 89:10915-10919 (1992) for the BLOSUM 62 comparison matrix) is also used by the algorithm.

In certain embodiments, for example, the parameters for a polypeptide sequence comparison can be made with the following: Algorithm: Needleman et al., J. Mol. Biol., 48:443-453 (1970); Comparison matrix: BLOSUM 62 from Henikoff et al., supra (1992); Gap Penalty: 12; Gap Length Penalty: 4; Threshold of Similarity: 0, along with no penalty for end gaps.

In certain embodiments, the parameters for polynucleotide molecule sequence (as opposed to an amino acid sequence) comparisons can be made with the following: Algorithm: Needleman et al., supra (1970); Comparison matrix: matches=+10, mismatch=0; Gap Penalty: 50: Gap Length Penalty: 3

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Stereoisomers (e.g., D-amino acids) of the twenty conventional (naturally occurring) amino acids, non-naturally occurring amino acids such as α-, α-disubstituted amino acids, N-alkyl amino acids, lactic acid, and other unconventional amino acids may also be suitable components for peptides of the present invention. Examples of non-naturally occurring amino acids include, for example: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylaspargine, N-ethylasparagine, hyroxylysine, all0-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

Naturally occurring residues may be divided into (overlapping) classes based on common side chain properties:
1) neutral hydrophobic: Met, Ala, Val, Leu, Ile, Pro, Trp, Met, Phe;
2) neutral polar: Cys, Ser, Thr, Asn, Gln, Tyr, Gly;
3) acidic: Asp, Glu;
4) basic: His, Lys, Arg;
5) residues that influence chain orientation: Gly, Pro; and
6) aromatic: Trp, Tyr, Phe.

Substitutions of amino acids may be conservative, which produces peptides having functional and chemical characteristics similar to those of the original peptide. Conservative amino acid substitutions involve exchanging a member of one of the above classes for another member of the same class. Conservative changes may encompass unconventional amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. These changes can result in substantial modification in the functional and/or chemical characteristics of the peptides. In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.,* 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional peptibody or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1 below.

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln, Glu, Asp | Gln |
| Asp | Glu, Gln, Asp | Glu |
| Cys | Ser, Ala | Ser |
| Gln | Asn, Glu, Asp | Asn |
| Glu | Asp, Gln, Asn | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

One skilled in the art will be able to produce variants of the peptides and peptibodies of the present invention by random substitution, for example, and testing the resulting peptide or peptibody for binding activity using the assays described herein.

Additionally, one skilled in the art can review structure-function studies or three-dimensional structural analysis in order to identify residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues. The variants can then be screened using activity assays as described herein.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al. *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a protein's structure. See Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given protein and that once a critical number of structures have been resolved, structural prediction will become dramatically more accurate.

Additional methods of predicting secondary structure include "threading" (Jones, D., *Curr. Opin. Struct. Biol.*, 7(3): 377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997)).

In certain embodiments, peptide or peptibody variants include glycosylation variants wherein one or more glycosylation sites such as a N-linked glycosylation site, has been added to the peptibody. An N-linked glycosylation site is characterized by the sequence: Asn-X-Ser or Asn-X-Thr, wherein the amino acid residue designated as X may be any amino acid residue except proline. The substitution or addition of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

The invention also provides "derivatives" of the peptides or peptibodies of the present invention. As used herein the term "derivative" refers to modifications other than, or in addition to, insertions, deletions, or substitutions of amino acid residues which retain the ability to bind to myostatin.

Preferably, the modifications made to the peptides of the present invention to produce derivatives are covalent in nature, and include for example, chemical bonding with polymers, lipids, other organic, and inorganic moieties. Derivatives of the invention may be prepared to increase circulating half-life of a peptibody, or may be designed to improve targeting capacity for the peptibody to desired cells, tissues, or organs.

The invention further embraces derivative binding agents covalently modified to include one or more water soluble polymer attachments, such as polyethylene glycol, polyoxyethylene glycol, or polypropylene glycol, as described U.S. Pat. Nos.: 4,640,835; 4,496,689; 4,301,144; 4,670,417; 4,791,192; and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers. Particularly preferred are peptibodies covalently modified with polyethylene glycol (PEG) subunits. Water-soluble polymers may be bonded at specific positions, for example at the amino terminus of the peptibodies, or randomly attached to one or more side chains of the polypeptide. The use of PEG for improving the therapeutic capacity for binding agents, e.g. peptibodies, and for humanized antibodies in particular, is described in U.S. Pat. No. 6,133,426 to Gonzales et al., issued Oct. 17, 2000.

The invention also contemplates derivatizing the peptide and/or vehicle portion of the myostatin binding agents. Such derivatives may improve the solubility, absorption, biological half-life, and the like of the compounds. The moieties may alternatively eliminate or attenuate any undesirable side-effect of the compounds and the like. Exemplary derivatives include compounds in which:

1. The derivative or some portion thereof is cyclic. For example, the peptide portion may be modified to contain two or more Cys residues (e.g., in the linker), which could cyclize by disulfide bond formation.

2. The derivative is cross-linked or is rendered capable of cross-linking between molecules. For example, the peptide portion may be modified to contain one Cys residue and thereby be able to form an intermolecular disulfide bond with a like molecule. The derivative may also be cross-linked through its C-terminus.

3. One or more peptidyl [—C(O)NR—] linkages (bonds) is replaced by a non-peptidyl linkage. Exemplary non-peptidyl linkages are —$CH_2$-carbamate [—$CH_2$—OC(O)NR—], phosphonate, —$CH_2$-sulfonamide [—$CH_2$—S(O)$_2$NR—], urea [—NHC(O)NH—], —$CH_2$-secondary amine, and alkylated peptide [—C(O)$NR_6$— wherein $R_6$ is lower alkyl].

4. The N-terminus is derivatized. Typically, the N-terminus may be acylated or modified to a substituted amine. Exemplary N-terminal derivative groups include —$NRR_1$ (other than —$NH_2$), —NRC(O)$R_1$, —NRC(O)$OR_1$, —NRS(O)$_2R_1$, —NHC(O)$NHR_1$, succinimide, or benzyloxycarbonyl-NH—(CBZ-NH—), wherein R and R1 are each independently hydrogen or lower alkyl and wherein the phenyl ring may be substituted with 1 to 3 substituents selected from the group consisting of $C_1$-$C_4$ alkyl, $C_1$-$C_4$ alkoxy, chloro, and bromo.

5. The free C-terminus is derivatized. Typically, the C-terminus is esterified or amidated. For example, one may use methods described in the art to add (NH—$CH_2$—$CH_2$—$NH_2$)$_2$ to compounds of this invention at the C-terminus. Likewise, one may use methods described in the art to add —$NH_2$, (or "capping" with an —$NH_2$ group) to compounds of this invention at the C-terminus. Exemplary C-terminal derivative groups include, for example, —C(O)$R_2$ wherein $R_2$ is lower alkoxy or —$NR_3R_4$ wherein $R_3$ and $R_4$ are independently hydrogen or $C_1$-$C_8$ alkyl (preferably $C_1$-$C_4$ alkyl).

6. A disulfide bond is replaced with another, preferably more stable, cross-linking moiety (e.g., an alkylene). See, e.g., Bhatnagar et al., *J Med Chem* 39: 3814-9 (1996), Alberts et al., *Thirteenth Am Pep Symp*, 357-9 (1993).

7. One or more individual amino acid residues is modified. Various derivatizing agents are known to react specifically with selected side chains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side chain groups (aspartyl or glutamyl) may be selectively modified by reaction with carbodiimides (R'—N=C=N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar et al., (supra).

Derivatization with bifunctional agents is useful for cross-linking the peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate(oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains [see, for example, Creighton, Proteins: Structure and Molecule Properties (W. H. Freeman & Co., San Francisco), pp. 79-86 (1983)].

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Additional derivatives include non-peptide analogs that provide a stabilized structure or lessened biodegradation, are also contemplated. Peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g., bioactive, confirmation which retains the ability to recognize and bind myostatin. In one aspect, the resulting analog/mimetic exhibits increased binding affinity for myostatin. One example of methods for preparation of nonpeptide mimetic analogs from peptides is described in Nachman et al., *Regul Pept* 57:359-370 (1995). If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptibodies also can be modified to create peptide derivatives by forming covalent or noncovalent complexes with other moieties. Covalently-bound complexes can be prepared by linking the chemical moieties to functional groups on the side chains of amino acids comprising the peptibodies, or at the N— or C-terminus.

In particular, it is anticipated that the peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising a peptibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. Nos. 3,817,837; 3,850,752; 3,996,345; and 4,277,437. Other labels that will be useful include but are not limited to radioactive labels, fluorescent labels and chemiluminescent labels. U.S. Patents concerning use of such labels include, for example, U.S. Pat. Nos. 3,817,837; 3,850,752; 3,939,350; and 3,996,345. Any of the peptibodies of the present invention may comprise one, two, or more of any of these labels.

Methods of Making Peptides and Peptibodies

The peptides of the present invention can be generated using a wide variety of techniques known in the art. For example, such peptides can be synthesized in solution or on a solid support in accordance with conventional techniques. Various automatic synthesizers are commercially available and can be used in accordance with known protocols. See, for example, Stewart and Young (supra); Tam et al., *J Am Chem Soc,* 105:6442, (1983); Merrifield, *Science* 232:341-347 (1986); Barany and Merrifield, *The Peptides*, Gross and Meienhofer, eds, Academic Press, New York, 1-284; Barany et al., *Int J Pep Protein Res,* 30:705-739 (1987); and U.S. Pat. No. 5,424,398, each incorporated herein by reference.

Solid phase peptide synthesis methods use a copoly(styrene-divinylbenzene) containing 0.1-1.0 mM amines/g polymer. These methods for peptide synthesis use butyloxycarbonyl (t-BOC) or 9-fluorenylmethyloxy-carbonyl(FMOC) protection of alpha-amino groups. Both methods involve stepwise syntheses whereby a single amino acid is added at each step starting from the C-terminus of the peptide (See, Coligan et al., *Curr Prot Immunol*, Wiley Interscience, 1991, Unit 9). On completion of chemical synthesis, the synthetic peptide can be deprotected to remove the t-BOC or FMOC amino acid blocking groups and cleaved from the polymer by treatment with acid at reduced temperature (e.g., liquid HF-10% anisole for about 0.25 to about 1 hours at 0° C.). After evaporation of the reagents, the peptides are extracted from the polymer with 1% acetic acid solution that is then lyophilized to yield the crude material. This can normally be purified by such techniques as gel filtration on Sephadex G-15 using 5% acetic acid as a solvent. Lyophilization of appropriate fractions of the column will yield the homogeneous peptides or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Phage display techniques can be particularly effective in identifying the peptides of the present invention as described above. Briefly, a phage library is prepared (using e.g. ml 13, fd, or lambda phage), displaying inserts from 4 to about 80 amino acid residues. The inserts may represent, for example, a completely degenerate or biased array. Phage-bearing inserts that bind to the desired antigen are selected and this process repeated through several cycles of reselection of phage that bind to the desired antigen. DNA sequencing is conducted to identify the sequences of the expressed peptides. The minimal linear portion of the sequence that binds to the desired antigen can be determined in this way. The procedure can be repeated using a biased library containing inserts containing part or all of the minimal linear portion plus one or more additional degenerate residues upstream or downstream thereof. These techniques may identify peptides of the invention with still greater binding affinity for myostatin than agents already identified herein.

Regardless of the manner in which the peptides are prepared, a nucleic acid molecule encoding each such peptide can be generated using standard recombinant DNA procedures. The nucleotide sequence of such molecules can be manipulated as appropriate without changing the amino acid sequence they encode to account for the degeneracy of the nucleic acid code as well as to account for codon preference in particular host cells.

The present invention also provides nucleic acid molecules comprising polynucleotide sequences encoding the peptides and peptibodies of the present invention. These nucleic acid molecules include vectors and constructs containing polynucleotides encoding the peptides and peptibodies of the present invention, as well as peptide and peptibody variants and derivatives. Exemplary nucleic acid molecules are provided in the Examples below.

Recombinant DNA techniques also provide a convenient method for preparing full length peptibodies and other large polypeptide binding agents of the present invention, or fragments thereof. A polynucleotide encoding the peptibody or fragment may be inserted into an expression vector, which can in turn be inserted into a host cell for production of the binding agents of the present invention. Preparation of exemplary peptibodies of the present invention are described in Example 2 below.

A variety of expression vector/host systems may be utilized to express the peptides and peptibodies of the invention. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. One preferred host cell line is *E.coli* strain 2596 (ATCC #202174), used for expression of peptibodies as described below in Example 2. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells.

The term "expression vector" refers to a plasmid, phage, virus or vector, for expressing a polypeptide from a polynucleotide sequence. An expression vector can comprise a transcriptional unit comprising an assembly of (1) a genetic element or elements having a regulatory role in gene expression, for example, promoters or enhancers, (2) a structural or sequence that encodes the binding agent which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionyl residue. This residue may or may not be subsequently cleaved from the expressed recombinant protein to provide a final peptide product.

For example, the peptides and peptibodies may be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted peptide is purified from the yeast growth medium using the methods used to purify the peptide from bacterial and mammalian cell supernatants.

Alternatively, the cDNA encoding the peptide and peptibodies may be cloned into the baculovirus expression vector pVL1393 (PharMingen, San Diego, Calif.). This vector can be used according to the manufacturer's directions (PharMingen) to infect *Spodoptera frugiperda* cells in sF9 protein-free media and to produce recombinant protein. The recombinant protein can be purified and concentrated from the media using a heparin-Sepharose column (Pharmacia).

Alternatively, the peptide or peptibody may be expressed in an insect system. Insect systems for protein expression are well known to those of skill in the art. In one such system, *Autographa californica* nuclear polyhedrosis virus (AcNPV) can be used as a vector to express foreign genes in *Spodoptera frugiperda* cells or in *Trichoplusia larvae*. The peptide coding sequence can be cloned into a nonessential region of the virus, such as the polyhedrin gene, and placed under control of the polyhedrin promoter. Successful insertion of the peptide will render the polyhedrin gene inactive and produce recombinant virus lacking coat protein coat. The recombinant viruses can be used to infect *S. frugiperda* cells or *Trichoplusia larvae* in which the peptide is expressed (Smith et al., *J Virol* 46: 584 (1983); Engelhard et al., *Proc Nat Acad Sci (USA)* 91: 3224-7 (1994)).

In another example, the DNA sequence encoding the peptide can be amplified by PCR and cloned into an appropriate vector for example, pGEX-3X (Pharmacia). The pGEX vector is designed to produce a fusion protein comprising glutathione-S-transferase (GST), encoded by the vector, and a protein encoded by a DNA fragment inserted into the vector's cloning site. The primers for PCR can be generated to include for example, an appropriate cleavage site. Where the fusion moiety is used solely to facilitate expression or is otherwise not desirable as an attachment to the peptide of interest, the recombinant fusion protein may then be cleaved from the GST portion of the fusion protein. The pGEX-3X/specific binding agent peptide construct is transformed into *E. coli* XL-1 Blue cells (Stratagene, La Jolla Calif.), and individual transformants isolated and grown. Plasmid DNA from individual transformants can be purified and partially sequenced using an automated sequencer to confirm the presence of the desired specific binding agent encoding nucleic acid insert in the proper orientation.

The fusion protein, which may be produced as an insoluble inclusion body in the bacteria, can be purified as follows. Host cells are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. The lysate can be cleared by sonication, and cell debris can be pelleted by centrifugation for 10 minutes at 12,000×g. The fusion protein-containing pellet can be resuspended in 50 mM Tris, pH 8, and 10 mM EDTA, layered over 50% glycerol, and centrifuged for 30 min. at 6000×g. The pellet can be resuspended in standard phosphate buffered saline solution (PBS) free of Mg++ and Ca++. The fusion protein can be further purified by fractionating the resuspended pellet in a denaturing SDS-PAGE (Sambrook et al., supra). The gel can be soaked in 0.4 M KCl to visualize the protein, which can be excised and electroeluted in gel-running buffer lacking SDS. If the GST/fusion protein is produced in bacteria as a soluble protein, it can be purified using the GST Purification Module (Pharmacia).

The fusion protein may be subjected to digestion to cleave the GST from the peptide of the invention. The digestion reaction (2040 mg fusion protein, 20-30 units human thrombin (4000 U/mg, Sigma) in 0.5 ml PBS can be incubated 16-48 hrs at room temperature and loaded on a denaturing SDS-PAGE gel to fractionate the reaction products. The gel can be soaked in 0.4 M KCl to visualize the protein bands. The identity of the protein band corresponding to the expected molecular weight of the peptide can be confirmed by amino acid sequence analysis using an automated sequencer (Applied Biosystems Model 473A, Foster City, Calif.). Alternatively, the identity can be confirmed by performing HPLC and/or mass spectometry of the peptides.

Alternatively, a DNA sequence encoding the peptide can be cloned into a plasmid containing a desired promoter and, optionally, a leader sequence (Better et al., *Science* 240:1041-43 (1988)). The sequence of this construct can be confirmed by automated sequencing. The plasmid can then be transformed into *E. coli* strain MC1061 using standard procedures employing CaCl2 incubation and heat shock treatment of the bacteria (Sambrook et al., supra). The transformed bacteria can be grown in LB medium supplemented with carbenicillin, and production of the expressed protein can be induced by growth in a suitable medium. If present, the leader sequence can effect secretion of the peptide and be cleaved during secretion.

Mammalian host systems for the expression of recombinant peptides and peptibodies are well known to those of skill in the art. Host cell strains can be chosen for a particular ability to process the expressed protein or produce certain post-translation modifications that will be useful in providing protein activity. Such modifications of the protein include, but are not limited to, acetylation, carboxylation, glycosylation, phosphorylation, lipidation and acylation. Different host cells such as CHO, HeLa, MDCK, 293, WI38, and the like have specific cellular machinery and characteristic mechanisms for such post-translational activities and can be chosen to ensure the correct modification and processing of the introduced, foreign protein.

It is preferable that transformed cells be used for long-term, high-yield protein production. Once such cells are transformed with vectors that contain selectable markers as well as the desired expression cassette, the cells can be allowed to grow for 1-2 days in an enriched media before they are switched to selective media. The selectable marker is designed to allow growth and recovery of cells that successfully express the introduced sequences. Resistant clumps of stably transformed cells can be proliferated using tissue culture techniques appropriate to the cell line employed.

A number of selection systems can be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr which confers resistance to methotrexate; gpt which confers resistance to mycophenolic acid; neo which confers resistance to the aminoglycoside G418 and confers resistance to chlorsulfuron; and hygro which confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Purification and Refolding of Binding Agents

In some cases, the binding agents such as the peptides and/or peptibodies of this invention may need to be "refolded" and oxidized into a proper tertiary structure arid disulfide linkages generated in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization, however a chaotrope is typically used at a lower concentration. Exemplary chaotropic agents are guanidine and urea. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a cosolvent may be used to increase the efficiency of the refolding. Commonly used cosolvents include glycerol, polyethylene glycol of various molecular weights, and arginine.

It may be desirable to purify the peptides and peptibodies of the present invention. Protein purification techniques are well known to those of skill in the art. These techniques involve, at one level, the crude fractionation of the proteinaceous and non-proteinaceous fractions. Having separated the peptide and/or peptibody from other proteins, the peptide or polypeptide of interest can be further purified using chromatographic and electrophoretic techniques to achieve partial or complete purification (or purification to homogeneity). Analytical methods particularly suited to the preparation of peptibodies and peptides or the present invention are ion-exchange chromatography, exclusion chromatography; polyacrylamide gel electrophoresis; isoelectric focusing. A particularly efficient method of purifying peptides is fast protein liquid chromatography or eyen HPLC.

Certain aspects of the present invention concern the purification, and in particular embodiments, the substantial purification, of a peptibody or peptide of the present invention. The term "purified peptibody or peptide" as used herein, is intended to refer to a composition, isolatable from other components, wherein the peptibody or peptide is purified to any degree relative to its naturally-obtainable state. A purified peptide or peptibody therefore also refers to a peptibody or peptide that is free from the environment in which it may naturally occur.

Generally, "purified" will refer to a peptide or peptibody composition that has been subjected to fractionation to remove various other components, and which composition substantially retains its expressed biological activity. Where the term "substantially purified" is used, this designation will refer to a peptide or peptibody composition in which the peptibody or peptide forms the major component of the composition, such as constituting about 50%, about 60%, about 70%, about 80%, about 90%, about 95% or more of the proteins in the composition.

Various methods for quantifying the degree of purification of the peptide or peptibody will be known to those of skill in the art in light of the present disclosure. These include, for example, determining the specific binding activity of an active fraction, or assessing the amount of peptide or peptibody within a fraction by SDS/PAGE analysis. A preferred method for assessing the purity of a peptide or peptibody fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the peptibody or peptide exhibits a detectable binding activity.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified binding agent.

There is no general requirement that the binding agents of the present invention always be provided in their most purified state. Indeed, it is contemplated that less substantially purified binding agent products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of the peptide or peptibody, or in maintaining binding activity of the peptide or peptibody.

It is known that the migration of a peptide or polypeptide can vary, sometimes significantly, with different conditions of SDS/PAGE (Capaldi et al., *Biochem Biophys Res Comm*, 76: 425 (1977)). It will therefore be appreciated that under differing electrophoresis conditions, the apparent molecular weights of purified or partially purified binding agent expression products may vary.

Activity of Myostatin Binding Agents

After the construction of the binding agents of the present invention, they are tested for their ability to bind myostatin and inhibit or block myostatin activity. Any number of assays or animal tests may be used to determine the ability of the agent to inhibit or block myostatin activity. Several assays used for characterizing the peptides and peptibodies of the present invention are described in the Examples below. One assay is the C2C12 pMARE-luc assay which makes use of a myostatin-responsive cell line (C2C12 myoblasts) transfected with a luciferase reporter vector containing myostatin/activin response elements (MARE). Exemplary peptibodies are assayed by pre-incubating a series of peptibody dilutions with myostatin, and then exposing the cells to the incubation mixture. The resulting luciferase activity is determined, and a titration curve is generated from the series of peptibody dilutions. The $IC_{50}$ (the concentration of peptibody to achieve 50% inhibition of myostatin activity as measured by luciferase activity) was then determined. A second assay described below is a BIAcore® assay to determine the kinetic parameters $k_a$ (association rate constant), $k_d$ (dissociation rate constant), and $K_D$ (dissociation equilibrium constant) for the myostatin binding agents. Lower dissociation equilibrium constants ($K_D$, expressed in nM) indicated a greater affinity of the peptibody for myostatin. Additional assays include blocking assays, to determine whether a binding agent such as a peptibody is neutralizing (prevents binding of myostatin to its receptor), or non-neutralizing (does not prevent binding of myostatin to its receptor); selectivity assays, which determine if the binding agents of the present invention bind selectively to myostatin and not to other TGFβ family members; and KinEx A™ assays or solution-based equilibrium assays, which also determine $K_D$ and are considered to be more sensitive in some circumstances. These assays are described in Example 3.

FIG. 1 shows the $IC_{50}$ of a peptide compared with the $IC_{50}$ of the peptibody form of the peptide. This demonstrates that the peptibody is significantly more effective at inhibiting myostatin activity than the peptide alone. In addition, affinity-matured peptibodies generally exhibit improved $IC_{50}$ and $K_D$ values compared with the parent peptides and peptibodies. The $IC_{50}$ values for a number of exemplary affinity matured peptibodies are shown in Table VII, Example 7 below. Additionally, in some instances, making a 2× version of a peptibody, where two peptides are attached in tandem, increase the activity of the peptibody both in vitro and in vivo.

In vivo activities are demonstrated in the Examples below. The activities of the binding agents include anabolic acitivity increasing lean muscle mass in animal models, as well as decreasing the fat mass with respect to total body weight in treated animal models, and increasing muscular strength in animal models.

Uses of the Myostatin Binding Agents

The myostatin binding agents of the present invention bind to myostatin and block or inhibit myostatin signaling within targeted cells. The present invention provides methods and reagents for reducing the amount or activity of myostatin in an animal by administering an effective dosage of one or more myostatin binding agents to the animal. In one aspect, the present invention provides methods and reagents for treating myostatin-related disorders in an animal comprising administering an effective dosage of one or more binding agents to the animal. These myostatin-related disorders include but are not limited to various forms of muscle wasting, as well as metabolic disorders such as diabetes and related disorders, and bone degenerative diseases such as osteoporosis.

As shown in the Example 8 below, exemplary peptibodies of the present invention dramatically increases lean muscle mass in the CD1 nu/nu mouse model. This in vivo activity correlates to the in vitro binding and inhibitory activity described below for the same peptibodies.

Muscle wasting disorders include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. For example, blocking myostatin through use of antibodies in vivo improved the dystrophic phenotype of the mdx mouse model of Duchenne muscular dystrophy (Bogdanovich et al, *Nature* 420, 28 (2002)). The peptibodies of the present invention increase lean muscle mass as a percentage of body weight and decrease fat mass as percentage of body weight when administered to an aged mdx mouse model.

Additional muscle wasting disorders arise from chronic disease such as amyotrophic lateral sclerosis, congestive obstructive pulmonary disease, cancer, AIDS, renal failure, and rheumatoid arthritis. For example, cachexia or muscle wasting and loss of body weight was induced in athymic nude mice by a systemically administered myostatin (Zimmers et al., supra). In another example, serum and intramuscular concentrations of myostatin-immunoreactive protein was found to be increased in men exhibiting AIDS-related muscle wasting and was inversely related to fat-free mass (Gonzalez-Cadavid et al., *PNAS USA* 95: 14938-14943 (1998)). Additional conditions resulting in muscle wasting may arise from inactivity due to disability such as confinement in a wheelchair, prolonged bedrest due to stroke, illness, spinal chord injury, bone fracture or trauma, and muscular atrophy in a microgravity environment (space flight). For example, plasma myostatin immunoreactive protein was found to increase after prolonged bedrest (Zachwieja et al. *J Gravit Physiol.* 6(2): 11(1999). It was also found that the muscles of rats exposed to a microgravity environment during a space shuttle flight expressed an increased amount of myostatin compared with the muscles of rats which were not exposed (Lalani et al., *J.Endocrin* 167 (3):417-28 (2000)).

In addition, age-related increases in fat to muscle ratios, and age-related muscular atrophy appear to be related to myostatin. For example, the average serum myostatin-immunoreactive protein increased with age in groups of young (19-35 yr old), middle-aged (36-75 yr old), and elderly (76-92 yr old) men and women, while the average muscle mass and fat-free mass declined with age in these groups (Yarasheski et al. *J Nutr Aging* 6(5):343-8 (2002)). It has also been shown that myostatin gene knockout in mice increased myogenesis and decreased adipogenesis (Lin et al., *Biochem Biophys Res Commun* 291(3):701-6 (2002), resulting in adults with increased muscle mass and decreased fat accumulation and leptin secretion. Exemplary peptibodies improve the lean muscle mass to fat ratio in aged mdx mice as shown below.

In addition, myostatin has now been found to be expressed at low levels in heart muscle and expression is upregulated in cardiomyocytes after infarct (Sharma et al., *J Cell Physiol.* 180 (1): 1-9 (1999)). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. supra). It has been demonstrated in the Examples below that decreasing myostatin activity by administering the inhibitors of the present invention will decrease the fat to muscle ratio in an animal, including aged animal models. Therefore, decreasing fat composition by administering the inhibitors of the present invention will improve diabetes, obesity, and hyperglycemic conditions in animals.

In addition, increasing muscle mass by reducing myostatin levels may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick et al. *Calcif Tissue Int* 71(1):63-8 (2002)).

The present invention also provides methods and reagents for increasing muscle mass in food animals by administering an effective dosage of the myostatin binding agent to the animal. Since the mature C-terminal myostatin polypeptide is identical in all species tested, myostatin binding agents would be expected to be effective for increasing muscle mass and reducing fat in any agriculturally important species including cattle, chicken, turkeys, and pigs.

The binding agents of the present invention may be used alone or in combination with other therapeutic agents to enhance their therapeutic effects or decrease potential side effects. The binding agents of the present invention possess one or more desirable but unexpected combination of properties to improve the therapeutic value of the agents. These properties include increased activity, increased solubility, reduced degradation, increased half-life, reduced toxicity, and reduced immunogenicity. Thus the binding agents of the present invention are useful for extended treatment regimes. In addition, the properties of hydrophilicity and hydrophobicity of the compounds of the invention are well balanced, thereby enhancing their utility for both in vitro and especially in vivo uses. Specifically, compounds of the invention have an appropriate degree of solubility in aqueous media that permits absorption and bioavailability in the body, while also having a degree of solubility in lipids that permits the compounds to traverse the cell membrane to a putative site of action, such as a particular muscle mass.

The binding agents of the present invention are useful for treating a "subject" or any animal, including humans, when administered in an effective dosage in a suitable composition.

In addition, the mystatin binding agents of the present invention are useful for detecting and quantitating myostatin in a number of assays. These assays are described in more detail below.

In general, the binding agents of the present invention are useful as capture agents to bind and immobilize myostatin in a variety of assays, similar to those described, for example, in Asai, ed., Methods in Cell Biology, 37, *Antibodies in Cell Biology*, Academic Press, Inc., New York (1993). The binding agent may be labeled in some manner or may react with a third molecule such as an anti-binding agent antibody which is labeled to enable myostatin to be detected and quantitated. For example, a binding agent or a third molecule can be modified with a detectable moiety, such as biotin, which can then be bound by a fourth molecule, such as enzyme-labeled streptavidin, or other proteins. (Akerstrom, *J Immunol* 135: 2589 (1985); Chaubert, *Mod Pathol* 10:585 (1997)).

Throughout any particular assay, incubation and/or washing steps may be required after each combination of reagents. Incubation steps can vary from about 5 seconds to several hours, preferably from about 5 minutes to about 24 hours. However, the incubation time will depend upon the assay format, volume of solution, concentrations, and the like. Usually, the assays will be carried out at ambient temperature, although they can be conducted over a range of temperatures.

Non-Competitive Binding Assays:

Binding assays can be of the non-competitive type in which the amount of captured myostatin is directly measured. For example, in one preferred "sandwich" assay, the binding agent can be bound directly to a solid substrate where it is immobilized. These immobilized agents then bind to myostatin present in the test sample. The immobilized myostatin is then bound with a labeling agent, such as a labeled antibody against myostatin, which can be detected In another preferred "sandwich" assay, a second agent specific for the binding agent can be added which contains a detectable moiety, such as biotin, to which a third labeled molecule can specifically bind, such as streptavidin. (See, Harlow and Lane, Antibodies, A Laboratory Manual, Ch 14, *Cold Spring Harbor Laboratory*, NY (1988), which is incorporated herein by reference).

Competitive Binding Assays:

Binding assays can be of the competitive type. The amount of myostatin present in the sample is measured indirectly by measuring the amount of myostatin displaced, or competed away, from a binding agent by the myostatin present in the sample. In one preferred competitive binding assay, a known amount of myostatin, usually labeled, is added to the sample and the sample is then contacted with the binding agent. The amount of labeled myostatin bound to the binding agent is inversely proportional to the concentration of myostatin present in the sample (following the protocols found in, for example Harlow and Lane, Antibodies, *A Laboratory Manual*, Ch 14, pp. 579-583, supra).

In another preferred competitive binding assay, the binding agent is immobilized on a solid substrate. The amount of myostastin bound to the binding agent may be determined either by measuring the amount of myostatin present in a myostatin/binding agent complex, or alternatively by measuring the amount of remaining uncomplexed myostatin.

Other Binding Assays

The present invention also provides Western blot methods to detect or quantify the presence of myostatin in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with the binding agents or fragments thereof that bind myostatin and the resulting complex is detected. These binding agents may be directly labeled or alternatively may be subsequently detected using labeled antibodies that specifically bind to the binding agent.

Diagnostic Assays

The binding agents or fragments thereof of the present invention may be useful for the diagnosis of conditions or diseases characterized by increased amounts of myostatin. Diagnostic assays for high levels of myostatin include methods utilizing a binding agent and a label to detect myostatin in human body fluids, extracts of cells or specific tissue extracts. For example, serum levels of myostatin may be measured in an individual overtime to determine the onset of muscle wasting associated with aging or inactivity, as described, for example, in Yarasheski et al., supra. Increased myostatin levels were shown to correlate with average decreased muscle mass and fat-free mass in groups of men and women of increasing ages (Yarasheski et al., supra). The binding agents of the present invention may be useful for monitoring increases or decreases in the levels of myostatin with a given individual over time, for example. The binding agents can be used in such assays with or without modification. In a preferred diagnostic assay, the binding agents will be labeled by attaching, e.g., a label or a reporter molecule. A wide variety of labels and reporter molecules are known, some of which have been already described herein. In particular, the present invention is useful for diagnosis of human disease.

A variety of protocols for measuring myostatin proteins using binding agents of myostatin are known in the art. Examples include enzyme-linked immunosorbent assay (ELISA), radioimmunoassay (RIA) and fluorescence activated cell sorting (FACS).

For diagnostic applications, in certain embodiments the binding agents of the present invention typically will be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, βgalactosidase, or horseradish peroxidase (Bayer et al., *Meth Enz,* 184: 138 (1990)).

Pharmaceutical Compositions

Pharmaceutical compositions of myostatin binding agents such as peptibodies described herein are within the scope of the present invention. Such compositions comprise a therapeutically or prophylactically effective amount of a myostatin binding agent, fragment, variant, or derivative thereof as described herein, in admixture with a pharmaceutically acceptable agent. In a preferred embodiment, pharmaceutical compositions comprise antagonist binding agents that inhibit myostatin partially or completely in admixture with a pharmaceutically acceptable agent. Typically, the myostatin binding agents will be sufficiently purified for administration to an animal.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18$^{th}$ Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the binding agent.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly (2-hydroxyethyl-methacrylate) (Langer et al., J. Biomed. Mater. Res., 15:167-277, (1981); Langer et al., Chem. Tech., 12:98-105(1982)), ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al.,PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s); reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent of the present invention such as a peptibody can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Pharmaceutical compositions containing the binding agents of the present invention are administered to a subject to treat any myostatin-related disorders. These include muscle-wasting disorders including but not limited to muscular dystrophy, muscle wasting in cancer, AIDS, muscle atrophy, rheumatoid arthritis, renal failure/uremia, chronic heart failure, prolonged bed-rest, spinal chord injury, stroke, and aging related sarcopenia. In addition these compositions are administered to treat obesity, diabetes, hyperglycemia, and increase bone density, The invention having been described, the following examples are offered by way of illustration, and not limitation.

EXAMPLE 1

Identification of Myostatin-Binding Peptides

Three filamentous phage libraries, TN8-IX ($5 \times 10^9$ independent transformants), TN12-I ($1.4 \times 10^9$ independent transformants), and linear ($2.3 \times 10^9$ independent transformants) (Dyax Corp.) were used to select for myostatin binding phage. Each library was incubated on myostatin-coated surfaces and subjected to different panning conditions: non-specific elution, and specific elution using recombinant human activin receptor IIB/Fc chimera (R&D Systems, Inc., Minneapolis, Minn.), or myostatin propeptide elution as described below. For all three libraries, the phages were eluted in a non-specific manner for the first round of selection, while the receptor and promyostatin was used in the second and third rounds of selection. The selection procedures were carried out as described below.

Preparation of Myostatin

Myostatin protein was produced recombinantly in the *E.coli* K-12 strain 2596 (ATCC #202174) as follows. Polynucleotides encoding the human promyostatin molecule were cloned into the pAMG21 expression vector (ATCC No. 98113), which was derived from expression vector pCFM1656 (ATCC No. 69576) and the expression vector system described in U.S. Pat. No. 4,710,473, by following the procedure described in published International Patent Application WO 00/24782. The polynucleotides encoding promyostatin were obtained from a mammalian expression vector. The coding region was amplified using a standard PCR method and the following PCR primers to introduce the restriction site for NdeI and BamHI.

5' primer: 5'-GAGAGAGAGCATATGAATGAGAACAGTGAGCAAAAAG-3' (Seq ID No: 292)

3' primer: 5'-AGAGAGGGATCCATTATGAGCACCCACAGCGGTC-3' (Seq ID No: 293)

The PCR product and vector were digested with both enzymes, mixed and ligated. The product of the ligation was transformed into *E. coli* strain #2596. Single colonies were checked microscopically for recombinant protein expression in the form of inclusion bodies. The plasmid was isolated and sequenced through the coding region of the recombinant gene to verify genetic fidelity.

Bacterial paste was generated from a 10L fermentation using a batch method at 37° C. The culture was induced with HSL at a cell density of 9.6 $OD_{600}$ and harvested six hours later at a density of 104 $OD_{600}$. The paste was stored at −80° C. *E.coli* paste expressing promyostatin was lysed in a microfluidizer at 16,000 psi, centrifuged to isolate the insoluble inclusion body fraction. Inclusion bodies were resuspended in guanidine hydrochloride containing dithiothreitol and solubilized at room temperature. This was then diluted 30 fold in an aqueous buffer. The refolded promyostatin was then concentrated and buffer exchanged into 20 mM Tris pH 8.0, and applied to an anion exchange column. The anion exchange column was eluted with an increasing sodium chloride gradient. The fractions containing promyostatin were pooled. The promyostatin produced in *E.coli* is missing the first 23 amino acids and begins with a methionine before the residue 24 asparagine. To produce mature myostatin, the pooled promyostatin was enzymatically cleaved between the propeptide and mature myostatin C terminal. The resulting mixture was then applied to a C4-rpHPLC column using a increasing gradient of acetonitrile containing 0.1% trifluoroacetic acid. Fractions containing mature myostatin were pooled and dried in a speed-vac.

The recombinant mature myostatin produced from *E. coli* was tested in the myoblast C2C12 based assay described below and found to be fully active when compared with recombinant murine myostatin commercially produced in a mammalian cell system (R&D Systems, Inc., Minneapolis, Minn.). The *E.coli*-produced mature myostatin was used in the phage-display and screening assays described below.

Preparation of Myostatin-Coated Tubes

Myostatin was immobilized on 5 ml Immuno™ Tubes (NUNC) at a concentration of 8 ug of myostatin protein in 1 ml of 0.1M sodium carbonate buffer (pH 9.6). The myostatin-coated Immuno™ Tube was incubated with orbital shaking for 1 hour at room temperature. Myostatin-coated Immuno™ Tube was then blocked by adding 5 ml of 2% milk-PBS and incubating at room temperature for 1 hour with rotation. The resulting myostatin-coated Immuno™ Tube was then washed three times with PBS before being subjected to the selection procedures. Additional Immuno™ Tubes were also prepared for negative selections (no myostatin). For each panning condition, five to ten Immuno™ Tubes were subjected to the above procedure except that the Immuno™ Tubes were coated with 1 ml of 2% BSA-PBS instead of myostatin protein.

Negative Selection

For each panning condition, about 100 random library equivalents for TN8-1X and TN12-I libraries ($5 \times 10^{11}$ pfu for TN8-IX, and $1.4 \times 10^{11}$ pfu for TN12-I) and about 10 random library equivalents for the linear library ($2.3 \times 10^{10}$ pfu) were aliquoted from the library stock and diluted to 1 ml with PBST (PBS with 0.05% Tween-20). The 1 ml of diluted library stock was added to an Immuno™ Tube prepared for the negative selection, and incubated for 10 minutes at room temperature with orbital shaking. The phage supernatant was drawn out and added to the second Immuno™ Tube for another negative selection step. In this way, five to ten negative selection steps were performed.

Selection for Myostatin Binding

After the last negative selection step above, the phage supernatant was added to the prepared myostatin coated Immuno™ Tubes. The Immuno™ Tube was incubated with orbital shaking for one hour at room temperature, allowing specific phage to bind to myostatin. After the supernatant was discarded, the Immuno™ Tube was washed about 15 times with 2% milk-PBS, 10 times with PBST and twice with PBS for the three rounds of selection with all three libraries (TN8-IX, TN12-I, and Linear libraries) except that for the second round of selections with TN8-IX and TN12-I libraries, the Immuno™ Tube was washed about 14 times with 2% milk-PBS, twice with 2% BSA-PBS, 10 times with PBST and once with PBS.

Non-Specific Elution

After the last washing step, the bound phages were eluted from the Immuno™ Tube by adding 1 ml of 100 mM triethylamine solution (Sigma, St. Louis, Mo.) with 10-minute incubation with orbital shaking. The pH of the phage containing solution was then neutralized with 0.5 ml of 1 M Tris-HCl (pH 7.5).

Receptor (Human Activin Receptor) Elution of Bound Phage

For round 2 and 3, after the last washing step, the bound phages were eluted from the Immuno™ Tube by adding 1 ml of 1 μM of receptor protein (recombinant human activin receptor IIB/Fc chimera, R&D Systems, Inc., Minneapolis, Minn.) with a 1-hour incubation for each condition.

Propeptide Elution of Bound Phage

For round 2 and 3, after the last washing step, the bound phages were eluted from the Immuno™ Tube by adding 1 ml of 1 μM propeptide protein (made as described above) with a 1-hour incubation for each condition.

Phage Amplification

Fresh *E.coli*. (XL-1 Blue MRF') culture was grown to $OD_{600}$=0.5 in LB media containing 12.5 ug/ml tetracycline. For each panning condition, 20 ml of this culture was chilled on ice and centrifuged. The bacteria pellet was resuspended in 1 ml of the min A salts solution.

Each mixture from different elution methods was added to a concentrated bacteria sample and incubated at 37° C. for 15 minutes. 2 ml of NZCYM media (2×NZCYM, 50 ug/ml Ampicillin) was added to each mixture and incubated at 37° C. for 15 minutes. The resulting 4 ml solution was plated on a large NZCYM agar plate containing 50 ug/ml ampicillin and incubated overnight at 37° C.

Each of the bacteria/phage mixture that was grown overnight on a large NZCYM agar plate was scraped off in 35 ml of LB media, and the agar plate was further rinsed with additional 35 ml of LB media. The resulting bacteria/phage mixture in LB media was centrifuged to pellet the bacteria away. 50 ul of the phage supernatant was transferred to a fresh tube, and 12.5 ml of PEG solution (20% PEG8000, 3.5M ammonium acetate) was added and incubated on ice for 2 hours to precipitate phages. The precipitated phages were centrifuged down and resuspended in 6 ml of the phage resuspension buffer (250 mM NaCl, 100 mM Tris pH8, 1 mM EDTA). This phage solution was further purified by centrifuging away the remaining bacteria and precipitating the phage for the second time by adding 1.5 ml of the PEG solution. After a centrifugation step, the phage pellet was resuspended in 400 ul of PBS. This solution was subjected to a final centrifugation to rid of remaining bacteria debris. The resulting phage preparation was titered by a standard plaque formation assay (Molecular Cloning, Maniatis et al., $3^{rd}$ Edition).

Additional Rounds of Selection and Amplification

In the second round, the amplified phage ($10^{11}$ pfu) from the first round was used as the input phage to perform the selection and amplification steps. The amplified phage ($10^{11}$ pfu) from the second round in turn was used as the input phage to perform third round of selection and amplification. After the elution steps of the third round, a small fraction of the eluted phage was plated out as in the plaque formation assay above. Individual plaques were picked and placed into 96 well microtiter plates containing 100 ul of TE buffer in each well. These master plates were incubated at 4° C. overnight to allow phages to elute into the TE buffer.

Clonal Analysis

Phase ELISA

The phage clones were subjected to phage ELISA and then sequenced. The sequences were ranked as discussed below.

Phage ELISA was performed as follows. An *E. Coli* XL-1 Blue MRF' culture was grown until $OD_{600}$ reached 0.5. 30 ul of this culture was aliquoted into each well of a 96 well microtiter plate. 10 ul of eluted phage was added to each well and allowed to infect bacteria for 15 min at room temperature. About 120 ul of LB media containing 12.5 ug/ml of tetracycline and 50 ug/ml of ampicillin were added to each well. The microtiter plate was then incubated with shaking overnight at 37° C. Myostatin protein (2 ug/ml in 0.1M sodium carbonate buffer, pH 9.6) was allowed to coat onto a 96 well Maxisorp™ plates (NUNC) overnight at 4° C. As a control, a separate Maxisorp™ plate was coated with 2% BSA prepared in PBS.

On the following day, liquid in the protein coated Maxisorp™ plates was discarded, washed three times with PBS and each well was blocked with 300 ul of 2% milk solution at room temperature for 1 hour. The milk solution was discarded, and the wells were washed three times with the PBS solution. After the last washing step, about 50 ul of PBST-4% milk was added to each well of the protein-coated Maxisorp™ plates. About 50 ul of overnight cultures from each well in the 96 well microtiter plate was transferred to the corresponding wells of the myostatin coated plates as well as the control 2% BSA coated plates. The 100 ul mixture in the two kinds of plates were incubated for 1 hour at room temperature. The liquid was discarded from the Maxisorp™ plates, and the wells were washed about three times with PBST followed by two times with PBS. The HRP-conjugated anti-M13 antibody (Amersham Pharmacia Biotech) was diluted to about 1:7,500, and 100 ul of the diluted solution was added to each well of the Maxisorp™ plates for 1 hour incubation at room temperature. The liquid was again discarded and the wells were washed about three times with PBST followed by two time with PBS. 100 ul of LumiGlo™ Cheminluminescent substrate (KPL) was added to each well of the Maxisorp™ plates and incubated for about 5 minutes for reaction to occur. The chemiluminescent unit of the Maxisorp™ plates was read on a plate reader (Lab System).

Sequencing of the Phase Clones

For each phage clone, the sequencing template was prepared by a PCR method. The following oligonucleotide pair was used to amplify a 500 nucleotide fragment: primer #1: 5'-CGGCGCAACTATGGTATCAAGCTG-3' (Seq ID No: 294) and primer #2: 5'-CATGTACCGTAACACT-GAGTTTCGTC-3' (Seq ID No: 295). The following mixture was prepared for each clone.

| Reagents | Volume (μL)/tube |
|---|---|
| distilled $H_2O$ | 26.25 |
| 50% glycerol | 10 |
| 10× PCR Buffer (w/o $MgCl_2$) | 5 |
| 25 mM $MgCl_2$ | 4 |
| 10 mM dNTP mix | 1 |
| 100 μM primer 1 | 0.25 |
| 100 μM primer 2 | 0.25 |
| Taq polymerase | 0.25 |
| Phage in TE (section 4) | 3 |
| Final reaction volume | 50 |

A thermocycler (GeneAmp PCR System 9700, Applied Biosystem) was used to run the following program: [94° C. for 5 min; 94° C. for 30 sec, 55° C. for 30 sec, 72° C. for 45 sec.]×30 cycles; 72° C. for 7 min; cool to 4° C. The PCR product from each reaction was cleaned up using the QIAquick Multiwell PCR Purification kit (Qiagen), following the manufacturer's protocol. The PCR cleaned up product was checked by running 10 ul of each PCR reaction mixed with 1 ul of dye (10×BBXS agarose gel loading dye) on a 1% agarose gel. The remaining product was then sequenced using the ABI 377 Sequencer (Perkin Elmer) following the manufacturer recommended protocol.

Sequence Ranking and Analysis

The peptide sequences that were translated from the nucleotide sequences were correlated to ELISA data. The clones that showed high chemiluminescent units in the myostatin-coated wells and low chemiluminescent units in the 2% BSA-coated wells were identified. The sequences that occurred multiple times were identified. Candidate sequences chosen based on these criteria were subjected to further analysis as peptibodies. Approximately 1200 individual clones were analyzed. Of these approximately 132 peptides were chosen for generating the peptibodies of the present invention. These are shown in Table I below. The peptides having SEQ ID NO: 1 to 129 were used to generate peptibodies of the same name. The peptides having SEQ ID NO: 130 to 141 shown in Table 1 comprise two or more peptides from SEQ ID NO: 1 to 132 attached by a linker sequence. SEQ ID NO: 130 to 141 were also used to generate peptibodies of the same name.

Consensus sequences were determined for the TN-8 derived group of peptides. These are as follows:

KDXCXXWHWMCKPX (Seq ID No: 142)

WXXCXXXGFWCXNX (Seq ID No: 143)

IXGCXWWDXXCYXX (Seq ID No: 144)

XXWCVSPXWFCXXX (Seq ID No: 145)

XXXCPWFAXXCVDW (Seq ID No: 146)

For all of the above consensus sequences, the underlined "core sequences" from each consensus sequence are the amino acid which always occur at that position. "X" refers to any naturally occurring or modified amino acid. The two cysteines contained with the core sequences were fixed amino acids in the TN8-IX library.

TABLE I

| PEPTIBODY NAME | SEQ.ID No | PEPTIDE SEQUENCE |
| --- | --- | --- |
| Myostatin-TN8-Con1 | 1 | KDKCMWHWMCKPP |
| Myostatin-TN8-Con2 | 2 | KDLCAMWHWMCKPP |
| Myostatin-TN8-Con3 | 3 | KDLCKMWKWMCKPP |
| Myostatin-TN8-Con4 | 4 | KDLCKMWHWMCKPK |
| Myostatin-TN8-Con5 | 5 | WYPCYEFHFWCYDL |
| Myostatin-TN8-Con6 | 6 | WYPCYEGHFWCYDL |
| Myostatin-TN8-Con7 | 7 | IFGCKWWDVQCYQF |
| Myostatin-TN8-Con8 | 8 | IFGCKWWDVDCYQF |
| Myostatin-TN8-Con9 | 9 | ADWCVSPNWFCMVM |
| Myostatin-TN8-Con10 | 10 | HKFCPWWALFCWDF |
| Myostatin-TN8-1 | 11 | KDLCKMWHWMGKPP |
| Myostatin-TN8-2 | 12 | IDKCAIWGWMCPPL |
| Myostatin-TN8-3 | 13 | WYPCGEFGMWCLNV |
| Myostatin-TN8-4 | 14 | WFTCLWNCDNE |
| Myostatin-TN8-5 | 15 | HTPCPWFAPLCVEW |
| Myostatin-TN8-6 | 16 | KEWCRWKWMCKPE |
| Myostatin-TN8-7 | 17 | FETCPSWAYFCLDI |
| Myostatin-TN8-8 | 18 | AYKCEANDWGCWWL |
| Myostatin-TN8-9 | 19 | NSWCEDQWHRCWWL |
| Myostatin-TN8-10 | 20 | WSACYAGHFWCYDL |
| Myostatin-TN8-11 | 21 | ANWCVSPNWFCMVM |
| Myostatin-TN8-12 | 22 | WTECYQQEFWCWNL |
| Myostatin-TN8-13 | 23 | ENTCERWKWMCPPK |
| Myostatin-TN8-14 | 24 | WLPCHQEGFWCMNF |
| Myostatin-TN8-15 | 25 | STMCSQWHWMCNPF |
| Myostatin-TN8-16 | 26 | IFGCHWWDVDCYQF |
| Myostatin-TN8-17 | 27 | IYGCKWWDIQCYDI |
| Myostatin-TN8-18 | 28 | PDWCIDPDWWCKFW |
| Myostatin-TN8-19 | 29 | QGHCTRWPWMCPPY |
| Myostatin-TN8-20 | 30 | WQECYREGFWCLQT |
| Myostatin-TN8-21 | 31 | WFDCYGPGFKCWSP |

TABLE I-continued

| PEPTIBODY NAME | SEQ.ID No | PEPTIDE SEQUENCE |
|---|---|---|
| Myostatin-TN8-22 | 32 | GVRCPKGHLWCLYP |
| Myostatin-TN8-23 | 33 | HWACGYWPWSCKWV |
| Myostatin-TN8-24 | 34 | GPACHSPWWWCVFG |
| Myostatin-TN8-25 | 35 | TTWCISPMWFCSQQ |
| Myostatin-TN8-26 | 36 | HKFCPPWAIFCWDF |
| Myostatin-TN8-27 | 37 | PDWCVSPRWYCNMW |
| Myostatin-TN8-28 | 38 | VWKCHWFGMDCEPT |
| Myostatin-TN8-29 | 39 | KKHCQIWTWMCAPK |
| Myostatin-TN8-30 | 40 | WFQCGSTLFWCYNL |
| Myostatin-TN8-31 | 41 | WSPCYDHYFYCYTI |
| Myostatin-TN8-32 | 42 | SWMCGFFKEVCMWV |
| Myostatin-TN8-33 | 43 | EMLCMIHPVFCNPH |
| Myostatin-TN8-34 | 44 | LKTCNLWPWMCPPL |
| Myostatin-TN8-35 | 45 | VVGCKWYEAWCYNK |
| Myostatin-TN8-36 | 46 | PIHCTQWAWMCPPT |
| Myostatin-TN8-37 | 47 | DSNCPWYFLSCVIF |
| Myostatin-TN8-38 | 48 | HIWCNLAMMKCVEM |
| Myostatin-TN8-39 | 49 | NLQCIYFLGKCIYF |
| Myostatin-TN8-40 | 50 | AWRCMWFSDVCTPG |
| Myostatin-TN8-41 | 51 | WFRCFLDADWCTSV |
| Myostatin-TN8-42 | 52 | EKICQMWSWMCAPP |
| Myostatin-TN8-43 | 53 | WFYCHLNKSECTEP |
| Myostatin-TN8-44 | 54 | FWRCAIGIDKCKRV |
| Myostatin-TN8-45 | 55 | NLGCKWYEVWCFTY |
| Myostatin-TN8-46 | 56 | IDLCNMWDGMCYPP |
| Myostatin-TN8-47 | 57 | EMPCNIWGWMCPPV |
| Myostatin-TN12-1 | 58 | WFRCVLTGIVDWSECFGL |
| Myostatin-TN12-2 | 59 | GFSCTFGLDEFYVDCSPF |
| Myostatin-TN12-3 | 60 | LPWCHDQVNADWGFCMLW |
| Myostatin-TN12-4 | 61 | YPTCSEKFWIYGQTCVLW |
| Myostatin-TN12-5 | 62 | LGPCPIHHGPWPQYCVYW |
| Myostatin-TN12-6 | 63 | PFPCETHQISWLGHCLSF |
| Myostatin-TN12-7 | 64 | HWGCEDLMWSWHPLCRRP |
| Myostatin-TN12-8 | 65 | LPLCDADMMPTIGFCVAY |
| Myostatin-TN12-9 | 66 | SHWCETTFWMNYAKCVHA |
| Myostatin-TN12-10 | 67 | LPKCTHVPFDQGGFCLWY |
| Myostatin-TN12-11 | 68 | FSSCWSPVSRQDMFCVFY |
| Myostatin-TN12-13 | 69 | SHKCEYSGWLQPLCYRP |
| Myostatin-TN12-14 | 70 | PWWCQDNYVQHMLHCDSP |

TABLE I-continued

| PEPTIBODY NAME | SEQ.ID No | PEPTIDE SEQUENCE |
|---|---|---|
| Myostatin-TN12-15 | 71 | WFRCMLMNSFDAFQCVSY |
| Myostatin-TN12-16 | 72 | PDACRDQPWYMFMGCMLG |
| Myostatin-TN12-17 | 73 | FLACFVEFELCFDS |
| Myostatin-TN12-18 | 74 | SAYCIITESDPYVLCVPL |
| Myostatin-TN12-19 | 75 | PSICESYSTMWLPMCQHN |
| Myostatin-TN12-20 | 76 | WLDCHDDSWAWTKMCRSH |
| Myostatin-TN12-21 | 77 | YLNCVMMNTSPFVECVFN |
| Myostatin-TN12-22 | 78 | YPWCDGFMIQQGITCMFY |
| Myostatin-TN12-23 | 79 | FDYCTWLNGFKDWKCWSR |
| Myostatin-TN12-24 | 80 | LPLCNLKEISHVQACVLF |
| Myostatin-TN12-25 | 81 | SPECAFARWLGIEQCQRD |
| Myostatin-TN12-26 | 82 | YPQCFNLHLLEWTECDWF |
| Myostatin-TN12-27 | 83 | RWRCEIYDSEFLPKCWFF |
| Myostatin-TN12-28 | 84 | LVGCDNVWHRCKLF |
| Myostatin-TN12-29 | 85 | AGWCHVWGEMFGMGCSAL |
| Myostatin-TN12-30 | 86 | HHECEWMARWMSLDCVGL |
| Myostatin-TN12-31 | 87 | FPMCGIAGMKDFDFCVWY |
| Myostatin-TN12-32 | 88 | RDDCTFWPEWLWKLCERP |
| Myostatin-TN12-33 | 89 | YNFCSYLFGVSKEACQLP |
| Myostatin-TN12-34 | 90 | AHWCEQGPWRYGNICMAY |
| Myostatin-TN12-35 | 91 | NLVCGKISAWGDEACARA |
| Myostatin-TN12-36 | 92 | HNVCTIMGPSMKWFCWND |
| Myostatin-TN12-37 | 93 | NDLCAMWGWRNTIWCQNS |
| Myostatin-TN12-38 | 94 | PPFCQNDNDMLQSLCKLL |
| Myostatin-TN12-39 | 95 | WYDCNVPNELLSGLCRLF |
| Myostatin-TN12-40 | 96 | YGDCDQNHWMWPFTCLSL |
| Myostatin-TN12-41 | 97 | GWMCHFDLHDWGATCQPD |
| Myostatin-TN12-42 | 98 | YFHCMFGGHEFEVHCESF |
| Myostatin-TN12-43 | 99 | AYWCWHGQCVRF |
| Myostatin-Linear-1 | 100 | SEHWTFTDWDGNEWWVRPF |
| Myostatin-Linear-2 | 101 | MEMLDSLFELLKDMVPISKA |
| Myostatin-Linear-3 | 102 | SPPEEALMEWLGWQYGKFT |
| Myostatin-Linear-4 | 103 | SPENLLNDLYILMTKQEWYG |
| Myostatin-Linear-5 | 104 | FHWEEGIPFHVVTPYSYDRM |
| Myostatin-Linear-6 | 105 | KRLLEQFMNDLAELVSGHS |
| Myostatin-Linear-7 | 106 | DTRDALFQEFYEFVRSRLVI |
| Myostatin-Linear-8 | 107 | RMSAAPRPLTYRDIMDQYWH |
| Myostatin-Linear-9 | 108 | NDKAHFFEMFMFDVHNFVES |

TABLE I-continued

| PEPTIBODY NAME | SEQ.ID No | PEPTIDE SEQUENCE |
|---|---|---|
| Myostatin-Linear-10 | 109 | QTQAQKIDGLWELLQSIRNQ |
| Myostatin-Linear-11 | 110 | MLSEFEEFLGNLVHRQEA |
| Myostatin-Linear-12 | 111 | YTPKMGSEWTSFWHNRIHYL |
| Myostatin-Linear-13 | 112 | LNDTLLRELKMVLNSLSDMK |
| Myostatin-Linear-14 | 113 | FDVERDLMRWLEGFMQSAAT |
| Myostatin-Linear-15 | 114 | HHGWNYLRKGSAPQWFEAWV |
| Myostatin-Linear-16 | 115 | VESLHQLQMWLDQKLASGPH |
| Myostatin-Linear-17 | 116 | RATLLKDFWQLVEGYGDN |
| Myostatin-Linear-18 | 117 | EELLREFYRFVSAFDY |
| Myostatin-Linear-19 | 118 | GLLDEFSHFIAEQFYQMPGG |
| Myostatin-Linear-20 | 119 | YREMSMLEGLLDVLERLQHY |
| Myostatin-Linear-21 | 120 | HNSSQMLLSELIMLVGSMMQ |
| Myostatin-Linear-22 | 121 | WREHFLNSDYIRDKLIAIDG |
| Myostatin-Linear-23 | 122 | QFPFYVFDDLPAQLEYWIA |
| Myostatin-Linear-24 | 123 | EFFHWLHNHRSEVNHWLDMN |
| Myostatin-Linear-25 | 124 | EALFQNFFRDVLTLSEREY |
| Myostatin-Linear-26 | 125 | QYWEQQWMTYFRENGLHVQY |
| Myostatin-Linear-27 | 126 | NQRMMLEDLWRIMTPMFGRS |
| Myostatin-Linear-29 | 127 | FLDELKAELSRHYALDDLDE |
| Myostatin-Linear-30 | 128 | GKLIEGLLNELMQLETFMPD |
| Myostatin-Linear-31 | 129 | ILLLDEYKKDWKSWF |
| Myostatin-2xTN8-19 kc | 130 | QGHCTRWPWMCPPYGSGSATGGSGSTASSGSGSATGQGHCTRWPWMCPPY |
| Myostatin-2xTN8-con6 | 131 | WYPCYEGHFWCYDLGSGSTASSGSGSATGWYPCYEGHFWCYDL |
| Myostatin-2xTN8-5 kc | 132 | HTPCPWFAPLCVEWGSGSATGGSGSTASSGSGSATGHTPCPWFAPLCVEW |
| Myostatin-2xTN8-18 kc | 133 | PDWCIDPDWWCKFWGSGSATGGSGSTASSGSGSATGPDWCIDPDWWCKFW |
| Myostatin-2xTN8-11 kc | 134 | ANWCVSPNWFCMVMGSGSATGGSGSTASSGSGSATGANWCVSPNWFCMVM |
| Myostatin-2xTN8-25 kc | 135 | PDWCIDPDWWCKFWGSGSATGGSGSTASSGSGSATGPDWCIDPDWWCKFW |
| Myostatin-2xTN8-23 kc | 136 | HWACGYWPWSCKWVGSGSATGGSGSTASSGSGSATGHWACGYWPWSCKWV |
| Myostatin-TN8-29-19 kc | 137 | KKHCQIWTWMCAPKGSGSATGGSGSTASSGSGSATGQGHCTRWPWMCPPY |
| Myostatin-TN8-19-29 kc | 138 | QGHCTRWPWMCPPYGSGSATGGSGSTASSGSGSATGKKHCQIWTWMCAPK |

TABLE I-continued

| PEPTIBODY NAME | SEQ.ID No | PEPTIDE SEQUENCE |
|---|---|---|
| Myostatin-TN8-29-19 kn | 139 | KKHCQIWTWMCAPKGSGSATGGS GSTASSGSGSATGQGHCTRWPWM CPPY |
| Myostatin-TN8-29-19-8g | 140 | KKHCQIWTWMCAPKGGGGGGGG QGHCTRWPWMCPPY |
| Myostatin-TN8-19-29-6gc | 141 | QGHCTRWPWMCPPYGGGGGGKK HCQIWTWMCAPK |

EXAMPLE 2

Generating Peptibodies

Construction of DNA Encoding Peptide-Fc Fusion Proteins

Peptides capable of binding myostatin were used alone or in combination with each other to construct fusion proteins in which a peptide was fused to the Fc domain of human IgG1. The amino acid sequence of the Fc portion of each peptibody is as follows (from amino terminus to carboxyl terminus):

```
DKTHTCPPCPAPELLGGPSVFLFPPKPKDTLMISRTPEVTCVVVDV    (Seq ID No: 296)
SHEDPEVKFNWYVDGVEVHNAKTKPREEQYNSTYRVVSVLTVL
HQDWLNGKEYKCKVSNKALPAPIEKTISKAKGQPREPQVYTLPPS
RDELTKNQVSLTCLVKGFYPSDIAVEWESNGQPENNYKTTPPVL
DSDGSFFLYSKLTVDKSRWQQGNVFSCSVMHEALHNHYTQKSLS
LSPGK
```

The peptide was fused in the N configuration (peptide was attached to the N-terminus of the Fc region), the C configuration (peptide was attached to the C-terminus of the Fc region), or the N,C configuration (peptide attached both at the N and C terminus of the Fc region). Separate vectors were used to express N-terminal fusions and C-terminal fusions. Each peptibody was constructed by annealing pairs of oligonucleotides ("oligos") to the selected phage nucleic acid to generate a double stranded nucleotide sequence encoding the peptide. These polynucleotide molecules were constructed as ApaL to XhoI fragments. The fragments were ligated into either the pAMG21-Fc N-terminal vector for the N-terminal orientation, or the pAMG21-Fc-C-terminal vector for the C-terminal orientation which had been previously digested with ApaLI and XhoI. The resulting ligation mixtures were transformed by electroporation into E. coli strain 2596 or 4167 cells (a hsdR-variant of strain 2596 cells) using standard procedures. Clones were screened for the ability to produce the recombinant protein product and to possess the gene fusion having a correct nucleotide sequence. A single such clone was selected for each of the modified peptides.

Many of constructs were created using an alternative vector designated pAMG21-2xBs-N(ZeoR)Fc. This vector is simlar to the above-described vector except that the vector digestion was performed with BsmBI. Some constructs fused peptide sequences at both ends of the Fc. In those cases the vector was a composite of pAMG21-2xBs-N(ZeoR) Fc and pAMG21-2xBs-C-Fc.

Construction of pAMG21

Expression plasmid pAMG21 (ATCC No. 98113) is derived from expression vector pCFM1656 (ATCC No. 69576) and the expression vector system described in U.S. Pat. No. 4,710,473, by following the procedure described in published International Patent Application WO 00/24782, all of which are incorporated herein by reference.

Fc N-terminal Vector

The Fc N-terminal vector was constructed using the pAMG21 Fc_Gly5_Tpo vector as a template. A 5' PCR primer (below) was designed to remove the Tpo peptide sequence in pAMG Tpo Gly5 and replace it with a polylinker containing ApaLI and XhoI sites. Using this vector as a template, PCR was performed with Expand Long Polymerase, using the following 5' primer and a universal 3' primer:

```
5' primer:  5'-ACAAACAAACATATGGGTGCACAGAAAGCGGCCGCAAAAAAA   (Seq ID No: 297)
            CTCGAGGGTGGAGGCGGTGGGGACA-3'

3' primer:  5'-GGTCATTACTGGACCGGATC-3'                     (Seq ID No: 298)
```

The resulting PCR product was gel purified and digested with restriction enzymes NdeI and BsrGI. Both the plasmid and the polynucleotide encoding the peptide of interest together with its linker were gel purified using Qiagen (Chatsworth, Calif.) gel purification spin columns. The plasmid and insert were then ligated using standard ligation procedures, and the resulting ligation mixture was transformed into E. coli cells (strain 2596). Single clones were selected and DNA sequencing was performed. A correct clone was identified and this was used as a vector source for the modified peptides described herein.

Construction of Fc C-terminal Vector

The Fc C-terminal vector was constructed using pAMG21 Fc_Gly5_Tpo vector as a template. A 3' PCR primer was designed to remove the Tpo peptide sequence and to replace it with a polylinker containing ApaLI and XhoI sites. PCR was performed with Expand Long Polymerase using a universal 5' primer and the 3' primer.

```
5' Primer:   5'-CGTACAGGTTTACGCAAGAAAATGG-3'            (Seq ID No: 299)

3' Primer:   5'-TTTGTTGGATCCATTACTCGAGTTTTTTTGCGGCCGCT  (Seq ID No: 300)
             TTCTGTGCACCACCACCTCCACCTTTAC-3'
```

The resulting PCR product was gel purified and digested with restriction enzymes BsrGI and BamHI. Both the plasmid and the polynucleotide encoding each peptides of interest with its linker were gel purified via Qiagen gel purification spin columns. The plasmid and insert were then ligated using standard ligation procedures, and the resulting ligation mixture was transformed into E. coli (strain 2596) cells. Strain 2596 (ATCC #202174) is a strain of E. coli K-12 modified to contain the lux promoter and two lambda temperature sensitive repressors, the cI857s7 and the lac I$^Q$ repressor. Single clones were selected and DNA sequencing was performed. A correct clone was identified and used as a source of each peptibody described herein.

Expression in E. coli.

Cultures of each of the pAMG21-Fc fusion constructs in E. coli strain 2596 were grown at 37° C. in Terrific Broth medium (See Tartof and Hobbs, "Improved media for growing plasmid and cosmid clones", Bethesda Research Labs Focus, Volume 9, page 12, 1987, cited in aforementioned Sambrook et al. reference). Induction of gene product expression from the luxPR promoter was achieved following the addition of the synthetic autoinducer, N-(3-oxohexanoyl)-DL-homoserine lactone, to the culture medium to a final concentration of 20 nanograms per milliliter (ng/ml). Cultures were incubated at 37° C. for an additional six hours. The bacterial cultures were then examined by microscopy for the presence of inclusion bodies and collected by centrifugation. Refractile inclusion bodies were observed in induced cultures, indicating that the Fc-fusions were most likely produced in the insoluble fraction in E. coli. Cell pellets were lysed directly by resuspension in Laemmli sample buffer containing 10% β-mercaptoethanol and then analyzed by SDS-PAGE. In most cases, an intense coomassie-stained band of the appropriate molecular weight was observed on an SDS-PAGE gel.

Folding and Purifying Peptibodies

Cells were broken in water (1/10 volume per volume) by high pressure homogenization (3 passes at 15,000 PSI) and inclusion bodies were harvested by centrifugation (4000 RPM in J-6B for 30 minutes). Inclusion bodies were solubilized in 6 M guanidine, 50 mM Tris, 8 mM DTT, pH 8.0 for 1 hour at a 1/10 ratio at ambient temperature. The solubilized mixture was diluted 25 times into 4 M urea, 20% glycerol, 50 mM Tris, 160 mM arginine, 3 mM cysteine, 1 mM cystamine, pH 8.5. The mixture was incubated overnight in the cold. The mixture was then dialyzed against 10 mM Tris pH 8.5, 50 mM NaCl, 1.5 M urea. After an overnight dialysis the pH of the dialysate was adjusted to pH 5 with acetic acid. The precipitate was removed by centrifugation and the supernatant was loaded onto a SP-Sepharose Fast Flow column equilibrated in 10 mM NaAc, 50 mM NaCl, pH 5, 4° C.). After loading the column was washed to baseline with 10 mM NaAc, 50 mM NaCl, pH 5.2. The column was developed with a 20 column volume gradient from 50 mM-500 mM NaCl in the acetate buffer. Alternatively, after the wash to baseline, the column was washed with 5 column volumes of 10 mM sodium phosphate pH 7.0 and the column developed with a 15 column volume gradient from 0-400 mM NaCl in phosphate buffer. Column fractions were analyzed by SDS-PAGE. Fractions containing dimeric peptibody were pooled. Fractions were also analyzed by gel filtration to determine if any aggregate was present.

A number of peptibodies were prepared from the peptides of Table I. The peptides were attached to the human IgG1 Fc molecule to form the peptibodies in Table II. Regarding the peptibodies in Table II, the C configuration indicates that the peptide named was attached at the C-termini of the Fc. The N configuration indicates that the peptide named was attached at the N-termini of the Fc. The N,C configuration indicates that one peptide was attached at the N-termini and one at the C-termini of each Fc molecule. The 2× designation indicates that the two peptides named were attached in tandem to each other and also attached at the N or the C termini, or both the N,C of the Fc, separated by the linker indicated. Two peptides attached in tandem separated by a linker, are indicated, for example, as Myostatin-TN8-29-19-8 g, which indicates that TN8-29 peptide is attached via a (gly)$_8$ linker to TN8-19 peptide. The peptide(s) were attached to the Fc via a (gly)$_5$ linker sequence unless otherwise specified. In some instances the peptide(s) were attached via a k linker. The linker designated k or 1k refers to the gsgsatggsgstassgsgsatg (Seq ID No: 301) linker sequence, with kc referring to the linker attached to the C-terminus of the Fc, and kn referring to the linker attached to the N-terminus of the Fc. In Table II below, column 4 refers to the linker sequence connecting the Fc to the first peptide and the fifth column refers to the configuration N or C or both.

Since the Fc molecule dimerizes in solution, a peptibody constructed so as to have one peptide will actually be a dimer with two copies of the peptide and two Fc molecules, and the 2× version having two peptides in tandem will actually be a dimer with four copies of the peptide and two Fc molecules.

Since the peptibodies given in Table II are expressed in E. coli, the first amino acid residue is Met (M). Therefore, the peptibodies in the N configuration are Met-peptide-linker-Fc, or Met-peptide-linker-peptide-linker-Fc, for example. Peptibodies in the C configuration are arranged as Met-Fc-linker-peptide or Met-Fc-linker-peptide-linker-peptide, for example. Peptibodies in the C,N configuration are a combination of both, for example, Met-peptide-linker-Fc-linker-peptide.

Nucleotide sequences encoding exemplary peptibodies are provided below in Table II. The polynucleotide sequences encoding an exemplary peptibody of the present invention includes a nucleotide sequence encoding the Fc polypeptide sequence such as the following:

```
5'-GACAAAACTCACACATGTCCACCTTGCCCAGCACCTGAACTC           (Seq ID No: 301)
CTGGGGGGACCGTCAGTTTTCCTCTTCCCCCCAAAACCCAAGGACACCCTCA
TGATCTCCCGGACCCCTGAGGTCACATGCGTGGTGGTGGACGTGAGCCACG
AAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTG
GTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCA
TCCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCCG
GAGAACAACTACAAGACCACGCCTCCCGTGCTGGACTCCGACGGCTCCTTCT
TCCTCTACAGCAAGCTCACCGTGGACAAGAGCAGGTGGCAGCAGGGGAACG
TCTTCTCATGCTCCGTGATGCATGAGGCTCTGCACAACCACTACACGCAGAA
GAGCCTCTCCCTGTCTCCGGGTAAA-3'
```

In addition, the polynucleotides encoding the (Gly)₅ linker such as the following are included:

```
5'-GGTGGAGGTGGTGGT-3'.    (Seq ID No: 302)
```

The polynucleotide encoding the peptibody also includes the codon encoding the methionine ATG and a stop codon such as TAA.

Therefore, the structure of the first peptibody in Table II is TN8-Con 1 with a C configuration and a (gly)₅ linker is as follows: M-Fc-GGGGG-KDKCKMWHWMCKPP (Seq ID No: 303).

Exemplary polynucleotides encoding this peptibody would be:

```
5'- ATGGACAAAACTCACACATGTCCACCTTGCCCAGCACCTGAA         (Seq ID No: 304)
CTCCTGGGGGGACCGTCAGTTTTCCTCTTCCCCCCAAAACCCAAGGACACCC
TCATGATCTCCCGGACCCCTGAGGTCACATGCGTGGTGGTGGACGTGAGCC
ACGAAGACCCTGAGGTCAAGTTCAACTGGTACGTGGACGGCGTGGAGGTGC
ATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACC
ATCTCCAAAGCCAAAGGGCAGCCCCGAGAACCACAGGTGTACACCCTGCCC
CCATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCAG
CCGGAGAACAACTACAAGACCACGCCTCCCGTGCTGGACTCCGACGGCTCC
TTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGC
AGAAGAGCCTCTCCCTGTCTCCGGGTAAAGGTGGAGGTGGTGGTAAGACAA
ATGCAAAATGTGGCACTGGATGTGCAAACCGCCG-3'
```

TABLE II

| Peptibody Name | Peptide | Nucleotide Sequence (Seq ID No) | | L | |
|---|---|---|---|---|---|
| Myostatin-TN8-con1 | KDKCKMWHWMCKPP (SEQ ID NO:1) | AAAGACAAATGCAAAATGTGGCACTG GATGTGCAAACCGCCG | (Seq. ID No: 147) | 5 gly | C |
| Myostatin-TN8-con2 | KDLCAMWHWMCKPP (SEQ ID NO:2) | AAAGACCTGTGCGCTATGTGGCACTG GATGTGCAAACCGCCG | (Seq. ID No: 148) | 5 gly | C |
| Myostatin-TN8-con3 | KDLCKMWKWMCKPP (SEQ ID NO:3) | AAAGACCTGTGCAAAATGTGGAAATG GATGTGCAAACCGCCG | (Seq ID No: 149) | 5 gly | C |
| Myostatin-TN8-con4 | KDLCKMWHWMCKPK (SEQ ID NO:4) | AAAGACCTGTGCAAAATGTGGCACTG GATGTGCAAACCGAAA | (Seq ID No: 150) | 5 gly | C |
| Myostatin-TN8-con5 | WYPCYEFHFWCYDL (SEQ ID NO:5) | TGGTACCCGTGCTACGAATTCCACTTC TGGTGCTACGACCTG | (Seq ID No: 151) | 5 gly | C |
| Myostatin-TN8-con5 | WYPCYEFHFWCYDL (SEQ ID NO:5) | TGGTACCCGTGCTACGAATTCCACTTC TGGTGCTACGACCTG | (Seq ID No: 152) | 5 gly | N |
| Myostatin-TN8-con6 | WYPCYEGHFWCYDL (SEQ ID NO:6) | TGGTACCCGTGCTACGAAGGTCACTT CTGGTGCTACGACCTG | (Seq ID No: 153) | 5 gly | C |
| Myostatin-TN8-con6 | WYPCYEGHFWCYDL (SEQ ID NO:6) | TGGTACCCGTGCTACGAAGGTCACTT CTGGTGCTACGACCTG | (Seq ID No: 154) | 5 gly | N |
| Myostatin-TN8-con7 | IFGCKWWDVQCYQF (SEQ ID NO:7) | ATCTTCGGTTGCAAATGGTGGGACGT TCAGTGCTACCAGTTC | (Seq ID No: 155) | 5 gly | C |
| Myostatin-TN8-con8 | IFGCKWWDVDCYQF (SEQ ID NO:8) | ATCTTCGGTTGCAAATGGTGGGACGT TGACTGCTACCAGTTC | (Seq ID No: 156) | 5 gly | C |
| Myostatin-TN8-con8 | IFGCKWWDVDCYQF (SEQ ID NO:8) | ATCTTCGGTTGCAAATGGTGGGACGT TGACTGCTACCAGTTC | (Seq ID No: 157) | 5 gly | N |
| Myostatin-TN8-con9 | ADWCVSPNWFCMVM (SEQ ID NO:9) | GCTGACTGGTGCGTTTCCCCGAACTG GTTCTGCATGGTTATG | (Seq ID No: 158) | 5 gly | C |
| Myostatin-TN8-con10 | HKFCPWWALFCWDF (SEQ ID NO:10) | CACAAATTCTGCCCGTGGTGGGCTCT GTTCTGCTGGGACTTC | (Seq ID No: 159) | 5 gly | C |
| Myostatin-TN8-1 | KDLCKMWHWMCKPP (SEQ ID NO:11) | AAAGACCTGTGCAAAATGTGGCACTG GATGTGCAAACCGCCG | (Seq ID No: 160) | 5 gly | C |
| Myostatin-TN8-2 | IDKCAIWGWMCPPL (SEQ ID NO:12) | ATCGACAAATGCGCTATCTGGGGTTG GATGTGCCCGCCGCTG | (Seq ID No: 161) | 5 gly | C |
| Myostatin-TN8-3 | WYPCGEFGMWCLNV (SEQ ID NO:13) | TGGTACCCGTGCGGTGAATTCGGTAT GTGGTGCCTGAACGTT | (Seq ID No: 162) | 5 gly | C |
| Myostatin-TN8-4 | WFTCLWNCDNE (SEQ ID NO:14) | TGGTTCACCTGCCTGTGGAACTGCGA CAACGAA | (Seq ID No: 163) | 5 gly | C |
| Myostatin-TN8-5 | HTPCPWFAPLCVEW (SEQ ID NO:15) | CACACCCCGTGCCCGTGGTTCGCTCC GCTGTGCGTTGAATGG | (Seq ID No: 164) | 5 gly | C |
| Myostatin-TN8-6 | KEWCRWKWMCKPE (SEQ ID NO:16) | AAAGAATGGTGCTGGCGTTGGAAATG GATGTGCAAACCGGAA | (Seq ID No: 165) | 5 gly | C |
| Myostatin-TN8-7 | FETCPSWAYFCLDI (SEQ ID NO:17) | TTCGAACCTGCCCGTCCTGGGCTTA CTTCTGCCTGGACATC | (Seq ID No: 166) | 5 gly | C |
| Myostatin-TN8-7 | FETCPSWAYFCLDI (SEQ ID NO:17) | TTCGAACCTGCCCGTCCTGGGCTTA CTTCTGCCTGGACATC | (Seq ID No: 167) | 5 gly | N |
| Myostatin-TN8-8 | AYKCEANDWGCWWL (SEQ ID NO:18) | GCTTACAAATGCGAAGCTAACGACTG GGGTTGCTGGTGGCTG | (Seq ID No: 168) | 5 gly | C |
| Myostatin-TN8-9 | NSWCEDQWHRCWWL (SEQ ID NO:19) | AACTCCTGGTGCGAAGACCAGTGGCA CCGTTGCTGGTGGCTG | (Seq ID No: 169) | 5 gly | C |
| Myostatin-TN8-10 | WSACYAGHFWCYDL (SEQ ID NO:20) | TGGTCCGCTTGCTACGCTGGTCACTTC TGGTGCTACGACCTG | (Seq ID No: 170) | 5 gly | C |
| Myostatin-TN8-11 | ANWCVSPNWFCMVM (SEQ ID NO:21) | GCTAACTGGTGCGTTTCCCCGAACTG GTTCTGCATGGTTATG | (Seq ID No: 171) | 5 gly | C |
| Myostatin-TN8-12 | WTECYQQEFWCWNL (SEQ ID NO:22) | TGGACCGAATGCTACCAGCAGGAATT CTGGTGCTGGAACCTG | (Seq ID No: 172) | 5 gly | C |

TABLE II-continued

| Peptibody Name | Peptide | Nucleotide Sequence (Seq ID No) | | L | |
|---|---|---|---|---|---|
| Myostatin-TN8-13 | ENTCERWKWMCPPK (SEQ ID NO:23) | GAAAACACCTGCGAACGTTGGAAATG GATGTGCCCGCCGAAA | (Seq ID No: 173) | 5 gly | C |
| Myostatin-TN8-14 | WLPCHQEGFWCMNF (SEQ ID NO:24) | TGGCTGCCGTGCCACCAGGAAGGTTT CTGGTGCATGAACTTC | (Seq ID No: 174) | 5 gly | C |
| Myostatin-TN8-15 | STMCSQWHWMCNPF (SEQ ID NO:25) | TCCACCATGTGCTCCCAGTGGCACTG GATGTGCAACCCGTTC | (Seq ID No: 175) | 5 gly | C |
| Myostatin-TN8-16 | IFGCHWWDVDCYQF (SEQ ID NO:26) | ATCTTCGGTTGCCACTGGTGGGACGT TGACTGCTACCAGTTC | (Seq ID No: 176) | 5 gly | C |
| Myostatin-TN8-17 | IYGCKWWDIQCYDI (SEQ ID NO:27) | ATCTACGGTTGCAAATGGTGGGACAT CCAGTGCTACGACATC | (Seq ID No: 177) | 5 gly | C |
| Myostatin-TN8-18 | PDWCIDPDWWCKFW (SEQ ID NO:28) | CCGGACTGGTGCATCGATCCGGACTG GTGGTGCAAATTCTGG | (Seq ID No: 178) | 5 gly | C |
| Myostatin-TN8-19 | QGHCTRWPWMCPPY (SEQ ID NO:29) | CAGGGTCACTGCACCCGTTGGCCGTG GATGTGCCCGCCGTAC | (Seq ID No: 179) | 5 gly | C |
| Myostatin-TN8-20 | WQECYREGFWCLQT (SEQ ID NO:30) | TGGCAGGAATGCTACCGTGAAGGTTT CTGGTGCCTGCAGACC | (Seq ID No: 180) | 5 gly | C |
| Myostatin-TN8-21 | WFDCYGPGFKCWSP (SEQ ID NO:31) | TGGTTCGACTGCTACGGTCCGGGTTTC AAATGCTGGTCCCCG | (Seq ID No: 181) | 5 gly | C |
| Myostatin-TN8-22 | GVRCPKGHLWCLYP (SEQ ID NO:32) | GGTGTTCGTTGCCCGAAAGGTCACCT GTGGTGCCTGTACCCG | (Seq ID No: 182) | 5 gly | C |
| Myostatin-TN8-23 | HWACGYWPWSCKWV (SEQ ID NO:33) | CACTGGGCTTGCGGTTACTGGCCGTG GTCCTGCAAATGGGTT | (Seq ID No: 183) | 5 gly | C |
| Myostatin-TN8-24 | GPACHSPWWWCVFG (SEQ ID NO:34) | GGTCCGGCTTGCCACTCCCCGTGGTG GTGGTGCGTTTTCGGT | (Seq ID No: 184) | 5 gly | C |
| Myostatin-TN8-25 | TTWCISPMWFCSQQ (SEQ ID NO:35) | ACCACCTGGTGCATCTCCCCGATGTG GTTCTGCTCCCAGCAG | (Seq ID No: 185) | 5 gly | C |
| Myostatin-TN8-26 | HKFCPPWAIFCWDF (SEQ ID NO:36) | CACAAATTCTGCCCGCCGTGGGCTAT CTTCTGCTGGGACTTC | (Seq ID No: 186) | 5 gly | N |
| Myostatin-TN8-27 | PDWCVSPRWYCNMW (SEQ ID NO:37) | CCGGACTGGTGCGTTTCCCCGCGTTG GTACTGCAACATGTGG | (Seq ID No: 187) | 5 gly | N |
| Myostatin-TN8-28 | VWKCHWFGMDCEPT (SEQ ID NO:38) | GTTTGGAAATGCCACTGGTTCGGTAT GGACTGCGAACCGACC | (Seq ID No: 188) | 5 gly | N |
| Myostatin-TN8-29 | KKHCQIWTWMCAPK (SEQ ID NO:39) | AAAAAACACTGCCAGATCTGGACCTG GATGTGCGCTCCGAAA | (Seq ID No: 189) | 5 gly | N |
| Myostatin-TN8-30 | WFQCGSTLFWCYNL (SEQ ID NO:40) | TGGTTCCAGTGCGGTTCCACCCTGTTC TGGTGCTACAACCTG | (Seq ID No: 190) | 5 gly | N |
| Myostatin-TN8-31 | WSPCYDHYFYCYTI (SEQ ID NO:41) | TGGTCCCCGTGCTACGACCACTACTTC TACTGCTACACCATC | (Seq ID No: 191) | 5 gly | N |
| Myostatin-TN8-32 | SWMCGFFKEVCMWV (SEQ ID NO:42) | TCCTGGATGTGCGGTTTCTTCAAAGA AGTTTGCATGTGGGTT | (Seq ID No: 192) | 5 gly | N |
| Myostatin-TN8-33 | EMLCMIHPVFCNPH (SEQ ID NO:43) | GAAATGCTGTGCATGATCCACCCGGT TTTCTGCAACCCGCAC | (Seq ID No: 193) | 5 gly | N |
| Myostatin-TN8-34 | LKTCNLWPWMCPPL (SEQ ID NO:44) | CTGAAAACCTGCAACCTGTGGCCGTG GATGTGCCCGCCGCTG | (Seq ID No: 194) | 5 gly | N |
| Myostatin-TN8-35 | VVGCKWYEAWCYNK (SEQ ID NO:45) | GTTGTTGGTTGCAAATGGTACGAAGC TTGGTGCTACAACAAA | (Seq ID No: 195) | 5 gly | N |
| Myostatin-TN8-36 | PIHCTQWAWMCPPT (SEQ ID NO:46) | CCGATCCACTGCACCCAGTGGGCTTG GATGTGCCCGCCGACC | (Seq ID No: 196) | 5 gly | N |
| Myostatin-TN8-37 | DSNCPWYFLSCVIF (SEQ ID NO:47) | GACTCCAACTGCCCGTGGTACTTCCT GTCCTGCGTTATCTTC | (Seq ID No: 197) | 5 gly | N |
| Myostatin-TN8-38 | HIWCNLAMMKCVEM (SEQ ID NO:48) | CACATCTGGTGCAACCTGGCTATGAT GAAATGCGTTGAAATG | (Seq ID No: 198) | 5 gly | N |

TABLE II-continued

| Peptibody Name | Peptide | Nucleotide Sequence (Seq ID No) | L | | |
|---|---|---|---|---|---|
| Myostatin-TN8-39 | NLQCIYFLGKCIYF (SEQ ID NO:49) | AACCTGCAGTGCATCTACTTCCTGGG TAAATGCATCTACTTC (Seq ID No: 199) | 5 gly | N | |
| Myostatin-TN8-40 | AWRCMWFSDVCTPG (SEQ ID NO:50) | GCTTGGCGTTGCATGTGGTTCTCCGAC GTTTGCACCCCGGGT (Seq ID No: 200) | 5 gly | N | |
| Myostatin-TN8-41 | WFRCFLDADWCTSV (SEQ ID NO:51) | TGGTTTCGTTGTTTTCTTGATGCTGAT TGGTGTACTTCTGTT (Seq ID No: 201) | 5 gly | N | |
| Myostatin-TN8-42 | EKICQMWSWMCAPP (SEQ ID NO:52) | GAAAAAATTTGTCAAATGTGGTCTTG GATGTGTGCTCCACCA (Seq ID No: 202) | 5 gly | N | |
| Myostatin-TN8-43 | WFYCHLNKSECTEP (SEQ ID NO:53) | TGGTTTTATTGTCATCTTAATAAATCT GAATGTACTGAACCA (Seq ID No: 203) | 5 gly | N | |
| Myostatin-TN8-44 | FWRCAIGIDKCKRV (SEQ ID NO:54) | TTTTGGCGTTGTGCTATTGGTATTGAT AAATGTAAACGTGTT (Seq ID No: 204) | 5 gly | N | |
| Myostatin-TN8-45 | NLGCKWYEVWCFTY (SEQ ID NO:55) | AATCTTGGTTGTAAATGGTATGAAGT TTGGTGTTTTACTTAT (Seq ID No: 205) | 5 gly | N | |
| Myostatin-TN8-46 | IDLCNMWDGMCYPP (SEQ ID NO:56) | ATTGATCTTTGTAATATGTGGGATGGT ATGTGTTATCCACCA (Seq ID No: 206) | 5 gly | N | |
| Myostatin-TN8-47 | EMPCNIWGWMCPPV (SEQ ID NO:57) | GAAATGCCATGTAATATTTGGGGTTG GATGTGTCCACCAGTT (Seq ID No: 207) | 5 gly | N | |
| Myostatin-TN12-1 | WFRCVLTGIVDWSECF GL (SEQ ID NO:58) | TGGTTCCGTTGCGTTCTGACCGGTATC GTTGACTGGTCCGAATGCTTCGGTCT G (Seq ID No: 208) | 5 gly | N | |
| Myostatin-TN12-2 | GFSCTFGLDEFYVDCSP F (SEQ ID NO:59) | GGTTTCTCCTGCACCTTCGGTCTGGAC GAATTCTACGTTGACTGCTCCCCGTTC (Seq ID No: 209) | 5 gly | N | |
| Myostatin-TN12-3 | LPWCHDQVNADWGFC MLW (SEQ ID NO:60) | CTGCCGTGGTGCCACGACCAGGTTAA CGCTGACTGGGGTTTCTGCATGCTGT GG (Seq ID No: 210) | 5 gly | N | |
| Myostatin-TN12-4 | YPTCSEKFWIYGQTCV LW (SEQ ID NO:61) | TACCCGACCTGCTCCGAAAAATTCTG GATCTACGGTCAGACCTGCGTTCTGT GG (Seq ID No: 211) | 5 gly | N | |
| Myostatin-TN12-5 | LGPCPIHHGPWPQYCV YW (SEQ ID NO:62) | CTGGGTCCGTGCCCGATCCACCACGG TCCGTGGCCGCAGTACTGCGTTTACT GG (Seq ID No: 212) | 5 gly | N | |
| Myostatin-TN12-6 | PFPCETHQISWLGHCLS F (SEQ ID NO:63) | CCGTTCCCGTGCGAAACCCACCAGAT CTCCTGGCTGGGTCACTGCCTGTCCTT C (Seq ID No: 213) | 5 gly | N | |
| Myostatin-TN12-7 | HWGCEDLMWSWHPLC RRP (SEQ ID NO:64) | CACTGGGGTTGCGAAGACCTGATGTG GTCCTGGCACCCGCTGTGCCGTCGTC CG (Seq ID No: 214) | 5 gly | N | |
| Myostatin-TN12-8 | LPLCDADMMPTIGFCV AY (SEQ ID NO:65) | CTGCCGCTGTGCGACGCTGACATGAT GCCGACCATCGGTTTCTGCGTTGCTTA C (Seq ID No: 215) | 5 gly | N | |
| Myostatin-TN12-9 | SHWCETTFWMNYAKC VHA (SEQ ID NO:66) | TCCCACTGGTGCGAAACCACCTTCTG GATGAACTACGCTAAATGCGTTCACG CT (Seq ID No: 216) | 5 gly | N | |
| Myostatin-TN12-10 | LPKCTHVPFDQGGFCL WY (SEQ ID NO:67) | CTGCCGAAATGCACCCACGTTCCGTT CGACCAGGGTGGTTTCTGCCTGTGGT AC (Seq ID No: 217) | 5 gly | N | |
| Myostatin-TN12-11 | FSSCWSPVSRQDMFCV FY (SEQ ID NO:68) | TTCTCCTCCTGCTGGTCCCCGGTTTCC CGTCAGGACATGTTCTGCGTTTTCTAC (Seq ID No: 218) | 5 gly | N | |
| Myostatin-TN12-13 | SHKCEYSGWLQPLCYR P (SEQ ID NO:69) | TCCCACAAATGCGAATACTCCGGTTG GCTGCAGCCGCTGTGCTACCGTCCG (Seq ID No: 219) | 5 gly | N | |
| Myostatin-TN12-14 | PWWCQDNYVQHMLH CDSP (SEQ ID NO:70) | CCGTGGTGGTGCCAGGACAACTACGT TCAGCACATGCTGCACTGCGACTCCC CG (Seq ID No: 220) | 5 gly | N | |

TABLE II-continued

| Peptibody Name | Peptide | Nucleotide Sequence (Seq ID No) | | L | |
|---|---|---|---|---|---|
| Myostatin-TN12-15 | WFRCMLMNSFDAFQCVSY (SEQ ID NO:71) | TGGTTCCGTTGCATGCTGATGAACTCCTTCGACGCTTTCCAGTGCGTTTCCTAC | (Seq ID No: 221) | 5 gly | N |
| Myostatin-TN12-16 | PDACRDQPWYMFMGCMLG (SEQ ID NO:72) | CCCGGACGCTTGCCGTGACCAGCCGTGGTACATGTTCATGGGTTGCATGCTGGGT | (Seq ID No: 222) | 5 gly | N |
| Myostatin-TN12-17 | FLACFVEFELCFDS (SEQ ID NO:73) | TTCCTGGCTTGCTTCGTTGAATTCGAACTGTGCTTCGACTCC | (Seq ID No: 223) | 5 gly | N |
| Myostatin-TN12-18 | SAYCIITESDPYVLCVPL (SEQ ID NO:74) | TCCGCTTACTGCATCATCACCGAATCCGACCCGTACGTTCTGTGCGTTCCGCTG | (Seq ID No: 224) | 5 gly | N |
| Myostatin-TN12-19 | PSICESYSTMWLPMCQHN (SEQ ID NO:75) | CCGTCCATCTGCGAATCCTACTCCACCATGTGGCTGCCGATGTGCCAGCACAAC | (Seq ID No: 225) | 5 gly | N |
| Myostatin-TN12-20 | WLDCHDDSWAWTKMCRSH (SEQ ID NO:76) | TGGCTGGACTGCCACGACGACTCCTGGGCTTGGACCAAAATGTGCCGTTCCCAC | (Seq ID No: 226) | 5 gly | N |
| Myostatin-TN12-21 | YLNCVMMNTSPFVECVFN (SEQ ID NO:77) | TACCTGAACTGCGTTATGATGAACACCTCCCCGTTCGTTGAATGCGTTTTCAAC | (Seq ID No: 227) | 5 gly | N |
| Myostatin-TN12-22 | YPWCDGFMIQQGITCMFY (SEQ ID NO:78) | TACCCGTGGTGCGACGGTTTCATGATCCAGCAGGGTATCACCTGCATGTTCTAC | (Seq ID No: 228) | 5 gly | N |
| Myostatin-TN12-23 | FDYCTWLNGFKDWKCWSR (SEQ ID NO:79) | TTCGACTACTGCACCTGGCTGAACGGTTTCAAAGACTGGAAATGCTGGTCCCGT | (Seq ID No: 229) | 5 gly | N |
| Myostatin-TN12-24 | LPLCNLKEISHVQACVLF (SEQ ID NO:80) | CTGCCGCTGTGCAACCTGAAAGAAATCTCCCACGTTCAGGCTTGCGTTCTGTTC | (Seq ID No: 230) | 5 gly | N |
| Myostatin-TN12-25 | SPECAFARWLGIEQCQRD (SEQ ID NO:81) | TCCCCGGAATGCGCTTTCGCTCGTTGGCTGGGTATCGAACAGTGCCAGCGTGAC | (Seq ID No: 231) | 5 gly | N |
| Myostatin-TN12-26 | YPQCFNLHLLEWTECDWF (SEQ ID NO:82) | TACCCGCAGTGCTTCAACCTGCACCTGCTGGAATGGACCGAATGCGACTGGTTC | (Seq ID No: 232) | 5 gly | N |
| Myostatin-TN12-27 | RWRCEIYDSEFLPKCWFF (SEQ ID NO:83) | CGTTGGCGTTGCGAAATCTACGACTCCGAATTCCTGCCGAAATGCTGGTTCTTC | (Seq ID No: 233) | 5 gly | N |
| Myostatin-TN12-28 | LVGCDNVWHRCKLF (SEQ ID NO:84) | CTGGTTGGTTGCGACAACGTTTGGCACCGTTGCAAACTGTTC | (Seq ID No: 234) | 5 gly | N |
| Myostatin-TN12-29 | AGWCHVWGEMFGMGCSAL (SEQ ID NO:85) | GCTGGTTGGTGCCACGTTTGGGGTGAAATGTTCGGTATGGGTTGCTCCGCTCTG | (Seq ID No: 235) | 5 gly | N |
| Myostatin-TN12-30 | HHECEWMARWMSLDCVGL (SEQ ID NO:86) | CACCACGAATGCGAATGGATGGCTCGTTGGATGTCCCTGGACTGCGTTGGTCTG | (Seq ID No: 236) | 5 gly | N |
| Myostatin-TN12-31 | FPMCGIAGMKDFDFCVWY (SEQ ID NO:87) | TTCCCGATGTGCGGTATCGCTGGTATGAAAGACTTCGACTTCTGCGTTTGGTAC | (Seq ID No: 237) | 5 gly | N |
| Myostatin-TN12-32 | RDDCTFWPEWLWKLCERP (SEQ ID NO:88) | CGTGATGATTGTACTTTTTGGCCAGAATGGCTTTGGAAACTTTGTGAACGTCCA | (Seq ID No: 238) | 5 gly | N |
| Myostatin-TN12-33 | YNFCSYLFGVSKEACQLP (SEQ ID NO:89) | TATAATTTTTGTTCTTATCTTTTTGGTGTTTCTAAAGAAGCTTGTCAACTTCCA | (Seq ID No: 239) | 5 gly | N |
| Myostatin-TN12-34 | AHWCEQGPWRYGNICMAY (SEQ ID NO:90) | GCTCATTGGTGTGAACAAGGTCCATGGCGTTATGGTAATATTTGTATGGCTTAT | (Seq ID No: 240) | 5 gly | N C |

TABLE II-continued

| Peptibody Name | Peptide | Nucleotide Sequence (Seq ID No) | | L | |
| --- | --- | --- | --- | --- | --- |
| Myostatin-TN12-35 | NLVCGKISAWGDEACARA (SEQ ID NO:91) | AATCTTGTTTGTGGTAAAATTTCTGCTTGGGGTGATGAAGCTTGTGCTCGTGCT | (Seq ID No: 241) | 5 gly | N |
| Myostatin-TN12-36 | HNVCTIMGPSMKWFCWND (SEQ ID NO:92) | CATAATGTTTGTACTATTATGGGTCCATCTATGAAATGGTITTTGTTGGAATGAT | (Seq ID No: 242) | 5 gly | N C |
| Myostatin-TN12-37 | NDLCAMWGWRNTIWCQNS (SEQ ID NO:93) | AATGATCTTTGTGCTATGTGGGGTTGGCGTAATACTATTTGGTGTCAAAATTCT | (Seq ID No: 243) | 5 gly | N C |
| Myostatin-TN12-38 | PPFCQNDNDMLQSLCKLL (SEQ ID NO:94) | CCACCATTTTGTCAAAATGATAATGATATGCTTCAATCTCTTTGTAAACTTCTT | (Seq ID No: 244) | 5 gly | N |
| Myostatin-TN12-39 | WYDCNVPNELLSGLCRLF (SEQ ID NO:95) | TGGTATGATTGTAATGTTCCAAATGAACTTCTTTCTGGTCTTTGTCGTCTTTTT | (Seq ID No: 245) | 5 gly | N |
| Myostatin-TN12-40 | YGDCDQNHWMWPFTCLSL (SEQ ID NO:96) | TATGGTGATTGTGATCAAAATCATTGGATGTGGCCATTTACTTGTCTTTCTCTT | (Seq ID No: 246) | 5 gly | N C |
| Myostatin-TN12-41 | GWMCHFDLHDWGATCQPD (SEQ ID NO:97) | GGTTGGATGTGTCATTTTGATCTTCATGATTGGGGTGCTACTTGTCAACCAGAT | (Seq ID No: 247) | 5 gly | N |
| Myostatin-TN12-42 | YFHCMFGGHEFEVHCESF (SEQ ID NO:98) | TATTTTCATTGTATGTTTGGTGGTCATGAATTTGAAGTTCATTGTGAATCTTTT | (Seq ID No: 248) | 5 gly | N C |
| Myostatin-TN12-43 | AYWCWHGQCVRF (SEQ ID NO:99) | GCTTATTGGTGTTGGCATGGTCAATGTGTTCGTTTT | (Seq ID No: 249) | 5 gly | N |
| Myostatin-Linear-1 | SEHWTFTDWDGNEWWVRPF (SEQ ID NO:100) | TCCGAACACTGGACCTTCACCGACTGGGACGGTAACGAATGGTGGGTTCGTCCGTTC | (Seq ID No: 250) | 5 gly | N |
| Myostatin-Linear-2 | MEMLDSLFELLKDMVPISKA (SEQ ID NO:101) | ATGGAAATGCTGGACTCCCTGTTCGAACTGCTGAAAGACATGGTTCCGATCTCCAAAGCT | (Seq ID No: 251) | 5 gly | N |
| Myostatin-Linear-3 | SPPEEALMEWLGWQYGKFT (SEQ ID NO:102) | TCCCCGCCGGAAGAAGCTCTGATGGAATGGCTGGGTTGGCAGTACGGTAAATTCACC | (Seq ID No: 252) | 5 gly | N |
| Myostatin-Linear-4 | SPENLLNDLYILMTKQEWYG (SEQ ID NO:103) | TCCCCGGAAAACCTGCTGAACGACCTGTACATCCTGATGACCAAACAGGAATGGTACGGT | (Seq ID No: 253) | 5 gly | N |
| Myostatin-Linear-5 | FHWEEGIPFHVVTPYSYDRM (SEQ ID NO:104) | TTCCACTGGGAAGAAGGTATCCCGTTCCACGTTGTTACCCCGTACTCCTACGACCGTATG | (Seq ID No: 254) | 5 gly | N |
| Myostatin-Linear-6 | KRLLEQFMNDLAELVSGHS (SEQ ID NO:105) | AAACGTCTGCTGGAACAGTTCATGAACGACCTGGCTGAACTGGTTTCCGGTCACTCC | (Seq ID No: 255) | 5 gly | N |
| Myostatin-Linear-7 | DTRDALFQEFYEFVRSRLVI (SEQ ID NO:106) | GACACCCGTGACGCTCTGTTCCAGGAATTCTACGAATTCGTTCGTTCCCGTCTGGTTATC | (Seq ID No: 256) | 5 gly | N |
| Myostatin-Linear-8 | RMSAAPRPLTYRDIMDQYWH (SEQ ID NO:107) | CGTATGTCCGCTGCTCCGCGTCCGCTGACCTACCGTGACATCATGGACCAGTACTGGCAC | (Seq ID No: 257) | 5 gly | N |
| Myostatin-Linear-9 | NDKAHFFEMFMFDVHNFVES (SEQ ID NO:108) | AACGACAAAGCTCACTTCTTCGAAATGTTCATGTTCGACGTTCACAACTTCGTTGAATCC | (Seq ID No: 258) | 5 gly | N |
| Myostatin-Linear-10 | QTQAQKIDGLWELLQSIRNQ (SEQ ID NO:109) | CAGACCCAGGCTCAGAAAATCGACGGTCTGTGGGAACTGCTGCAGTCCATCCGTAACCAG | (Seq ID No: 259) | 5 gly | N |
| Myostatin-Linear-11 | MLSEFEEFLGNLVHRQEA (SEQ ID NO:110) | ATGCTGTCCGAATTCGAAGAATTCCTGGGTAACCTGGTTCACCGTCAGGAAGCT | (Seq ID No: 260) | 5 gly | N |

TABLE II-continued

| Peptibody Name | Peptide | Nucleotide Sequence | (Seq ID No) | L | |
|---|---|---|---|---|---|
| Myostatin-Linear-12 | YTPKMGSEWTSFWHNRIHYL (SEQ ID NO:111) | TACACCCCGAAAATGGGTTCCGAATGGACCTCCTTCTGGCACAACCGTATCCACTACCTG | (Seq ID No: 261) | 5 gly | N |
| Myostatin-Linear-13 | LNDTLLRELKMVLNSLSDMK (SEQ ID NO:112) | CTGAACGACACCCTGCTGCGTGAACTGAAAATGGTTCTGAACTCCCTGTCCGACATGAAA | (Seq ID No: 262) | 5 gly | N |
| Myostatin-Linear-14 | FDVERDLMRWLEGFMQSAAT (SEQ ID NO:113) | TTCGACGTTGAACGTGACCTGATGCGTTGGCTGGAAGGTTTCATGCAGTCCGCTGCTACC | (Seq ID No: 263) | 5 gly | N |
| Myostatin-Linear-15 | HHGWNYLRKGSAPQWFEAWV (SEQ ID NO:114) | CACCACGGTTGGAACTACCTGCGTAAAGGTTCCGCTCCGCAGTGGTTCGAAGCTTGGGTT | (Seq ID No: 264) | 5 gly | N |
| Myostatin-Linear-16 | VESLHQLQMWLDQKLASGPH (SEQ ID NO:115) | GTTGAATCCCTGCACCAGCTGCAGATGTGGCTGGACCAGAAACTGGCTTCCGGTCCGCAC | (Seq ID No: 265) | 5 gly | N |
| Myostatin-Linear-17 | RATLLKDFWQLVEGYGDN (SEQ ID NO:116) | CGTGCTACCCTGCTGAAAGACTTCTGGCAGCTGGTTGAAGGTTACGGTGACAAC | (Seq ID No: 266) | 5 gly | N |
| Myostatin-Linear-18 | EELLREFYRFVSAFDY (SEQ ID NO:117) | GAAGAACTGCTGCGTGAATTCTACCGTTTCGTTTCCGCTTTCGACTAC | (Seq ID No: 267) | 5 gly | N |
| Myostatin-Linear-19 | GLLDEFSHFIAEQFYQMPGG (SEQ ID NO:118) | GGTCTGCTGGACGAATTCTCCCACTTCATCGCTGAACAGTTCTACCAGATGCCGGGTGGT | (Seq ID No: 268) | 5 gly | N |
| Myostatin-Linear-20 | YREMSMLEGLLDVLERLQHY (SEQ ID NO:119) | TACCGTGAAATGTCCATGCTGGAAGGTCTGCTGGACGTTCTGGAACGTCTGCAGGACTAC | (Seq ID No: 269) | 5 gly | N |
| Myostatin-Linear-21 | HNSSQMLLSELIMLVGSMMQ (SEQ ID NO:120) | CACAACTCCTCCCAGATGCTGCTGTCCGAACTGATCATGCTGGTTGGTTCCATGATGCAG | (Seq ID No: 270) | 5 gly | N |
| Myostatin-Linear-22 | WREHFLNSDYIRDKLIAIDG (SEQ ID NO:121) | TGGCGTGAACACTTCCTGAACTCCGACTACATCCGTGACAAACTGATCGCTATCGACGGT | (Seq ID No: 271) | 5 gly | N |
| Myostatin-Linear-23 | QFPFYVFDDLPAQLEYWIA (SEQ ID NO:122) | CAGTTCCCGTTCTACGTTTTCGACGACCTGCCGGCTCAGCTGGAATACTGGATCGCT | (Seq ID No: 272) | 5 gly | N |
| Myostatin-Linear-24 | EFFHWLHNHRSEVNHWLDMN (SEQ ID NO:123) | GAATTCTTCCACTGGCTGCACAACCACCGTTCCGAAGTTAACCACTGGCTGGACATGAAC | (Seq ID No: 273) | 5 gly | N |
| Myostatin-Linear-25 | EALFQNFFRDVLTLSEREY (SEQ ID NO:124) | GAAGCTCTTTTTCAAAATTTTTTCGTGATGTTCTTACTCTTTCTGAACGTGAATAT | (Seq ID No: 274) | 5 gly | N C |
| Myostatin-Linear-26 | QYWEQQWMTYFRENGLHVQY (SEQ ID NO:125) | CAATATTGGGAACAACAATGGATGACTTATTTTCGTGAAAATGGTCTTCATGTTCAATAT | (Seq ID No: 275) | 5 gly | N |
| Myostatin-Linear-27 | NQRMMLEDLWRIMTPMFGRS (SEQ ID NO:126) | AATCAACGTATGATGCTTGAAGATCTTTGGCGTATTATGACTCCAATGTTTGGTCGTTCT | (Seq ID No: 276) | 5 gly | N C |
| Myostatin-Linear-29 | FLDELKAELSRHYALDDLDE (SEQ ID NO:127) | TTTCTTGATGAACTTAAAGCTGAACTTTCTCGTCATTATGCTCTTGATGATCTTGATGAA | (Seq ID No: 277) | 5 gly | N |
| Myostatin-Linear-30 | GKLIEGLLNELMQLETFMPD (SEQ ID NO:128) | GGTAAACTTATTGAAGGTCTTCTTAATGAACTTATGCAACTTGAAACTTTTATGCCAGAT | (Seq ID No: 278) | 5 gly | N C |
| Myostatin-Linear-31 | ILLLDEYKKDWKSWF (SEQ ID NO:129) | ATTCTTCTTCTTGATGAATATAAAAAAGATTGGAAATCTTGGTTT | (Seq ID No: 279) | 5 gly | N |
| Myostatin-2XTN8-19 kc | QGHCTRWPWMCPPYGSGSATGGSGSTASSGSGSATGQGHCTRWPWMC | CAGGGCCACTGTACTCGCTGGCCGTGGATGTGCCCGCCGTACGGTTCTGGTTCCGCTACCGGTGGTTCTGGTTCCACTG | (Seq ID No: 280) | 1k | N |

TABLE II-continued

| Peptibody Name | Peptide | Nucleotide Sequence (Seq ID No) | | L | |
|---|---|---|---|---|---|
| | PPY<br>(SEQ ID NO:130) | CTTCTTCTGGTTCCGGTTCTGCTACTG<br>GTCAGGGTCACTGCACTCGTTGGCCA<br>TGGATGTGTCCACCGTAT | | | |
| Myostatin-<br>2XTN8-CON6 | WYPCYEGHFWCYDLG<br>SGSTASSGSGSATGWY<br>PCYEGHFWCYDL<br>(SEQ ID NO:131) | TGGTATCCGTGTTATGAGGGTCACTTC<br>TGGTGCTACGATCTGGGTTCTGGTTCC<br>ACTGCTTCTTCTGGTTCCGGTTCCGCT<br>ACTGGTTGGTACCCGTGCTACGAAGG<br>TCACTTTTGGTGTTATGATCTG | (Seq ID No: 281) | 5 gly | C |
| Myostatin-<br>2XTN8-5 kc | HTPCPWFAPLCVEWGS<br>GSATGGSGSTASSGSGS<br>ATGHTPCPWFAPLCVE<br>W<br>(SEQ ID NO:132) | CACACTCCGTGTCCGTGGTTTGCTCCG<br>CTGTGCGTTGAATGGGGTTCTGGTTCC<br>GCTACTGGTGGTTCCGGTTCCACTGCT<br>TCTTCTGGTTCCGGTTCTGCAACTGGT<br>CACACCCCGTGCCCGTGGTTTGCACC<br>GCTGTGTGTAGAGTGG | (Seq ID No: 282) | 1k | C |
| Myostatin-<br>2XTN8-18 kc | PDWCIDPDWWCKFWG<br>SGSATGGSGSTASSGSG<br>SATGPDWCIDPDWWC<br>KFW<br>(SEQ ID NO:133) | CCGGATTGGTGTATCGACCCGGACTG<br>GTGGTGCAAATTCTGGGGTTCTGGTTC<br>CGCTACCGGTGGTTCCGGTTCCACTG<br>CTTCTTCTGGTTCCGGTTCTGCAACTG<br>GTCCGGACTGGTGCATCGACCCGGAT<br>TGGTGGTGTAAATTTTGG | (Seq ID No: 283) | 1k | C |
| Myostatin-<br>2XTN8-11 kc | ANWCVSPNWFCMVM<br>GSGSATGGSGSTASSGS<br>GSATGANWCVSPNWF<br>CMVM<br>(SEQ ID NO:134) | CCGGATTGGTGTATCGACCCGGACTG<br>GTGGTGCAAATTCTGGGGTTCTGGTTC<br>CGCTACCGGTGGTTCCGGTTCCACTG<br>CTTCTTCTGGTTCCGGTTCTGCAACTG<br>GTCCGGACTGGTGCATCGACCCGGAT<br>TGGTGGTGTAAATTTTGG | (Seq ID No; 284) | 1k | C |
| Myostatin-<br>2XTN8-25 kc | PDWCIDPDWWCKFWG<br>SGSATGGSGSTASSGSG<br>SATGPDWCIDPDWWC<br>KFW<br>(SEQ ID NO:135) | ACCACTTGGTGCATCTCTCCGATGTG<br>GTTCTGCTCTCAGCAGGGTTCTGGTTC<br>CACTGCTTCTTCTGGTTCCGGTTCTGC<br>AACTGGTACTACTGGTGTATCTCTCC<br>AATGTGGTTTTGTTCTCAGCAA | (Seq ID No: 285) | 1k | C |
| Myostatin-<br>2XTN8-23 kc | HWACGYWPWSCKWV<br>GSGSATGGSGSTASSGS<br>GSATGHWACGYWPWS<br>CKWV<br>(SEQ ID NO:136) | CACTGGGCATGTGGCTATTGGCCGTG<br>GTCCTGCAAATGGGTTGGTTCTGGTTC<br>CGCTACCGGTGGTTCCGGTTCCACTG<br>CTTCTTCTGGTTCCGGTTCTGCAACTG<br>GTCACTGGGCTTGCGGTTACTGGCCG<br>TGGTCTTGTAAATGGGTT | (Seq ID No: 286) | 1k | C |
| Myostatin-TN8-<br>29-19 kc | KKHCQIWTWMCAPKG<br>SGSATGGSGSTASSGSG<br>SATGQGHCTRWPWMC<br>PPY<br>(SEQ ID NO:137) | AAAAAACACTGTCAGATCTGGACTTG<br>GATGTGCGCTCCGAAAGGTTCTGGTT<br>CCGCTACCGGTGGTTCTGGTTCCACTG<br>CTTCTTCTGGTTCCGGTTCCGCTACTG<br>GTCAGGGTCACTGCACTCGTTGGCCA<br>TGGATGTGTCCGCCGTAT | (Seq ID No: 287) | 1k | C |
| Myostatin-TN8-<br>19-29 kc | QGHCTRWPWMCPPYG<br>SGSATGGSGSTASSGSG<br>SATGKKHCQIWTWMC<br>APK<br>(SEQ ID NO:138) | CAGGGTCACTGCACCCGTTGGCCGTG<br>GATGTGCCCGCCGTACGGTTCTGGTT<br>CCGCTACCGGTGGTTCTGGTTCCACTG<br>CTTCTTCTGGTTCCGGTTCTGCTACTG<br>GTAAAAAACACTGCCAGATCTGGACT<br>TGGATGTGCGCTCCGAAA | (Seq ID No: 288) | 1k | C |
| Myostatin-TN8-<br>29-19 kn | KKHCQIWTWMCAPKG<br>SGSATGGSGSTASSGSG<br>SATGQGHCTRWPWMC<br>PPY<br>(SEQ ID NO:139) | AAAAAACACTGTCAGATCTGGACTTG<br>GATGTGCGCTCCGAAAGGTTCTGGTT<br>CCGCTACCGGTGGTTCTGGTTCCACTG<br>CTTCTTCTGGTTCCGGTTCCGCTACTG<br>GTCAGGGTCACTGCACTCGTTGGCCA<br>TGGATGTGTCCGCCGTAT | (Seq ID No: 289) | 1k | N |
| Myostatin-TN8-<br>29-19-8g | KKHCQIWTWMCAPKG<br>GGGGGGQGHCTRWP<br>WMCPPY<br>(SEQ ID NO:140) | AAAAAACACTGCCAGATCTGGACTTG<br>GATGTGCGCTCCGAAAGGTGGTGGTG<br>GTGGTGGCGGTGGCCAGGGTCACTGC<br>ACCCGTTGGCCGTGGATGTGTCCGCC<br>GTAT | (Seq ID No: 290) | 8 gly | C |
| Myostatin-TN8-<br>19-29-6gc | QGHCTRWPWMCPPYG<br>GGGGGKKHCQIWTWM<br>CAPK<br>(SEQ ID NO:141) | CAGGGTCACTGCACCCGTTGGCCGTG<br>GATGTGCCCGCCGTACGGTGGTGGTG<br>GTGGTGGCAAAAAACACTGCCAGATC<br>TGGACTTGGATGTGCGCTCCGAAA | (Seq ID No: 291) | 6 gly | C |

EXAMPLE 3

In Vitro Assays

C2C12 Cell Based Myostatin Activity Assay

This assay demonstrates the myostatin neutralizing capability of the inhibitor being tested by measuring the extent that binding of myostatin to its receptor is inhibited.

A myostatin-responsive reporter cell line was generated by transfection of C2C12 myoblast cells (ATCC No: CRL-1772) with a pMARE-luc construct. The pMARE-luc construct was made by cloning twelve repeats of the CAGA sequence, representing the myostatin/activin response elements (Dennler et al. EMBO 17: 3091-3100 (1998)) into a pLuc-MCS reporter vector (Stratagene cat #219087) upstream of the TATA box. The myoblast C2C12 cells naturally express myostatin/activin receptors on its cell-surface. When myostatin binds the cell receptors, the Smad pathway is activated, and phosphorylated Smad binds to the response element (Macias-Silva et al. Cell 87:1215 (1996)), resulting in the expression of the lucerase gene. Luciferase activity is then measured using a commercial luciferase reporter assay kit (cat #E4550, Promega, Madison, Wis.) according to manufacturer's protocol. A stable line of C2C12 cells that had been transfected with pMARE-luc (C2C12/pMARE clone #44) was used to measure myostatin activity according to the following procedure.

Equal numbers of the reporter cells (C2C12/pMARE clone #44) were plated into 96 well cultures. A first round screening using two dilutions of peptibodies was performed with the myostatin concentration fixed at 4 nM. Recombinant mature myostatin was pre-incubated for 2 hours at room temperature with peptibodies at 40 nM and 400 nM respectively. The reporter cell culture was treated with the myostatin with or without peptibodies for six hours. Myostatin activity was measured by determining the luciferase activity in the treated cultures. This assay was used to initially identify peptibody hits that inhibited the myostatin signaling activity in the reporter assay. Subsequently, a nine point titration curve was generated with the myostatin concentration fixed at 4 nM. The myostatin was preincubated with each of the following nine concentrations of peptibodies: 0.04 mM, 0.4 nM, 4 nM, 20 nM, 40 nM, 200 nM, 400 nM, 2 uM and 4 uM for two hours before adding the mixture to the reporter cell culture. The $IC_{50}$ values were for a number of examplary peptibodies are provided in Tables III and for affinity matured peptibodies, in Table VIII.

BIAcore® Assay

An affinity analysis of each candidate myostatin peptibody was performed on a BIAcore®3000 (Biacore, Inc., Piscataway, N.J.), apparatus using sensor chip CM5, and 0.005 percent P20 surfactant (Biacore, Inc.) as running buffer. Recombinant mature myostatin protein was immobilized to a research grade CM5 sensor chip (Biacore, Inc.) via primary amine groups using the Amine Coupling Kit (Biacore, Inc.) according to the manufacturer's suggested protocol.

Direct binding assays were used to screen and rank the peptibodies in order of their ability to bind to immobilized myostatin. Binding assays were carried by injection of two concentrations (40 and 400 nM) of each candidate myostatin-binding peptibody to the immobilized myostatin surface at a flow rate of 50 μl/min for 3 minutes. After a dissociation time of 3 minutes, the surface was regenerated. Binding curves were compared qualitatively for binding signal intensity, as well as for dissociation rates. Peptibody binding kinetic parameters including $k_a$ (association rate constant), $k_d$ (dissociation rate constant) and $K_D$ (dissociation equilibrium constant) were determined using the BIA evaluation 3.1 computer program (Biacore, Inc.). The lower the dissociation equilibrium constants (expressed in nM), the greater the affinity of the peptibody for myostatin. Examples of peptibody $K_D$ values are shown in Table III and Table VI for affinity-matured peptibodies below.

Blocking Assay on ActRIIB/Fc Surface

Blocking assays were carried out using immobilized ActRIIB/Fc (R&D Systems, Minneapolis, Minn.) and myostatin in the presence and absence of peptibodies with the BIAcore® assay system. Assays were used to classify peptibodies as non-neutralizing (those which did not prevent myostatin binding to ActRIIB/Fc) or neutralizing (those that prevented myostatin binding to ActRIIB/Fc). Baseline myostatin-ActRIIB/Fc binding was first determined in the absence of any peptibody.

For early screening studies, peptibodies were diluted to 4 nM, 40 nM, and 400 nM in sample buffer and incubated with 4 nM myostatin (also diluted in sample buffer). The peptibody: ligand mixtures were allowed to reach equilibrium at room temperature (at least 5 hours) and then were injected over the immobilized ActRIIB/Fc surface for 20 to 30 minutes at a flow rate of 10 uL/min. An increased binding response (over control binding with no peptibody) indicated that peptibody binding to myostatin was non-neutralizing. A decreased binding response (compared to the control) indicated that peptibody binding to myostatin blocked the binding of myostatin to ActRIIB/Fc. Selected peptibodies were further characterized using the blocking assay of a full concentration series in order to derive $IC_{50}$ values (for neutralizing peptibodies) or $EC_{50}$ (for non-neutralizing peptibodies). The peptibody samples were serially diluted from 200 nM to 0.05 mM in sample buffer and incubated with 4 mM myostatin at room temperature to reach equilibrium (minimum of five hours) before injected over the immobilized ActRIIB/Fc surface for 20 to 30 minutes at a flow rate of 10 uL/min. Following the sample injection, bound ligand was allowed to dissociate from the receptor for 3 minutes. Plotting the binding signal vrs. peptibody concentration, the $IC_{50}$ values for each peptibody in the presence of 4 nM myostatin were calculated. It was found, for example, that the peptibodies TN8-19, L2 and L17 inhibit myostatin activity in cell-based assay, but binding of TN-8-19 does not block myostatin/ActRIIB/Fc interactions, indicating that TN-8-19 binds to a different epitope than that observed for the other two peptibodies.

Epitope Binning for Peptibodies

A purified peptibody was immobilized on a BIAcore chip to capture myostatin before injection of a second peptibody, and the amount of secondary peptibody bound to the captured myostatin was determined. Only peptibodies with distinct epitopes will bind to the captured myostatin, thus enabling the binning of peptibodies with similar or distinct epitope binding properties. For example, it was shown that peptibodies TN8-19 and L23 bind to different epitopes on myostatin.

Selectivity Assays

These assays were performed using BIAcore® technology, to determine the selectivity of binding of the peptibodies to other TGFβ family members. ActRIIB/Fc, TGFβRII/Fc and BMPR-1A/Fc (all obtained from R & D Systems, Minneapolis, Minn.) were covalently coupled to research grade sensor chips according to manufacturer's suggested protocol. Because BIAcore assays detects changes in the refractive index, the difference between the response detected with injection over the immobilized receptor surfaces compared with the response detected with injection over the control surface in the absence of any peptibody represents the actual binding of Activin A, TGFβ1, TGFβ3, and BMP4 to the receptors, respectively. With pre-incubation of peptibodies and TGFβ molecules, a change (increase or decrease) in binding response indicates peptibody binding to the TGFβ family of molecules. The peptibodies of the present invention all bind to myostatin but not to Activin A, TGFβ1, TGFβ3, or BMP4.

KinEx A™ Equilibrium Assays

Solution-based equilibrium-binding assays using KinExA™ technology (Sapidyne Instruments, Inc.) were used to determine the dissociation equilibrium ($K_D$) of myostatin binding to peptibody molecules. This solution-based assay is considered to be more sensitive than the BIAcore assay in some instances. Reacti-Gel™ 6× was pre-coated with about 50 ug/ml myostatin for over-night, and then blocked with BSA. 30 pM and 100 pM of peptibody samples were incubated with various concentrations (0.5 pM to 5 nM) of myostatin in sample buffer at room temperature for 8 hours before being run through the myostatin-coated beads. The amount of the bead-bound peptibody was quantified by fluorescent (Cy5) labeled goat anti-human-Fc antibody at 1 mg/ml in superblock. The binding signal is proportional to the concentration of free peptibody at equilibrium with a given myostatin concentration. $K_D$ was obtained from the nonlinear regression of the competition curves using a dual-curve one-site homogeneous binding model provided in the KinEx A™ software (Sapidyne Instruments, Inc.).

EXAMPLE 4

Comparison of Myostatin Inhibitors

The ability of three exemplary first-round peptibodies to bind to ($K_D$) and inhibit ($IC_{50}$) were compared with the $K_D$ and $IC_{50}$ values obtained for the soluble receptor fusion protein actRIIB/Fc (R &D Systems, Inc., Minneapolis, Minn.). The $IC_{50}$ values were determined using the pMARE luc cell-based assay described in Example 3 and the $K_D$ values were determined using the Biacore® assay described in Example 3.

TABLE III

| Inhibitor | $IC_{50}$ (nM) | $K_D$ (nM) |
| --- | --- | --- |
| ActRIIB/Fc | ~83 | ~7 |
| 2xTN8-19-kc | ~9 | ~2 |
| TN8-19 | ~23 | ~2 |
| TN8-29 | ~26 | ~60 |
| TN12-34 | ~30 | — |
| Linear-20 | ~11 | — |

The peptibodies have an $IC_{50}$ that is improved over the receptor/Fc inhibitor and binding affinities which are comparable in two peptibodies with the receptor/Fc.

EXAMPLE 5

Comparison of Ability of Peptide and Peptibody to Inhibit Myostatin

The following peptide sequence: QGHCTRWPWMCPPY (TN8-19) (SEQ ID NO: 33) was used to construct the corresponding peptibody TN8-19(pb) according to the procedure described in Example 2 above. Both the peptide alone and the peptibody were screened for myostatin inhibiting activity using the C2C12 based assay described in Example 3 above. It can be seen from FIG. 1 the $IC_{50}$ (effective concentration for fifty percent inhibition of myostatin) for the peptibody is significantly less than that of the peptide, and thus the ability of the peptide to inhibit myostatin activity has been substantially improved by placing it in the peptibody configuration.

EXAMPLE 6

Generation of Affinity-Matured Peptides and Peptibodies

Several of the first round peptides used for peptibody generation were chosen for affinity maturation. The selected peptides included the following: the cysteine constrained TN8-19, QGHCTRWPWMCPPY (SEQ ID NO: 33), and the linear peptides Linear-2 MEMLDSLFELLKDMVPISKA (SEQ ID NO: 104); Linear-15 HHGWNYLRKGSAPQWFEAWV (SEQ ID NO: 117); Linear-17 RATLLKDFWQLVEGYGDN (SEQ ID NO: 119); Linear-20 YREMSMLEGLLDVLERLQHY (SEQ ID NO: 122), Linear-21 HNSSQMLLSELIMLVGSMMQ (SEQ ID NO: 123), Linear-24 EFFHWLHNHRSEVNHWLDMN (SEQ ID NO: 126). Based on a consensus sequence, directed secondary phage display libraries were generated in which the "core" amino acids (determined from the consensus sequence) were either held constant or biased in frequency of occurrence. Alternatively, an individual peptide sequence could be used to generate a biased, directed phage display library. Panning of such libraries under more stringent conditions can yield peptides with enhanced binding to myostatin, selective binding to myostatin, or with some additional desired property.

Production of Doped Oligos for Libraries

Oligonucleotides were synthesized in a DNA synthesizer which were 91% "doped" at the core sequences, that is, each solution was 91% of the represented base (A, G, C, or T), and 3% of each of the other 3 nucleotides. For the TN8-19 family, for example, a 91% doped oligo used for the construction of a secondary phage library was the following:

```
5'-CAC AGT GCA CAG GGT NNK NNK NNK caK ggK caK tgK acK cgK tgK    (SEQ ID NO: 634)

ccK tgK atK tgK ccK ccK taK NNK NNK NNK CAT TCT CTC GAG ATC A-3'
``` wherein "N" indicates that each of the four nucleotides A, T, C, and G were equally represented, K indicates that G and T were equally represented, and the lower case letter represents a mixture of 91% of the indicated base and 3% of each of the other bases. The family of oligonucleotides prepared in this manner were PCR amplified as described above, ligated into a phagemid vectors, for example, a modified pCES1 plasmid (Dyax), or any available phagemid vector according to the protocol described above. The secondary phage libraries generated were all 91% doped and had between 1 and $6.5 \times 10^9$ independent transformants. The libraries were panned as described above, but with the following conditions:

Round 1 Panning:
Input phage number: $10^{12}$-$10^{13}$ cfu of phagemid
Selection method: Nunc Immuno Tube selection
Negative selection: 2× with Nunc Immuno Tubes coated with 2% BSA at 10 min. each
Panning coating: Coat with 1 μg of Myostatin protein in 1 ml of 0.1M Sodium carbonate buffer (pH 9.6)
Binding time: 3 hours
Washing conditions: 6×2%-Milk-PBST; 6×PBST; 2×PBS
Elution condition: 100 mM TEA elution Round 2 Panning:
Input phage number: $10^{11}$ cfu of phagemid
Selection method: Nunc Immuno Tube selection
Negative selection: 2× with Nunc Immuno Tubes coated with 2%.BSA at 30 min. each
Panning coating: Coat with 1 μg of Myostatin protein in 1 ml of 0.1M Sodium carbonate buffer (pH 9.6)
Binding time: 1 hour
Washing conditions: 15×2%-Milk-PBST, 1×2%-Milk-PBST for 1 hr., 10×2%-BSA-PBST, 1×2%-BSA-PBST for 1 hr., 10×PBST and 3×PBS
Elution condition: 100 mM TEA elution Round 3 Panning:
Input phage number: $10^{10}$ cfu of phagemid
Selection method: Nunc Immuno Tube selection
Negative selection: 6× with Nunc Immuno Tubes coated with 2% BSA at 10 min. each
Panning coating: Coat with 0.1 μg of Myostatin protein in 1 ml of 0.1M Sodium carbonate buffer (pH 9.6)
Binding time: 1 hour
Washing conditions: 15×2%-Milk-PBST, 1×2%-Milk-PBST for 1 hr., 10×2%-BSA-PBST, 1×2%-BSA-PBST for 1 hr., 10×PBST and 3×PBS
Elution condition: 100 mM TEA elution Panning of the secondary libraries yielded peptides with enhanced binding to myostatin. Individual selected clones were subjected phage ELISA, as described above, and sequenced.

The following affinity matured TN8-19 family of peptides are shown in Table IV below.

TABLE IV

| Affinity-matured peptibody | SEQ ID NO: | Peptide sequence |
|---|---|---|
| mTN8-19-1 | 305 | VALHGQCTRWPWMCPPQREG |
| mTN8-19-2 | 306 | YPEQGLCTRWPWMCPPQTLA |
| mTN8-19-3 | 307 | GLNQGHCTRWPWMCPPQDSN |
| mTN8-19-4 | 308 | MITQGQCTRWPWMCPPQPSG |
| mTN8-19-5 | 309 | AGAQEHCTRWPWMCAPNDWI |
| mTN8-19-6 | 310 | GVNQGQCTRWRWMCPPNGWE |
| mTN8-19-7 | 311 | LADHGQCIRWPWMCPPEGWE |
| mTN8-19-8 | 312 | ILEQAQCTRWPWMCPPQRGG |
| mTN8-19-9 | 313 | TQTHAQCTRWPWMCPPQWEG |
| mTN8-19-10 | 314 | VVTQGHCTLWPWMCPPQRWR |
| mTN8-19-11 | 315 | IYPHDQCTRWPWMCPPQPYP |
| mTN8-19-12 | 316 | SYWQGQCTRWPWMCPPQWRG |
| mTN8-19-13 | 317 | MWQQGHCTRWPWMCPPQGWG |
| mTN8-19-14 | 318 | EFTQWHCTRWPWMCPPQRSQ |
| mTN8-19-15 | 319 | LDDQWQCTRWPWMCPPQGFS |
| mTN8-19-16 | 320 | YQTQGLCTRWPWMCPPQSQR |
| mTN8-19-17 | 321 | ESNQGQCTRWPWMCPPQGGW |
| mTN8-19-18 | 322 | WTDRGPCTRWPWMCPPQANG |
| mTN8-19-19 | 323 | VGTQGQCTRWPWMCPPYETG |
| mTN8-19-20 | 324 | PYEQGKCTRWPWMCPPYEVE |
| mTN8-19-21 | 325 | SEYQGLCTRWPWMCPPQGWK |
| mTN8-19-22 | 326 | TFSQGHCTRWPWMCPPQGWG |
| mTN8-19-23 | 327 | PGAHDHCTRWPWMCPPQSRY |
| mTN8-19-24 | 328 | VAEEWHCRRWPWMCPPQDWR |
| mTN8-19-25 | 329 | VGTQGHCTRWPWMCPPQPAG |
| mTN8-19-26 | 330 | EEDQAHCRSWPWMCPPQGWV |
| mTN8-19-27 | 331 | ADTQGHCTRWPWMCPPQHWF |
| mTN8-19-28 | 332 | SGPQGHCTRWPWMCAPQGWF |
| mTN8-19-29 | 333 | TLVQGHCTRWPWMCPPQRWV |
| mTN8-19-30 | 334 | GMAHGKCTRWAWMCPPQSWK |
| mTN8-19-31 | 335 | ELYHGQCTRWPWMCPPQSWA |
| mTN8-19-32 | 336 | VADHGHCTRWPWMCPPQGWG |
| mTN8-19-33 | 337 | PESQGHCTRWPWMCPPQGWG |
| mTN8-19-34 | 338 | IPAHGHCTRWPWMCPPQRWR |
| mTN8-19-35 | 339 | FTVHGHCTRWPWMCPPYGWV |
| mTN8-19-36 | 340 | PDFPGHCTRWRWMCPPQGWE |
| mTN8-19-37 | 341 | QLWQGPCTQWPWMCPPKGRY |
| mTN8-19-38 | 342 | HANDGHCTRWQWMCPPQWGG |
| mTN8-19-39 | 343 | ETDHGLCTRWPWMCPPYGAR |
| mTN8-19-40 | 344 | GTWQGLCTRWPWMCPPQGWQ |
| mTN8-19 con1 | 345 | VATQGQCTRWPWMCPPQGWG |
| mTN8-19 con2 | 346 | VATQGQCTRWPWMCPPQRWG |
| mTN8 con6-1 | 347 | QREWYPCYGGHLWCYDLHKA |

TABLE IV-continued

| Affinity- matured peptibody | SEQ ID NO: | Peptide sequence |
|---|---|---|
| mTN8 con6-2 | 348 | ISAWYSCYAGHFWCWDLKQK |
| mTN8 con6-3 | 349 | WTGWYQCYGGHLWCYDLRRK |
| mTN8 con6-4 | 350 | KTFWYPCYDGHFWCYNLKSS |
| mTN8 con6-5 | 351 | ESRWYPCYEGHLWCFDLTET |

The consensus sequence derived from the affinity-matured TN-8-19-1 through Con2 (excluding the mTN8 con6 sequences) shown above is: $\underline{C}a_1a_2\underline{W}a_3\underline{WMCPP}$ (SEQ ID NO: 352). All of these peptides comprise the sequence WMCPP (SEQ ID NO: 633). The underlined amino acids represent the core amino acids present in all embodiments, and $a_1$, $a_2$ and $a_3$ are selected from a neutral hydrophobic, neutral polar, or basic amino acid. In one embodiment of this consensus sequence, $\underline{C}b_1b_2\underline{W}b_3\underline{WMCPP}$ (SEQ ID NO: 353), $b_1$ is selected from any one of the amino acids T, I, or R; $b_2$ is selected from any one of R, S, Q; and $b_3$ is selected from any one of P, R and Q. All of the peptides comprise the sequence WMCPP (SEQ ID NO: 633). A more detailed analysis of the affinity matured TN8 sequences comprising SEQ ID NO: 352 provides the following formula:

$$c_1c_2c_3c_4c_5c_6\underline{C}c_7c_8\underline{W}c_9\underline{WMCPP}c_{10}c_{11}c_{12}c_{13} \quad \text{(SEQ ID NO: 354)},$$

wherein:

$c_1$ is absent or any amino acid;

$c_2$ is absent or a neutral hydrophobic, neutral polar, or acidic amino acid;

$c_3$ is absent or a neutral hydrophobic, neutral polar, or acidic amino acid;

$c_4$ is absent or any amino acid;

$c_5$ is absent or a neutral hydrophobic, neutral polar, or acidic amino acid;

$c_6$ is absent or a neutral hydrophobic, neutral polar, or basic amino acid;

$c_7$ is a neutral hydrophobic, neutral polar, or basic amino acid;

$c_8$ is a neutral hydrophobic, neutral polar, or basic amino acid;

$c_9$ is a neutral hydrophobic, neutral polar or basic amino acid; and wherein $c_{10}$ to $c_{13}$ is any amino acid.

In one embodiment of the above formulation, $b_7$ is selected from any one of the amino acids T, I, or R; $b_8$ is selected from any one of R, S, Q; and $b_9$ is selected from any one of P, R and Q. This provides the following sequence:

$$d_1d_2d_3d_4d_5d_6\underline{C}d_7d_8\underline{W}d_9\underline{WMCPP}d_{10}d_{11}d_{12}d_{13} \quad \text{(SEQ ID NO: 355)},$$

$d_1$ is absent or any amino acid;

$d_2$ is absent or a neutral hydrophobic, neutral polar, or acidic amino acid;

$d_3$ is absent or a neutral hydrophobic, neutral polar, or acidic amino acid;

$d_4$ is absent or any amino acid;

$d_5$ is absent or a neutral hydrophobic, neutral polar, or acidic amino acid;

$d_6$ is absent or a neutral hydrophobic, neutral polar, or basic amino acid;

$d_7$ is selected from any one of the amino acids T, I, or R;

$d_8$ is selected from any one of R, S, Q;

$d_9$ is selected from any one of P, R and Q and $d_{10}$ through $d_{13}$ are selected from any amino acid.

The consensus sequence of the mTN8 con6 series is $\underline{W}\underline{Y}e_1e_2\underline{Y}e_3\underline{G}$, (SEQ ID NO: 356) wherein $e_1$ is P, S or Y; $e_2$ is C or Q, and $e_3$ is G or H.

In addition to the TN-19 affinity matured family, additional affinity matured peptides were produced from the linear L-2, L-15, L-17, L-20, L-21, and L-24 first round peptides. These families are presented in Table V below.

TABLE V

| Affinity matured peptibody | SEQ ID NO: | Peptide Sequence |
|---|---|---|
| L2 | 104 | MEMLDSLFELLKDMVPISKA |
| mL2-Con1 | 357 | RMEMLESLLELLKEIVPMSKAG |
| mL2-Con2 | 358 | RMEMLESLLELLKEIVPMSKAR |
| mL2-1 | 359 | RMEMLESLLELLKDIVPMSKPS |
| mL2-2 | 360 | GMEMLESLFELLQEIVPMSKAP |
| mL2-3 | 361 | RMEMLESLLELLKDIVPISNPP |
| mL2-4 | 362 | RIEMLESLLELLQEIVPISKAE |
| mL2-5 | 363 | RMEMLQSLLELLKDIVPMSNAR |
| mL2-6 | 364 | RMEMLESLLELLKEIVPTSNGT |
| mL2-7 | 365 | RMEMLESLFELLKEIVPMSKAG |
| mL2-8 | 366 | RMEMLGSLLELLKEIVPMSKAR |
| mL2-9 | 367 | QMELLDSLFELLKEIVPKSQPA |
| mL2-10 | 368 | RMEMLDSLLELLKEIVPMSNAR |
| mL2-11 | 369 | RMEMLESLLELLHEIVPMSQAG |
| mL2-12 | 370 | QMEMLESLLQLLKEIVPMSKAS |
| mL2-13 | 371 | RMEMLDSLLELLKDMVPMTTGA |
| mL2-14 | 372 | RIEMLESLLELLKDMVPMANAS |
| mL2-15 | 373 | RMEMLESLLQLLNEIVPMSRAR |
| mL2-16 | 374 | RMEMLESLFDLLKELVPMSKGV |
| mL2-17 | 375 | RIEMLESLLELLKDIVPIQKAR |
| mL2-18 | 376 | RMELLESLFELLKDMVPMSDSS |
| mL2-19 | 377 | RMEMLESLLEVLQEIVPRAKGA |
| mL2-20 | 378 | RMEMLDSLLQLLNEIVPMSHAR |
| mL2-21 | 379 | RMEMLESLLELLKDIVPMSNAG |
| mL2-22 | 380 | RMEMLQSLFELLKGMVPISKAG |
| mL2-23 | 381 | RMEMLESLLELLKEIVPNSTAA |
| mL2-24 | 382 | RMEMLQSLLELLKEIVPISKAG |
| mL2-25 | 383 | RIEMLDSLLELLNELVPMSKAR |
| L-15 | 117 | HHGWNYLRKGSAPQWFEAWV |
| mL15-con1 | 384 | QVESLQQLLMWLDQKLASGPQG |
| mL15-1 | 385 | RMELLESLFELLKEMVPRSKAV |
| mL15-2 | 386 | QAVSLQHLLMWLDQKLASGPQH |

TABLE V-continued

| Affinity matured peptibody | SEQ ID NO: | Peptide Sequence |
|---|---|---|
| mL15-3 | 387 | DEDSLQQLLMWLDQKLASGPQL |
| mL15-4 | 388 | DVASLQQLLIWLDQKLAQGPHA |
| mL15-5 | 389 | EVDELQQLLNWLDHKLASGPLQ |
| mL15-6 | 390 | DVESLEQLLMWLDHQLASGPHG |
| mL15-7 | 391 | QVDSLQQVLLWLEHKLALGPQV |
| mL15-8 | 392 | GDESLQHLLMWLEQKLALGPHG |
| mL15-9 | 393 | QIEMLESLLDLLRDMVPMSNAF |
| mL15-10 | 394 | EVDSLQQLLMWLDQKLASGPQA |
| mL15-11 | 395 | EDESLQQLLIYLDKMLSSGPQV |
| mL15-12 | 396 | AMDQLHQLLIWLDHKLASGPQA |
| mL15-13 | 397 | RIEMLESLLELLDEIALIPKAW |
| mL15-14 | 398 | EVVSLQHLLMWLEHKLASGPDG |
| mL15-15 | 399 | GGESLQQLLMWLDQQLASGPQR |
| mL15-16 | 400 | GVESLQQLLIFLDHMLVSGPHD |
| mL15-17 | 401 | NVESLEHLMMWLERLLASGPYA |
| mL15-18 | 402 | QVDSLQQLLIWLDHQLASGPKR |
| mL15-19 | 403 | EVESLQQLLMWLEHKLAQGPQG |
| mL15-20 | 404 | EVDSLQQLLMWLDQKLASGPHA |
| mL15-21 | 405 | EVDSLQQLLMWLDQQLASGPQK |
| mL15-22 | 406 | GVEQLPQLLMWLEQKLASGPQR |
| mL15-23 | 407 | GEDSLQQLLMWLDQQLAAGPQV |
| mL15-24 | 408 | ADDSLQQLLMWLDRKLASGPHV |
| mL15-25 | 409 | PVDSLQQLLIWLDQKLASGPQG |
| L-17 | 119 | RATLLKDFWQLVEGYGDN |
| mL17-con1 | 410 | DWRATLLKEFWQLVEGLGDNLV |
| mL17-con2 | 411 | QSRATLLKEFWQLVEGLGDKQA |
| mL17-1 | 412 | DGRATLLTEFWQLVQGLGQKEA |
| mL17-2 | 413 | LARATLLKEFWQLVEGLGEKVV |
| mL17-3 | 414 | GSRDTLLKEFWQLVVGLGDMQT |
| mL17-4 | 415 | DARATLLKEFWQLVDAYGDRMV |
| mL17-5 | 416 | NDRAQLLRDFWQLVDGLGVKSW |
| mL17-6 | 417 | GVRETLLYELWYLLKGLGANQG |
| mL17-7 | 418 | QARATLLKEFCQLVGCQGDKLS |
| mL17-8 | 419 | QERATLLKEFWQLVAGLGQNMR |
| mL17-9 | 420 | SGRATLLKEFWQLVQGLGEYRW |
| mL17-10 | 421 | TMRATLLKEFWLFVDGQREMQW |
| mL17-11 | 422 | GERATLLNDFWQLVDGQGDNTG |
| mL17-12 | 423 | DERETLLKEFWQLVHGWGDNVA |
| mL17-13 | 424 | GGRATLLKELWQLLEGQGANLV |
| mL17-14 | 425 | TARATLLNELVQLVKGYGDKLV |
| mL17-15 | 426 | GMRATLLQEFWQLVGGQGDNWM |
| mL17-16 | 427 | STRATLLNDLWQLMKGWAEDRG |
| mL17-17 | 428 | SERATLLKELWQLVGGWGDNFG |
| mL17-18 | 429 | VGRATLLKEFWQLVEGLVGQSR |
| mL17-19 | 430 | EIRATLLKEFWQLVDEWREQPN |
| mL17-20 | 431 | QLRATLLKEFLQLVHGLGETDS |
| mL17-21 | 432 | TQRATLLKEFWQLIEGLGGKHV |
| mL17-22 | 433 | HYRATLLKEFWQLVDGLREQGV |
| mL17-23 | 434 | QSRVTLLREFWQLVESYRPIVN |
| mL17-24 | 435 | LSRATLLNEFWQFVDGQRDKRM |
| mL17-25 | 436 | WDRATLLNDFWHLMEELSQKPG |
| mL17-26 | 437 | QERATLLKEFWRMVEGLGKNRG |
| mL17-27 | 438 | NERATLLREFWQLVGGYGVNQR |
| L-20 | 122 | YREMSMLEGLLDVLERLQHY |
| mL20-1 | 439 | HQRDMSMLWELLDVLDGLRQYS |
| mL20-2 | 440 | TQRDMSMLDGLLEVLDQLRQQR |
| mL20-3 | 441 | TSRDMSLLWELLEELDRLGHQR |
| mL20-4 | 442 | MQHDMSMLYGLVELLESLGHQI |
| mL20-5 | 443 | WNRDMRMLESLFEVLDGLRQQV |
| mL20-6 | 444 | GYRDMSMLEGLLAVLDRLGPQL |
| mL20 con1 | 445 | TQRDMSMLEGLLEVLDRLGQQR |
| mL20 con2 | 446 | WYRDMSMLEGLLEVLDRLGQQR |
| L-21 | 123 | HNSSQMLLSELIMLVGSMMQ |
| mL21-1 | 447 | TQNSRQMLLSDFMMLVGSMIQG |
| mL21-2 | 448 | MQTSRHILLSEFMMLVGSLMHG |
| mL21-3 | 449 | HDNSRQMLLSDLLHLVGTMIQG |
| mL21-4 | 450 | MENSRQNLLRELIMLVGNMSHQ |
| mL21-5 | 451 | QDTSRHMLLREFMMLVGEMIQG |
| mL21 con1 | 452 | DQNSRQMLLSDLMILVGSMIQG |
| L-24 | 126 | EFFHWLHNHRSEVNHWLDMN |
| mL24-1 | 453 | NVFFQWVQKHGRVVYQWLDINV |
| mL24-2 | 454 | FDFLQWLQNHRSEVEHWLVMDV |

The affinity matured peptides provided in Tables IV and V are then assembed into peptibodies as described above and assayed using the in vivo assays.

The affinity matured L2 peptides comprise a consensus sequence of f$_1$EMLf$_2$SLf$_3$f$_4$LL, (SEQ ID NO: 455), wherein f$_1$ is M or I; f$_2$ is any amino acid; f$_3$ is L or F; and f$_4$ is E, Q or D.

The affinity matured L15 peptide family comprise the sequence Lg$_1$g$_2$LLg$_3$g$_4$L, (SEQ ID NO: 456), wherein g$_1$ is Q, D or E, g$_2$ is S, Q, D or E, g$_3$ is any amino acid, and g$_4$ is L, W, F, or Y. The affinity matured L17 family comprises the sequence: h$_1$h$_2$h$_3$h$_4$h$_5$h$_6$h$_7$h$_8$h$_9$ (SEQ ID NO: 457) wherein h$_1$ is R or D; h$_2$ is any amino acid; h$_3$ is A, T S or Q; h$_4$ is L or M; h$_5$ is L or S; h$_6$ is any amino acid; h$_7$ is F or E; h$_8$ is W, F or C; and h$_9$ is L, F, M or K. Consensus sequences may also be determined for the mL20, mL21 and mL24 families of peptides shown above.

Peptibodies were constructed from these affinity matured peptides as described above, using a linker attached to the Fc domain of human IgG1, having SEQ ID NO: 296, at the N-terminus (N configuration), at the C terminus (C configuration) of the Fc, or at both the N and C terminals (N,C configurations), as described in Example 2 above. The peptides named were attached to the C or N terminals via a 5 glycine (5G), 8 glycine or k linker sequence. In the 2× peptibody version the peptides were linked with linkers such as 5 gly, 8 gly or k. Affinity matured peptides and peptibodies are designated with a small "m" such as mTN8-19-22 for example. Peptibodies of the present invention further contain two splice sites where the peptides were spliced into the phagemid vectors. The position of these splice sites are AQ—peptide—LE. The peptibodies generally include these additional amino acids (although they are not included in the peptide sequences listed in the tables). In some peptibodies the LE amino acids were removed from the peptides sequences. These peptibodies are designated—LE.

Exemplary peptibodies, and exemplary polynucleotide sequences encoding them, are provided in Table VI below. This table includes examples of peptibody sequences (as opposed to peptide only), such as the 2× mTN8-19-7 (SEQ ID NO: 615) and the peptibody with the LE sequences deleted (SEQ ID NO: 617). By way of explanation, the linker sequences in the 2× versions refer to the linker between the tandem peptides. These peptibody sequences contain the Fc, linkers, AQ and LE sequences. The accompanying nucleotide sequence encodes the peptide sequence in addition to the AQ/LE linker sequences, if present, but does not encode the designated linker.

TABLE VI

| Peptibody Name | Peptide | Nucleotide Sequence | (SEQ ID No) | Linker | Terminus |
|---|---|---|---|---|---|
| mL2-Con1 | RMEMLESLLELL KEIVPMSKAG (SEQ ID NO:357) | CGTATGGAAATGCTTGAATCTCTTC TTGAACTTCTTAAAGAAATTGTTCC AATGTCTAAAGCTGGT | (SEQ ID NO: 458) | 5 gly | N |
| mL2-Con2 | RMEMLESLLELL KEIVPMSKAR (SEQ ID NO:358) | CGTATGGAAATGCTTGAATCTCTTC TTGAACTTCTTAAAGAAATTGTTCC AATGTCTAAAGCTCGT | (SEQ ID NO: 459) | 5 gly | N |
| mL2-1 | RMEMLESLLELL KDIVPMSKPS (SEQ ID NO:359) | CGTATGGAAATGCTTGAATCTCTTC TTGAACTTCTTAAAGATATTGTTCC AATGTCTAAACCATCT | (SEQ ID NO: 460) | 5 gly | N |
| mL2-2 | GMEMLESLFELL QEIVPMSKAP (SEQ ID NO:360) | GGTATGGAAATGCTTGAATCTCTTT TTGAACTTCTTCAAGAAATTGTTCC AATGTCTAAAGCTCCA | (SEQ ID NO: 461) | 5 gly | N |
| mL2-3 | RMEMLESLLELL KDIVPISNPP (SEQ ID NO:361) | CGTATGGAAATGCTTGAATCTCTTC TTGAACTTCTTAAAGATATTGTTCC AATTTCTAATCCACCA | (SEQ ID NO: 462) | 5 gly | N |
| mL2-4 | RIEMLESLLELLQ EIVPISKAE (SEQ ID NO:362) | CGTATTGAAATGCTTGAATCTCTTC TTGAACTTCTTCAAGAAATTGTTCC AATTTCTAAAGCTGAA | (SEQ ID NO: 463) | 5 gly | N |
| mL2-5 | RMEMLQSLLELL KDIVPMSNAR (SEQ ID NO:363) | CGTATGGAAATGCTTCAATCTCTTC TTGAACTTCTTAAAGATATTGTTCC AATGTCTAATGCTCGT | (SEQ ID NO: 464) | 5 gly | N |
| mL2-6 | RMEMLESLLELL KEIVPTSNGT (SEQ ID NO:364) | CGTATGGAAATGCTTGAATCTCTTC TTGAACTTCTTAAAGAAATTGTTCC AACTTCTAATGGTACT | (SEQ ID NO: 465) | 5 gly | N |
| m12-7 | RMEMLESLFELL KEIVPMSKAG (SEQ ID NO:365) | CGTATGGAAATGCTTGAATCTCTTT TTGAACTTCTTAAAGAAATTGTTCC AATGTCTAAAGCTGGT | (SEQ ID NO: 466) | 5 gly | N |
| mL2-8 | RMEMLGSLLELL KEIVPMSKAR (SEQ ID NO:366) | CGTATGGAAATGCTTGGTTCTCTTC TTGAACTTCTTAAAGAAATTGTTCC AATGTCTAAAGCTCGT | (SEQ ID NO: 467) | 5 gly | N |
| mL2-9 | QMELLDSLFELL KEIVPKSQPA (SEQ ID NO:367) | CAAATGGAACTTCTTGATTCTCTTT TTGAACTTCTTAAAGAAATTGTTCC AAAATCTCAACCAGCT | (SEQ ID NO: 468) | 5 gly | N |

TABLE VI-continued

| Peptibody Name | Peptide | Nucleotide Sequence | (SEQ ID No) | Linker | Terminus |
|---|---|---|---|---|---|
| mL2-10 | RMEMLDSLLELL KEIVPMSNAR (SEQ ID NO:368) | CGTATGGAAATGCTTGATTCTCTTC TTGAACTTCTTAAAGAAATTGTTCC AATGTCTAATGCTCGT | (SEQ ID NO: 469) | 5 gly | N |
| mL2-11 | RMEMLESLLELL HEIVPMSQAG (SEQ ID NO:369) | CGTATGGAAATGCTTGAATCTCTTC TTGAACTTCTTCATGAAATTGTTCC AATGTCTCAAGCTGGT | (SEQ ID NO: 470) | 5 gly | N |
| mL2-12 | QMEMLESLLQLL KEIVPMSKAS (SEQ ID NO:370) | CAAATGGAAATGCTTGAATCTCTTC TTCAACTTCTTAAAGAAATTGTTCC AATGTCTAAAGCTTCT | (SEQ ID NO: 471) | 5 gly | N |
| mL2-13 | RMEMLDSLLELL KDMVPMTTGA (SEQ ID NO:371) | CGTATGGAAATGCTTGATTCTCTTC TTGAACTTCTTAAAGATATGGTTCC AATGACTACTGGTGCT | (SEQ ID NO: 472) | 5 gly | N |
| mL2-14 | RIEMLESLLELLK DMVPMANAS (SEQ ID NO:372) | CGTATTGAAATGCTTGAATCTCTTC TTGAACTTCTTAAAGATATGGTTCC AATGGCTAATGCTTCT | (SEQ ID NO: 473) | 5 gly | N |
| mL2-15 | RMEMLESLLQLL NEIVPMSRAR (SEQ ID NO:373) | CGTATGGAAATGCTTGAATCTCTTC TTCAACTTCTTAATGAAATTGTTCC AATGTCTCGTGCTCGT | (SEQ ID NO: 474) | 5 gly | N |
| mL2-16 | RMEMLESLFDLL KELVPMSKGV (SEQ ID NO:374) | CGTATGGAAATGCTTGAATCTCTTT TTGATCTTCTTAAAGAACTTGTTCC AATGTCTAAAGGTGTT | (SEQ ID NO: 475) | 5 gly | N |
| mL2-17 | RIEMLESLLELLK DIVPIQKAR (SEQ ID NO:375) | CGTATTGAAATGCTTGAATCTCTTC TTGAACTTCTTAAAGATATTGTTCC AATTCAAAAAGCTCGT | (SEQ ID NO: 476) | 5 gly | N |
| mL2-18 | RMELLESLFELLK DMVPMSDSS (SEQ ID NO:376) | CGTATGGAACTTCTTGAATCTCTTT TTGAACTTCTTAAAGATATGGTTCC AATGTCTGATTCTTCT | (SEQ ID NO: 477) | 5 gly | N |
| mL2-19 | RMEMLESLLEVL QEIVPRAKGA (SEQ ID NO:377) | CGTATGGAAATGCTTGAATCTCTTC TTGAAGTTCTTCAAGAAATTGTTCC ACGTGCTAAAGGTGCT | (SEQ ID NO: 478) | 5 gly | N |
| mL2-20 | RMEMLDSLLQLL NEIVPMSHAR (SEQ ID NO:378) | CGTATGGAAATGCTTGATTCTCTTC TTCAACTTCTTAATGAAATTGTTCC AATGTCTCATGCTCGT | (SEQ ID NO: 479) | 5 gly | N |
| mL2-21 | RMEMLESLLELL KDIVPMSNAG (SEQ ID NO:379) | CGTATGGAAATGCTTGAATCTCTTC TTGAACTTCTTAAAGATATTGTTCC AATGTCTAATGCTGGT | (SEQ ID NO: 480) | 5 gly | N |
| mL2-22 | RMEMLQSLFELL KGMVPISKAG (SEQ ID NO:380) | CGTATGGAAATGCTTCAATCTCTTT TTGAACTTCTTAAAGGTATGGTTCC AATTTCTAAAGCTGGT | (SEQ ID NO: 481) | 5 gly | N |
| mL2-23 | RMEMLESLLELL KEIVPNSTAA (SEQ ID NO:381) | CGTATGGAAATGCTTGAATCTCTTC TTGAACTTCTTAAAGAAATTGTTCC AAATTCTACTGCTGCT | (SEQ ID NO: 482) | 5 gly | N |
| mL2-24 | RMEMLQSLLELL KEIVPISKAG (SEQ ID NO:382) | CGTATGGAAATGCTTCAATCTCTTC TTGAACTTCTTAAAGAAATTGTTCC AATTTCTAAAGCTGGT | (SEQ ID NO: 483) | 5 gly | N |
| mL2-25 | RIEMLDSLLELLN ELVPMSKAR (SEQ ID NO:383) | CGTATTGAAATGCTTGATTCTCTTC TTGAACTTCTTAATGAACTTGTTCC AATGTCTAAAGCTCGT | (SEQ ID NO: 484) | 5 gly | N |
| mL17-Con1 | DWRATLLKEFW QLVEGLGDNLV (SEQ ID NO:384) | GATTGGCGTGCTACTCTTCTTAAAG AATTTTGGCAACTTGTTGAAGGTCT TGGTGATAATCTTGTT | (SEQ ID NO: 485) | 5 gly | N |
| mL17-1 | DGRATLLTEFWQ LVQGLGQKEA (SEQ ID NO:412) | GATGGTCGTGCTACTCTTCTTACTG AATTTTGGCAACTTGTTCAAGGTCT TGGTCAAAAAGAAGCT | (SEQ ID NO: 486) | 5 gly | N |
| mL17-2 | LARATLLKEFWQ LVEGLGEKVV (SEQ ID NO:413) | CTTGCTCGTGCTACTCTTCTTAAAG AATTTTGGCAACTTGTTGAAGGTCT TGGTGAAAAAGTTGTT | (SEQ ID NO: 487) | 5 gly | N |

TABLE VI-continued

| Peptibody Name | Peptide | Nucleotide Sequence | (SEQ ID No) | Linker | Terminus |
|---|---|---|---|---|---|
| mL17-3 | GSRDTLLKEFWQ LVVGLGDMQT (SEQ ID NO:414) | GGTTCTCGTGATACTCTTCTTAAAG AATTTTGGCAACTTGTTGTTGGTCT TGGTGATATGCAAACT | (SEQ ID NO: 488) | 5 gly | N |
| mL17-4 | DARATLLKEFWQ LVDAYGDRMV (SEQ ID NO:415) | GATGCTCGTGCTACTCTTCTTAAAG AATTTTGGCAACTTGTTGATGCTTA TGGTGATCGTATGGTT | (SEQ ID NO: 489) | 5 gly | N |
| mL17-5 | NDRAQLLRDFWQ LVDGLGVKSW (SEQ ID NO:416) | AATGATCGTGCTCAACTTCTTCGTG ATTTTTGGCAACTTGTTGATGGTCT TGGTGTTAAATCTTGG | (SEQ ID NO: 490) | 5 gly | N |
| mL17-6 | GVRETLLYELWY LLKGLGANQG (SEQ ID NO:417) | GGTGTTCGTGAAACTCTTCTTTATG AACTTTGGTATCTTCTTAAAGGTCT TGGTGCTAATCAAGGT | (SEQ ID NO: 491) | 5 gly | N |
| mL17-7 | QARATLLKEFCQ LVGCQGDKLS (SEQ ID NO:418) | CAAGCTCGTGCTACTCTTCTTAAAG AATTTTGTCAACTTGTTGGTTGTCA AGGTGATAAACTTTCT | (SEQ ID NO: 492) | 5 gly | N |
| mL17-8 | QERATLLKEFWQ LVAGLGQNMR (SEQ ID NO:419) | CAAGAACGTGCTACTCTTCTTAAA GAATTTTGGCAACTTGTTGCTGGTC TTGGTCAAAATATGCGT | (SEQ ID NO: 493) | 5 gly | N |
| mL17-9 | SGRATLLKEFWQ LVQGLGEYRW (SEQ ID NO:420) | TCTGGTCGTGCTACTCTTCTTAAAG AATTTTGGCAACTTGTTCAAGGTCT TGGTGAATATCGTTGG | (SEQ ID NO: 494) | 5 gly | N |
| mL17-10 | TMRATLLKEFWL FVDGQREMQW (SEQ ID NO:421) | ACTATGCGTGCTACTCTTCTTAAAG AATTTTGGCTTTTTGTTGATGGTCA ACGTGAAATGCAATGG | (SEQ ID NO: 495) | 5 gly | N |
| mL17-11 | GERATLLNDFWQ LVDGQGDNTG (SEQ ID NO:422) | GGTGAACGTGCTACTCTTCTTAATG ATTTTTGGCAACTTGTTGATGGTCA AGGTGATAATACTGGT | (SEQ ID NO: 496) | 5 gly | N |
| mL17-12 | DERETLLKEFWQ LVHGWGDNVA (SEQ ID NO:423) | GATGAACGTGAAACTCTTCTTAAA GAATTTTGGCAACTTGTTCATGGTT GGGGTGATAATGTTGCT | (SEQ ID NO: 497) | 5 gly | N |
| mL17-13 | GGRATLLKELWQ LLEGQGANLV (SEQ ID NO:424) | GGTGGTCGTGCTACTCTTCTTAAAG AACTTTGGCAACTTCTTGAAGGTCA AGGTGCTAATCTTGTT | (SEQ ID NO: 498) | 5 gly | N |
| mL17-14 | TARATLLNELVQ LVKGYGDKLV (SEQ ID NO:425) | ACTGCTCGTGCTACTCTTCTTAATG AACTTGTTCAACTTGTTAAAGGTTA TGGTGATAAACTTGTT | (SEQ ID NO: 499) | 5 gly | N |
| mL17-15 | GMRATLLQEFWQ LVGGQGDNWM (SEQ ID NO:426) | GGTATGCGTGCTACTCTTCTTCAAG AATTTTGGCAACTTGTTGGTGGTCA AGGTGATAATTGGATG | (SEQ ID NO: 500) | 5 gly | N |
| mL17-16 | STRATLLNDLWQ LMKGWAEDRG (SEQ ID NO:427) | TCTACTCGTGCTACTCTTCTTAATG ATCTTTGGCAACTTATGAAAGGTTG GGCTGAAGATCGTGGT | (SEQ ID NO: 501) | 5 gly | N |
| mL17-17 | SERATLLKELWQ LVGGWGDNFG (SEQ ID NO:428) | TCTGAACGTGCTACTCTTCTTAAAG AACTTTGGCAACTTGTTGGTGGTTG GGGTGATAATTTTGGT | (SEQ ID NO: 502) | 5 gly | N |
| mL17-18 | VGRATLLKEFWQ LVEGLVGQSR (SEQ ID NO:429) | GTTGGTCGTGCTACTCTTCTTAAAG AATTTTGGCAACTTGTTGAAGGTCT TGTTGGTCAATCTCGT | (SEQ ID NO: 503) | 5 gly | N |
| 2x mTN8-Con6-(N)-1K | M-GAQ-WYPCYEGHFWC YDL-GSGSATGGSGST ASSGSGSATG-WYPCYEGHFWC YDL-LE-5G-FC (SEQ ID NO:504) | TGGTATCCGTGTTATGAGGGTCACT TCTGGTGCTACGATCTGGGTTCTGG TTCCACTGCTTCTTCTGGTTCCGGT TCCGCTACTGGTTGGTACCCGTGCT ACGAAGGTCACTTTTGGTGTTATGA TCTG | (SEQ ID NO: 505) | 1K | N |
| 2x mTN8-Con6-(C)-1K | FC-5G-AQ-WYPCYEGHFWC YDL- | TGGTATCCGTGTTATGAGGGTCACT TCTGGTGCTACGATCTGGGTTCTGG TTCCACTGCTTCTTCTGGTTCCGGT | (SEQ ID NO: 507) | 1K | C |

TABLE VI-continued

| Peptibody Name | Peptide | Nucleotide Sequence | (SEQ ID No) | Linker | Terminus |
|---|---|---|---|---|---|
| | GSGSATGGSGST ASSGSGSATG- WYPCYEGHFWC YDL-LE (SEQ ID NO:506) | TCCGCTACTGGTTGGTACCCGTGCT ACGAAGGTCACTTTTGGTGTTATGA TCTG | | | |
| 2x mTN8-Con7- (N)-1K | M-GAQ- IFGCKWWDVQC YQF- GSGSATGGSGST ASSGSGSATG- IFGCKWWDVQC YQF-LE-5G-FC (SEQ ID NO:508) | ATCTTTGGCTGTAAATGGTGGGAC GTTCAGTGCTACCAGTTCGGTTCTG GTTCCACTGCTTCTTCTGGTTCCGG TTCCGCTACTGGTATCTTCGGTTGC AAGTGGTGGGATGTACAGTGTTAT CAGTTT | (SEQ ID NO: 509) | 1K | N |
| 2x mTN8-Con7- (C)-1K | FC-5G-AQ- IFGCKWWDVQC YQF- GSGSATGGSGST ASSGSGSATG- IFGCKWWDVQC YQF-LE (SEQ ID NO:510) | ATCTTTGGCTGTAAATGGTGGGAC GTTCAGTGCTACCAGTTCGGTTCTG GTTCCACTGCTTCTTCTGGTTCCGG TTCCGCTACTGGTATCTTCGGTTGC AAGTGGTGGGATGTACAGTGTTAT CAGTTT | (SEQ ID NO: 511) | 1K | C |
| 2x mTN8-Con8- (N)-1K | M-GAQ- IFGCKWWDVDC YQF- GSGSATGGSGST ASSGSGSATG- IFGCKWWDVDC YQF-LE-5G-FC (SEQ ID NO:512) | ATCTTTGGCTGTAAGTGGTGGGAC GTTGACTGCTACCAGTTCGGTTCTG GTTCCACTGCTTCTTCTGGTTCCGG TTCCGCTACTGGTATCTTCGGTTGC AAATGGTGGGACGTTGATTGTTAT CAGTTT | (SEQ ID NO: 513) | 1K | N |
| 2x mTN8-Con8- (C)-1K | FC-5G-AQ- IFGCKWWDVDC YQF- GSGSATGGSGST ASSGSGSATG- IFGCKWWDVDC YQF-LE (SEQ ID NO:514) | ATCTTTGGCTGTAAGTGGTGGGAC GTTGACTGCTACCAGTTCGGTTCTG GTTCCACTGCTTCTTCTGGTTCCGG TTCCGCTACTGGTATCTTCGGTTGC AAATGGTGGGACGTTGATTGTTAT CAGTTT | (SEQ ID NO: 515) | 1K | C |
| mL15-Con1 | QVESLQQLLMWL DQKLASGPQG (SEQ ID NO:384) | CAGGTTGAATCCCTGCAGCAGCTG CTGATGTGGCTGGACCAGAAACTG GCTTCCGGTCCGCAGGGT | (SEQ ID NO: 516) | 5 gly | C |
| mL15-1 | RMELLESLFELLK EMVPRSKAV (SEQ ID NO:385) | CGTATGGAACTGCTGGAATCCCTG TTCGAACTGCTGAAAGAAATGGTT CCGCGTTCCAAAGCTGTT | (SEQ ID NO: 517) | 5 gly | C |
| mL15-2 | QAVSLQHLLMW LDQKLASGPQH (SEQ ID NO:386) | CAGGCTGTTTCCCTGCAGCACCTGC TGATGTGGCTGGACCAGAAACTGG CTTCCGGTCCGCAGCAC | (SEQ ID NO: 518) | 5 gly | C |
| mL15-3 | DEDSLQQLLMWL DQKLASGPQL (SEQ ID NO:387) | GACGAAGACTCCCTGCAGCAGCTG CTGATGTGGCTGGACCAGAAACTG GCTTCCGGTCCGCAGCTG | (SEQ ID NO: 519) | 5 gly | C |
| mL15-4 | PVASLQQLLIWL DQKLAQGPHA (SEQ ID NO:388) | CCGGTTGCTTCCCTGCAGCAGCTGC TGATCTGGCTGGACCAGAAACTGG CTCAGGGTCCGCACGCT | (SEQ ID NO: 520) | 5 gly | C |
| mL15-5 | EVDELQQLLNWL DHKLASGPLQ (SEQ ID NO:389) | GAAGTTGACGAACTGCAGCAGCTG CTGAACTGGCTGGACCACAAACTG GCTTCCGGTCCGCTGCAG | (SEQ ID NO: 521) | 5 gly | C |
| mL15-6 | DVESLEQLLMWL DHQLASGPHG (SEQ ID NO:390) | GACGTTGAATCCCTGGAACAGCTG CTGATGTGGCTGGACCACCAGCTG GCTTCCGGTCCGCACGGT | (SEQ ID NO: 522) | 5 gly | C |
| mL15-7 | QVDSLQQVLLWL EHKLALGPQV (SEQ ID NO:391) | CAGGTTGACTCCCTGCAGCAGGTT CTGCTGTGGCTGGAACACAAACTG GCTCTGGGTCCGCAGGTT | (SEQ ID NO: 523) | 5 gly | C |

TABLE VI-continued

| Peptibody Name | Peptide | Nucleotide Sequence | (SEQ ID No) | Linker | Terminus |
|---|---|---|---|---|---|
| mL15-8 | GDESLQHLLMWL EQKLALGPHG (SEQ ID NO:392) | GGTGACGAATCCCTGCAGCACCTG CTGATGTGGCTGGAACAGAAACTG GCTCTGGGTCCGCACGGT | (SEQ ID NO: 524) | 5 gly | C |
| mL15-9 | QIEMLESLLDLLR DMVPMSNAF (SEQ ID NO:393) | CAGATCGAAATGCTGGAATCCCTG CTGGACCTGCTGCGTGACATGGTTC CGATGTCCAACGCTTTC | (SEQ ID NO: 525) | 5 gly | C |
| mL15-10 | EVDSLQQLLMWL DQKLASGPQA (SEQ ID NO:394) | GAAGTTGACTCCCTGCAGCAGCTG CTGATGTGGCTGGACCAGAAACTG GCTTCCGGTCCGCAGGCT | (SEQ ID NO: 526) | 5 gly | C |
| mL15-11 | EDESLQQLLIYLD KMLSSGPQV (SEQ ID NO:395) | GAAGACGAATCCCTGCAGCAGCTG CTGATCTACCTGGACAAAATGCTG TCCTCCGGTCCGCAGGTT | (SEQ ID NO: 527) | 5 gly | C |
| mL15-12 | AMDQLHQLLIWL DHKLASGPQA (SEQ ID NO:396) | GCTATGGACCAGCTGCACCAGCTG CTGATCTGGCTGGACCACAAACTG GCTTCCGGTCCGCAGGCT | (SEQ ID NO: 528) | 5 gly | C |
| mL15-13 | RIEMLESLLELLD EIALIPKAW (SEQ ID NO:397) | CGTATCGAAATGCTGGAATCCCTG CTGGAACTGCTGGACGAAATCGCT CTGATCCCGAAAGCTTGG | (SEQ ID NO: 529) | 5 gly | C |
| mL15-14 | EVVSLQHLLMWL EHKLASGPDG (SEQ ID NO:398) | GAAGTTGTTTCCCTGCAGCACCTGC TGATGTGGCTGGAACACAAACTGG CTTCCGGTCCGGACGGT | (SEQ ID NO: 530) | 5 gly | C |
| mL15-15 | GGESLQQLLMWL DQQLASGPQR (SEQ ID NO:399) | GGTGGTGAATCCCTGCAGCAGCTG CTGATGTGGCTGGACCAGCAGCTG GCTTCCGGTCCGCAGCGT | (SEQ ID NO: 531) | 5 gly | C |
| mL15-16 | GVESLQQLLIFLD HMLVSGPHD (SEQ ID NO:400) | GGTGTTGAATCCCTGCAGCAGCTG CTGATCTTCCTGGACCACATGCTGG TTTCCGGTCCGCACGAC | (SEQ ID NO: 532) | 5 gly | C |
| mL15-17 | NVESLEHLMMW LERLLASGPYA (SEQ ID NO:401) | AACGTTGAATCCCTGGAACACCTG ATGATGTGGCTGGAACGTCTGCTG GCTTCCGGTCCGTACGCT | (SEQ ID NO: 533) | 5 gly | C |
| mL15-18 | QVDSLQQLLIWL DHQLASGPKR (SEQ ID NO:402) | CAGGTTGACTCCCTGCAGCAGCTG CTGATCTGGCTGGACCACCAGCTG GCTTCCGGTCCGAAACGT | (SEQ ID NO: 534) | 5 gly | C |
| mL15-19 | EVESLQQLLMWL EHKLAQGPQG (SEQ ID NO:403) | GAAGTTGAATCCCTGCAGCAGCTG CTGATGTGGCTGGAACACAAACTG GCTCAGGGTCCGCAGGGT | (SEQ ID NO: 535) | 5 gly | C |
| mL15-20 | EVDSLQQLLMWL DQKLASGPHA (SEQ ID NO:404) | GAAGTTGACTCCCTGCAGCAGCTG CTGATGTGGCTGGACCAGAAACTG GCTTCCGGTCCGCACGCT | (SEQ ID NO: 536) | 5 gly | C |
| mL15-21 | EVDSLQQLLMWL DQQLASGPQK (SEQ ID NO:405) | GAAGTTGACTCCCTGCAGCAGCTG CTGATGTGGCTGGACCAGCAGCTG GCTTCCGGTCCGCAGAAA | (SEQ ID NO: 537) | 5 gly | C |
| mL15-22 | GVEQLPQLLMWL EQKLASGPQR (SEQ ID NO:406) | GGTGTTGAACAGCTGCCGCAGCTG CTGATGTGGCTGGAACAGAAACTG GCTTCCGGTCCGCAGCGT | (SEQ ID NO: 538) | 5 gly | C |
| mL15-23 | GEDSLQQLLMWL DQQLAAGPQV (SEQ ID NO:407) | GGTGAAGACTCCCTGCAGCAGCTG CTGATGTGGCTGGACCAGCAGCTG GCTGCTGGTCCGCAGGTT | (SEQ ID NO: 539) | 5 gly | C |
| mL15-24 | ADDSLQQLLMW LDRKLASGPHV (SEQ ID NO:408) | GCTGACGACTCCCTGCAGCAGCTG CTGATGTGGCTGGACCGTAAACTG GCTTCCGGTCCGCACGTT | (SEQ ID NO: 540) | 5 gly | C |
| mL15-25 | PVDSLQQLLIWL DQKLASGPQG (SEQ ID NO:409) | CCGGTTGACTCCCTGCAGCAGCTG CTGATCTGGCTGGACCAGAAACTG GCTTCCGGTCCGCAGGGT | (SEQ ID NO: 541) | 5 gly | C |
| mL17-Con2 | QSRATLLKEFWQ LVEGLGDKQA (SEQ ID NO:411) | CAGTCCCGTGCTACCCTGCTGAAA GAATTCTGGCAGCTGGTTGAAGGT CTGGGTGACAAACAGGCT | (SEQ ID NO: 542) | 5 gly | C |

TABLE VI-continued

| Peptibody Name | Peptide | Nucleotide Sequence (SEQ ID No) | | Linker | Terminus |
|---|---|---|---|---|---|
| mL17-19 | EIRATLLKEFWQL VDEWREQPN (SEQ ID NO:430) | GAAATCCGTGCTACCCTGCTGAAA GAATTCTGGCAGCTGGTTGACGAA TGGCGTGAACAGCCGAAC | (SEQ ID NO: 543) | 5 gly | C |
| mL17-20 | QLRATLLKEFLQL VHGLGETDS (SEQ ID NO:431) | CAGCTGCGTGCTACCCTGCTGAAA GAATTCCTGCAGCTGGTTCACGGTC TGGGTGAAACCGACTCC | (SEQ ID NO: 544) | 5 gly | C |
| mL17-21 | TQRATLLKEFWQ LIEGLGGKHV (SEQ ID NO:432) | ACCCAGCGTGCTACCCTGCTGAAA GAATTCTGGCAGCTGATCGAAGGT CTGGGTGGTAAACACGTT | (SEQ ID NO: 545) | 5 gly | C |
| mL17-22 | HYRATLLKEFWQ LVDGLREQGV (SEQ ID NO:433) | CACTACCGTGCTACCCTGCTGAAA GAATTCTGGCAGCTGGTTGACGGT CTGCGTGAACAGGGTGTT | (SEQ ID NO: 546) | 5 gly | C |
| mL17-23 | QSRVTLLREFWQ LVESYRPIVN (SEQ ID NO:434) | CAGTCCCGTGTTACCCTGCTGCGTG AATTCTGGCAGCTGGTTGAATCCTA CCGTCCGATCGTTAAC | (SEQ ID NO: 547) | 5 gly | C |
| mL17-24 | LSRATLLNEFWQ FVDGQRDKRM (SEQ ID NO:435) | CTGTCCCGTGCTACCCTGCTGAACG AATTCTGGCAGTTCGTTGACGGTCA GCGTGACAAACGTATG | (SEQ ID NO: 548) | 5 gly | C |
| mL17-25 | WDRATLLNDFW HLMEELSQKPG (SEQ ID NO:436) | TGGGACCGTGCTACCCTGCTGAAC GACTTCTGGCACCTGATGGAAGAA CTGTCCCAGAAACCGGGT | (SEQ ID NO: 549) | 5 gly | C |
| mL17-26 | QERATLLKEFWR MVEGLGKNRG (SEQ ID NO:437) | CAGGAACGTGCTACCCTGCTGAAA GAATTCTGGCGTATGGTTGAAGGT CTGGGTAAAAACCGTGGT | (SEQ ID NO: 550) | 5 gly | C |
| mL17-27 | NERATLLREFWQ LVGGYGVNQR (SEQ ID NO:438) | AACGAACGTGCTACCCTGCTGCGT GAATTCTGGCAGCTGGTTGGTGGTT ACGGTGTTAACCAGCGT | (SEQ ID NO: 551) | 5 gly | C |
| mTN8Con6-1 | QREWYPCYGGHL WCYDLHKA (SEQ ID NO:347) | CAGCGTGAATGGTACCCGTGCTAC GGTGGTCACCTGTGGTGCTACGAC CTGCACAAAGCT | (SEQ ID NO: 552) | 5 gly | C |
| mTN8Con6-2 | ISAWYSCYAGHF WCWDLKQK (SEQ ID NO:348) | ATCTCCGCTTGGTACTCCTGCTACG CTGGTCACTTCTGGTGCTGGGACCT GAAACAGAAA | (SEQ ID NO: 553) | 5 gly | C |
| mTN8Con6-3 | WTGWYQCYGGH LWCYDLRRK (SEQ ID NO:349) | TGGACCGGTTGGTACCAGTGCTAC GGTGGTCACCTGTGGTGCTACGAC CTGCGTCGTAAA | (SEQ ID NO: 554) | 5 gly | C |
| mTN8Con6-4 | KTFWYPCYDGHF WCYNLKSS (SEQ ID NO:350) | AAAACCTTCTGGTACCCGTGCTAC GACGGTCACTTCTGGTGCTACAAC CTGAAATCCTCC | (SEQ ID NO: 545) | 5 gly | C |
| mTN8Con6-5 | ESRWYPCYEGHL WCFDLTET (SEQ ID NO:351) | GAATCCCGTTGGTACCCGTGCTAC GAAGGTCACCTGTGGTGCTTCGAC CTGACCGAAACC | (SEQ ID NO: 546) | 5 gly | C |
| mL24-1 | NVFFQWVQKHG RVVYQWLDINV (SEQ ID NO:453) | AATGTTTTTTTCAATGGGTTCAAA AACATGGTCGTGTTGTTTATCAATG GCTTGATATTAATGTT | (SEQ ID NO: 557) | 5 gly | C |
| mL24-2 | FDFLQWLQNHRS EVEHWLVMDV (SEQ ID NO:454) | TTTGATTTTCTTCAATGGCTTCAAA ATCATCGTTCTGAAGTTGAACATTG GCTTGTTATGGATGTT | (SEQ ID NO: 558) | 5 gly | C |
| mL20-1 | HQRDMSMLWEL LDVLDGLRQYS (SEQ ID NO:439) | CATCAACGTGATATGTCTATGCTTT GGGAACTTCTTGATGTTCTTGATGG TCTTCGTCAATATTCT | (SEQ ID NO: 559) | 5 gly | C |
| mL20-2 | TQRDMSMLDGLL EVLDQLRQQR (SEQ ID NO:440) | ACTCAACGTGATATGTCTATGCTTG ATGGTCTTCTTGAAGTTCTTGATCA ACTTCGTCAACAACGT | (SEQ ID NO: 560) | 5 gly | C |
| mL20-3 | TSRDMSLLWELL EELDRLGHQR (SEQ ID NO:441) | ACCTCCCGTGACATGTCCCTGCTGT GGGAACTGCTGGAAGAACTGGACC GTCTGGGTCACCAGCGT | (SEQ ID NO: 561) | 5 gly | C |

TABLE VI-continued

| Peptibody Name | Peptide | Nucleotide Sequence | (SEQ ID No) | Linker | Terminus |
|---|---|---|---|---|---|
| mL20-4 | MQHDMSMLYGL VELLESLGHQI (SEQ ID NO:442) | ATGCAACATGATATGTCTATGCTTT ATGGTCTTGTTGAACTTCTTGAATC TCTTGGTCATCAAATT | (SEQ ID NO: 562) | 5 gly | C |
| mL20-5 | WNRDMRMLESL FEVLDGLRQQV (SEQ ID NO:443) | TGGAATCGTGATATGCGTATGCTTG AATCTCTTTTTGAAGTTCTTGATGG TCTTCGTCAACAAGTT | (SEQ ID NO: 563) | 5 gly | C |
| mL20-6 | GYRDMSMLEGLL AVLDRLGPQL (SEQ ID NO:444) | GGTTATCGTGATATGTCTATGCTTG AAGGTCTTCTTGCTGTTCTTGATCG TCTTGGTCCACAACTT | (SEQ ID NO: 564) | 5 gly | C |
| mL20 Con1 | TQRDMSMLEGLL EVLDRLGQQR (SEQ ID NO:445) | ACTCAACGTGATATGTCTATGCTTG AAGGTCTTCTTGAAGTTCTTGATCG TCTTGGTCAACAACGT | (SEQ ID NO: 565) | 5 gly | C |
| mL20 Con2 | WYRDMSMLEGL LEVLDRLGQQR (SEQ ID NO:446) | TGGTACCGTGACATGTCCATGCTG GAAGGTCTGCTGGAAGTTCTGGAC CGTCTGGGTCAGCAGCGT | (SEQ ID NO: 566) | 5 gly | C |
| mL21-1 | TQNSRQMLLSDF MMLVGSMIQG (SEQ ID NO:447) | ACTCAAAATTCTCGTCAAATGCTTC TTTCTGATTTTATGATGCTTGTTGG TTCTATGATTCAAGGT | (SEQ ID NO: 567) | 5 gly | C |
| mL21-2 | MQTSRHILLSEFM MLVGSIMHG (SEQ ID NO:448) | ATGCAAACTTCTCGTCATATTCTTC TTTCTGAATTTATGATGCTTGTTGG TTCTATTATGCATGGT | (SEQ ID NO: 568) | 5 gly | C |
| mL21-3 | HDNSRQMLLSDL LHLVGTMIQG (SEQ ID NO:449) | CACGACAACTCCCGTCAGATGCTG CTGTCCGACCTGCTGCACCTGGTTG GTACCATGATCCAGGGT | (SEQ ID NO: 569) | 5 gly | C |
| mL21-4 | MENSRQNLLRELI MLVGNMSHQ (SEQ ID NO:450) | ATGGAAAACTCCCGTCAGAACCTG CTGCGTGAACTGATCATGCTGGTTG GTAACATGTCCCACCAG | (SEQ ID NO: 570) | 5 gly | C |
| mL21-5 | QDTSRHMLLREF MMLVGEMIQG (SEQ ID NO:451) | CAGGACACCTCCCGTCACATGCTG CTGCGTGAATTCATGATGCTGGTTG GTGAAATGATCCAGGGT | (SEQ ID NO: 571) | 5 gly | C |
| mL21 Con1 | DQNSRQMLLSDL MILVGSMIQG (SEQ ID NO:452) | GACCAGAACTCCCGTCAGATGCTG CTGTCCGACCTGATGATCCTGGTTG GTTCCATGATCCAGGGT | (SEQ ID NO: 572) | 5 gly | C |
| mTN8-19-1 | VALHGQCTRWP WMCPPQREG (SEQ ID NO:305) | GTTGCTCTTCATGGTCAATGTACTC GTTGGCCATGGATGTGTCCACCAC AACGTGAAGGT | (SEQ ID NO: 573) | 5 gly | C |
| mTN8-19-2 | YPEQGLCTRWPW MCPPQTLA (SEQ ID NO:306) | TATCCAGAACAAGGTCTTTGTACTC GTTGGCCATGGATGTGTCCACCAC AAACTCTTGCT | (SEQ ID NO: 574) | 5 gly | C |
| mTN8-19-3 | GLNQGHCTRWP WMCPPQDSN (SEQ ID NO:307) | GGTCTGAACCAGGGTCACTGCACC CGTTGGCCGTGGATGTGCCCGCCG CAGGACTCCAAC | (SEQ ID NO: 575) | 5 gly | C |
| mTN8-19-4 | MITQGQCTRWPW MCPPQPSG (SEQ ID NO:308) | ATGATTACTCAAGGTCAATGTACTC GTTGGCCATGGATGTGTCCACCAC AACCATCTGGT | (SEQ ID NO: 576) | 5 gly | C |
| mTN8-19-5 | AGAQEHCTRWP WMCAPNDWI (SEQ ID NO:309) | GCTGGTGCTCAGGAACACTGCACC CGTTGGCCGTGGATGTGCGCTCCG AACGACTGGATC | (SEQ ID NO: 577) | 5 gly | C |
| mTN8-19-6 | GVNQGQCTRWR WMCPPNGWE (SEQ ID NO:310) | GGTGTTAACCAGGGTCAGTGCACC CGTTGGCCGTTGGATGTGCCCGCCG AACGGTTGGGAA | (SEQ ID NO: 578) | 5 gly | C |
| mTN8-19-7 | LADHGQCIRWPW MCPPEGWE (SEQ ID NO:311) | CTGGCTGACCACGGTCAGTGCATC CGTTGGCCGTGGATGTGCCCGCCG GAAGGTTGGGAA | (SEQ ID NO: 579) | 5 gly | C |
| mTN8-19-8 | ILEQAQCTRWPW MCPPQRGG (SEQ ID NO:312) | ATCCTGGAACAGGCTCAGTGCACC CGTTGGCCGTGGATGTGCCCGCCG CAGCGTGGTGGT | (SEQ ID NO: 580) | 5 gly | C |

TABLE VI-continued

| Peptibody Name | Peptide | Nucleotide Sequence | (SEQ ID No) | Linker | Terminus |
|---|---|---|---|---|---|
| mTN8-19-9 | TQTHAQCTRWP WMCPPQWEG (SEQ ID NO:313) | ACTCAAACTCATGCTCAATGTACTC GTTGGCCATGGATGTGTCCACCAC AATGGGAAGGT | (SEQ ID NO: 581) | 5 gly | C |
| mTN8-19-10 | VVTQGHCTLWP WMCPPQRWR (SEQ ID NO:314) | GTTGTTACTCAAGGTCATTGTACTC TTTGGCCATGGATGTGTCCACCACA ACGTTGGCGT | (SEQ ID NO: 582) | 5 gly | C |
| mTN8-19-11 | IYPHDQCTRWPW MCPPQPYP (SEQ ID NO:315) | ATTTATCCACATGATCAATGTACTC GTTGGCCATGGATGTGTCCACCAC AACCATATCCA | (SEQ ID NO: 583) | 5 gly | C |
| mTN8-19-12 | SYWQGQCTRWP WMCPPQWRG (SEQ ID NO:316) | TCTTATTGGCAAGGTCAATGTACTC GTTGGCCATGGATGTGTCCACCAC AATGGCGTGGT | (SEQ ID NO: 584) | 5 gly | C |
| mTN8-19-13 | MWQQGHCTRWP WMCPPQGWG (SEQ ID NO:317) | ATGTGGCAACAAGGTCATTGTACT CGTTGGCCATGGATGTGTCCACCA CAAGGTTGGGGT | (SEQ ID NO: 585) | 5 gly | C |
| mTN8-19-14 | EFTQWHCTRWP WMCPPQRSQ (SEQ ID NO:318) | GAATTCACCCAGTGGCACTGCACC CGTTGGCCGTGGATGTGCCCGCCG CAGCGTTCCCAG | (SEQ ID NO: 586) | 5 gly | C |
| mTN8-19-15 | LDDQWQCTRWP WMCPPQGFS (SEQ ID NO:319) | CTGGACGACCAGTGGCAGTGCACC CGTTGGCCGTGGATGTGCCCGCCG CAGGGTTTCTCC | (SEQ ID NO: 587) | 5 gly | C |
| mTN8-19-16 | YQTQGLCTRWP WMCPPQSQR (SEQ ID NO:320) | TATCAAACTCAAGGTCTTTGTACTC GTTGGCCATGGATGTGTCCACCAC AATCTCAACGT | (SEQ ID NO: 588) | 5 gly | C |
| mTN8-19-17 | ESNQGQCTRWP WMCPPQGGW (SEQ ID NO:321) | GAATCTAATCAAGGTCAATGTACT CGTTGGCCATGGATGTGTCCACCA CAAGGTGGTTGG | (SEQ ID NO: 589) | 5 gly | C |
| mTN8-19-18 | WTDRGPCTRWP WMCPPQANG (SEQ ID NO:322) | TGGACCGACCGTGGTCCGTGCACC CGTTGGCCGTGGATGTGCCCGCCG CAGGCTAACGGT | (SEQ ID NO: 590) | 5 gly | C |
| mTN8-19-19 | VGTQGQCTRWP WMCPPYETG (SEQ ID NO:323) | GTTGGTACCCAGGGTCAGTGCACC CGTTGGCCGTGGATGTGCCCGCCG TACGAAACCGGT | (SEQ ID NO: 591) | 5 gly | C |
| mTN8-19-20 | PYEQGKCTRWP WMCPPYEVE (SEQ ID NO:324) | CCGTACGAACAGGGTAAATGCACC CGTTGGCCGTGGATGTGCCCGCCG TACGAAGTTGAA | (SEQ ID NO: 592) | 5 gly | C |
| mTN8-19-21 | SEYQGLCTRWPW MCPPQGWK (SEQ ID NO:325) | TCCGAATACCAGGGTCTGTGCACC CGTTGGCCGTGGATGTGCCCGCCG CAGGGTTGGAAA | (SEQ ID NO: 593) | 5 gly | C |
| mTN8-19-22 | TFSQGHCTRWPW MCPPQGWG (SEQ ID NO:326) | ACCTTCTCCCAGGGTCACTGCACCC GTTGGCCGTGGATGTGCCCGCCGC AGGGTTGGGGT | (SEQ ID NO: 594) | 5 gly | C |
| mTN8-19-23 | PGAHDHCTRWP WMCPPQSRY (SEQ ID NO:327) | CCGGGTGCTCACGACCACTGCACC CGTTGGCCGTGGATGTGCCCGCCG CAGTCCCGTTAC | (SEQ ID NO: 595) | 5 gly | C |
| mTN8-19-24 | VAEEWHCRRWP WMCPPQDWR (SEQ ID NO:328) | GTTGCTGAAGAATGGCACTGCCGT CGTTGGCCGTGGATGTGCCCGCCG CAGGACTGGCGT | (SEQ ID NO: 596) | 5 gly | C |
| mTN8-19-25 | VGTQGHCTRWP WMCPPQPAG (SEQ ID NO:329) | GTTGGTACCCAGGGTCACTGCACC CGTTGGCCGTGGATGTGCCCGCCG CAGCCGGCTGGT | (SEQ ID NO: 597) | 5 gly | C |
| mTN8-19-26 | EEDQAHCRSWP WMCPPQGWV (SEQ ID NO:330) | GAAGAAGACCAGGCTCACTGCCGT TCCTGGCCGTGGATGTGCCCGCCG CAGGGTTGGGTT | (SEQ ID NO: 598) | 5 gly | C |
| mTN8-19-27 | ADTQGHCTRWP WMCPPQHWF (SEQ ID NO:331) | GCTGACACCCAGGGTCACTGCACC CGTTGGCCGTGGATGTGCCCGCCG CAGCACTGGTTC | (SEQ ID NO: 599) | 5 gly | C |

TABLE VI-continued

| Peptibody Name | Peptide | Nucleotide Sequence | (SEQ ID No) | Linker | Terminus |
|---|---|---|---|---|---|
| mTN8-19-28 | SGPQGHCTRWPW MCAPQGWF (SEQ ID NO:332) | TCCGGTCCGCAGGGTCACTGCACC CGTTGGCCGTGGATGTGCGCTCCG CAGGGTTGGTTC | (SEQ ID NO: 600) | 5 gly | C |
| mTN8-19-29 | TLVQGHCTRWP WMCPPQRWV (SEQ ID NO:333) | ACCCTGGTTCAGGGTCACTGCACC CGTTGGCCGTGGATGTGCCCGCCG CAGCGTTGGGTT | (SEQ ID NO: 601) | 5 gly | C |
| mTN8-19-30 | GMAHGKCTRWA WMCPPQSWK (SEQ ID NO:334) | GGTATGGCTCACGGTAAATGCACC CGTTGGGCTTGGATGTGCCCGCCG CAGTCCTGGAAA | (SEQ ID NO: 602) | 5 gly | C |
| mTN8-19-31 | ELYHGQCTRWP WMCPPQSWA (SEQ ID NO:335) | GAACTGTACCACGGTCAGTGCACC CGTTGGCCGTGGATGTGCCCGCCG CAGTCCTGGGCT | (SEQ ID NO: 603) | 5 gly | C |
| mTN8-19-32 | VADHGCTRWP WMCPPQGWG (SEQ ID NO:336) | GTTGCTGACCACGGTCACTGCACC CGTTGGCCGTGGATGTGCCCGCCG CAGGGTTGGGGT | (SEQ ID NO: 604) | 5 gly | C |
| mTN8-19-33 | PESQGHCTRWPW MCPPQGWG (SEQ ID NO:337) | CCGGAATCCCAGGGTCACTGCACC CGTTGGCCGTGGATGTGCCCGCCG CAGGGTTGGGGT | (SEQ ID NO: 605) | 5 gly | C |
| mTN8-19-34 | IPAHGHCTRWPW MCPPQRWR (SEQ ID NO:338) | ATCCCGGCTCACGGTCACTGCACC CGTTGGCCGTGGATGTGCCCGCCG CAGCGTTGGCGT | (SEQ ID NO: 606) | 5 gly | C |
| mTN8-19-35 | FTVHGHCTRWP WMCPPYGWV (SEQ ID NO:339) | TTCACCGTTCACGGTCACTGCACCC GTTGGCCGTGGATGTGCCCGCCGT ACGGTTGGGTT | (SEQ ID NO: 607) | 5 gly | C |
| mTN8-19-36 | PDFPGHCTRWRW MCPPQGWE (SEQ ID NO:340) | CCAGATTTTCCAGGTCATTGTACTC GTTGGCGTTGGATGTGTCCACCAC AAGGTTGGGAA | (SEQ ID NO: 608) | 5 gly | C |
| mTN8-19-37 | QLWQGPCTQWP WMCPPKGRY (SEQ ID NO:341) | CAGCTGTGGCAGGGTCCGTGCACC CAGTGGCCGTGGATGTGCCCGCCG AAAGGTCGTTAC | (SEQ ID NO: 609) | 5 gly | C |
| mTN8-19-38 | HANDGHCTRWQ WMCPPQWGG (SEQ ID NO:342) | CACGCTAACGACGGTCACTGCACC CGTTGGCAGTGGATGTGCCCGCCG CAGTGGGGTGGT | (SEQ ID NO: 610) | 5 gly | C |
| mTN8-19-39 | ETDHGLCTRWPW MCPPYGAR (SEQ ID NO:343) | GAAACCGACCACGGTCTGTGCACC CGTTGGCCGTGGATGTGCCCGCCG TACGGTGCTCGT | (SEQ ID NO: 611) | 5 gly | C |
| mTN8-19-40 | GTWQGLCTRWP WMCPPQGWQ (SEQ ID NO:344) | GGTACCTGGCAGGGTCTGTGCACC CGTTGGCCGTGGATGTGCCCGCCG CAGGGTTGGCAG | (SEQ ID NO: 612) | 5 gly | C |
| mTN8-19 Con1 | VATQGQCTRWP WMCPPQGWG (SEQ ID NO:345) | GTTGCTACCCAGGGTCAGTGCACC CGTTGGCCGTGGATGTGCCCGCCG CAGGGTTGGGGT | (SEQ ID NO: 613) | 5 gly | C |
| mTN8-19 Con2 | VATQGQCTRWP WMCPPQRWG (SEQ ID NO:346) | GTTGCTACCCAGGGTCAGTGCACC CGTTGGCCGTGGATGTGCCCGCCG CAGCGTTGGGGT | (SEQ ID NO: 614) | 5 gly | C |
| 2X mTN8-19-7 | FC-5G-AQ- LADHGQCIRWPW MCPPEGWELEGS GSATGGSGSTASS GSGSATGLADHG QCIRWPWMCPPE GWE-LE (SEQ ID NO:615) | CTTGCTGATCATGGTCAATGTATTC GTTGGCCATGGATGTGTCCACCAG AAGGTTGGGAACTCGAGGGTTCCG GTTCCGCTACCGGCGGCTCTGGCTC CACTGCTTCTTCCGGTTCCGGTTCT GCTACTGGTCTGGCTGACCACGGT CAGTGCATCCGTTGGCCGTGGATG TGCCCGCCGGAAGGTTGGGAACTG GAA | (SEQ ID NO: 616) | 1K | C |
| 2X mTN8-19-7 ST-GG del2x LE | FC-5G-AQ- LADHGQCIRWPW MCPPEGWEGSGS ATGGSGGGASSG SGSATGLADHGQ CIRWPWMCPPEG | CTTGCTGATCATGGTCAATGTATTC GTTGGCCATGGATGTGTCCACCAG AAGGTTGGGAAGGTTCCGGTTCCG CTACCGGCGGCTCTGGCGGTGGCG CTTCTTCCGGTTCCGGTTCTGCTAC TGGTCTGGCTGACCACGGTCAGTG | (SEQ ID NO: 618) | 1K | C |

TABLE VI-continued

| Peptibody Name | Peptide | Nucleotide Sequence | (SEQ ID No) | Linker | Terminus |
|---|---|---|---|---|---|
| | WE (SEQ ID NO:617) | CATCCGTTGGCCGTGGATGTGTCCA CCAGAAGGTTGGGAA | | | |
| 2X mTN8-19-21 | FC-5G-AQ-SEYQGLCTRWPW MCPPQGWKLEGS GSATGGSGSTASS GSGSATGSEYQG LCTRWPWMCPPQ GWK-LE (SEQ ID NO:619) | TCTGAATATCAAGGTCTTTGTACTC GTTGGCCATGGATGTGTCCACCAC AAGGTTGGAAACTCGAGGGTTCCG GTTCCGCTACCGGCGGCTCTGGCTC CACTGCTTCTTCCGGTTCCGGTTCT GCTACTGGTTCTGAGTATCAAGGC CTCTGTACTCGCTGGCCATGGATGT GTCCACCACAAGGCTGGAAGCTGG AA | (SEQ ID NO: 620) | 1K | C |
| 2X mTN8-19-21 ST-GG del2x LE | FC-5G-AQ-SEYQGLCTRWPW MCPPQGWKGSGS ATGGSGGGASSG SGSATGSEYQGL CTRWPWMCPPQ GWK (SEQ ID NO:621) | TCTGAATATCAAGGTCTTTGTACTC GTTGGCCATGGATGTGTCCACCAC AAGGTTGGAAAGGTTCCGGTTCCG CTACCGGCGGCTCTGGCGGTGGTG CTTCTTCCGGTTCCGGTTCTGCTAC TGGTTCTGAGTATCAAGGCCTCTGT ACTCGCTGGCCATGGATGTGTCCA CCACAAGGTTGGAAA | (SEQ ID NO: 622) | 1K | C |
| 2X mTN8-19-22 | FC-5G-AQ-TFSQGHCTRWPW MCPPQGWLEGS GSATGGSGSTASS GSGSATGTFSQG HCTRWPWMCPP QGWG-L E (SEQ ID NO:623) | ACTTTTTCTCAAGGTCATTGTACTC GTTGGCCATGGATGTGTCCACCAC AAGGTTGGGGTCTCGAGGGTTCCG GTTCCGCTACCGGCGGCTCTGGCTC CACTGCTTCTTCCGGTTCCGGTTCT GCTACTGGTACTTTTTCTCAAGGC ATTGTACTCGCTGGCCATGGATGTG TCCACCACAAGGCTGGGGCCTGGA A | (SEQ ID NO: 624) | 1K | C |
| 2X mTN8-19-32 | FC-5G-AQ-VADHGHCTRWP WMCPPQGWGLE GSGSATGGSGST ASSGSGSATGVA DHGHCTRWPWM CPPQGWG-LE (SEQ ID NO:625) | GTTGCTGATCATGGTCATTGTACTC GTTGGCCATGGATGTGTCCACCAC AAGGTTGGGGTCTCGAGGGTTCCG GTTCCGCAACCGGCGGCTCTGGCT CCACTGCTTCTTCCGGTTCCGGTTC TGCTACTGGTGTTGCTGACCACGGT CACTGCACCCGTTGGCCGTGGATG TGCCCGCCGCAGGGTTGGGGTCTG GAA | (SEQ ID NO: 626) | 1K | C |
| 2X mTN8-19-32 ST-GG del2x LE | FC-5G-AQ-VADHGHCTRWP WMCPPQGWGGS GSATGGSGGGAS SGSGSATGVADH GHCTRWPWVCPP QGWG (SEQ ID NO:627) | GTTGCTGATCATGGTCATTGTACTC GTTGGCCATGGATGTGTCCACCAC AAGGTTGGGGTGGTTCCGGTTCCG CTACCGGCGGCTCTGGCGGTGGTG CTTCTTCCGGTTCCGGTTCTGCTAC TGGTGTTGCTGACCACGGTCACTGC ACCCGTTGGCCGTGGGTGTGTCCA CCACAAGGTTGGGGT | (SEQ ID NO: 628) | 1K | C |
| 2X mTN8-19-33 | FC-5G-AQ-PESQGHCTRWPW MCPPQGWLEGS GSATGGSGSTASS GSGSATGPESQG HCTRWPWMCPP QGWGLE (SEQ ID NO:629) | CCAGAATCTCAAGGTCATTGTACTC GTTGGCCATGGATGTGTCCACCAC AAGGTTGGGGTCTCGAGGGTTCCG GTTCCGCTACCGGCGGCTCTGGCTC CACTGCTTCTTCCGGTTCCGGTTCT GCTACTGGTCCGGAATCCCAGGGT CACTGCACCCGTTGGCCGTGGATG TGCCCGCCGCAGGGTTGGGGTCTG GAA | (SEQ ID NO: 630) | 1K | C |
| 2X mTN8-19-33 ST-GG del2x LE | FC-5G-AQ-PESQGHCTRWPW MCPPQGWGGSGS ATGGSGGGASSG SGSATGPESQGH CTRWPWMCP PQGWG (SEQ ID NO:631) | CCAGAATCTCAAGGTCATTGTACTC GTTGGCCATGGATGTGTCCACCAC AAGGTTGGGGTGGTTCCGGTTCCG CTACCGGCGGCTCTGGCGGTGGTG CTTCTTCCGGTTCCGGTTCTGCTAC TGGTCCGGAATCCCAGGGTCACTG CACCCGTTGGCCGTGGATGTGTCC ACCACAAGGTTGGGGT | (SEQ ID NO: 632) | 1K | C |

EXAMPLE 7

In Vitro Screening of Affinity Matured Peptibodies

The following exemplary peptibodies were screened according to the protocols set forth above to obtain the following $K_D$ and $IC_{50}$ values. Table VII shows the range of $K_D$ values for selected affinity matured peptibodies compared with the parent peptibodies, as determined by KinExA™ solution based assays or BIAcore® assays. These values demonstrate increased binding affinity of the affinity matured peptibodies for myostatin compared with the parent peptibodies. Table VIII shows $IC_{50}$ values for a number of affinity matured peptibodies. A range of values is given in this table.

TABLE VII

| peptibodies | $K_D$ |
| --- | --- |
| TN8-19 (parent) | >1 nM |
| 2xmTN8-19 (parent) | >1 nM |
| 1x mTN8-19-7 | 10 pM |
| 2x mTN8-19-7 | 12 pM |
| 1x mTN8-19-21 | 6 pM |
| 2x mTN8-19-21 | 6 pM |
| 1x mTN8-19-32 | 9 pM |
| 1x mTN8-19-33 | 21 pM |
| 2x mTN8-19-33 | 3 pM |
| 1x mTN8-19-22 | 4 pM |
| 1x mTN8-19-con1 | 20 pM |

TABLE VIII

| Affinity Matured Peptibody | $IC_{50}$ (nM) |
| --- | --- |
| mTN8-19 Con1 | 1.0-4.4 |
| mTN8-19-2 | 7.508-34.39 |
| mTN8-19-4 | 16.74 |
| mTN8-19-5 | 7.743-3.495 |
| mTN8-19-6 | 17.26 |
| mTN8-19-7 | 1.778 |
| mTN8-19-9 | 22.96-18.77 |
| mTN8-19-10 | 5.252-7.4 |
| mTN8-19-11 | 28.66 |
| mTN8-19-12 | 980.4 |
| mTN8-19-13 | 20.04 |
| mTN8-19-14 | 4.065-6.556 |
| mTN8-19-16 | 4.654 |
| mTN8-19-21 | 2.767-3.602 |
| mTN8-19-22 | 1.927-3.258 |
| mTN8-19-23 | 6.584 |
| mTN8-19-24 | 1.673-2.927 |
| mTN8-19-27 | 4.837-4.925 |
| mTN8-19-28 | 4.387 |
| mTN8-19-29 | 6.358 |
| mTN8-19-32 | 1.842-3.348 |
| mTN8-19-33 | 2.146-2.745 |
| mTN8-19-34 | 5.028-5.069 |
| mTN8Con6-3 | 86.81 |
| mTN8Con6-5 | 2385 |
| mTN8-19-7(-LE) | 1.75-2.677 |
| mTN8-19-21(-LE) | 2.49 |
| mTN8-19-33(-LE) | 1.808 |
| 2xmTN8-19-7 | 0.8572-2.649 |
| 2xmTN8-19-9 | 1.316-1.228 |
| 2xmTN8-19-14 | 1.18-1.322 |
| 2xmTN8-19-16 | 0.9903-1.451 |
| 2xmTN8-19-21 | 0.828-1.434 |
| 2xmTN8-19-22 | 0.9937-1.22 |
| 2xmTN8-19-27 | 1.601-3.931 |
| 2xmTN8-19-7(-LE) | 1.077-1.219 |
| 2xmTN8-19-21(-LE) | 0.8827-1.254 |
| 2xmTN8-19-33(-LE) | 1.12-1.033 |
| mL2-7 | 90.24 |
| mL2-9 | 105.5 |
| mL15-7 | 32.75 |
| mL15-9 | 354.2 |
| mL20-2 | 122.6 |
| mL20-3 | 157.9 |
| mL20-4 | 160 |

EXAMPLE 8

In Vivo Anabolic Activity of Exemplary Peptibodies

The CD1 nu/nu mouse model (Charles River Laboratories, Massachusettes) was used to determine the in vivo efficacy of the peptibodies of the present invention which included the human Fc region (huFc). This model responded to the inhibitors of the present invention with a rapid anabolic response which was associated with increased dry muscle mass and an increase in myofibrillar proteins but was not associated with accumulation in body water content.

Figure 2:
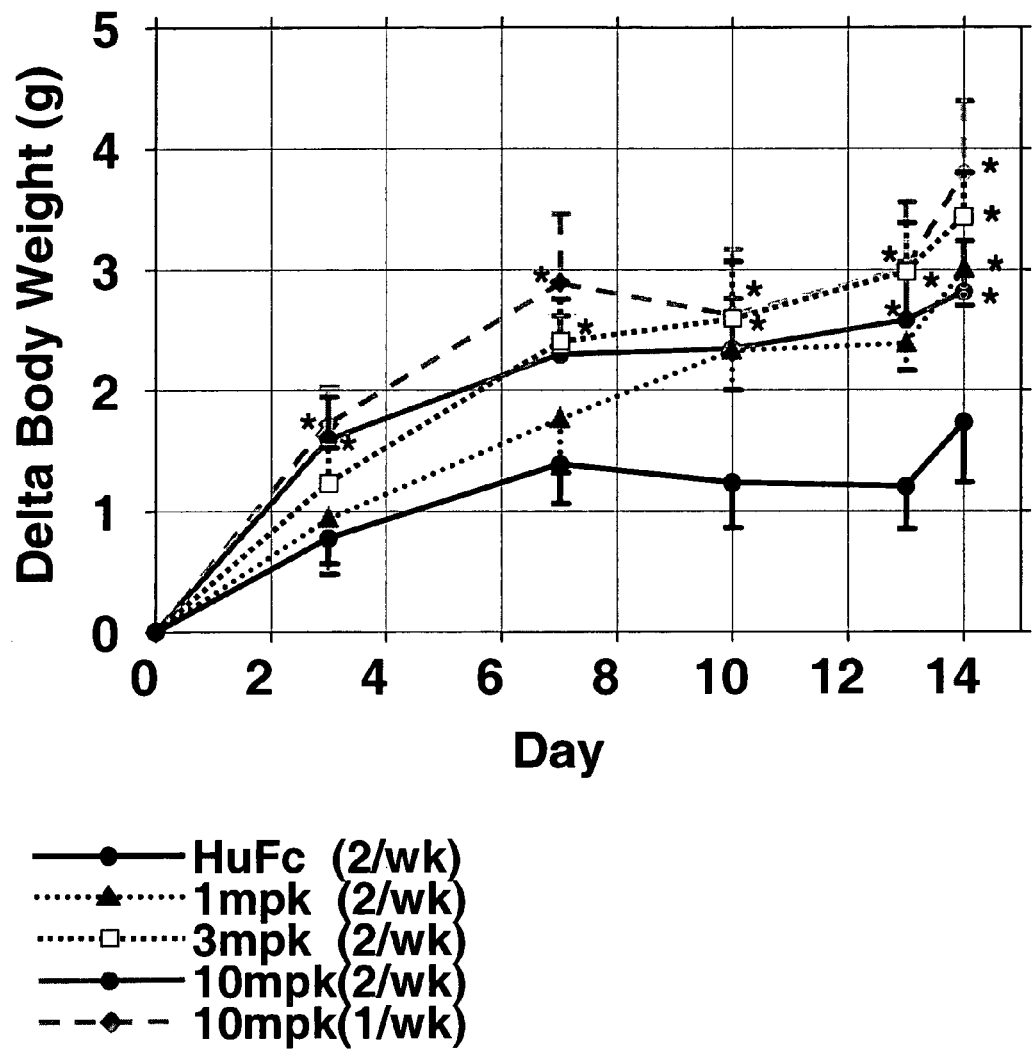
FIG. 2 is a graph showing the increase in total body weight for CD1 nu/nu mice treated with increasing dosages of the 1×mTN8-19-21 peptibody over a fourteen day period compared with mice treated with a huFc control, as described in Example 8.
Figure 3A:
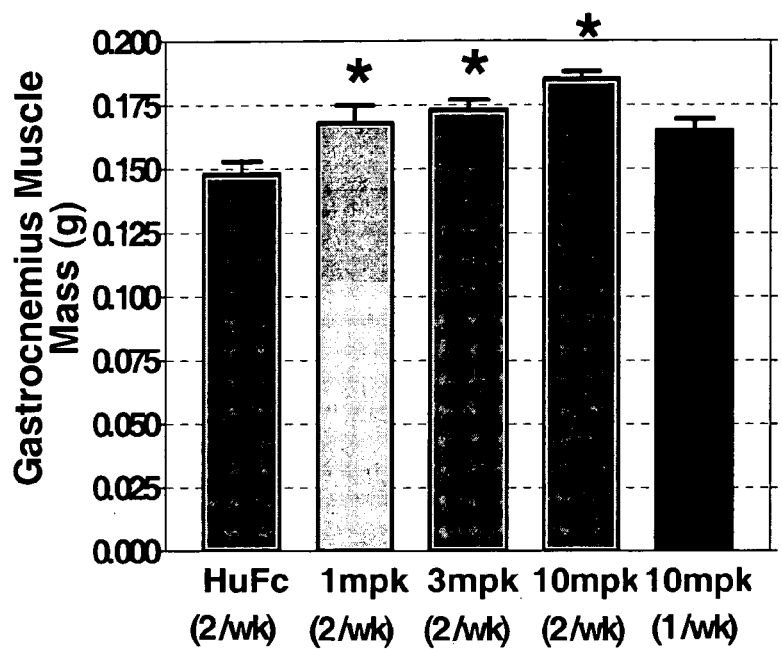
FIG. 3A shows the increase in the mass of the gastrocnemius muscle mass at necropsy of the mice treated in FIG. 2 (Example 8).
Figure 3B:
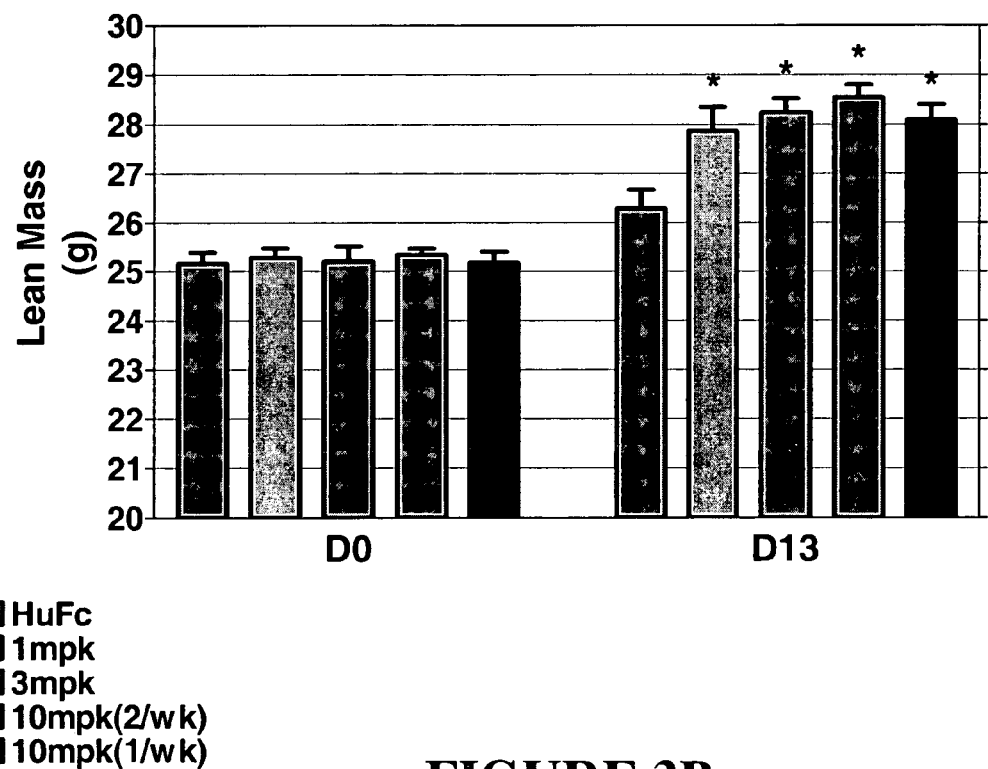
FIG. 3B shows the increase in lean mass as determined by NMR on day 0 compared with day 13 of the experiment described in Example 8.

In one example, the efficacy of 1× peptibody mTN8-19-21 in vivo was demonstrated by the following experiment. A group of 10 8 week old CD1 nu/nu mice were treated twice weekly or once weekly with dosages of 1 mg/kg, 3 mg/kg and 10 mg/kg (subcutaneous injection). The control group of 10 8 week old CD1 nu/nu mice received a twice weekly (subcutaneous) injection of huFc (vehicle) at 10 mg/kg. The animals were weighed every other day and lean body mass determined by NMR on day 0 and day 13. The animals are then sacrificed at day 14 and the size of the gastrocnemius muscle determined. The results are shown in FIGS. 2 and 3. FIG. 2 shows the increase in total body weight of the mice over 14 days for the various dosages of peptibody compared with the control. As can be seen from FIG. 2, all of the dosages have show an increase in body weight compared with the control, with all of the dosages showing statistically significant increases over the control by day 14. FIG. 3 shows the change in lean body mass on day 0 and day 13 as determined by NMR, as well as the change in weight of the gastrocnemius muscle dissected from the animals at day 14.

Figure 4:
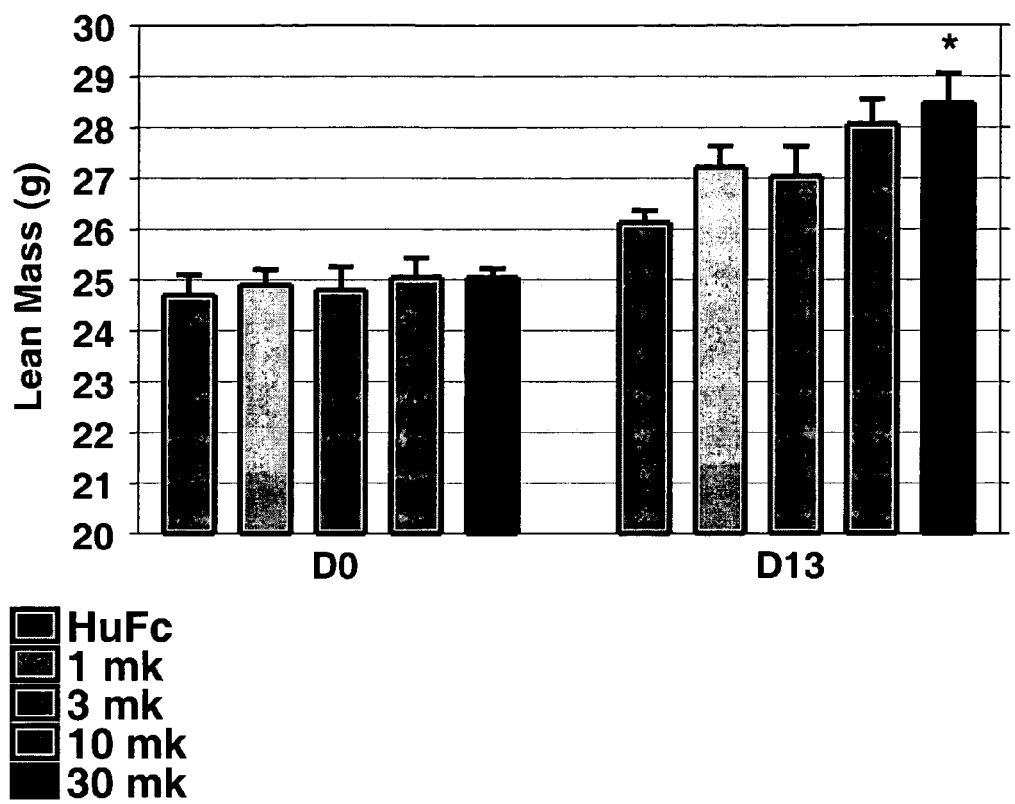
FIG. 4 shows the increase in lean body mass as for CD1 nu/nu mice treated with biweekly injections of increasing dosages of 1×mTN8-19-32 peptibody as determined by NMR on day 0 and day 13 of the experiment described in Example 8.

In another example, the 1× mTN8-19-32 peptibody was administered to CD1 nu/nu mice in a biweekly injection of 1 mg/kg, 3 mg/kg, 10 mg/kg, and 30 mg/kg compared with the huFc control (vehicle). The peptibody-treated animals show an increase in total body weight (not shown) as well as lean body mass on day 13 compared with day 0 as determined by NMR measurement. The increase in lean body mass is shown in FIG. 4.

Figure 5A:
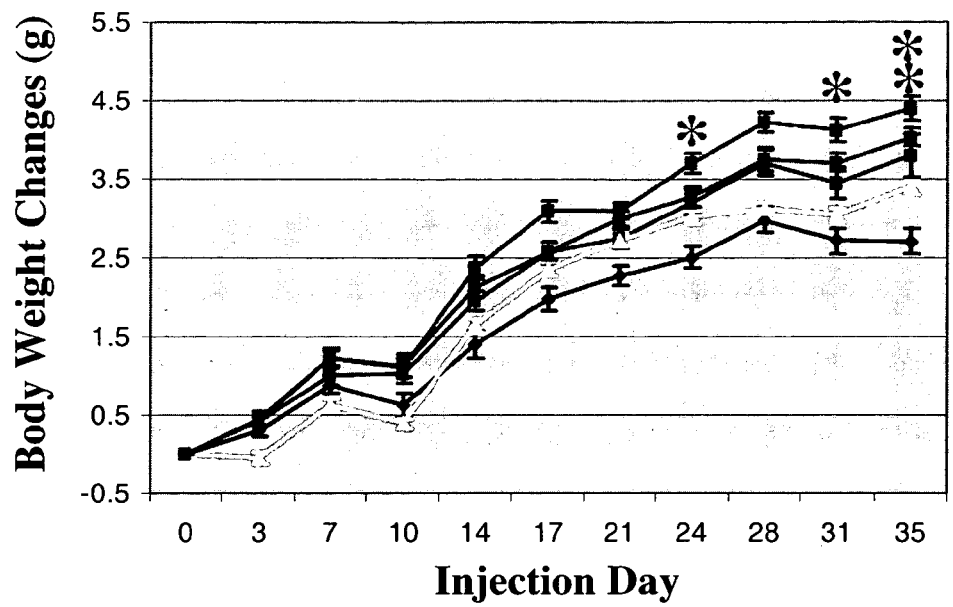
FIG. 5A shows the increase in body weight for CD1 nu/nu mice treated with biweekly injections of 1×mTN8-19-7 compared with 2×mTN8-19-7 and the control animal for 35 days as described in Example 8.
Figure 5B:
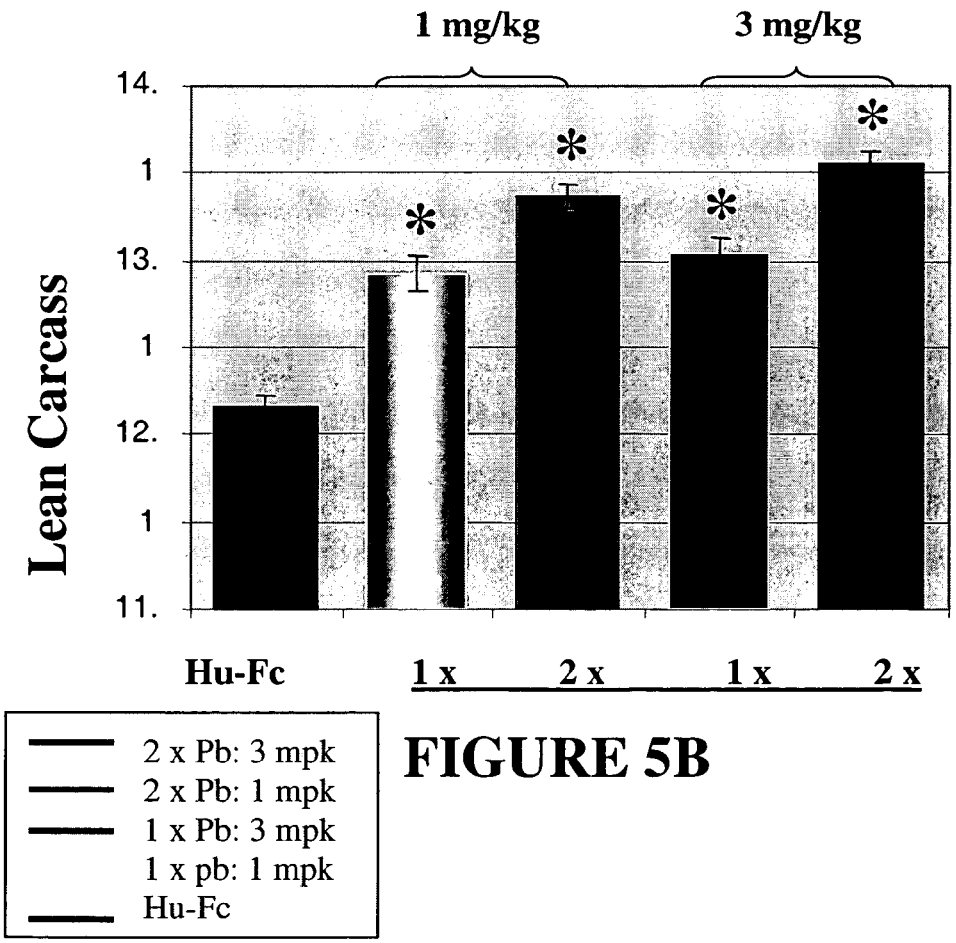
FIG. 5B shows the increase in lean carcass weight at necropsy for the 1× and 2× versions at 1 mg/kg and 3 mg/kg compared with the animals receiving the vehicle (huFc) (controls).

In another example, a 1× affinity-matured peptibody was compared with a 2× affinity-matured peptibody for in vivo anabolic efficacy. CD1 nu/nu male mice (10 animals per group) were treated with twice weekly injections of 1 mg/kg and 3 mg/kg of 1× mTN8-19-7 and 2× mTN8-19-7 for 35 days, while the control group (10 animals) received twice weekly injections of huFc (3 mg/kg). As shown in FIG. 5, treatment with the 2× peptibody resulted in a greater body weight gain and lean carcass weight at necropsy compared with the 1× peptibody or control.

EXAMPLE 9

Increase in Muscular Strength

Normal age-matched 4 month old male C57B/6 mice were treated for 30 days with 2 injections per week subcutaneous injections 5 mg/kg per week of 2× mTN8-19-33, 2× mTN8-19-7, and huFc vehicle control group (10 animals/group). The animals were allowed to recover without any further injections. Gripping strength was measured on day 18 of the recovery period. Gripping strength was measured using a Columbia Instruments meter, model 1027 dsm (Columbus, Ohio). Peptibody treatment resulted in significant increase in gripping strength, with 2× mTN8-19-33 pretreated animals showing a 14% increase in gripping strength compared with the control-treated mice, while 2× mTN8-19-7 showed a 15% increase in gripping strength compared with the control treated mice.

EXAMPLE 10

Pharmacokinetics

In vivo phamacokinetics experiments were performed using representative peptibodies without the LE sequences. 10 mg/kg and 5mg/kg dosages were administered to CD1 nu/nu mice and the following parameters determined: Cmax (ug/mL), area under the curve (AUC) (ug-hr/mL), and half-life (hr). It was found that the 2× versions of the affinity matured peptibodies have a significantly longer half-life than the 1× versions. For example 1× affinity matured mTN8-19-22 has a half-life in the animals of about 50.2 hours, whereas 2× mTN8-19-22 has a half-life of about 85.2 hours. Affinity matured 1× mTN8-7 has a half-life of about 65 hours, whereas 2× mTN8-19-7 has a half-life of about 106 hours.

EXAMPLE 11

Treatment of mdx Mice

Figure 6A:
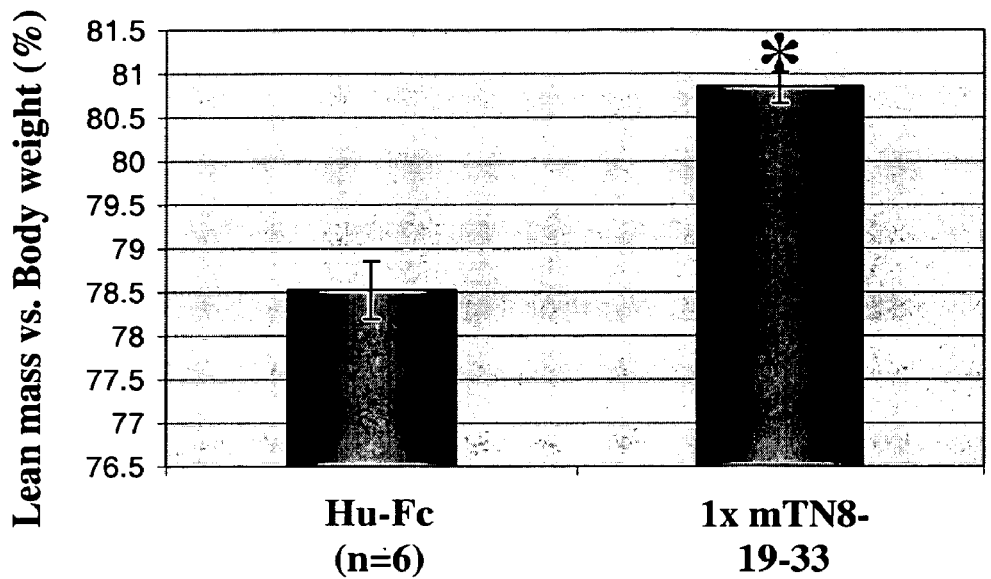
FIG. 6A shows the increase in lean muscle mass vs. body weight for aged mdx mice treated with either affinity matured 1×mTN8-19-33 peptibody or huFc vehicle at 10 mg/kg subcutaneously every other day for three months.
Figure 6B:
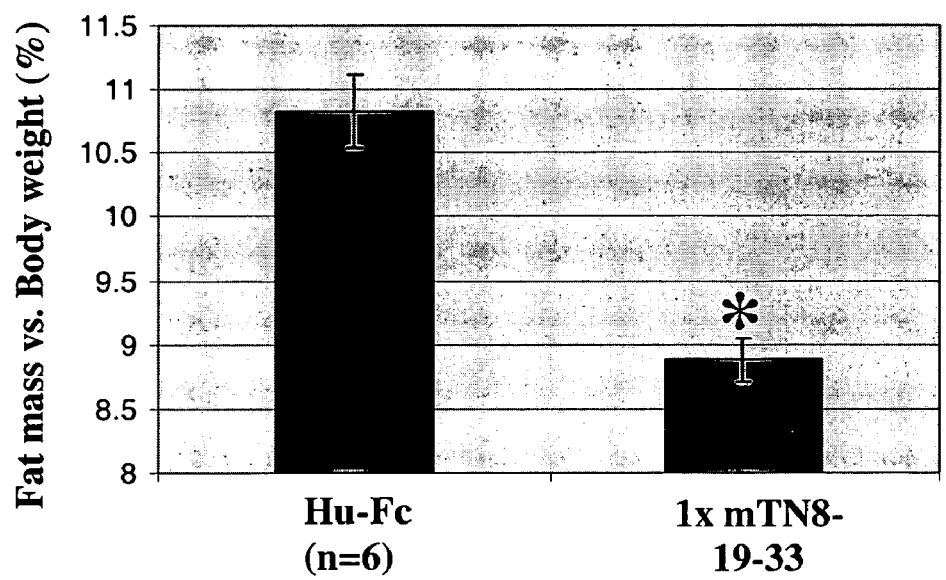
FIG. 6B shows the change in fat mass compared to body weight as determined by NMR for the same mice after 3 months of treatment.

The peptibodies of the present invention have been shown to increase lean muscle mass in an animal and are useful for the treatment of a variety of disorders which involve muscle wasting. Muscular dystrophy is one of those disorders. The mouse model for Duchenne's muscular dystrophy is the Duchenne mdx mouse (Jackson Laboratories, Bar Harbor, Me.). Aged (10 month old) mdx mice were injected with either the peptibody 1× mTN8-19-33 (n=8/group) or with the vehicle huFc protein (N=6/group) for a three month period of time. The dosing schedule was every other day, 10 mg/kg, by subcutaneous injection. The peptibody treatment had a positive effect on increasing and maintaining body mass for the aged mdx mice. Significant increases in body weight were observed in the peptibody-treated group compared to the hu-Fc-treated control group, as shown in FIG. 6A. In addition, NMR analysis revealed that the lean body mass to fat mass ratio was also significantly increased in the aged mdx mice as a result of the peptibody treatment compared with the control group, and that the fat percentage of body weight decreased in the peptibody treated mice compared with the control group, as shown in FIG. 6B.

The present invention is not to be limited in scope by the specific embodiments described herein, which are intended as single illustrations of individual aspects of the invention, and functionally equivalent methods and components of the invention. Indeed, various modifications of the invention, in addition to those shown and described herein will become apparent to those skilled in the art from the foregoing description and accompanying drawings. Such modifications are intended to fall within the scope of the appended claims.

---

What is claimed is:

1. A binding agent comprising at least one peptide capable of binding myostatin, wherein the peptide comprises the sequence $Cb_1b_2Wb_3WMCPP$ (SEQ ID NO: 353), wherein
   $b_1$ is selected from any one of the amino acids T, I, or R;
   $b_2$ is selected from any one of R, S, or Q;
   $b_3$ is selected from any one of P, R or Q,
and physiologically acceptable salts thereof.

2. A myostatin binding agent wherein said agent has the structure:

$(X^1)_a$-$F^1$-$(X^2)_b$, or multimers thereof;

wherein $F^1$ is a vehicle; and $X^1$ and $X^2$ are each independently selected from $-(L^1)_c$-$P^1$;

$-(L^1)_c$-$P^1$-$(L^2)_d$-$P^2$;

$-(L^1)_c$-$P^1$-$(L^2)_d$-$P^2$-$(L^3)_e$-$P^3$;

and $-(L)_c$-$P^1$-$(L^2)_d$-$P^2$-$(L^3)_e$-$P^3$-$(L^4)_f$-$P^4$;

wherein $P^1$, $P^2$, $P^3$, and $P^4$ are peptides capable of binding myostatin, and each comprise the sequence $Cb_1b_2Wb_3WMCPP$ (SEQ ID NO: 353),
wherein
   $b_1$ is selected from any one of the amino acids T, I, or R;
   $b_2$ is selected from any one of R, S, or Q;
   $b_3$ is selected from any one of P, R or Q,
wherein $L^1$, $L^2$, $L^3$, and $L^4$ are each linkers;
and wherein a, b, c, d, e, and f are each independently 0 or 1, provided that at least one of a and b is 1, and physiologically acceptable salts thereof.

3. The binding agent of claim 2, wherein the vehicle is an Fc domain.

4. A pharmaceutical composition comprising a therapeutically effective amount of the binding agent of any one of claims 1 or 2 in admixture with a pharmaceutically acceptable carrier thereof.

5. The pharmaceutical composition of claim 4, wherein the vehicle is an Fc domain.

6. The myostatin binding agent of claim 2, wherein a is 0 and b is 1.

7. The binding agent of claim 3, wherein the Fc is a human IgG Fc.

8. The binding agent of claim 2 wherein a is 1 and b is 0.

9. The binding agent of claim 1, wherein the peptide is between 10 and 50 amino acids in length.

10. The binding agent of claim 2, wherein the peptide is between 10 and 50 amino acids in length.

11. The binding agent of claim 2, wherein the binding agent has the structure $F^1$-$(L^1)_c$-$P^1$ or $F^1$-$(L^1)_c$-$P^1$-$(L^2)_d$-$P^2$.

12. The binding agent of claim 11, wherein the linkers $L^1$ and $L^2$ are $(Gly)_5$.

13. The binding agent of claim 12, wherein the vehicle is an Fc domain.

14. The binding agent of claim 13, wherein the Fc domain is a human IgG Fc.

15. The binding agent of claim 1, wherein the peptide is selected from any one of SEQ ID NO: 305-308, 310-313, 315-331, 333, 335-346.

16. The binding agent of claim 2, wherein the peptide is independently selected from any one of SEQ ID NO: 305-308, 310-313, 315-331, 333, 335-346.

17. The binding agent of claim 14, wherein the peptide is independently selected from any one of SEQ ID NO: 305-308, 310-313, 315-331, 333, 335-346.

18. The binding agent of claim 17, wherein the binding agent further comprises AQ.

19. The binding agent of claim 2, wherein the binding agent further comprises LE and AQ.

20. The binding agent of claim 2, wherein the binding agent has the structure $F^1$-$(L^1)_c$-$P^1$, wherein $F^1$ is a human IgG Fc, wherein $L^1$ is $(Gly)_5$, wherein the binding agent further comprises AQ and wherein $P^1$ is selected from SEQ ID NO: 311, SEQ ID NO: 325, SEQ ID NO: 326, SEQ ID NO: 336, SEQ ID NO: 337, and SEQ ID NO: 345.

21. A binding agent capable of binding myostatin comprising the structure $F^1$-$(L^1)$-$P^1$, wherein $F^1$ is a human IgG Fc, wherein $L^1$ is $(Gly)_5$, wherein the binding agent further comprises AQ and wherein $P^1$ is selected from SEQ ID NO: 311, SEQ ID NO: 325, SEQ ID NO: 326, SEQ ID NO: 336, SEQ ID NO: 337, and SEQ ID NO: 345.

22. A pharmaceutical composition comprising a therapeutically effective amount of the binding agent of claim 21 in admixture with a pharmaceutically acceptable carrier thereof.

* * * * *

UNITED STATES PATENT AND TRADEMARK OFFICE
CERTIFICATE OF CORRECTION

| | | |
|---|---|---|
| PATENT NO. | : 7,511,012 B2 | Page 1 of 1 |
| APPLICATION NO. | : 10/742379 | |
| DATED | : March 31, 2009 | |
| INVENTOR(S) | : Han et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1110 days.

Signed and Sealed this
Twenty-third Day of August, 2011

David J. Kappos
*Director of the United States Patent and Trademark Office*